United States Patent
Bartholomew et al.

(10) Patent No.: US 12,377,206 B2
(45) Date of Patent: *Aug. 5, 2025

(54) FLUIDICS CONTROL SYSTEM FOR MULTI CATHETER STACK

(71) Applicant: Imperative Care, Inc., Campbell, CA (US)

(72) Inventors: Kyle Bartholomew, Campbell, CA (US); Tabish Mustufa, Sunnyvale, CA (US); Vedant Chhaya, Campbell, CA (US)

(73) Assignee: Imperative Care, Inc., Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/666,217

(22) Filed: May 16, 2024

(65) Prior Publication Data

US 2024/0382668 A1    Nov. 21, 2024

Related U.S. Application Data

(60) Provisional application No. 63/550,926, filed on Feb. 7, 2024, provisional application No. 63/528,038, filed
(Continued)

(51) Int. Cl.
*A61M 5/00* (2006.01)
*A61M 5/14* (2006.01)
(Continued)

(52) U.S. Cl.
CPC .......... *A61M 5/007* (2013.01); *A61M 5/1408* (2013.01); *A61M 5/1411* (2013.01);
(Continued)

(58) Field of Classification Search
CPC .. A61M 5/007; A61M 5/1408; A61M 5/1411; A61M 5/14212; A61M 5/16827;
(Continued)

(56) References Cited

U.S. PATENT DOCUMENTS 4,819,653 A   4/1989   Marks
4,925,444 A   5/1990   Orkin
(Continued)

FOREIGN PATENT DOCUMENTS

AU   2006268156   4/2012
CN   102462533    5/2012
(Continued)

OTHER PUBLICATIONS

US 12,076,032 B1, 09/2024, Teigen et al. (withdrawn)
(Continued)

*Primary Examiner* — Bhisma Mehta
*Assistant Examiner* — Hamza A Darb
(74) *Attorney, Agent, or Firm* — Knobbe, Martens, Olson & Bear, LLP

(57) ABSTRACT

A fluidics system includes a cassette having a saline subsystem, a contrast subsystem, and a vacuum subsystem. The fluidics system further includes a splitter and a first tubing set coupled to the cassette and splitter, the first tubing set having a single saline channel, a single contrast channel, and a single vacuum channel. The fluidics system further includes two or more hub assemblies, at least one of the two or more hub assemblies configured to have a third saline flow-path, a third contrast flow-path, and a third vacuum flow-path to provide saline, contrast and vacuum to the lumen of a catheter coupled to the at least one of the two or more hub assemblies. The fluidics system further includes a second tubing set having a plurality of tube groups, each tube group coupled to the splitter and to one of the two or more hub assemblies.

24 Claims, 87 Drawing Sheets

Related U.S. Application Data on Jul. 20, 2023, provisional application No. 63/467,251, filed on May 17, 2023.

(51) Int. Cl.
*A61M 5/142* (2006.01)
*A61M 5/168* (2006.01)

(52) U.S. Cl.
CPC .... *A61M 5/14212* (2013.01); *A61M 5/16827* (2013.01); *A61M 5/16831* (2013.01); *A61M 2205/3393* (2013.01)

(58) Field of Classification Search
CPC ...... A61M 5/16831; A61M 2205/3393; A61M 5/168; A61M 5/1407; A61M 5/142
See application file for complete search history.

(56) References Cited

U.S. PATENT DOCUMENTS

| | | |
|---|---|---|
| 5,037,404 A | 8/1991 | Gold et al. |
| 5,131,391 A | 7/1992 | Sakai et al. |
| 5,380,268 A | 1/1995 | Wheeler |
| 5,638,818 A | 6/1997 | Diab et al. |
| 5,882,333 A | 3/1999 | Schaer et al. |
| 5,989,208 A | 11/1999 | Nita |
| 6,096,004 A | 8/2000 | Meglan et al. |
| 6,375,471 B1 | 4/2002 | Wendlandt et al. |
| 6,400,971 B1 | 6/2002 | Firanov et al. |
| 7,192,433 B2 | 3/2007 | Osypka et al. |
| 7,331,967 B2 | 2/2008 | Lee et al. |
| 7,379,790 B2 | 5/2008 | Toth et al. |
| 7,556,611 B2 | 7/2009 | Kolenbrander et al. |
| 7,567,233 B2 | 7/2009 | Garibaldi et al. |
| 7,608,083 B2 | 10/2009 | Lee et al. |
| 7,615,042 B2 | 11/2009 | Beyar et al. |
| 7,727,185 B2 | 6/2010 | Weitzner |
| 7,747,960 B2 | 6/2010 | Garibaldi et al. |
| 7,756,308 B2 | 7/2010 | Viswanathan |
| 7,761,133 B2 | 7/2010 | Viswanathan et al. |
| 7,789,874 B2 | 9/2010 | Yu et al. |
| D626,250 S | 10/2010 | Wenderow et al. |
| 7,818,076 B2 | 10/2010 | Viswanathan |
| 7,831,294 B2 | 11/2010 | Viswanathan |
| 7,850,640 B2 | 12/2010 | Williams et al. |
| 7,850,642 B2 | 12/2010 | Moll et al. |
| 7,853,306 B2 | 12/2010 | Viswanathan et al. |
| 7,884,727 B2 | 2/2011 | Tran |
| 7,886,743 B2 | 2/2011 | Cooper et al. |
| 7,887,549 B2 | 2/2011 | Wenderow et al. |
| 7,909,798 B2 | 3/2011 | Osypka |
| 7,951,243 B2 | 5/2011 | Boyle, Jr. et al. |
| 7,955,316 B2 | 6/2011 | Weitzner et al. |
| 7,963,288 B2 | 6/2011 | Rosenberg et al. |
| 8,004,229 B2 | 8/2011 | Nowlin et al. |
| 8,021,326 B2 | 9/2011 | Moll et al. |
| RE42,804 E | 10/2011 | Dedig et al. |
| 8,052,636 B2 | 11/2011 | Moll et al. |
| 8,083,753 B2 | 12/2011 | Solar et al. |
| 8,108,069 B2 | 1/2012 | Stahler et al. |
| 8,114,032 B2 | 2/2012 | Ferry et al. |
| 8,123,726 B2 | 2/2012 | Searfoss et al. |
| 8,131,379 B2 | 3/2012 | Hauck |
| 8,137,317 B2 | 3/2012 | Osypka |
| 8,146,874 B2 | 4/2012 | Yu |
| 8,165,684 B2 | 4/2012 | Putz et al. |
| 8,190,238 B2 | 5/2012 | Moll et al. |
| 8,220,468 B2 | 7/2012 | Cooper et al. |
| 8,242,972 B2 | 8/2012 | Garibaldi et al. |
| 8,244,824 B2 | 8/2012 | Garibaldi et al. |
| 8,257,302 B2 | 9/2012 | Beyar et al. |
| 8,262,671 B2 | 9/2012 | Osypka |
| 8,281,807 B2 | 10/2012 | Trombley et al. |
| 8,307,693 B2 | 11/2012 | Uram et al. |
| D674,484 S | 1/2013 | Murphy et al. |
| 8,343,096 B2 | 1/2013 | Kirschenman et al. |
| 8,343,098 B2 | 1/2013 | Nystrom et al. |
| 8,377,077 B2 | 2/2013 | Reis |
| 8,390,438 B2 | 3/2013 | Olson et al. |
| 8,399,871 B2 | 3/2013 | Beyar et al. |
| 8,403,909 B2 | 3/2013 | Spohn et al. |
| D680,645 S | 4/2013 | Murphy et al. |
| 8,409,172 B2 | 4/2013 | Moll et al. |
| 8,467,853 B2 | 6/2013 | Hunter et al. |
| D685,468 S | 7/2013 | Murphy et al. |
| 8,480,618 B2 | 7/2013 | Wenderow et al. |
| 8,498,691 B2 | 7/2013 | Moll et al. |
| 8,506,555 B2 | 8/2013 | Morales |
| 8,521,331 B2 | 8/2013 | Itkowitz |
| 8,529,582 B2 | 9/2013 | Devengenzo et al. |
| 8,540,698 B2 | 9/2013 | Spohn et al. |
| 8,551,084 B2 | 10/2013 | Hauck et al. |
| 8,613,730 B2 | 12/2013 | Hieb et al. |
| 8,617,102 B2 | 12/2013 | Moll et al. |
| 8,620,473 B2 | 12/2013 | Diolaiti et al. |
| 8,671,817 B1 | 3/2014 | Bogusky |
| 8,672,880 B2 | 3/2014 | Cohen et al. |
| 8,684,953 B2 | 4/2014 | Cabiri |
| 8,684,962 B2 | 4/2014 | Kirschenman et al. |
| 8,694,157 B2 | 4/2014 | Wenderow et al. |
| 8,894,610 B2 | 5/2014 | Macnamara et al. |
| 8,740,840 B2 | 6/2014 | Foley et al. |
| 8,747,358 B2 | 6/2014 | Trombley et al. |
| 8,790,297 B2 | 7/2014 | Bromander et al. |
| 8,799,792 B2 | 8/2014 | Garibaldi et al. |
| 8,800,881 B2 | 8/2014 | Biset et al. |
| 8,801,661 B2 | 8/2014 | Moll et al. |
| 8,806,359 B2 | 8/2014 | Garibaldi et al. |
| 8,828,021 B2 | 9/2014 | Wenderow et al. |
| 8,840,628 B2 | 9/2014 | Green et al. |
| 8,852,162 B2 | 10/2014 | Williams et al. |
| 8,852,167 B2 | 10/2014 | Trombley et al. |
| 8,905,969 B2 | 12/2014 | Nystrom et al. |
| 8,939,963 B2 | 1/2015 | Rogers et al. |
| 8,961,491 B2 | 2/2015 | Uber et al. |
| 8,968,333 B2 | 3/2015 | Yu et al. |
| 8,974,408 B2 | 3/2015 | Wallace et al. |
| 8,974,420 B2 | 3/2015 | Searfoss et al. |
| 8,986,246 B2 | 3/2015 | Foley et al. |
| 9,056,200 B2 | 6/2015 | Uber et al. |
| 9,066,740 B2 | 6/2015 | Carlson et al. |
| 9,070,486 B2 | 6/2015 | Guerrera et al. |
| 9,095,681 B2 | 8/2015 | Wenderow et al. |
| 9,101,379 B2 | 8/2015 | Au et al. |
| 9,111,016 B2 | 8/2015 | Besson et al. |
| 9,132,949 B2 | 9/2015 | Bidet et al. |
| 9,138,566 B2 | 9/2015 | Cabiri |
| 9,168,356 B2 | 10/2015 | Wenderow et al. |
| 9,186,046 B2 | 11/2015 | Ramamurthy et al. |
| 9,199,033 B1 | 12/2015 | Cowan et al. |
| 9,205,227 B2 | 12/2015 | Cohen et al. |
| 9,220,568 B2 | 12/2015 | Bromander et al. |
| 9,233,225 B2 | 1/2016 | Hebert |
| 9,241,768 B2 | 1/2016 | Sandhu et al. |
| 9,242,252 B2 | 1/2016 | Eberle et al. |
| 9,259,526 B2 | 2/2016 | Barron et al. |
| 9,295,527 B2 | 3/2016 | Kirschenman et al. |
| 9,314,306 B2 | 4/2016 | Yu |
| 9,314,307 B2 | 4/2016 | Richmond et al. |
| 9,314,310 B2 | 4/2016 | Kirschenman et al. |
| 9,314,311 B2 | 4/2016 | Wenderow et al. |
| 9,314,594 B2 | 4/2016 | Kirschenman |
| 9,320,479 B2 | 4/2016 | Wenderow et al. |
| 9,320,573 B2 | 4/2016 | Sandhu et al. |
| 9,333,324 B2 | 5/2016 | Cohen et al. |
| 9,345,859 B2 | 5/2016 | Blacker |
| 9,375,729 B2 | 6/2016 | Eberle et al. |
| 9,402,977 B2 | 8/2016 | Wenderow et al. |
| 9,408,669 B2 | 8/2016 | Kokish et al. |
| 9,427,515 B1 | 8/2016 | Nystrom |
| 9,427,562 B2 | 8/2016 | Blacker |
| 9,439,736 B2 | 9/2016 | Olson |
| 9,447,890 B2 | 9/2016 | Jennings et al. |
| 9,452,276 B2 | 9/2016 | Duindam et al. |

(56) References Cited

U.S. PATENT DOCUMENTS

| | | |
|---|---|---|
| 9,452,277 B2 | 9/2016 | Blacker |
| 9,474,857 B2 | 10/2016 | Riley et al. |
| 9,480,797 B1 | 11/2016 | Swantner et al. |
| 9,488,971 B2 | 11/2016 | Yip et al. |
| 9,498,291 B2 | 11/2016 | Balaji et al. |
| 9,510,912 B2 | 12/2016 | Bencteux et al. |
| 9,517,305 B2 | 12/2016 | Uram et al. |
| 9,532,840 B2 | 1/2017 | Wong et al. |
| 9,533,121 B2 | 1/2017 | Pacheco et al. |
| 9,545,497 B2 | 1/2017 | Wenderow et al. |
| 9,549,783 B2 | 1/2017 | Zirps |
| 9,566,201 B2 | 2/2017 | Yu |
| 9,566,414 B2 | 2/2017 | Wong et al. |
| 9,572,481 B2 | 2/2017 | Duindam et al. |
| 9,585,806 B2 | 3/2017 | Herrig |
| 9,586,029 B2 | 3/2017 | Shekalim et al. |
| 9,603,573 B2 | 3/2017 | Leininger et al. |
| 9,623,209 B2 | 4/2017 | Wenderow et al. |
| 9,629,595 B2 | 4/2017 | Walker et al. |
| 9,636,479 B2 | 5/2017 | Bencteux et al. |
| 9,687,304 B2 | 6/2017 | Bencteux et al. |
| 9,700,698 B2 | 7/2017 | Pacheco et al. |
| 9,707,377 B2 | 7/2017 | Cohen et al. |
| 9,744,305 B2 | 8/2017 | Cowan et al. |
| 9,750,576 B2 | 9/2017 | Murphy et al. |
| 9,750,953 B2 | 9/2017 | Kalafut |
| 9,764,114 B2 | 9/2017 | Murphy et al. |
| 9,770,301 B2 | 9/2017 | Bencteux et al. |
| 9,782,130 B2 | 10/2017 | Hauck et al. |
| 9,782,564 B2 | 10/2017 | Zirps et al. |
| 9,789,285 B1 | 10/2017 | Blacker |
| 9,814,534 B2 | 11/2017 | Wenderow et al. |
| 9,825,455 B2 | 11/2017 | Sandhu et al. |
| 9,827,410 B2 | 11/2017 | Cowan et al. |
| 9,828,157 B2 | 11/2017 | Roesler |
| 9,833,293 B2 | 12/2017 | Wenderow et al. |
| 9,839,481 B2 | 12/2017 | Blumenkranz et al. |
| 9,855,101 B2 | 1/2018 | Wenderow et al. |
| 9,943,321 B2 | 4/2018 | Nita |
| 9,943,958 B2 | 4/2018 | Blacker et al. |
| 9,949,799 B2 | 4/2018 | Hingwe et al. |
| 9,962,229 B2 | 5/2018 | Blacker et al. |
| 9,981,109 B2 | 5/2018 | Blacker et al. |
| 9,993,614 B2 | 6/2018 | Pacheco et al. |
| 9,993,615 B2 | 6/2018 | Blacker |
| 9,999,751 B2 | 6/2018 | Pacheco et al. |
| 10,010,699 B2 | 7/2018 | Cohen et al. |
| 10,029,072 B2 | 7/2018 | Hebert |
| 10,046,140 B2 | 8/2018 | Kokish et al. |
| 10,052,761 B2 | 8/2018 | Langenfeld et al. |
| 10,071,224 B2 | 9/2018 | Hebert |
| 10,071,225 B2 | 9/2018 | Hebert |
| 10,085,805 B1 | 10/2018 | Blacker |
| 10,086,167 B2 | 10/2018 | Hebert |
| 10,105,486 B2 | 10/2018 | Trombley et al. |
| 10,123,843 B2 | 11/2018 | Wong et al. |
| 10,123,844 B2 | 11/2018 | Nowlin et al. |
| 10,124,149 B2 | 11/2018 | Hebert |
| 10,130,427 B2 | 11/2018 | Tanner et al. |
| 10,138,025 B2 | 11/2018 | Nakamura |
| 10,145,747 B1 | 12/2018 | Lin et al. |
| 10,178,995 B2 | 1/2019 | Cragg |
| 10,201,314 B2 | 2/2019 | Frederick et al. |
| 10,231,788 B2 | 3/2019 | Olson et al. |
| 10,238,456 B2 | 3/2019 | Murphy et al. |
| 10,245,112 B2 | 4/2019 | Kottenstette et al. |
| 10,258,285 B2 | 4/2019 | Hauck et al. |
| 10,271,910 B2 | 4/2019 | Wenderow et al. |
| 10,299,867 B2 | 5/2019 | Wenderow et al. |
| 10,307,570 B2 | 6/2019 | Blacker |
| 10,322,277 B2 | 6/2019 | Nystrom |
| 10,342,953 B2 | 7/2019 | Wenderow et al. |
| 10,363,062 B2 | 7/2019 | Spencer et al. |
| 10,363,109 B2 | 7/2019 | Dachs, II et al. |
| 10,368,951 B2 | 8/2019 | Moll et al. |
| 10,391,234 B2 | 8/2019 | Sams et al. |
| 10,420,537 B2 | 9/2019 | Salahieh et al. |
| 10,426,557 B2 | 10/2019 | Amiri et al. |
| 10,426,559 B2 | 10/2019 | Graetzel et al. |
| 10,426,926 B2 | 10/2019 | Blacker et al. |
| 10,449,007 B2 | 10/2019 | Deboeuf et al. |
| 10,456,556 B2 | 10/2019 | Cabiri |
| 10,512,514 B2 | 12/2019 | Nowlin et al. |
| 10,522,250 B2 | 12/2019 | Spohn et al. |
| 10,531,883 B1 | 1/2020 | Deville et al. |
| 10,531,929 B2 | 1/2020 | Widenhouse et al. |
| 10,537,400 B2 | 1/2020 | Dachs, II et al. |
| 10,539,478 B2 | 1/2020 | Lin et al. |
| 10,549,071 B2 | 2/2020 | Falb et al. |
| 10,549,084 B2 | 2/2020 | Sokolov et al. |
| 10,555,780 B2 | 2/2020 | Tanner et al. |
| 10,556,092 B2 | 2/2020 | Yu et al. |
| 10,561,821 B2 | 2/2020 | Wenderow et al. |
| 10,568,539 B2 | 2/2020 | Kowshik et al. |
| 10,568,700 B2 | 2/2020 | Donhowe et al. |
| 10,583,276 B2 | 3/2020 | Zirps |
| 10,588,656 B2 | 3/2020 | Trosper et al. |
| 10,589,018 B2 | 3/2020 | Uber et al. |
| 10,611,391 B1 | 4/2020 | Klem et al. |
| 10,647,007 B2 | 5/2020 | Cordoba et al. |
| 10,653,863 B1 | 5/2020 | Blacker et al. |
| 10,660,814 B2 | 5/2020 | Soundararajan et al. |
| 10,661,453 B2 | 5/2020 | Koenig et al. |
| 10,687,903 B2 | 6/2020 | Lewis et al. |
| 10,695,140 B2 | 6/2020 | Overmyer et al. |
| 10,695,533 B2 | 6/2020 | Deboeuf et al. |
| 10,695,536 B2 | 6/2020 | Weitzner et al. |
| 10,709,510 B2 | 7/2020 | Kottenstette |
| 10,709,512 B2 | 7/2020 | Bajo et al. |
| 10,716,726 B2 | 7/2020 | Bergman et al. |
| 10,722,253 B2 | 7/2020 | Deville et al. |
| 10,729,825 B2 | 8/2020 | Boyle, Jr. et al. |
| 10,736,706 B2 | 8/2020 | Scheib |
| 10,737,061 B2 | 8/2020 | Parmar |
| 10,744,302 B2 | 8/2020 | Pacheco et al. |
| 10,765,303 B2 | 9/2020 | Graetzel et al. |
| 10,765,486 B2 | 9/2020 | Bajo et al. |
| 10,779,775 B2 | 9/2020 | Bergman et al. |
| 10,779,895 B2 | 9/2020 | Wenderow et al. |
| 10,783,993 B2 | 9/2020 | Spohn et al. |
| 10,799,305 B2 | 10/2020 | Murphy et al. |
| 10,806,905 B2 | 10/2020 | Asmus |
| 10,813,713 B2 | 10/2020 | Koch et al. |
| 10,814,102 B2 | 10/2020 | Laby et al. |
| 10,820,951 B2 | 11/2020 | Soundararajan et al. |
| 10,820,954 B2 | 11/2020 | Marsot et al. |
| 10,827,913 B2 | 11/2020 | Ummalaneni et al. |
| 10,828,463 B2 | 11/2020 | Blacker |
| 10,835,153 B2 | 11/2020 | Rafii-Tari et al. |
| 10,835,329 B2 | 11/2020 | Wenderow et al. |
| 10,835,668 B2 | 11/2020 | Novickoff et al. |
| 10,849,702 B2 | 12/2020 | Hsu et al. |
| 10,864,629 B2 | 12/2020 | Guerrera et al. |
| 10,874,468 B2 | 12/2020 | Wallace et al. |
| 10,881,472 B2 | 1/2021 | Sen et al. |
| 10,881,474 B2 | 1/2021 | Blacker et al. |
| 10,881,765 B2 | 1/2021 | Igarashi |
| 10,898,082 B2 | 1/2021 | Sandgaard |
| 10,898,288 B2 | 1/2021 | Dachs, II et al. |
| 10,900,771 B2 | 1/2021 | Kottenstette et al. |
| 10,912,624 B2 | 2/2021 | Prentakis et al. |
| 10,912,924 B2 | 2/2021 | Park et al. |
| 10,945,904 B2 | 3/2021 | de Jesus Ruiz et al. |
| 10,953,206 B2 | 3/2021 | Blacker |
| 10,959,789 B2 | 3/2021 | Yi et al. |
| 10,959,792 B1 | 3/2021 | Huang et al. |
| 10,987,179 B2 | 4/2021 | Ummalaneni et al. |
| 10,987,491 B2 | 4/2021 | Wenderow et al. |
| 10,994,102 B2 | 5/2021 | Blacker |
| 11,007,118 B2 | 5/2021 | Cowan et al. |
| 11,007,348 B2 | 5/2021 | Blacker |
| 11,040,147 B2 | 6/2021 | Wagner |
| 11,045,274 B2 | 6/2021 | Dachs, II et al. |
| 11,052,226 B2 | 7/2021 | Salahieh et al. |

(56) References Cited

U.S. PATENT DOCUMENTS

| | | |
|---|---|---|
| 11,058,508 B2 | 7/2021 | Scheib et al. |
| 11,076,924 B2 | 8/2021 | Kim et al. |
| 11,078,945 B2 | 8/2021 | Grout et al. |
| 11,083,842 B2 | 8/2021 | Chassot |
| 11,083,873 B2 | 8/2021 | Hebert |
| 11,083,882 B2 | 8/2021 | Schrauder et al. |
| 11,096,712 B2 | 8/2021 | Teigen et al. |
| 11,104,012 B2 | 8/2021 | Cordoba et al. |
| 11,109,919 B2 | 9/2021 | Murphy et al. |
| 11,109,920 B2 | 9/2021 | Al-Jadda et al. |
| 11,109,921 B2 | 9/2021 | Kottenstette et al. |
| 11,110,217 B2 | 9/2021 | O'Brien et al. |
| 11,114,918 B2 | 9/2021 | Zirps |
| 11,129,602 B2 | 9/2021 | Wong et al. |
| 11,141,566 B2 | 10/2021 | Cabiri |
| 11,147,950 B2 | 10/2021 | Destrebecq et al. |
| 11,179,213 B2 | 11/2021 | Huang et al. |
| 11,185,455 B2 | 11/2021 | Cagle et al. |
| 11,191,893 B2 | 12/2021 | Capone et al. |
| 11,197,683 B1 | 12/2021 | Teigen et al. |
| 11,207,147 B2 | 12/2021 | Diamond et al. |
| 11,209,300 B2 | 12/2021 | Johnson |
| 11,213,356 B2 | 1/2022 | Tanner et al. |
| 11,213,362 B2 | 1/2022 | Sharon et al. |
| 11,213,654 B2 | 1/2022 | Murphy et al. |
| 11,234,779 B2 | 2/2022 | Fuerst et al. |
| 11,234,781 B2 | 2/2022 | Penny et al. |
| 11,234,784 B2 | 2/2022 | Alden |
| 11,241,291 B2 | 2/2022 | Sharon et al. |
| 11,259,881 B2 | 3/2022 | Garcia Kilroy et al. |
| 11,266,424 B2 | 3/2022 | Hofmann et al. |
| 11,291,515 B2 | 4/2022 | Sharon et al. |
| 11,298,198 B2 | 4/2022 | Fournier et al. |
| 11,304,668 B2 | 4/2022 | Wenderow et al. |
| 11,318,618 B2 | 5/2022 | Desai |
| 11,331,157 B2 | 5/2022 | Russell et al. |
| 11,337,712 B2 | 5/2022 | Teigen et al. |
| 11,337,764 B2 | 5/2022 | Deboeuf et al. |
| 11,357,586 B2 | 6/2022 | Huang et al. |
| 11,357,597 B2 | 6/2022 | Jhaveri et al. |
| 11,359,156 B2 | 6/2022 | Long et al. |
| 11,376,086 B2 | 7/2022 | McGrogan et al. |
| 11,389,360 B2 | 7/2022 | Koenig et al. |
| 11,400,214 B2 | 8/2022 | Porter |
| 11,406,402 B2 | 8/2022 | Deville et al. |
| 11,413,101 B2 | 8/2022 | Sen et al. |
| 11,413,431 B2 | 8/2022 | Blacker |
| 11,419,977 B2 | 8/2022 | Cowan et al. |
| 11,426,246 B2 | 8/2022 | Asadian et al. |
| 11,432,835 B2 | 9/2022 | Shaffer et al. |
| 11,432,840 B2 | 9/2022 | Grothe et al. |
| 11,448,327 B2 | 9/2022 | Heffner et al. |
| 11,464,587 B2 | 10/2022 | Yu et al. |
| 11,464,589 B1 | 10/2022 | Roh et al. |
| 11,472,030 B2 | 10/2022 | Ho et al. |
| 11,478,329 B2 | 10/2022 | Gee et al. |
| 11,490,911 B2 | 11/2022 | Panian |
| 11,497,481 B2 | 11/2022 | Penny et al. |
| 11,497,523 B2 | 11/2022 | Trosper et al. |
| 11,497,568 B2 | 11/2022 | Ho et al. |
| 11,510,736 B2 | 11/2022 | Rafii-Tari et al. |
| D976,399 S | 1/2023 | Carmi |
| 11,547,426 B2 | 1/2023 | Deville et al. |
| 11,547,511 B2 | 1/2023 | Asadian et al. |
| 11,564,649 B2 | 1/2023 | Kedmi-Shahar et al. |
| 11,571,267 B2 | 2/2023 | Gonenc et al. |
| 11,576,743 B2 | 2/2023 | Venkataraman et al. |
| 11,577,382 B2 | 2/2023 | Cagle et al. |
| 11,589,931 B2 | 2/2023 | Desai et al. |
| 11,607,108 B2 | 3/2023 | Yu et al. |
| 11,628,024 B2 | 4/2023 | Kapadia |
| 11,633,247 B2 | 4/2023 | Johnson et al. |
| 11,642,181 B2 | 5/2023 | Nobles et al. |
| 11,653,905 B2 | 5/2023 | Wong et al. |
| 11,660,151 B2 | 5/2023 | Schena |
| 11,660,437 B2 | 5/2023 | Verma |
| 11,672,602 B2 | 6/2023 | Monteverde et al. |
| 11,678,943 B2 | 6/2023 | Zhou et al. |
| 11,678,948 B2 | 6/2023 | Vargas et al. |
| 11,684,759 B2 | 6/2023 | Hayzelden |
| 11,690,985 B2 | 7/2023 | Calhoun et al. |
| 11,696,808 B2 | 7/2023 | Blacker et al. |
| 11,696,810 B2 | 7/2023 | Asadian et al. |
| 11,701,196 B2 | 7/2023 | Scheib et al. |
| 11,703,604 B2 | 7/2023 | Dissertori et al. |
| 11,712,805 B2 | 8/2023 | Zhou et al. |
| 11,713,376 B2 | 8/2023 | Leroux et al. |
| 11,717,356 B2 | 8/2023 | Amiri et al. |
| 11,717,640 B2 | 8/2023 | Fantuzzi et al. |
| 11,723,739 B2 | 8/2023 | Asadian et al. |
| 11,723,744 B2 | 8/2023 | Ergueta Tejerina et al. |
| 11,730,499 B1 | 8/2023 | Thio et al. |
| 11,737,821 B2 | 8/2023 | Algawi et al. |
| 11,744,989 B2 | 9/2023 | Blacker |
| 11,759,269 B2 | 9/2023 | Zhou et al. |
| 11,764,873 B2 | 9/2023 | Burla et al. |
| 11,765,360 B2 | 9/2023 | Schroers et al. |
| 11,766,786 B2 | 9/2023 | Cordoba et al. |
| 11,780,092 B2 | 10/2023 | Desai et al. |
| 11,785,938 B2 | 10/2023 | Clavien et al. |
| 11,786,329 B2 | 10/2023 | Fuerst et al. |
| 11,789,315 B1 | 10/2023 | Yu et al. |
| 11,793,500 B2 | 10/2023 | Vargas |
| 11,793,597 B2 | 10/2023 | Vargas et al. |
| 11,801,365 B2 | 10/2023 | Blacker et al. |
| 11,813,203 B2 | 11/2023 | Timm et al. |
| 11,819,295 B2 | 11/2023 | Wenderow et al. |
| 11,832,904 B2 | 12/2023 | Wenderow et al. |
| 11,844,580 B2 | 12/2023 | Sen et al. |
| 11,844,732 B2 | 12/2023 | Klem et al. |
| 11,883,119 B2 | 1/2024 | Sen et al. |
| 11,883,245 B2 | 1/2024 | Fathollahi Ghezelghieh et al. |
| 11,890,024 B2 | 2/2024 | Panian |
| 11,890,432 B2 | 2/2024 | Awad et al. |
| 11,896,325 B2 | 2/2024 | Clark et al. |
| 11,903,669 B2 | 2/2024 | Cope et al. |
| 11,906,009 B2 | 2/2024 | Klem |
| 11,910,997 B2 | 2/2024 | Fuerst et al. |
| 11,911,120 B2 | 2/2024 | Freiin von Kapri et al. |
| 11,911,910 B2 | 2/2024 | Gonenc et al. |
| 11,918,240 B2 | 3/2024 | Deville et al. |
| 11,918,312 B2 | 3/2024 | Yu |
| 11,918,423 B2 | 3/2024 | Kottenstette et al. |
| 11,998,290 B2 | 6/2024 | Murphy et al. |
| 12,004,829 B2 | 6/2024 | Searfoss et al. |
| 12,005,589 B2 | 6/2024 | Rea et al. |
| 12,035,989 B2 | 7/2024 | Clark et al. |
| 12,046,363 B2 | 7/2024 | Shrivastava et al. |
| 12,059,161 B2 | 8/2024 | Deville et al. |
| 12,059,225 B2 | 8/2024 | Zhou et al. |
| 12,076,036 B2 | 9/2024 | Baron et al. |
| 12,076,099 B2 | 9/2024 | Shrivastava et al. |
| 12,076,497 B2 | 9/2024 | Fantuzzi et al. |
| 12,076,505 B2 | 9/2024 | Haubert |
| 12,082,982 B2 | 9/2024 | Jhaveri et al. |
| 12,087,024 B2 | 9/2024 | Djelouah et al. |
| 12,102,290 B2 | 10/2024 | Sharon et al. |
| 12,114,940 B2 | 10/2024 | Garcia Kilroy et al. |
| 12,117,624 B2 | 10/2024 | Fuerst et al. |
| 12,133,631 B2 | 11/2024 | Saadat et al. |
| 12,133,700 B2 | 11/2024 | Miller et al. |
| 12,133,702 B2 | 11/2024 | Nowlin et al. |
| 12,133,704 B2 | 11/2024 | Savall et al. |
| 12,133,707 B2 | 11/2024 | Zhang et al. |
| 12,133,965 B2 | 11/2024 | Chassot et al. |
| 12,136,867 B2 | 11/2024 | Zirps |
| 12,137,603 B2 | 11/2024 | Liu et al. |
| 12,137,874 B2 | 11/2024 | Deyanov et al. |
| 12,137,880 B2 | 11/2024 | Retailleau et al. |
| 12,137,926 B2 | 11/2024 | Cooper |
| 12,137,935 B2 | 11/2024 | Blumenkranz et al. |
| 12,137,936 B2 | 11/2024 | Litke et al. |
| 12,137,990 B2 | 11/2024 | Walker et al. |
| 12,138,002 B2 | 11/2024 | Fenech |

(56) References Cited

U.S. PATENT DOCUMENTS

| | | |
|---|---|---|
| 12,138,003 B2 | 11/2024 | Schuh |
| 12,138,004 B2 | 11/2024 | Cone et al. |
| 12,138,006 B2 | 11/2024 | Ramstad et al. |
| 12,138,012 B2 | 11/2024 | Barbagli et al. |
| 12,138,129 B2 | 11/2024 | Yuan et al. |
| 12,138,130 B2 | 11/2024 | Garbus et al. |
| 12,140,172 B2 | 11/2024 | Grout et al. |
| 12,140,788 B2 | 11/2024 | Samadani et al. |
| 12,144,564 B2 | 11/2024 | Barbagli et al. |
| 12,144,569 B2 | 11/2024 | Cone et al. |
| 12,144,574 B2 | 11/2024 | Griffiths et al. |
| 12,144,575 B2 | 11/2024 | Torabi |
| 12,144,690 B2 | 11/2024 | Fuerst et al. |
| 12,145,278 B2 | 11/2024 | Ho et al. |
| 12,148,320 B2 | 11/2024 | Alexander et al. |
| 12,150,645 B2 | 11/2024 | Meade et al. |
| 12,150,660 B1 | 11/2024 | Teigen et al. |
| 12,150,692 B2 | 11/2024 | Shah et al. |
| 12,150,718 B2 | 11/2024 | Barbagli et al. |
| 12,150,723 B2 | 11/2024 | Ayvali et al. |
| 12,150,796 B2 | 11/2024 | Wenderow et al. |
| 12,150,819 B2 | 11/2024 | Hazelton et al. |
| 12,156,654 B2 | 12/2024 | Wellman |
| 12,156,666 B2 | 12/2024 | Trosper et al. |
| 12,156,667 B2 | 12/2024 | Trosper et al. |
| 12,156,711 B2 | 12/2024 | Liao et al. |
| 12,156,755 B2 | 12/2024 | Walker et al. |
| 12,157,238 B2 | 12/2024 | Fredrickson et al. |
| 12,161,286 B2 | 12/2024 | Hazelton et al. |
| 12,161,290 B2 | 12/2024 | Liou et al. |
| 12,161,306 B2 | 12/2024 | Blumenkranz et al. |
| 12,161,321 B2 | 12/2024 | Weir et al. |
| 12,161,419 B2 | 12/2024 | Fuerst et al. |
| 12,161,423 B2 | 12/2024 | Chopra et al. |
| 12,161,434 B2 | 12/2024 | Panescu et al. |
| 12,161,435 B2 | 12/2024 | Abbott et al. |
| 12,161,512 B2 | 12/2024 | Shirazian et al. |
| 12,161,822 B2 | 12/2024 | Kim et al. |
| 12,162,143 B2 | 12/2024 | Dimaio et al. |
| 12,164,684 B2 | 12/2024 | Itkowitz et al. |
| 12,165,268 B2 | 12/2024 | Olson et al. |
| 12,165,317 B2 | 12/2024 | Proksch et al. |
| 12,167,943 B2 | 12/2024 | Azizian et al. |
| 12,171,398 B2 | 12/2024 | Halderman et al. |
| 12,171,401 B2 | 12/2024 | Brichard et al. |
| 12,171,435 B2 | 12/2024 | Kaufman et al. |
| 12,171,504 B2 | 12/2024 | Rafii-Tari |
| 12,171,505 B2 | 12/2024 | Barbagli et al. |
| 12,171,511 B2 | 12/2024 | Gonenc et al. |
| 12,171,514 B2 | 12/2024 | Soundararajan et al. |
| 12,171,516 B2 | 12/2024 | Abbott et al. |
| 12,171,543 B2 | 12/2024 | Duindam et al. |
| 12,171,955 B2 | 12/2024 | Wenderow et al. |
| 12,171,958 B2 | 12/2024 | Kim et al. |
| 12,175,018 B2 | 12/2024 | Freiin von Kapri et al. |
| 12,177,411 B2 | 12/2024 | Culman |
| 12,178,387 B2 | 12/2024 | McDowall et al. |
| 12,178,399 B2 | 12/2024 | Itkowitz et al. |
| 12,178,431 B2 | 12/2024 | Ueda et al. |
| 12,178,521 B2 | 12/2024 | Sramek et al. |
| 12,178,526 B2 | 12/2024 | McKenney et al. |
| 12,178,534 B2 | 12/2024 | Asadian et al. |
| 12,182,956 B2 | 12/2024 | Harris, Jr. |
| 2002/0192113 A1 | 12/2002 | Uffenheimer et al. |
| 2003/0071285 A1 | 4/2003 | Tsukernik |
| 2003/0100849 A1 | 5/2003 | Jang |
| 2003/0105451 A1 | 6/2003 | Westlund et al. |
| 2003/0114739 A1 | 6/2003 | Fuimaono et al. |
| 2003/0125673 A1 | 7/2003 | Houde et al. |
| 2004/0068248 A1 | 4/2004 | Mooney et al. |
| 2004/0097805 A1 | 5/2004 | Verard et al. |
| 2004/0143225 A1* | 7/2004 | Callan ................ A61M 39/22 604/247 |
| 2005/0077225 A1* | 4/2005 | Usher ................ B01D 63/14 604/9 |
| 2005/0107667 A1 | 5/2005 | Danitz |
| 2005/0165276 A1 | 7/2005 | Belson et al. |
| 2005/0277912 A1 | 12/2005 | John |
| 2006/0011501 A1 | 1/2006 | Itou et al. |
| 2006/0095022 A1 | 5/2006 | Moll et al. |
| 2006/0200026 A1 | 9/2006 | Wallace et al. |
| 2006/0200191 A1 | 9/2006 | Zadno-Azizi |
| 2007/0060915 A1 | 3/2007 | Kucklick |
| 2007/0106208 A1* | 5/2007 | Uber, III ............ A61M 31/005 220/500 |
| 2007/0270639 A1 | 11/2007 | Long |
| 2008/0027464 A1 | 1/2008 | Moll et al. |
| 2008/0086051 A1 | 4/2008 | Voegele |
| 2008/0262513 A1 | 10/2008 | Stahler et al. |
| 2008/0319387 A1 | 12/2008 | Amisar et al. |
| 2009/0076445 A1 | 3/2009 | Furnish |
| 2009/0131955 A1 | 5/2009 | Wenderow et al. |
| 2009/0153374 A1 | 6/2009 | Maw et al. |
| 2009/0171332 A1 | 7/2009 | Bonneau |
| 2009/0254083 A1 | 10/2009 | Wallace et al. |
| 2009/0264785 A1 | 10/2009 | Causevic et al. |
| 2010/0069833 A1 | 3/2010 | Wenderow et al. |
| 2010/0175701 A1 | 7/2010 | Reis et al. |
| 2010/0204712 A1 | 8/2010 | Mallaby |
| 2010/0204713 A1 | 8/2010 | Ruiz Morales |
| 2010/0280363 A1 | 11/2010 | Skarda et al. |
| 2011/0015484 A1 | 1/2011 | Alvarez et al. |
| 2011/0144658 A1 | 6/2011 | Wenderow et al. |
| 2011/0238010 A1 | 9/2011 | Kirschenman et al. |
| 2011/0288544 A1 | 11/2011 | Verin et al. |
| 2011/0313318 A1 | 12/2011 | Rule et al. |
| 2012/0071895 A1 | 3/2012 | Stahler et al. |
| 2012/0172798 A1 | 7/2012 | Miller et al. |
| 2012/0179032 A1 | 7/2012 | Bromander et al. |
| 2012/0316458 A1 | 12/2012 | Rahmany |
| 2013/0035537 A1 | 2/2013 | Wallace |
| 2013/0053704 A1 | 2/2013 | Bernak et al. |
| 2013/0096551 A1 | 4/2013 | Govari et al. |
| 2013/0131499 A1 | 5/2013 | Chan et al. |
| 2013/0214912 A1 | 8/2013 | Beyar et al. |
| 2013/0231678 A1 | 9/2013 | Wenderow |
| 2014/0058321 A1 | 2/2014 | Wenderow et al. |
| 2014/0066900 A1 | 3/2014 | Blacker |
| 2014/0228762 A1 | 8/2014 | Capone |
| 2014/0276233 A1 | 9/2014 | Murphy |
| 2014/0276389 A1 | 9/2014 | Walker |
| 2014/0276948 A1 | 9/2014 | Zirps |
| 2014/0318702 A1 | 10/2014 | Tegg |
| 2015/0005738 A1 | 1/2015 | Blacker |
| 2015/0005745 A1 | 1/2015 | Bergman et al. |
| 2015/0073391 A1 | 3/2015 | Hutchins et al. |
| 2015/0088002 A1 | 3/2015 | Podhajsky |
| 2015/0157252 A1 | 6/2015 | Sabesan |
| 2015/0272683 A1 | 10/2015 | Yang et al. |
| 2015/0374483 A1 | 12/2015 | Janardhan |
| 2016/0058513 A1 | 3/2016 | Giorgi |
| 2016/0067448 A1 | 3/2016 | Blacker et al. |
| 2016/0074057 A1 | 3/2016 | Jezierski et al. |
| 2016/0184032 A1 | 6/2016 | Romo |
| 2016/0310702 A1 | 10/2016 | Cabiri |
| 2016/0374590 A1 | 12/2016 | Wong et al. |
| 2017/0000576 A1 | 1/2017 | Zirps |
| 2017/0014998 A1 | 1/2017 | Langenfeld et al. |
| 2017/0020627 A1 | 1/2017 | Tesar et al. |
| 2017/0027653 A1 | 2/2017 | Kirschenman |
| 2017/0143416 A1 | 5/2017 | Guler et al. |
| 2017/0135773 A1 | 6/2017 | Lohmeier et al. |
| 2017/0224224 A1 | 8/2017 | Yu |
| 2017/0252025 A1 | 9/2017 | Cabiri et al. |
| 2017/0281054 A1 | 10/2017 | Stever et al. |
| 2017/0317937 A1 | 11/2017 | Dillon |
| 2017/0333000 A1 | 11/2017 | Nystrom et al. |
| 2017/0348060 A1 | 12/2017 | Blacker |
| 2018/0126122 A1 | 5/2018 | Cabiri |
| 2018/0153477 A1 | 6/2018 | Nagale et al. |
| 2018/0161001 A1 | 6/2018 | Seip |
| 2018/0168751 A1 | 6/2018 | Yi et al. |
| 2018/0185104 A1 | 7/2018 | Olson et al. |
| 2018/0199916 A1 | 7/2018 | Sugihara et al. |

(56) References Cited

U.S. PATENT DOCUMENTS

| | | |
|---|---|---|
| 2018/0250086 A1 | 9/2018 | Grubbs |
| 2018/0360398 A1 | 12/2018 | Wenderow et al. |
| 2019/0008360 A1 | 1/2019 | Peh et al. |
| 2019/0030324 A1 | 1/2019 | Grace et al. |
| 2019/0111237 A1 | 4/2019 | Cabiri et al. |
| 2019/0133666 A1 | 5/2019 | Johnson |
| 2019/0209026 A1 | 7/2019 | Han et al. |
| 2019/0231373 A1 | 8/2019 | Quick |
| 2019/0254690 A1 | 8/2019 | Cabiri et al. |
| 2019/0255297 A1 | 8/2019 | Fischell et al. |
| 2019/0269368 A1 | 9/2019 | Hauck et al. |
| 2019/0301913 A1 | 10/2019 | Johnson |
| 2019/0304108 A1 | 10/2019 | Carrell et al. |
| 2019/0336227 A1 | 11/2019 | Murphy et al. |
| 2019/0365485 A1 | 12/2019 | Kottenstette et al. |
| 2019/0380825 A1 | 12/2019 | Perkins et al. |
| 2020/0008891 A1 | 1/2020 | Wenderow et al. |
| 2020/0008896 A1 | 1/2020 | Cone et al. |
| 2020/0009354 A1 | 1/2020 | Wenderow et al. |
| 2020/0016371 A1 | 1/2020 | Blacker |
| 2020/0054403 A1 | 2/2020 | Zhou et al. |
| 2020/0085528 A1 | 3/2020 | Olson et al. |
| 2020/0129740 A1 | 4/2020 | Kottenstette et al. |
| 2020/0163726 A1 | 5/2020 | Tanner et al. |
| 2020/0170630 A1 | 6/2020 | Wong et al. |
| 2020/0242767 A1 | 7/2020 | Zhao et al. |
| 2020/0028181 A1 | 9/2020 | Cabiri |
| 2020/0282186 A1 | 9/2020 | Blacker et al. |
| 2020/0289219 A1 | 9/2020 | Denlinger et al. |
| 2020/0297444 A1 | 9/2020 | Camarillo et al. |
| 2020/0297973 A1 | 9/2020 | Blacker et al. |
| 2020/0306064 A1 | 10/2020 | Perkins et al. |
| 2020/0316340 A1 | 10/2020 | Wenderow et al. |
| 2020/0324084 A1 | 10/2020 | Falb et al. |
| 2020/0338308 A1 | 10/2020 | Saber et al. |
| 2020/0345979 A1 | 11/2020 | Loh et al. |
| 2020/0352494 A1 | 11/2020 | Gable et al. |
| 2020/0368494 A1 | 11/2020 | Parmar |
| 2020/0375671 A1 | 12/2020 | Wenderow et al. |
| 2020/0390503 A1 | 12/2020 | Casas et al. |
| 2020/0397451 A1 | 12/2020 | Feltyberger et al. |
| 2020/0405408 A1 | 12/2020 | Shelton, IV et al. |
| 2020/0405410 A1 | 12/2020 | Shelton, IV et al. |
| 2021/0007816 A1 | 1/2021 | Huang et al. |
| 2021/0022816 A1 | 1/2021 | DeBuys et al. |
| 2021/0030492 A1 | 2/2021 | Wenderow et al. |
| 2021/0045622 A1 | 2/2021 | Petroff et al. |
| 2021/0046284 A1 | 2/2021 | Mauch |
| 2021/0060767 A1 | 3/2021 | Guerrera et al. |
| 2021/0077211 A1 | 3/2021 | Blacker et al. |
| 2021/0093406 A1 | 4/2021 | Blacker et al. |
| 2021/0100980 A1 | 4/2021 | Blacker |
| 2021/0145532 A1 | 5/2021 | Tucker et al. |
| 2021/0178032 A1 | 6/2021 | Hsu et al. |
| 2021/0178036 A1 | 6/2021 | Nazarifar et al. |
| 2021/0186534 A1 | 6/2021 | Hunt et al. |
| 2021/0192759 A1 | 6/2021 | Lang |
| 2021/0196413 A1 | 7/2021 | Inoue |
| 2021/0212792 A1 | 7/2021 | Shelton et al. |
| 2021/0220064 A1 | 7/2021 | Kottenstette et al. |
| 2021/0228841 A1 | 7/2021 | Falb et al. |
| 2021/0247396 A9 | 8/2021 | Penny et al. |
| 2021/0251472 A1 | 8/2021 | Baez |
| 2021/0259884 A1 | 8/2021 | Heeren et al. |
| 2021/0282863 A1 | 9/2021 | Rafii-Tari et al. |
| 2021/0282867 A1 | 9/2021 | Tegg et al. |
| 2021/0282875 A1 | 9/2021 | Sharon et al. |
| 2021/0282893 A1 | 9/2021 | Leo et al. |
| 2021/0290310 A1 | 9/2021 | Laby et al. |
| 2021/0290320 A1 | 9/2021 | Mao et al. |
| 2021/0290324 A1 | 9/2021 | Mintz et al. |
| 2021/0298847 A1 | 9/2021 | Mao et al. |
| 2021/0298850 A1 | 9/2021 | Huang et al. |
| 2021/0298857 A1 | 9/2021 | Zheng et al. |
| 2021/0298954 A1 | 9/2021 | Alvarez et al. |
| 2021/0305639 A1 | 9/2021 | Ho et al. |
| 2021/0315596 A1 | 10/2021 | Buck et al. |
| 2021/0353129 A1 | 11/2021 | Roelle et al. |
| 2021/0361366 A1 | 11/2021 | Murphy et al. |
| 2021/0369370 A1 | 12/2021 | Malanoski |
| 2021/0393338 A1 | 12/2021 | Graetzel et al. |
| 2021/0401527 A1 | 12/2021 | Hassan |
| 2022/0031415 A1 | 2/2022 | Vargas et al. |
| 2022/0040450 A1 | 2/2022 | Haubert |
| 2022/0167984 A1 | 6/2022 | Shelton, IV |
| 2022/0168000 A1 | 6/2022 | Naglretter et al. |
| 2022/0168001 A1 | 6/2022 | Naglretter et al. |
| 2022/0168002 A1 | 6/2022 | Naglretter et al. |
| 2022/0168049 A1 | 6/2022 | Tanner et al. |
| 2022/0211452 A1 | 7/2022 | Clark et al. |
| 2022/0233263 A1 | 7/2022 | Canale et al. |
| 2022/0233820 A1 | 7/2022 | Clark et al. |
| 2022/0313375 A1 | 7/2022 | Zhang et al. |
| 2022/0323096 A1 | 10/2022 | Naglretter et al. |
| 2022/0331509 A1* | 10/2022 | Buck ............... A61M 25/0662 |
| 2022/0370161 A1 | 11/2022 | Yu |
| 2022/0370706 A1 | 11/2022 | Meganck |
| 2022/0378522 A1 | 12/2022 | Zemlok et al. |
| 2023/0000563 A1 | 1/2023 | Bell et al. |
| 2023/0035508 A1 | 2/2023 | Clark et al. |
| 2023/0035946 A1 | 2/2023 | Kapadia |
| 2023/0043432 A1 | 2/2023 | Kapadia |
| 2023/0046468 A1 | 2/2023 | Lau et al. |
| 2023/0047098 A1 | 2/2023 | Lau et al. |
| 2023/0048055 A1 | 2/2023 | Lau et al. |
| 2023/0048388 A1 | 2/2023 | Lau et al. |
| 2023/0052862 A1 | 2/2023 | Lau et al. |
| 2023/0107693 A1 | 4/2023 | Walker et al. |
| 2023/0116327 A1 | 4/2023 | Walker et al. |
| 2023/0116700 A1 | 4/2023 | Yu et al. |
| 2023/0117715 A1 | 4/2023 | Ho et al. |
| 2023/0126545 A1 | 4/2023 | Liu et al. |
| 2023/0202040 A1 | 6/2023 | Lin et al. |
| 2023/0209018 A1 | 6/2023 | Alexanderson et al. |
| 2023/0218816 A1 | 7/2023 | Germain et al. |
| 2023/0310100 A1 | 10/2023 | Wenderow et al. |
| 2023/0347110 A1 | 11/2023 | Wenderow et al. |
| 2023/0380914 A1 | 11/2023 | Meglan et al. |
| 2023/0380915 A1 | 11/2023 | Hundertmark |
| 2024/0001101 A1* | 1/2024 | Wallin ............... A61M 60/414 |
| 2024/0016560 A1 | 1/2024 | Canale et al. |
| 2024/0019042 A1 | 1/2024 | Lim |
| 2024/0032949 A1 | 2/2024 | Yang et al. |
| 2024/0033016 A1 | 2/2024 | Yang et al. |
| 2024/0033017 A1 | 2/2024 | Yang et al. |
| 2024/0033018 A1 | 2/2024 | Yang et al. |
| 2024/0033019 A1 | 2/2024 | Lau et al. |
| 2024/0033486 A1 | 2/2024 | Lau et al. |
| 2024/0041480 A1 | 2/2024 | Bartholomew |
| 2024/0042124 A1 | 2/2024 | Bartholomew |
| 2024/0042142 A1 | 2/2024 | Bartholomew |
| 2024/0122612 A1* | 4/2024 | Bartholomew ..... A61M 5/1408 |
| 2024/0165415 A1 | 5/2024 | Grosskopf et al. |
| 2024/0180635 A1 | 6/2024 | Lau et al. |
| 2024/0180640 A1 | 6/2024 | Lau et al. |
| 2024/0180641 A1 | 6/2024 | Lau et al. |
| 2024/0180642 A1 | 6/2024 | Lau et al. |
| 2024/0180643 A1 | 6/2024 | Lau et al. |
| 2024/0180650 A1 | 6/2024 | Lau et al. |
| 2024/0180651 A1 | 6/2024 | Lau et al. |
| 2024/0180652 A1 | 6/2024 | Lau et al. |
| 2024/0180653 A1 | 6/2024 | Lau et al. |
| 2024/0180654 A1 | 6/2024 | Lau et al. |
| 2024/0180658 A1 | 6/2024 | Lau et al. |
| 2024/0180659 A1 | 6/2024 | Lau et al. |
| 2024/0181207 A1 | 6/2024 | Lau et al. |
| 2024/0181208 A1 | 6/2024 | Lau et al. |
| 2024/0181213 A1 | 6/2024 | Lau et al. |
| 2024/0181214 A1 | 6/2024 | Lau et al. |
| 2024/0181224 A1 | 6/2024 | Lau et al. |
| 2024/0181298 A1 | 6/2024 | Lau et al. |
| 2024/0183382 A1 | 6/2024 | Lau et al. |
| 2024/0197416 A1 | 6/2024 | Gonzalez |

(56) References Cited

U.S. PATENT DOCUMENTS

2024/0197418 A1 6/2024 Jourdan
2024/0198051 A1 6/2024 Jourdan
2024/0207570 A1 6/2024 Mar

FOREIGN PATENT DOCUMENTS

| | | |
|---|---|---|
| CN | 103976766 | 8/2014 |
| CN | 104042259 | 9/2014 |
| CN | 203935213 | 11/2014 |
| CN | 204428157 | 7/2015 |
| CN | 105534599 | 5/2016 |
| CN | 105616008 | 6/2016 |
| CN | 105640648 | 6/2016 |
| CN | 105662586 | 6/2016 |
| CN | 105662588 | 6/2016 |
| CN | 105662589 | 6/2016 |
| CN | 105796179 | 7/2016 |
| CN | 205598007 | 9/2016 |
| CN | 106691414 | 5/2017 |
| CN | 107307909 | 11/2017 |
| CN | 107349514 | 11/2017 |
| CN | 107374737 | 11/2017 |
| CN | 107374738 | 11/2017 |
| CN | 107374739 | 11/2017 |
| CN | 107374740 | 11/2017 |
| CN | 107374741 | 11/2017 |
| CN | 107550570 | 1/2018 |
| CN | 107684459 | 2/2018 |
| CN | 107744405 | 3/2018 |
| CN | 107744406 | 3/2018 |
| CN | 107744616 | 3/2018 |
| CN | 107811624 | 3/2018 |
| CN | 108158656 | 6/2018 |
| CN | 108175504 | 6/2018 |
| CN | 207970143 | 10/2018 |
| CN | 207979770 | 10/2018 |
| CN | 207979771 | 10/2018 |
| CN | 207980153 | 10/2018 |
| CN | 109567947 | 4/2019 |
| CN | 208693445 | 4/2019 |
| CN | 109730779 A | 5/2019 |
| CN | 109821137 A | 5/2019 |
| CN | 208989133 | 6/2019 |
| CN | 209136865 | 7/2019 |
| CN | 209137698 | 7/2019 |
| CN | 110151310 A | 8/2019 |
| CN | 110236679 | 9/2019 |
| CN | 209713130 | 12/2019 |
| CN | 211271130 | 12/2019 |
| CN | 210056225 | 2/2020 |
| CN | 111035453 | 4/2020 |
| CN | 111110353 | 5/2020 |
| CN | 111110354 | 5/2020 |
| CN | 111407416 | 7/2020 |
| CN | 111437033 | 7/2020 |
| CN | 111449752 | 7/2020 |
| CN | 210962301 | 7/2020 |
| CN | 111658154 | 9/2020 |
| CN | 111772801 | 10/2020 |
| CN | 211610046 | 10/2020 |
| CN | 211723416 U | 10/2020 |
| CN | 111916214 | 11/2020 |
| CN | 111931626 | 11/2020 |
| CN | 111933268 | 11/2020 |
| CN | 112017516 | 12/2020 |
| CN | 212089719 | 12/2020 |
| CN | 212089720 | 12/2020 |
| CN | 112546396 | 3/2021 |
| CN | 112546397 | 3/2021 |
| CN | 112587241 | 4/2021 |
| CN | 213465314 | 6/2021 |
| CN | 113303913 | 8/2021 |
| CN | 113304393 | 8/2021 |
| CN | 113693733 | 11/2021 |
| EP | 1 776 057 | 11/2009 |
| EP | 2 124 705 | 5/2019 |
| FR | 3118406 | 7/2022 |
| WO | WO 2000/18290 | 4/2000 |
| WO | WO 2007/102134 | 9/2007 |
| WO | WO 2008/057887 | 10/2008 |
| WO | WO 2013/103885 | 7/2013 |
| WO | WO 2016/191307 | 12/2016 |
| WO | WO 2017/220010 | 12/2017 |
| WO | WO 2019/222641 | 11/2019 |
| WO | WO 2020/031147 | 2/2020 |
| WO | WO 2020/061240 | 3/2020 |
| WO | WO 2020/123671 | 6/2020 |
| WO | WO 2020/130924 | 6/2020 |
| WO | WO 2021/004255 | 6/2020 |
| WO | WO 2020/142340 | 7/2020 |
| WO | WO 2021/011551 | 7/2020 |
| WO | WO 2020/167749 | 8/2020 |
| WO | WO 2020/263630 | 12/2020 |
| WO | WO 2021/011533 | 1/2021 |
| WO | WO 2021/011554 | 1/2021 |
| WO | WO 2021/015990 | 1/2021 |
| WO | WO 2021/126698 | 6/2021 |
| WO | WO 2021/127426 | 6/2021 |
| WO | WO 2021/183444 | 9/2021 |
| WO | WO 2021/184444 | 9/2021 |
| WO | WO 2022/048984 | 3/2022 |
| WO | WO 2022/154979 | 7/2022 |
| WO | WO 2022/220899 | 10/2022 |
| WO | WO 2023/019117 | 2/2023 |
| WO | WO 2024/137632 | 6/2024 |

OTHER PUBLICATIONS

US 12,108,960 B1, 10/2024, Teigen et al. (withdrawn)
Bao et al., Apr. 2018, Operation evaluation in-human of a novel remote-controlled vascular interventional robot, Biomedical Microdevices, 20(2):34.
Bao et al., Feb. 2018, A cooperation of catheters and guidewires-based novel remote-controlled vascular interventional robot, Biomedical Microdevices, 20(1):20.
Bell, Apr. 4, 2019, Coding for Empathy, https://www.youtube.com/watch?v=13tzbxofDVc, screenshot of video.
Bency et al., Apr. 25, 2019, Neural Path Planning: Fixed Time, Near-Optimal Path Generation via Oracle Imitation, arXiv:1904.11102v1 [cs.RO], 8 pp.
Bergman et al., 2020, Robotic-assisted percutaneous coronary intervention, Handbook of Robotic and Image-Guided Surgery, doi: https.//doi.org/10.1016/B978-0-12-814245-5.00020-7.
Chen et al., Feb. 14, 2020, Deep learning robotic guidance for autonomous vascular access, Nature Machine Intelligence, https://doi.org/10.1038/s42256-020-0148-7, 12 pp.
Das et al., Feb. 21, 2019, Learning-Based Proxy Collision Detection for Robot Motion Planning Applications, arXiv:1902.08164v1 [cs.RO], 19 pp.
Das et al., May 29, 2020, Stochastic Modeling of Distance to Collision for Robot Manipulators, arXiv:2005.14391v1 [cs.RO], 8 pp.
Evard, Jun. 2018, Catheter localization utilizing a sensor-enabled guidewire design of a proof-of-concept system, Masters' Thesis, California Polytechnic State University, San Luis Obispo, 186 pp.
Fagogenis et al., Apr. 2019, Autonomous Robotic Intracardiac Catheter Navigation Using Haptic Vision, Science Robotics, 4(29):1-12.
Guo et al., Apr. 13, 2018, Study on real-time force feedback for a master-slave interventional surgical robotic system, Biomedical Microdevices, 20(2):37, 12 pp.
Guo et al., May 20, 2020, Machine learning-based operation skills assessment with vascular difficulty index for vascular intervention surgery, Medical & Biological Engineering & Computing, https://doi.org/10.1007/s11517-020-02195-9, 15 pp.
Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.

(56) References Cited

OTHER PUBLICATIONS

Jiang et al., 2018, Initial clinical trial of robot of endovascular treatment with force feedback and cooperating of catheter and guidewire, Applied Bionics and Biomechanics, vol. 2018, Article ID 9735979, 10 pp.

Johnson et al., Aug. 12, 2020, Dynamically Constrained Motion Planning Networks for Non-Holonomic Robots, arXiv:2008.05112v1 [cs.RO}, 7 pp.

Kagiyama et al., Jul. 31, 2019, First experience of robotic-assisted percutaneous coronary intervention in Japan, Intern Med Advance Publication, doi: 10/2016/internalmedicine.3272-19.

Kuang et al., Apr. 2020, Vibration-Based Multi-Axis Force Sensing: Design, Characterization, and Modeling, IEEE Robotics and Automation Letters, 5(2):3082-3089.

Li et al., 2022, An endovascular catheterization robotic system using collaborative operation with magnetically controlled haptic force feedback, Micromachines, 13:505.

Li et al., Jan. 17, 2021, MPC-MPNet: Model-Predictive Motion Planning Networks for Fast, Near-Optimal Planning Under Kinodynamic Constraints, arXiv:2101.06798v1 [cs.RO], 8 pp.

Liu et al., 2021, Animal experiment of a novel neurointerventional surgical robotic system with master-slave mode, Applied Bionics and Biomechanics, vol. 2021, Article ID 8836268, 8 pp.

Qureshi et al., Feb. 2021, Motion Planning Networks: Bridging the Gap Between Learning-Based and Classical Motion Planners, IEEE Transactions on Robotics, 37(1), 19 pp.

Qureshi et al., Jul. 3, 2021, Constrained Motion Planning Networks X, arXiv:2010.08702v2 [cs.RO), 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

Sganga et al., Sep. 15, 2018, OffsetNet: Deep Learning for Localization in the Lung using Rendered Images, arXiv:1809.05645v1 [cs.CV], 7 pp.

Sganga, May 22, 2020, Webinar: Autonomous Surgical Robots, https://www.youtube.com/watch?v=QRO2KnfGlgo, screenshot of video.

Wang et al., Feb. 3, 2018, Online measuring and evaluation of guidewire inserting resistance for robotic interventional surgery systems, Microsystem Technologies, https://doi/org/10.1007/s00542-018-03750-4.

Wilcox et al., Jan. 2020, SOLAR-GP: Sparse Online Locally Adaptive Regression Using Gaussian Processes for Bayesian Robot Model Learning and Control, EEE Robotics and Automation Letters, 5(2), 8 pp.

Yip et al., 2017, Autonomous Control of Continuum Robot Manipulators for Complex Cardiac Ablation Tasks, Journal of Medical Robotics Research, 2(1),: 1750002-1-1750002-13.

Yip et al., Jul. 10, 2017, Robot Autonomy for Surgery, https://arxiv.org/pdf/1707.03080.pdf, 33 pp.

Zhao et al., Apr. 2, 2018, Operating force information on-line acquisition of a novel slave manipulator for vascular interventional surgery, Biomedical Microdevices, 20(2):33, 13 pp.

Zhou et al., 2021, ADRC-based control method for the vascular intervention master-slave surgical robotic system, Micromachines, 12:1439.

* cited by examiner

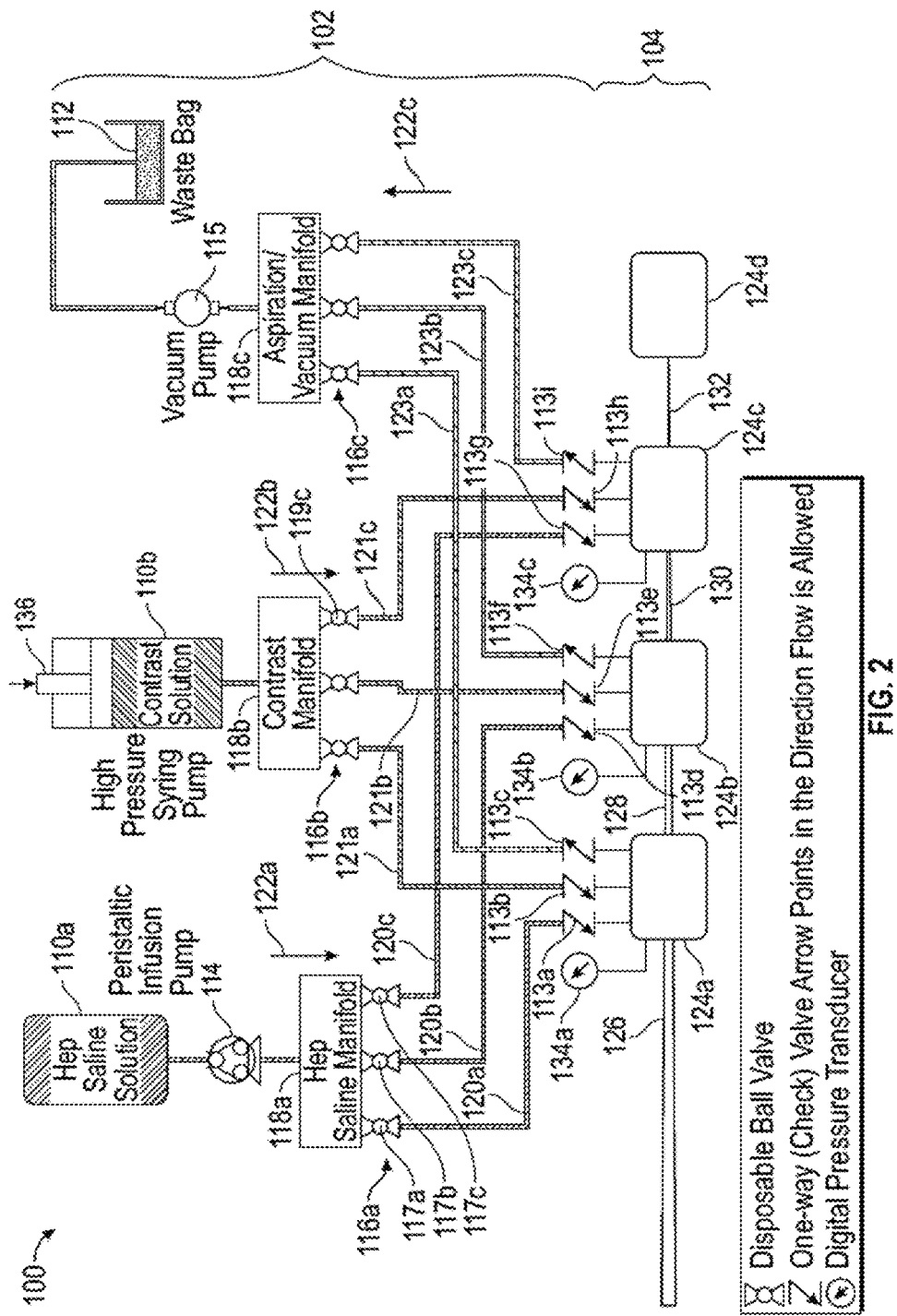

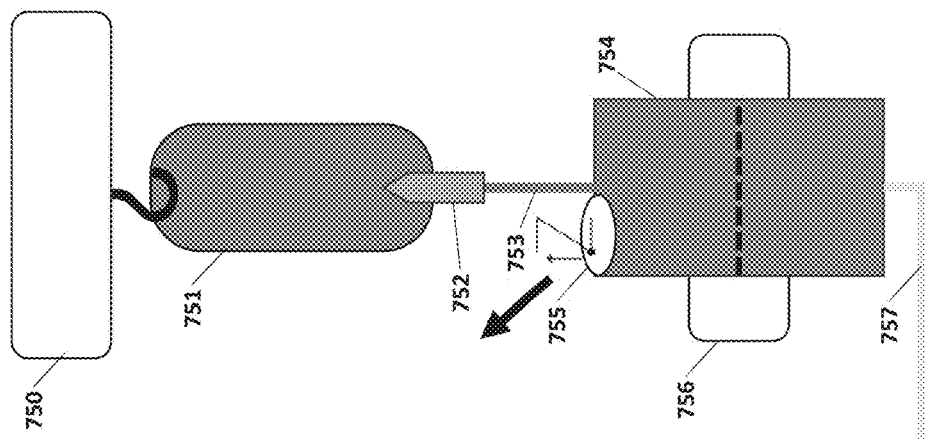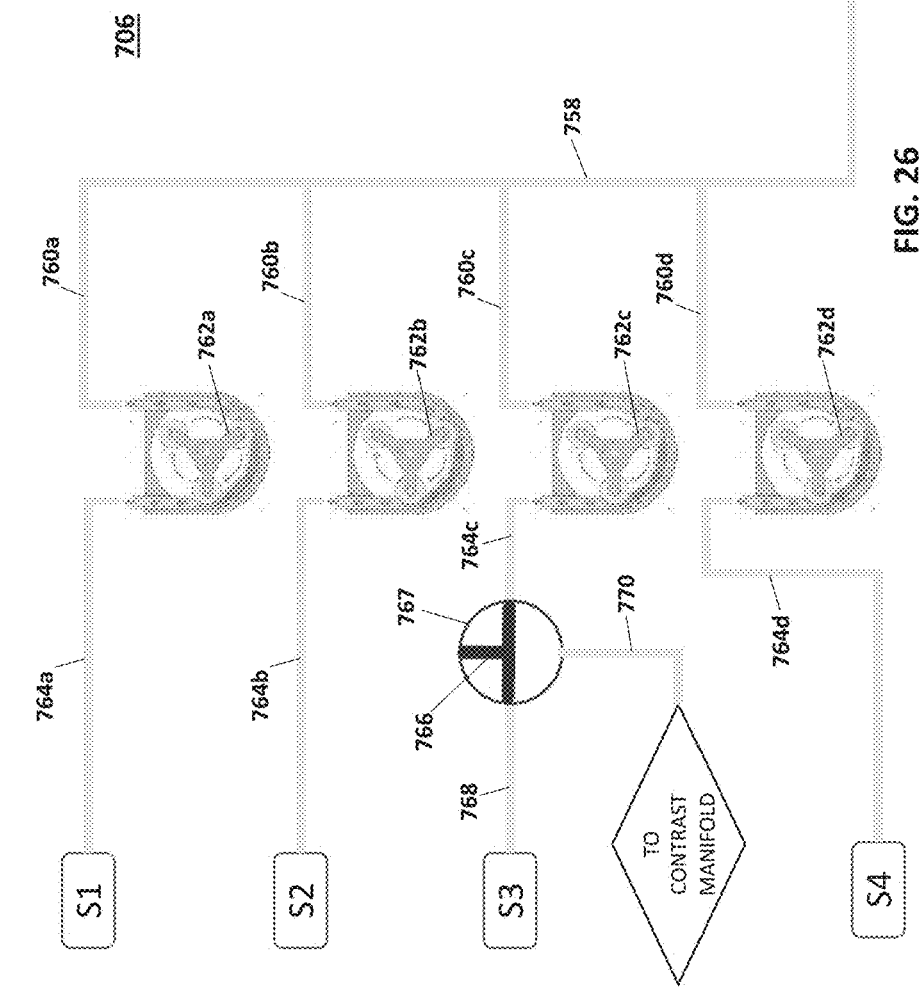
FIG. 26

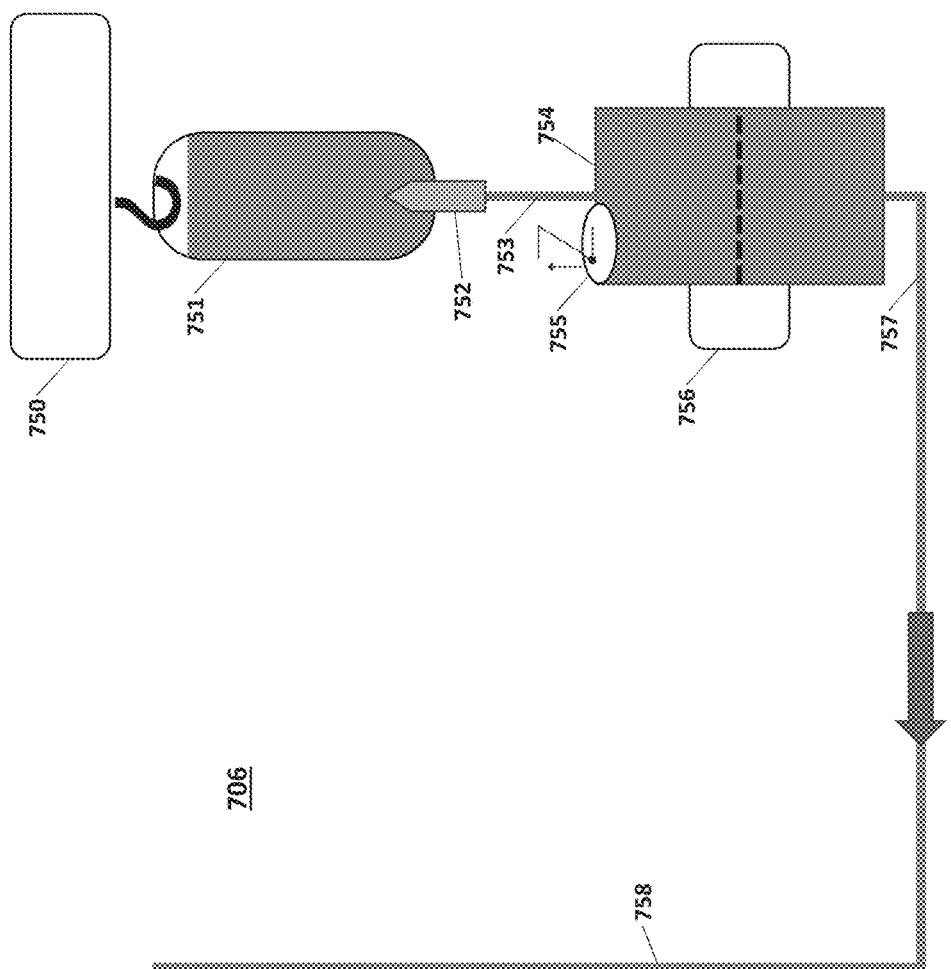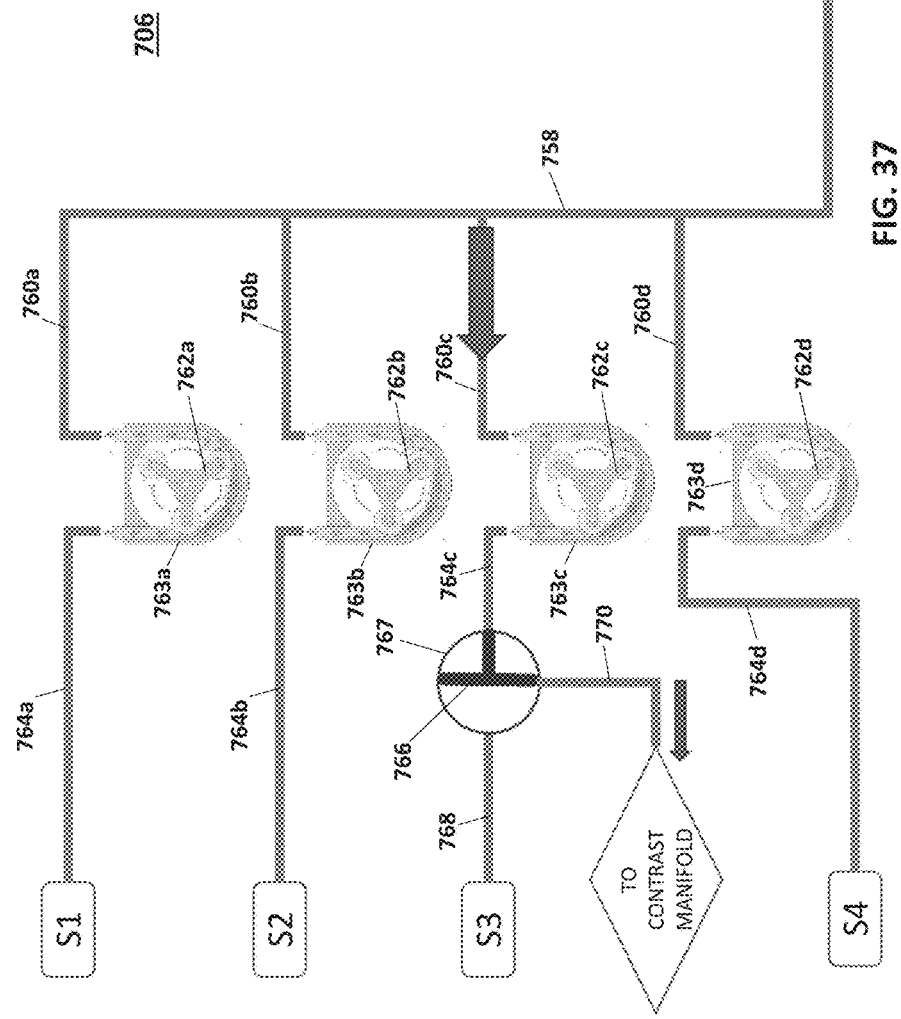
FIG. 37

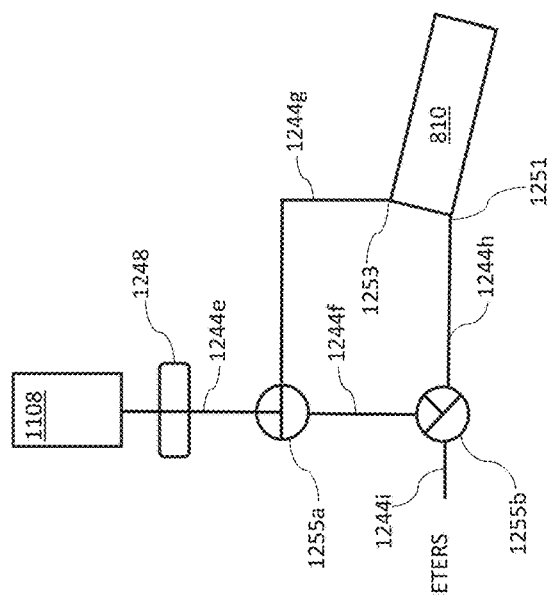
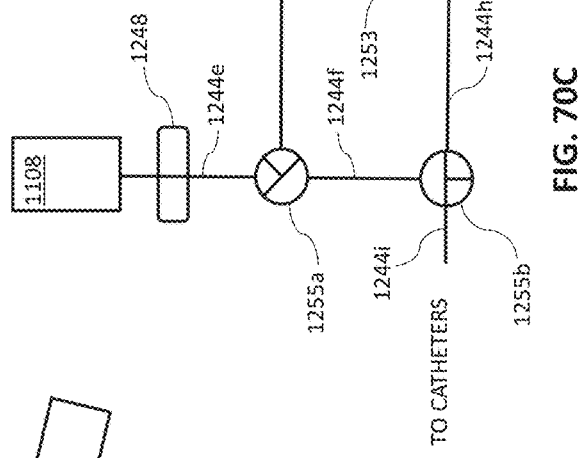
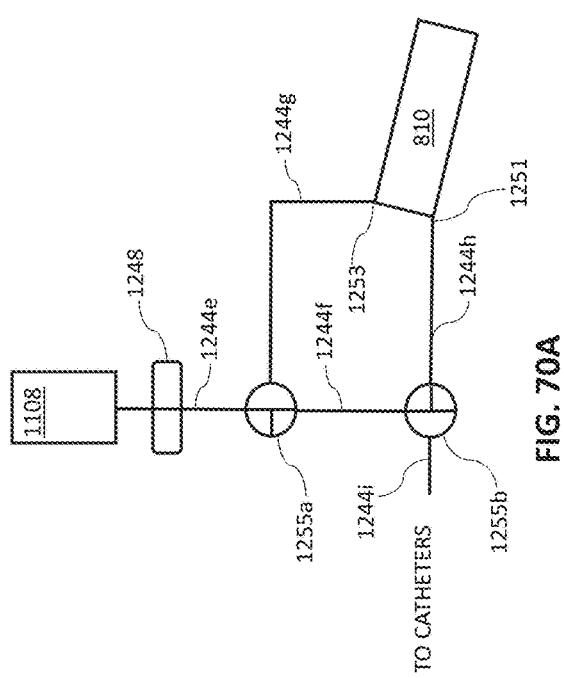

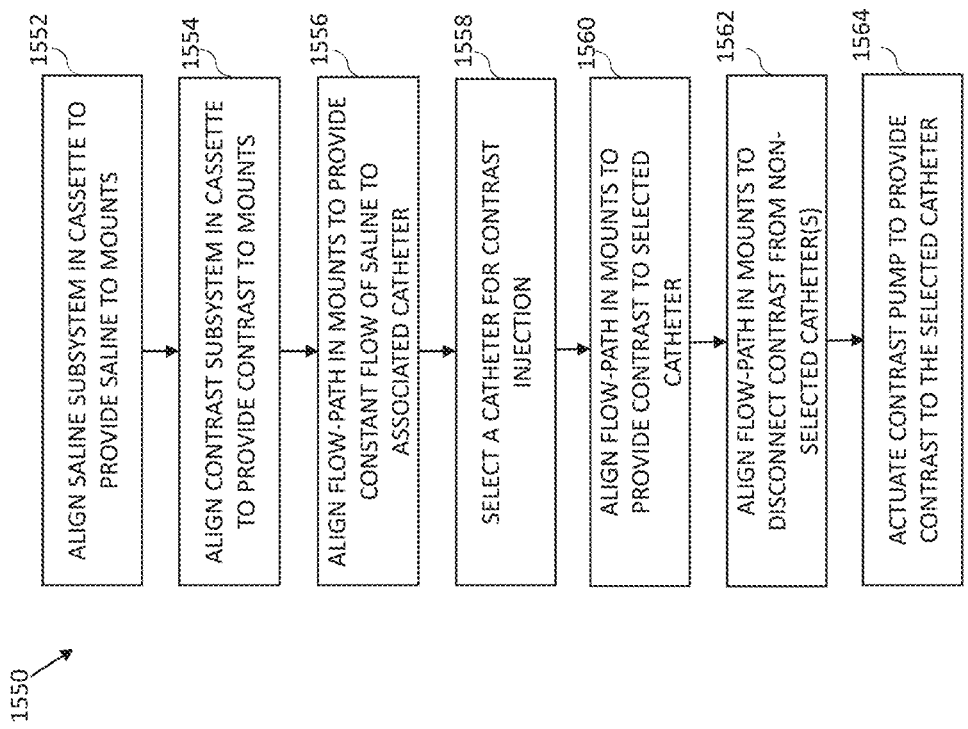

FLUIDICS CONTROL SYSTEM FOR MULTI CATHETER STACK

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims priority to U.S. Provisional Patent Application No. 63/467,251, filed May 17, 2023, titled FLUIDICS CONTROL SYSTEM FOR MULTI CATHETER STACK, U.S. Provisional Patent Application No. 63/528,038, filed Jul. 20, 2023, titled FLUIDICS CONTROL SYSTEM FOR MULTI CATHETER STACK, and U.S. Provisional Patent Application No. 63/550,926, filed Feb. 7, 2024, titled FLUIDICS CONTROL SYSTEM FOR MULTI CATHETER STACK, the entire content of each of which is incorporated by reference herein for all purposes and forms a part of this specification.

BACKGROUND

Field

This disclosure relates generally to the field of fluidics infrastructure, and more specifically to the field of fluid management and delivery during medical procedures, either manual or robotically driven. Described herein are systems and methods for fluidics management and delivery.

Description of the Related Art

Any of a variety of endoluminal or endovascular medical procedures may involve introduction of a number of tools such as catheters into the body either simultaneously or sequentially. Each catheter may require a unique connection to any of a variety of sources of aspiration, irrigation, drug, saline or contrast infusion. Such sources are conventionally placed in communication with the catheter via tubing ending in a connector for releasable connection to a complementary port on a catheter hub (mount).

A catheter exchange typically involves disconnecting tubing from a first catheter being removed and reconnecting the tubing to a second, replacement catheter. In addition, catheters typically have one luer connection port for injection of all fluids as well as for aspiration. During the course of a procedure, multiple different fluids and/or fluid volumes may be injected at different times in addition to aspiration. As such, fluid sources such as syringes are frequently connected and disconnected from the luer connection port. This conventional switching of components, syringes, and fluidic connections during a procedure can lead to a risk of air bubble introduction, errors at connection points, and/or errors in fluid selection.

Thus, there remains a need for an improved fluid and tool management system that overcomes one or more of the drawbacks of conventional fluid management and catheter exchange systems.

SUMMARY

An aspiration system with integrated fluidics management includes an elongate, flexible tubular body having a proximal end, a distal end and at least one lumen; a mount on the proximal end of the tubular body; a valve system which may be in the form of a valve manifold in communication with the mount; and first, second and third ports on the manifold. The valve manifold is configured to selectively place any one of the first, second and third ports into communication with the lumen while simultaneously blocking the other two ports from communicating with the lumen. The fluidics management system may be used with a two or three or four or more interventional device stack (e.g., concentrically mounted catheters over a guidewire) for either a manually operated or robotically driven intervention.

The valve manifold may include a first valve in communication with the first port; a second valve in communication with the second port; and a third valve in communication with the third port. The first port may be configured for connection to a source of vacuum, the second port may be configured for connection to a source of saline and the third port may be configured for connection to a source of contrast media. The valves may be electronically controlled.

The aspiration system may further comprise a control system having a processor configured to adjust the valve manifolds in response to human input. In one implementation, the control system is configured to adjust the manifolds into an aspiration mode in which the aspiration port is in communication with the catheter lumen, and communication between the lumen and the saline port and the contrast port is obstructed. The control system may further be configured to adjust the valve manifold into a contrast injection mode in which the contrast port is in communication with the lumen, and communication between the lumen and the saline port and the aspiration port is obstructed. The control system may be further configured to control the volume and rate of delivery of delivered contrast media or other fluid.

The first, second and third ports may comprise connectors for removable connection to tubing extending away from the mount. The first, second and third ports may alternatively comprise tubing non removably attached to and extending away from the mount.

The aspiration system may further comprise a hemostasis valve, permanently or removably carried by the mount. The hemostasis valve is adjustable between at least a low sealing force mode in which a catheter can slide through the valve and the valve prevents retrograde leakage of low pressure fluids, and a high sealing force mode in which the valve clamps tightly over the catheter to prevent retrograde escape of high pressure fluid. The control system may be configured to adjust the hemostasis valve between the low sealing force mode and the high sealing force mode.

The aspiration system may further comprise a contrast injection control.

The first port may be configured for connection to a source of vacuum, the second port may be configured for connection to a source of saline and the third port may be configured for connection to a source of contrast media.

In response to human instruction to enter a contrast injection mode, the control system may be configured to adjust the hemostasis valve into the high sealing force mode, and to adjust the valve manifold to selectively place the third port into communication with the lumen while simultaneously blocking the first and second ports from communicating with the lumen.

There is also provided a fluidics control system. The system comprises a processor; a valve manifold having a vacuum valve configured for connection between a catheter and a source of vacuum, a saline valve configured for connection between the catheter and a source of saline and a contrast valve configured for connection between the catheter and a source of contrast media; and a contrast control for initiating introduction of contrast media into the catheter. The processor may be configured to open the contrast valve, and close the saline and aspiration valves in response to manipulating the contrast control.

The fluidics control system may further comprise a catheter mount in fluid communication with the contrast valve, saline valve and aspiration valve. A hemostasis valve may be carried by the mount, or by an assembly (e.g., a hub) coupled to the mount.

The fluidics control system may further comprise a drive mechanism configured to adjust the sealing strength of the hemostatic valve in response to a signal from the processor. The processor may additionally be configured to increase the sealing strength of the hemostatic valve in response to the manipulation of the contrast control to introduce contrast into the catheter. The processor may additionally be configured to decrease the sealing strength of the hemostatic valve in response to the manipulation of the contrast control to stop introducing contrast into the catheter.

The valve manifold may be carried by the mount. Alternatively, the valve manifold may be remote from the mount, and in communication with the mount by way of a tubing set having vacuum, saline and contrast lines.

There is also provided a degassing method for a multiple catheter fluid management system. The method comprises injecting a first fluid at a low pressure from a first fluid source into a first fluid source connection of a hemostasis valve, and closing a first valve at the first fluid source connection. Vacuum is applied to a sink connection of the hemostasis valve to remove residual first fluid into the sink. A sink valve is closed and a second fluid is injected from a second fluid source into a second fluid source connection of the hemostasis valve.

The first fluid may comprise heparinized saline. The second fluid may comprise contrast.

The degassing method may further comprise actuating a gasket of the hemostasis valve to a high pressure configuration before injecting the second fluid. The method may further comprise actuating a gasket of the hemostasis valve to a low pressure configuration before injecting the first fluid.

There is also provided a catheter system with integrated fluidics management. The catheter system includes a first elongate, flexible tubular body having a proximal end, a distal end, and at least one lumen. The catheter system also includes a mount on the proximal end of the tubular body and a valve system in communication with the mount. The catheter system also includes a first port, a second port, and a third port in communication with the valve system. The valve system is configured to selectively place any one of the first port, the second port, and the third port into communication with the lumen while simultaneously blocking the other two ports from communicating with the lumen.

The first elongate, flexible tubular body can include an aspiration catheter. The valve system can include a first valve in communication with the first port, a second valve in communication with the second port, and a third valve in communication with the third port. The first port can be configured for connection to a source of vacuum. The second port can be configured for connection to a source of saline. The third port can be configured for connection to a source of contrast media. The catheter system can include a control system configured to adjust the valve system into an aspiration mode in which the first port is in communication with the lumen, and communication between the second port and the lumen and between the third port and the lumen are obstructed. The control system can be configured to adjust the valve system into a contrast injection mode in which the third port is in communication with the lumen, and communication between the first port and the lumen and between the second port and the lumen are obstructed. The control system can be configured to control a volume of delivered contrast media. The valve system can include a valve manifold, the valve manifold including the first port, the second port, and the third port. Each of the first port, the second port, and the third port can include a connector for removable connection to tubing extending away from the mount. Each of the first port, the second port, and the third port can include tubing attached to and extending away from the mount. The catheter system can include a hemostasis valve carried by the mount. The hemostasis valve can be adjustable between at least a low sealing force mode and a high sealing force mode. The control system can be configured to adjust the hemostasis valve between the low scaling force mode and the high sealing force mode. The system can include a contrast injection control. The control system can be configured to adjust the hemostasis valve into the high sealing force mode, and to adjust the valve system to selectively place the third port into communication with the lumen while simultaneously blocking the first port and the second port from communicating with the lumen, in response to a human input. The human input can be received through a contrast control on a user interface. The catheter system can include a second elongate, flexible tubular body extending through the hemostasis valve. The control system can be configured to adjust the valve system into a contrast injection mode in response to a human input in which the third port is in communication with the lumen, and communication between the second port and the lumen and between the first port and the lumen are obstructed. The control system can be configured to determine a sealing force of the hemostasis valve around the second elongate, flexible tubular body in response to the human input. The control system can be configured to increase the sealing force of the hemostasis valve if the control system determines that the sealing force of the hemostasis valve around the second elongate, flexible tubular body is low.

There is also provided a fluidics control system. The fluidics control system includes a first processor, a valve system including a first vacuum valve configured for connection between a first catheter and a first source of vacuum, a first saline valve configured for connection between the first catheter and a first source of saline, and a first contrast valve configured for connection between the first catheter and a first source of contrast media, and a first contrast control for initiating introduction of contrast media into the first catheter. The first processor is configured to open the first contrast valve and close the first saline valve and the first vacuum valve in response to actuation of the first contrast control.

The fluidics control system can include the first catheter. The first catheter can include a first catheter mount in fluid communication with the first contrast valve, the first saline valve, and the first vacuum valve. The fluidics control system can include a first hemostasis valve on the first catheter mount. The fluidics control system can include a second catheter configured to axially receive the first catheter therethrough (in its lumen). The second catheter can include a second catheter mount. The second catheter mount can include a second hemostasis valve. The second hemostasis valve can be adjustable between a low compression state and a high compression state against the first catheter. The first processor or a second processor can be configured to adjust the second hemostasis valve into the high compression state against the first catheter, in response to actuating the first contrast control. The first processor can be configured to adjust the second hemostasis valve into the high compression state against the first catheter, in response to actuating the first contrast control. The first processor can be configured to introduce contrast media into the first catheter in response to actuation of the first contrast control and when the second hemostasis valve is in the high compression state against the first catheter. The first processor can be configured to activate a first contrast media pump in response to actuation of the first contrast control. The fluidics control system can further include a drive circuit configured to adjust the compression state of the second hemostasis valve between the high compression state and the low compression state in response to a signal from the first processor. The first processor can be additionally configured to confirm that the second hemostasis valve is in the high compression state in response to actuation of the first contrast control to introduce contrast media into the first catheter. The first processor can be additionally configured to adjust the second hemostasis valve into the low compression state in response to actuation of the first contrast control to stop introduction of contrast media into the first catheter. The valve system can include a valve manifold carried by the first catheter mount. The first vacuum valve, the first saline valve, and the first contrast valve can be remote from the first catheter hub, and in communication with the first catheter hub by way of a tubing set having a vacuum line, a saline line, and a contrast line.

There is also provided a fluidics control system for multi catheter procedures. The fluidics control system includes a first catheter including a hemostasis valve which is adjustable between a low compression mode and a high compression mode, a second catheter extendable through the hemostasis valve and through the first catheter, a source of saline solution in communication with the first catheter through a saline valve, a source of contrast media in communication with the first catheter through a contrast valve, and a processor configured to, in response to human instruction, send a first control signal to place the hemostasis valve into the high compression mode, and send a second control signal to open the contrast valve.

The processor can be further configured to, in response to human instruction, send a third control signal to place the hemostasis valve into the low compression mode, and to send a fourth control signal to a robotic catheter drive system to axially adjust the second catheter with respect to the first catheter. The processor can be further configured to, in response to human instruction, send a fifth control signal to a robotic catheter drive system to axially, proximally withdraw a guidewire from the second catheter prior to opening the contrast valve.

There is also provided a degassing method for a multiple catheter fluid management system. The degassing method includes injecting a first fluid at a low pressure from a first fluid source into a first fluid source connection of a hemostasis valve, closing a first valve at the first fluid source connection, applying vacuum to a sink connection of the hemostasis valve to remove residual first fluid into a sink connected to the sink connection, closing a sink valve at the sink connection, and injecting a second fluid from a second fluid source into a second fluid source connection of the hemostasis valve.

The first fluid can be heparinized saline. The second fluid source can be contrast. The method can further include actuating a plunger of the hemostasis valve to a high compression state before injecting the second fluid. The method can further include actuating a plunger of the hemostasis valve to a low compression state before injecting the first fluid. The method can further include, before injecting the first fluid, applying vacuum to the sink connection of the hemostasis valve to remove luminal air from a catheter fluidly connected to the hemostasis valve while the first valve at the first fluid source connection of the hemostasis valve is closed, and closing the sink valve at the sink connection. Injecting the second fluid from the second fluid source into the second fluid source connection can include injecting the second fluid from the second fluid source into the second fluid source connection at a high pressure. The method can further include detecting, by an air bubble sensor, air bubbles in at least one of the first fluid or the second fluid.

There is also provided a degassing method for a multiple catheter fluid management system. The method includes applying vacuum to a sink connection of a hemostasis valve to remove luminal air from a catheter fluidly connected to the hemostasis valve while a first valve at a first fluid source connection of the hemostasis valve is closed, closing a sink valve at the sink connection, opening the first valve at the first fluid source connection of the hemostasis valve, and injecting a first fluid at a low pressure from a first fluid source into the first fluid source connection of the hemostasis valve.

The first fluid can be heparinized saline. The method can further include applying vacuum to the sink connection of the hemostasis valve to remove residual first fluid into a sink connected to the sink connection, and injecting a second fluid from a second fluid source into a second fluid source connection of the hemostasis valve. The second fluid can be contrast. Injecting the second fluid from the second fluid source into the second fluid source connection can include injecting the second fluid from the second fluid source into the second fluid source connection at a high pressure. The method can further include detecting, by an air bubble sensor, air bubbles in at least one of the first fluid or the second fluid.

There is also provided a degassing method for a multiple catheter fluid management system. The method includes receiving by a processor communicatively coupled to a hemostasis valve on a catheter hub a first input indicating injection of a first fluid at a low pressure from a first fluid source into a first fluid source connection of the hemostasis valve, transmitting by the processor a first output signal to close a first valve at the first fluid source connection, transmitting by the processor a second output signal to initiate vacuum at a sink connection of the hemostasis valve to remove residual first fluid into a sink, transmitting a third output signal to close a sink valve at the sink connection, and receiving a second input indicating injection of a second fluid from a second fluid source into a second fluid source connection of the hemostasis valve.

The first fluid can be heparinized saline. The second fluid can be contrast. The hemostasis valve can include a plunger. The method can further include transmitting by the processor a fourth output signal to cause the plunger to actuate to a high compression state before receiving the second input indicating injection of the second fluid. The method can further include transmitting by the processor a fifth output signal to cause the plunger to actuate to a low compression state before receiving the first input indicating injection of the first fluid. The method can further include detecting, by an air bubble sensor, air bubbles in at least one of the first fluid or the second fluid.

There is also provided a fluidics degassing system. The fluidics degassing system includes a first hemostasis valve on a first catheter hub. The first hemostasis valve includes a first fluid source connection including a first valve, a second fluid source connection including a second valve, and a sink connection including a sink valve. The fluidics degassing system also includes a first processor communicatively coupled to the first hemostasis valve. The first processor is configured to receive a first input indicating injection of a first fluid at a low pressure from a first fluid source into the first fluid source connection, transmit a first output to close the first valve at the first fluid source connection, transmit a second output to initiate vacuum at the sink connection to remove residual first fluid into a sink, transmit a third output to close the sink valve at the sink connection, and receive a second input indicating injection of a second fluid from a second fluid source into the second fluid source connection.

The first fluid can be heparinized saline. The second fluid can be contrast. The system can further include a manifold including a saline valve configured for connection between the first fluid source connection of the first hemostasis valve and a saline source, a contrast valve configured for connection between the second fluid source connection of the first hemostasis valve and a contrast media source, and a vacuum valve configured for connection between the sink connection of the first hemostasis valve and a vacuum source. The system can include a first catheter having the first catheter hub including the first hemostasis valve. The system can include a second catheter hub configured to axially, movably receive the first catheter therethrough. The second catheter hub can include a second hemostasis valve. The second hemostasis valve can be adjustable between a low compression state and a high compression state against the first catheter. The first hemostasis valve can include a plunger. The first processor can be further configured to transmit a fourth output to the plunger to cause the plunger to actuate to a high compression state before receiving the second input indicating injection of the second fluid. The first processor can be further configured to transmit a fifth output to the plunger to cause the plunger to actuate to a low compression state before receiving the first input indicating injection of the first fluid.

There is also provided a fluid management system for a robotically driven interventional device. The system includes a hub configured to be positioned on a proximal end of a first elongate body and to manipulate the first elongate body, and a first hemostasis valve at least partially disposed in the hub, wherein the hemostasis valve includes a first fluid source connection, a second fluid source connection, and a sink connection. The hemostasis valve is configured to be concurrently and fluidly connected to a first fluid source via the first fluid source connection, a second fluid source via the second fluid source connection, and a sink via the sink connection, such that the system is configured to automatically switch between permitting fluid into a lumen of the first elongate body through the hemostasis valve exclusively from the first fluid source or from the second fluid source or to permit fluid removal from the lumen to be collected in the sink.

The hemostasis valve can include a three-way connector including the first fluid source connection, the second fluid source connection, and the sink connection. The first fluid source can include one of saline, heparinized saline, or a pharmaceutical. The second fluid source can include contrast. The system can include a first manifold including a first input line configured to be connected to the first fluid source and a first output line configured to be connected to the first fluid source connection of the hemostasis valve. The system can include a second hub configured to receive and manipulate a second elongate body at least partially disposed in the lumen of the first elongate body, and a second hemostasis valve at least partially disposed in the second hub, wherein the second hemostasis valve includes a third fluid source connection, a fourth fluid source connection, and a second sink connection, wherein the first manifold includes a second output line that is configured to connect to the third fluid source connection. The first manifold can include a valve configured to activate one or both of the first output line and the second output line. One or more of the first input line, the first output line, and the second output line can include one or more of: a drip rate sensor, a bubble sensor, a bubble filter, or an inline pump. The system can further include a second manifold including a second input line configured to be connected to the second fluid source and a third output line configured to be connected to the second fluid source connection of the first hemostasis valve. The system can further include a second hub configured to receive and manipulate a second elongate body at least partially disposed in a lumen of the first elongate body, and a second hemostasis valve at least partially disposed in the second hub, wherein the second hemostasis valve includes a third fluid source connection, a fourth fluid source connection, and a second sink connection, wherein the second manifold further includes a fourth output line configured to connect to the fourth fluid source connection. One or more of: the second input line or the third output line includes one or more of: a bubble sensor or a bubble filter. The system can include a third manifold including a sink output line configured to be connected to the sink, and a sink input line configured to be connected to the sink connection of the hemostasis valve. The system can further include a second hub configured to receive and manipulate a second elongate body at least partially disposed in the lumen of the elongate body, and a second hemostasis valve at least partially disposed in the second hub, wherein the second hemostasis valve includes a third fluid source connection, a fourth fluid source connection, and a second sink connection, wherein the second manifold further includes a second sink input line that is configured to connect to the second sink connection. The sink input line can include an inline local filter. The sink can include an aspiration container such that the sink output line includes the aspiration container that is configured to be fluidly connected to an aspiration pump. The hemostasis valve can include an actuatable gasket that is movable between a first open configuration, a second low sealing force configuration for low pressure fluid transfer from the first fluid source or the second fluid source, and a third high sealing force configuration for high pressure fluid transfer from the second fluid source. The first fluid source can include saline and the second fluid source can include contrast. The system can include a driven magnet on the hub configured to cooperate with a drive magnet such that the driven magnet moves in response to movement of the drive magnet. The drive magnet can be axially movably carried by a support table. The system can include a second hub configured to receive and manipulate a second elongate body at least partially disposed in the lumen of the first elongate body, and a second hemostasis valve at least partially disposed in the second hub, wherein the second hemostasis valve includes a third fluid source connection, a fourth fluid source connection, and a second sink connection. The second hemostasis valve can be configured to be fluidly connected to: the first fluid source via the third fluid source connection, the second fluid source via the fourth fluid source connection, and the sink via the second sink connection, such that the second hemostasis valve is configured to permit fluid into the lumen of the second elongate body through the hemostasis valve from the first fluid source or from the second fluid source or to permit fluid removal from the lumen of the second elongate body to be collected in the sink. The second hemostasis valve can include a second three-way connector including the third fluid source connection, the fourth fluid source connection and a second sink connection.

There is also provided a fluid management system for a robotically driven medical device. The system includes a hub configured to receive and manipulate an interventional device, and a hemostasis valve carried by the hub. The hemostasis valves includes a first port including a three-way connector that is configured to be simultaneously fluidly connected to a first fluid source, a second fluid source, and a sink, and a second port including an actuatable hemostasis gasket configured to seal about a second interventional device configured to be disposed in a lumen of the interventional device. The gasket is actuatable between a first open state, a second low sealing force state for receiving low pressure fluid injections from the first fluid source or the second fluid source through the first port or for permitting fluid to flow through the first port to the sink, and a third high sealing force state for receiving high pressure fluid injections from the second fluid source through the first port.

There is also provided a method of providing contrast injection from a selected catheter of a robotic catheter system having at least a first catheter and a second catheter, the second catheter configured to be positioned in a lumen of the first catheter (for example, in part of the lumen or in the entire length of the lumen). The method can comprise receiving, by a controller, a signal indicating a selection of the first or second catheter for injecting contrast; controlling, by the controller, a position of a valve to place the lumen of the selected catheter in fluid communication to a contrast subsystem, determining, by the controller, that valves of non-selected catheters of the at least first and second catheters are aligned such that the non-selected catheters are not in fluid communication with the contrast subsystem, and actuating, by the controller, a contrast pump in fluid communication with the lumen of the selected catheter to inject contrast. Determining that valves of non-selected catheters of the at least first and second catheters are aligned such that the non-selected catheters are not in fluid communication with the contrast subsystem can include using stored information of the position of valves that connect the non-selected catheters to the contrast subsystem. Determining that valves of non-selected catheters of the at least first and second catheters are aligned such that the non-selected catheters are not in fluid communication with the contrast subsystem can include using information from a sensor on a valve of a non-selected catheter.

There is also provided a fluidics system that can comprise a cassette configured to be releasably coupled to a pump station, and configured to receive saline from a saline source, receive contrast from a contrast source, and receive vacuum from a vacuum source, the cassette comprising a saline subsystem having a first saline flow-path, a contrast subsystem having a first contrast flow-path, and a vacuum subsystem including a first vacuum flow-path. The system can further comprise a splitter having a second saline flow-path, a second contrast flow-path, and a second vacuum flow-path, each of the second saline, contrast, and vacuum flow-paths having a single proximal end and a plurality of distal ends. The system can further comprise a first tubing set having a first length and coupled to the cassette and splitter, the first tubing set including a single saline channel coupled to the first saline flow-path and the proximal end of the second saline flow-path, a single contrast channel coupled to the first contrast flow-path and the proximal end of the second contrast flow-path, and a single vacuum channel coupled to the first vacuum flow-path and the proximal end of the second vacuum flow-path. The system can also comprise two or more hub assemblies, at least one of the two or more hub assemblies configured to have a third saline flow-path, a third contrast flow-path, and a third vacuum flow-path to provide saline, contrast and vacuum to the lumen of a catheter coupled to the at least one of the two or more hub assemblies. The system can also comprise a second tubing set having a second length that is shorter than the first length, the second tubing set comprising a plurality of tube groups, each tube group coupled to the splitter on a proximal end of the tube group and to one of the two or more hub assemblies on a distal end of the tube group, at least one of the plurality of tube groups including a saline subchannel coupled to the distal end of the second saline flow-path of the splitter, a contrast subchannel coupled to the distal end of the second contrast flow-path of the splitter, and a vacuum subchannel coupled to the distal end of the second vacuum flow-path of the splitter.

In such fluidics systems, at least one of the two or more hub assemblies comprises a mount, and wherein the mount comprises the third saline flow-path, the third contrast flow-path, and the third vacuum flow-path. The mount can include a connector, wherein the mount is configured to provide saline, contrast, and vacuum through the connector to the lumen of the catheter. The at least one of the two or more hub assemblies can comprise one or more robotically actuated control valves controlled by a control system to selectively align the third saline flow-path, the third contrast flow-path, and the third vacuum flow-path to be in fluid communication with lumen of the catheter. The first length of the first tubing set can be at least twice as long as the second length of the second tubing set to minimize the length of tubing that needs to be visually inspected. In some examples, a ratio of the first length to the second length is greater than 1:4. The saline subsystem can be configured to receive saline from a first saline source and a second saline source, the saline subsystem including a robotically actuated valve controlled by a control system to place first saline flow-path in fluid communication with the first saline source or the second saline source. The control system can control the robotically actuated valve to switch to receiving saline from a different one of the first and second saline sources based on receiving a signal from a sensor. The sensor can be, for example, a weight sensor configured to sense the weight of the first saline source and the second saline source, or an air sensor configured to detect air in the first saline flow-path. The contrast subsystem can comprise a contrast pump actuatable by a control system to provide contrast to the at least one of the two or more hub assemblies. The vacuum subsystem can comprise a clot pod. The clot pod can include at least one transparent surface positioned such that contents of the clot pod are visible from outside of the cassette. The vacuum subsystem can include a drip chamber in fluid communication with the first vacuum flow-path, the vacuum subsystem comprising one or more robotically actuated valves controlled such that fluid aspirated by the vacuum subsystem is collected in the drip chamber. The drip chamber can include at least one transparent surface positioned such that contents of the drip chamber are visible from outside of the cassette. The drip chamber can be positioned in the first vacuum flow-path between the clot pod and the first tubing set. The vacuum subsystem can further comprise a plurality of robotically actuated valves configured to be controlled by a control system for controlling the vacuum flow-path through the drip chamber and the clot pod. The plurality of robotically actuated valves of the vacuum subsystem include a first valve positioned in the first vacuum flow-path between the drip chamber and the clot pod and a second valve positioned on an opposite side of the drip chamber in the first vacuum flow-path between the drip chamber and the first tubing set, wherein first valve and second valve are selectively controlled to control the flow of fluid and material from the two or more hub assemblies to the drip chamber and the clot pod. The fluidics system can further comprise a plurality of catheters, one of the plurality of catheters coupled to each of the two or more hub assemblies. Each of the two or more hub assemblies can include a saline air sensor positioned to detect air in the third saline flow-path, and a contrast air sensor positioned to detect air in the third contrast flow-path. The saline and contrast air sensors can be positioned in the saline and contrast third flow-paths, respectively, between the plurality of robotically actuated control valves and the second tubing set for detecting air in the saline and contrast flow-paths before it reaches the plurality of robotically actuated control valves. One or more of the plurality of robotically actuated control valves are controlled by a control system to block the saline and contrast flow-paths to the connector based on a signal from one of the saline and contrast air sensors. In such fluidics systems, each of the two or more hub assemblies can include a plurality of sensors, and wherein the first tubing set, the splitter, and each tube group of the second tubing set further comprises an electrical channel coupled to the plurality of sensors in the two or more hub assemblies, the electrical channel configured to communicate electrical signals from the plurality of sensors to an electrical interface on the cassette that is configured to electrically connect to a corresponding electrical interface on a pump station to provide the signals from the plurality of sensors in the hub assemblies to a control system. The plurality of sensors can include a saline air sensor positioned to detect air in the third saline flow-path, a contrast air sensor positioned to detect air in the third contrast flow-path, and a pressure sensor configured to sense pressure of fluid provided to the lumen of the catheter.

There is also provide a fluidics system, comprising two or more hub assemblies, each hub assembly including one or more robotically actuated control valves; a saline channel, a contrast channel, and a vacuum channel; and a primary channel configured to be coupled to a catheter, wherein the one or more robotically actuated control valves are controlled by a control system to selectively connect one or both of the saline channel and the contrast channel to be in fluid communication with the primary channel, or to connect the vacuum channel to be in fluid communication with the primary channel, for providing saline, contrast or vacuum to the catheter. At least one of the two or more hub assemblies can be a two part hub assembly and include a hub (first subassembly) and a mount (second subassembly). In the fluidics system, at least one of the two or more hub assemblies can comprise the one or more robotically actuated control valves, the saline channel, the contrast channel, the vacuum channel, and the primary channel. At least one of the two or more hub assemblies can further comprise a connector configured to be coupled to the catheter for providing fluid to the catheter through the connector. Such fluidics system can further comprise a catheter coupled to each of the two or more hub assemblies. The one or more robotically actuated control valves can comprise two robotically actuated valves. Each of the two or more hub assemblies can include a mount, and the two robotically actuated valves are located in the mount of each of the two or more hub assemblies. In fluidic systems two or more hub assemblies can include three hub assemblies. Such fluidic systems can further comprise a cassette configured to be releasably coupled to a pump station, the cassette comprising a saline subsystem configured to receive saline from a saline source, a contrast subsystem configured to receive contrast from a contrast source, and a vacuum subsystem configured to receive vacuum from a vacuum source; and communication channels coupled to the cassette and the two or more hub assemblies for providing saline, contrast, and vacuum to the hub assemblies. The cassette can include a portion of the saline subsystem, and wherein the pump station includes at least one actuator configured to operatively couple to the cassette to operate the portion of the saline subsystem in the cassette. The fluidics system can further include a controller configured to control the pump station based in part on a first user input received from an interface in communication with the fluidics system. The interface can be located in proximity to the fluidics system. The controller can be further configured to control the pump station based in part on a first user input received from a control console in communication with the fluidics system. The control console can be located in the same room as the fluidics system. The control console can be in a location remote from the fluidics system.

There is also provided a fluidics system, comprising two or more hub assemblies configured to be coupled to a catheter, at least one of the two or more hub assemblies comprising a robotically actuated first control valve; a saline channel in fluid communication with the first control valve; a saline-contrast channel in fluid communication with the first control valve; and a saline restricted-flow channel in fluid communication with the saline channel and the saline-contrast channel bypassing the first control valve. At least one of the two or more hub assemblies can further comprise a contrast channel in fluid communication with the first control valve, wherein the first control valve is robotically controlled to selectively connect one or both or neither of the saline channel and the contrast channel to be in fluid communication with the saline-contrast channel through the first control valve. The at least one of the two or more hub assemblies further comprise further comprise a vacuum channel; a robotically actuated second control valve coupled to the saline-contrast channel and a primary channel for providing saline, contrast and vacuum to a catheter, the robotically actuated second control valve configured to be controlled by a control system to connect and disconnect the vacuum channel and the primary channel; a first air sensor positioned to detect air in the saline channel and configured to generate a signal indicative of detected air in the saline channel; and a second air sensor positioned to detect air in the contrast channel and configured to generate a signal indicative of detected air in the contrast channel, wherein the second control valve is robotically actuated to disconnect the saline-contrast channel from the primary channel based at least in part on a signal from the first air sensor or the second air sensor. The at least one of the two or more hub assemblies can further comprise a check valve positioned in the saline channel between the first air sensor and the first control valve, the check valve configured to limit fluid flow in the saline channel in the direction from the first air sensor towards the first control valve. In such fluidic systems, wherein each hub assembly can further comprise a robotically actuated second control valve in fluid communication with the saline-contrast channel; a vacuum channel in fluid communication with the second control valve, wherein the second valve is robotically actuated to selectively connect either the vacuum channel or the saline-contrast channel to a primary channel in fluid communication with a catheter coupled to the hub assembly.

Each hub assembly can further comprise a primary channel in fluid communication with the lumen of a catheter coupled to the mount, wherein the fluidics system comprises a pressure sensor positioned to detect pressure in the primary channel and generate a signal indicative of the detected pressure, wherein the fluidics system is configured to determine to whether to inject contrast based at least in part on the signal indicative of the pressure in the primary channel.

There is also provided a method of selectively providing saline, contrast, and vacuum from a cassette releasable coupled to a pump station to a plurality of catheters, each catheter coupled to one of a plurality of hub assemblies in fluid communication with a primary channel in the respective hub assembly, the method comprising: providing saline through a saline communication channel coupled to the cassette and coupled to each one of the plurality of hub assemblies, wherein a portion of the saline communication channel coupled to each of the plurality of hub assemblies is the same; providing contrast through a contrast communication channel coupled to the cassette and coupled to each one of the plurality of hub assemblies, wherein a portion of the contrast communication channel coupled to each of the plurality of hub assemblies is the same; and providing vacuum through a vacuum communication channel coupled to the cassette and coupled to each one of the plurality of hub assemblies, wherein a portion of the vacuum communication channel coupled to each of the plurality of hub assemblies is the same. In such methods, the plurality of hub assemblies can comprise three hub assemblies. At least one of the plurality of hub assemblies can include a hub and a mount. Methods of selectively providing saline, contrast, and vacuum from a cassette releasable coupled to a pump station to a plurality of catheters can further comprise controlling by a control system, for each of the plurality of hub assemblies, one or more robotically actuated control valves located in the hub assembly to selectively connect the primary channel with the saline channel, the contrast channel, or the vacuum channel to provide saline, contrast or vacuum to the catheter.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIG. 2 shows a schematic of a three channel fluidics system.

FIG. 26 illustrates an example of a configuration of the saline subsystem after a saline bag has been coupled to a saline subsystem.

FIG. 37 illustrates actuating a saline/contrast connection valve to connect the saline subsystem to the contrast subsystem to prime fluid communication channels in the contrast subsystem with saline.

FIGS. 70A-70C are schematics illustrating another example of a contrast subsystem that can be included in a cassette.

FIG. 80 is a flowchart illustrating a process for performing contrast injection of the selected catheter in a robotic catheter system having multiple catheters coupled to a movable mounts with each of the movable mounts is being provided fluidic saline, contrast, and vacuum by the fluidics system.

FIG. 82 illustrates an example configuration of a fluidics system where "high" vacuum is provided to a catheter, for example, when the distal end of the catheter is positioned near a clot such that the clot can be ingested by the vacuum subsystem and captured in the clot pod.

FIG. 83 illustrates an example configuration of a fluidics system where "high" vacuum is provided to a catheter, illustrating blood flow through the catheter towards the clot pod assembly where air bubbles are formed in the aspirated blood as a result of the applied high vacuum.

FIG. 84 illustrates an example configuration of a fluidics system where "high" vacuum is provided to a catheter and the clot has been transported back through the catheter, mount, and vacuum line and captured in a clot pod of a clot pod assembly.

FIG. 85 illustrates an example configuration of a fluidics system where "high" vacuum is provided to a catheter and the clot has been aspirated and captured in a clot pod, and the system is configured to perform a saline flush of the clot pod and the vacuum communication channel between the mount and the clot pod.

FIG. 86 illustrates an example configuration of a fluidics system during backbleed, where "low" vacuum is provided to a catheter and to create a vacuum flow-path from the catheter to the clot pod to remove fluid containing air bubbles from the catheter and hub without decreasing the solubility of blood to the point where (additional) dissolved air comes out of the blood or saline in the catheter, hub, and/or mount.

DETAILED DESCRIPTION

Figure 1A:
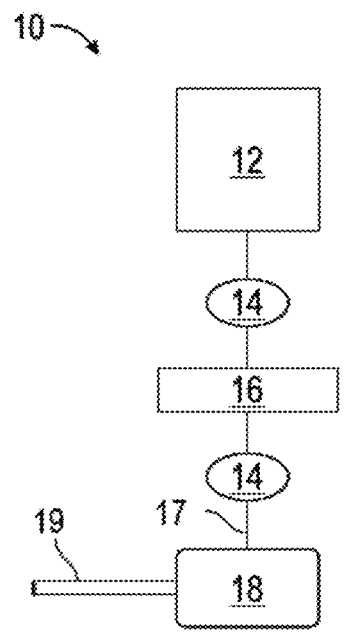
FIG. 1A illustrates one embodiment of a one channel fluidics management system.

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Properly injecting fluids into vessels of a living human body in a precise and predictable manner can be difficult without assisted fluid management systems. Such a desired preciseness for administering fluids, combined with the danger of delivery of improper volumes of fluid or fluid containing air bubbles, has led the medical industry to train physicians with a tactile feel for fluid administration combined with a visual volume and air bubble assessment. For example, when learning to inject fluids into the brain, physicians are trained to press a syringe with a specific coordinated pressure as well as how to manually prepare and review fluids for volume and air bubbles when injecting and/or removing fluids during particular procedures.

In catheterization procedures, air emboli represent a significant, even fatal, hazard for patients. Air can be introduced during fluid injection, during catheter switching or manipulation, or any other event that creates a pressure gradient that enables air to flow into the catheter and subsequently into the vessel. Reducing the number of times that connections are broken and created in a system during a catheterization procedure may reduce the likelihood of air embolism. The fluidics management systems and methods described herein are configured to reduce the likelihood of air embolism during a catheterization procedure.

Further, in the case of ischemic stroke or other occlusive or thrombus-related conditions, every minute that goes by without treatment may result in reduced recovery for the patient. Reducing manual switching between fluid administration and removal (e.g., aspiration) catheters as well as reducing the time needed for fluid preparation during a catheterization procedure, for example using a fluid management system, may improve patient survival and recovery post the stroke event. In some embodiments, reducing manual switching between fluid administration and removal catheters by using the fluid management systems described herein may provide an advantage of reducing workload for operating staff. In some embodiments, reducing manual switching between fluid administration and removal catheters by using the fluid management systems described herein may provide an advantage of enabling a remotely controlled procedure (in which an interventionalist is not onsite near to the fluid management system and/or catheters) to be carried out in a streamlined fashion because connection changes may not be part of the procedure when using the fluid management systems described herein. In some embodiments, reducing manual switching between fluid administration and removal catheters by using the fluid management systems described herein provides an advantage of improved safety and reliability (e.g., procedure step consistency). In addition, by using a consistent fluid management system, the risk of air embolization is reduced.

Disclosed herein are systems and methods for managing fluidics systems that administer and remove fluids during medical procedures. The fluidics systems described herein can be used with robotic catheter systems. The fluidics systems can be used with other device and methods as well. The fluidics systems may be coupled to robotically driven interventional devices, manually driven interventional devices, or any combination thereof. In particular, the systems and methods may be configured to control fluid administering equipment to ensure proper diagnostics and/or treatment is provided.

The systems and methods described herein may include a programmable and/or automated fluid injection and removal system that may assist a physician (e.g., surgeon, interventionalist, and the like) to perform procedures when fluidics are involved. For example, the devices, systems, and methods for operating fluid management systems described herein may automate fluid injected using programmable pumps, vacuums, catheter hubs, and the like, to allow consistent, precise, and timely injections. In some embodiments, the fluid lines are not swapped or disconnected during a procedure, but are instead configured once before a procedure and left intact throughout the procedure so as to avoid errors at connection points (e.g., valving errors), errors in fluid selection, and/or air bubble introduction issues that arise because of air introduced when switching between fluids.

In operation, the fluid management systems described herein may include multiple fluidics systems in which each system is for a separate fluid source and or fluid collection container. The multiple fluidics systems may be configured to flow from the same fluid management system and couple to interventional devices or medical tools. For example, each fluidics system may be configured to connect to each catheter hub (manual catheter hub or robotically driven hub) associated with the fluid management system. Each catheter hub ("hub") may connect to at least one interventional device, for example a catheter. The hub, or a control interface removed from the hub, may include controls to control fluid administration steps and/or catheter manipulation steps.

In some embodiments, the devices, systems, and methods described herein may be configured to provide an advantage of reducing the time and effort used to degas fluidics systems. For example, maintaining fully filled fluid lines and fluid tubing connections during procedures (i.e., avoiding switching of fluidics components) may ensure that a degassing procedure can be performed a single time for each fluid before the procedure. The methods described herein may include configuration methods, degassing methods, methods of treatment, fluid injection and/or fluid removal methods, and the like.

In some embodiments, the devices, systems, and methods described herein may be configured to reduce a number of sterile packages that have to be opened for a particular procedure. For example, because additional catheters, fluid lines, hubs, and/or other fluidly connected components are configured to connect to the system before the procedure and remain connected, the components may be packaged together or at least multiple packages opened and components assembled at one time before the procedure and there may be no need to open additional packages or install additional components during the procedure. For example, in certain embodiments, one or more catheters, hubs, and fluid lines may be provided in a single sterile package. In some embodiments, one or more catheters, hubs, and fluid lines may be provided in a single sterile package with a splitter and/or a cassette. In other embodiments, any of the foregoing components may be packaged in separate sterile packages.

In some embodiments, the devices, systems, and methods described herein may be configured to reduce time and/or steps used to flush fluid lines because such steps may be automated and performed in an automatic fashion when requested by the fluid management system.

In some embodiments, the devices, systems, and methods described herein may be configured to display fluidics management steps on a user interface to streamline configuration of the fluidics systems. For example, specific user interfaces may be configured for specific procedures. Each user interface may present instructions, information, or other data to a procedure staff while the fluidics management system is automatically executing next steps of the procedure with respect to fluidics management.

Systems and Devices

FIG. 1A illustrates one embodiment of one channel of a multi-channel fluidics management system 10. The fluidics management system 10 may be configured as an automated system to manage the delivery of fluids to or aspirate material from a patient via one or more interventional devices, for example catheters. As shown, the system 10 may manage fluid delivery to a patient during a medical procedure. The fluidics management system 10 includes at least one fluid source and/or sink 12 coupled to a valve 14, which is coupled to a manifold 16. The manifold 16 is either remote (e.g., on a support table or tower outside the sterile field) or coupled to a catheter hub 18, which is coupled to at least one source and/or sink line 17. The source and/or sink line 17 is coupled through the hub to at least one catheter 19.

Certain embodiments of hub assemblies described herein, such as hub assembly ("hub") 18, include a housing for coupling an interventional device thereto, components (e.g., rollers) for directly coupling to and moving along a drive table, and magnet(s) for magnetically coupling to a hub adapter across a sterile barrier. A hub (or hub assembly) can refer to a single assembly with a housing, or a hub (or hub assembly) can generally refer to an apparatus having two (or more) subassemblies (e.g., a first subassembly and a second subassembly). In some embodiments of a hub assembly having two subassemblies, a hub can refer to a first subassembly that can be configured to couple to and house an interventional device, and that may be removably attachable to a second subassembly (or mount) configured to magnetically couple to a hub adapter across a sterile barrier and move along a drive table. Such a hub and mount may together form a hub assembly. Such hub assemblies may allow for a hub (first subassembly) to be removed from a mount (second subassembly) which can be advantageous, for example, so that a different hub can be coupled to the same mount or so that the hub may be used separately from the mount (e.g., for a manual procedure). Certain components of advantageous example configurations of a mount are shown and described in reference to FIGS. 64-87. An arrangement of a hub assembly having a hub that is releasably couplable to mount can allow for replacement of a hub with a different hub having a different interventional device coupled thereto without breaking a magnetic connection with a hub adapter. For example, such an arrangement may allow for a hub coupled to an access catheter to be removed from a mount and replaced with a hub coupled to a procedure catheter without breaking a magnetic connection between active and passive magnetic sides of the coupling of the hub adapter and hub assembly (e.g., between the hub adapter and the mount). In some embodiments, the mount may be a magnetically driven member, an axially driven member, a puck, a slider, a shuttle, or a stage. The fluidics systems described herein can relate to various embodiments of systems that include a hub, or a hub and a mount, regardless of whether they are described in reference to a hub, or a hub and mount, unless explicitly indicated or indicated by context.

The fluidics management system 10 can provide multiple fluids (e.g., saline, contrast) and vacuum to one or more hubs. An elongated device can be attached to each of the one or more hubs for performing a medical procedure. For example, a catheter can be coupled to each of the one or more hubs that receive fluids and vacuum from the fluidics management system 10, and a guidewire can be coupled to a hub that does not receive fluids or vacuum. The one or more hubs can be controlled by a controller of the robotic catheter system to move along a drive table to correspondingly move the attached elongated device towards or into a patient, or to move the attached elongated device away from or out of a patient. In some preferred embodiments, the one or more hubs are moved in a longitudinal direction (e.g., along a line or straight path) during use in medical procedures.

Figure 18:
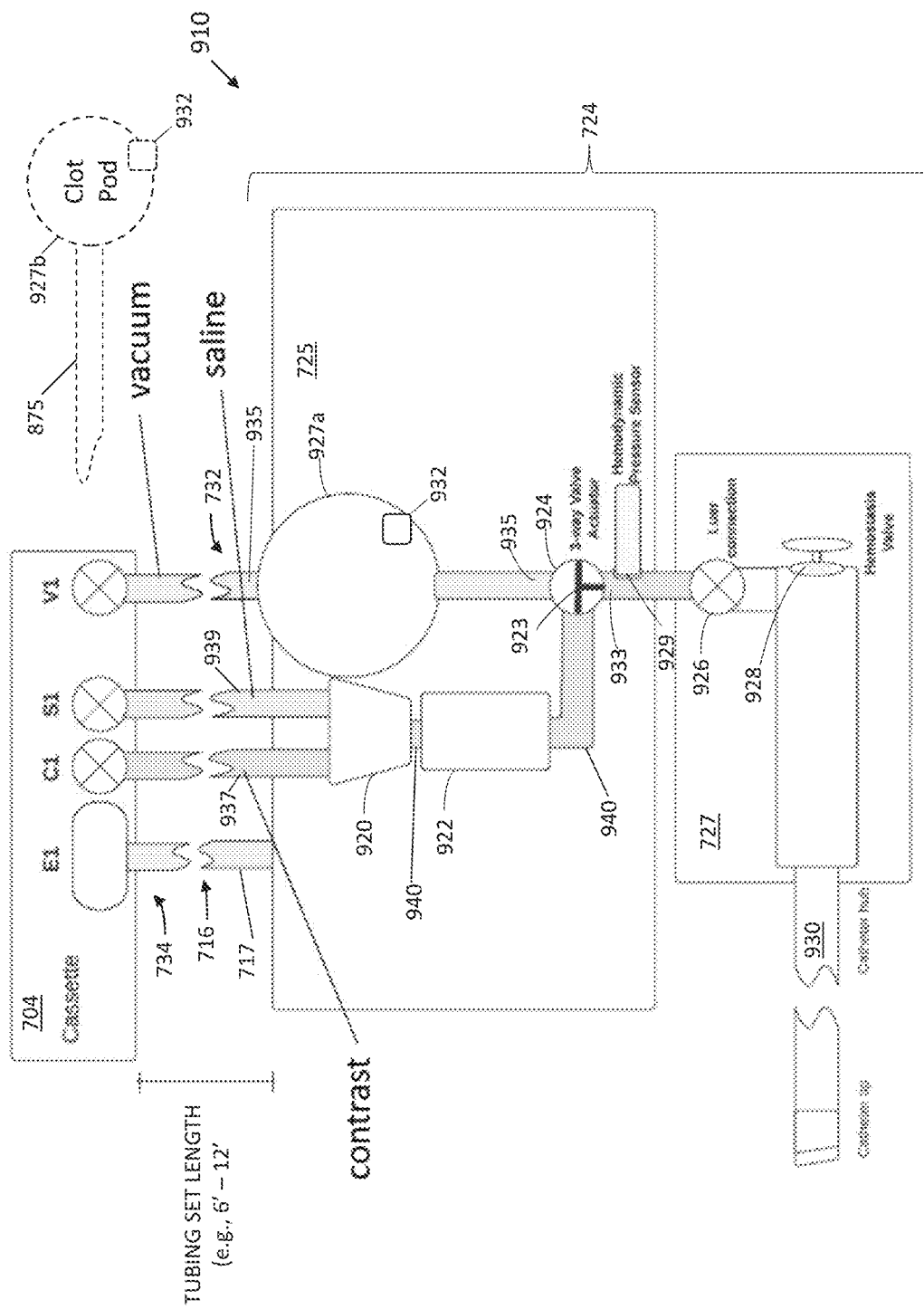
FIG. 18 illustrates an example of a catheter coupled to an embodiment of a hub, and a tubing set connected at a distal end to the hub and at a proximal end to a cassette, where the tubing set includes a saline tube, a contrast tube, and a vacuum tube, and can include electrical connections, where the tubing set forms a portion of a fluid communication system that connects the hub and to a saline subsystem, a contrast subsystem, and a vacuum subsystem, for example, the saline subsystem, a contrast subsystem, and vacuum subsystem as illustrated in FIGS. 15, 16, and 17, respectively.
Figure 69:
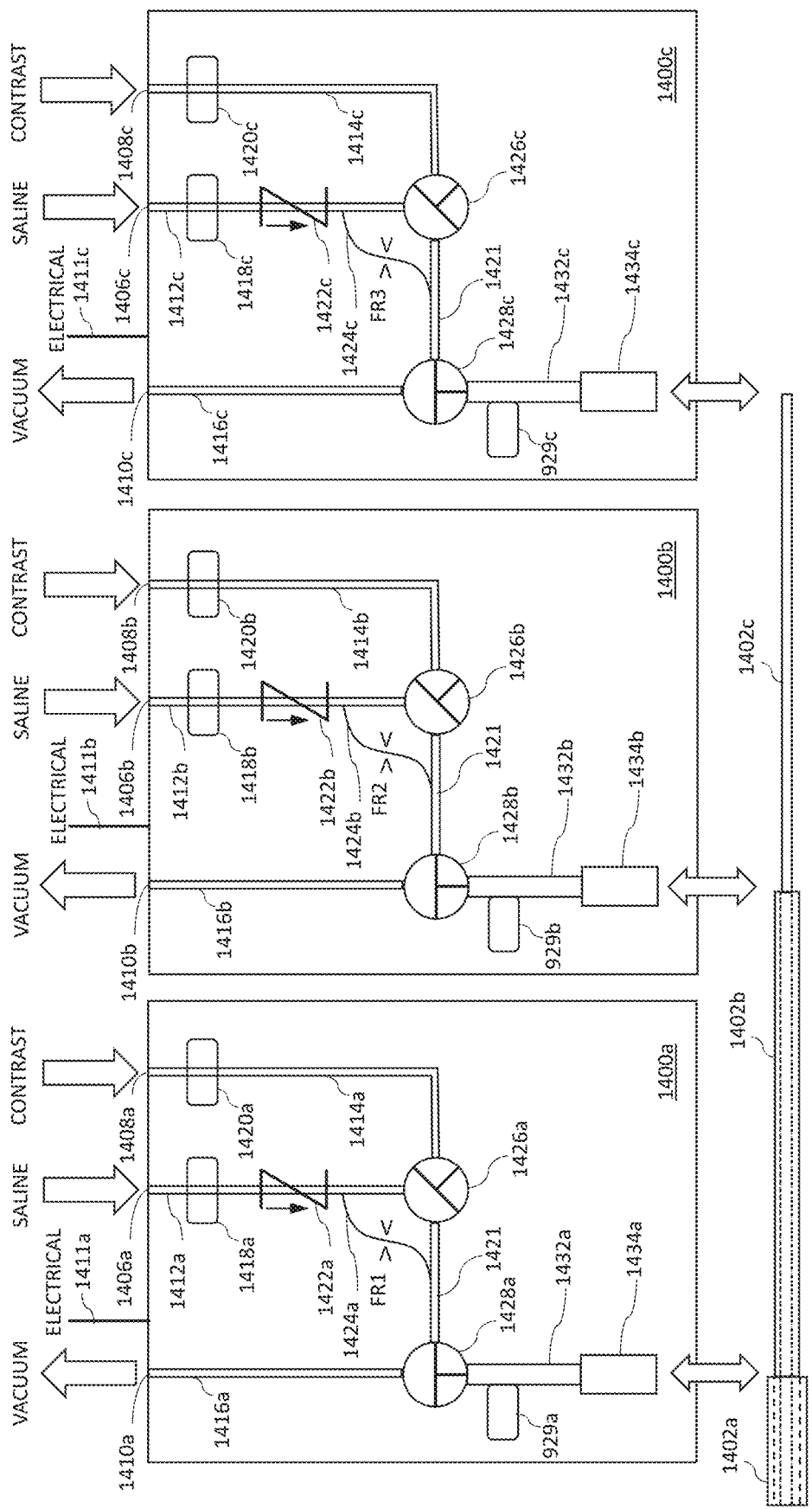
FIG. 69 is a schematic illustrating an example of a fluidic system components in one or more mounts, which can be coupled to the second tubing set, this particular example including three mounts each having a fluidic connection for saline, contrast, and vacuum, and an electrical connection that includes one or more electrical leads, the electrical connection coupled to one or more sensors in the mounts to communicate signals from the one or more sensors to the cassette, and ultimately a station (e.g., a pump station) when the cassette is coupled to the station.

As indicated above, in some embodiments, a hub is a two-part a hub. A two-part hub can include a first part (a hub or first subassembly) and a second part (a mount or second subassembly). An elongated device (e.g., a catheter, a guidewire, etc.) can be coupled to the hub. The hub can be, and typically is, mechanically coupled to the hub assembly when in use. In some preferred embodiments, the first and second subassemblies can be decoupled if necessary when during a medical procedure. In embodiments where a hub includes a first and second subassembly, different components can be included in each of the first and second subassemblies. In some embodiments, the first subassembly can include a hemostasis valve controllable by a controller of the robotic catheter system to open or close during a medical process. For example, the hemostasis valve can be controlled to close during a contrast injection process with a first catheter to control the flow of contrast through the catheter lumen to the distal tip of the first catheter and preventing the injected contrast from flowing in the opposite direction along the surface of another elongated device positioned at least partially in the lumen of the first catheter. The first subassembly can include rotational mechanisms for rotating the elongated device coupled to the first subassembly. The rotational mechanisms can be driven by actuators in the second assembly which couple to the rotational mechanisms when the first subassembly is coupled to the second subassembly. In various embodiments, the second subassembly can include fluidics components (e.g., air sensors, fluid connectors, air bubble filters, pressure sensors, control valves, channels, saline restricted-flow channels, and the like) that are used to provide fluids and vacuum to a catheter attached to the first subassembly. An example of a two-part hub is illustrated in FIG. 18, where the two-part hub 724 includes a first part (hub or first subassembly) 727 and a second part (mount or second subassembly) 725. Another example of a two-part hub is illustrated in FIG. 69, which illustrates an embodiment of a system that includes three second subassemblies (mounts) 1400a-c that provide fluids and vacuum to connectors 1434a-c, which can be connected to first subassemblies (not shown) which are coupled to catheters 1402a-c to provide saline, contrast, and vacuum to the catheters 1402*a-c*. Whether a hub includes a "single" hub assembly or includes a first subassembly and a second subassembly, all or nearly all of the fluidic operations are the same when the first subassembly and a second subassembly are coupled together. A two part hub may be referred to herein simply as a hub for case of reference. In some instances, for a hub having a first subassembly and a second subassembly, the first subassembly may be referred to herein as a "hub" and the second subassembly may be referred to as a "mount" to differentiate the two subassemblies.

In some embodiments, the fluid source and/or sink 12 includes both a reservoir of fluid volume and a means of propelling such fluid to another component of the system 10 or a means of retrieving fluid back to the source. Example propelling means may include one or more propellers, impellers, and/or pumps to circulate and/or retrieve fluid throughout system 10. In some embodiments, the propelling means can be used to control the volume, flow rate, and/or pressure. In certain embodiments, the propelling means can be activated to propel fluid to another component of the system or retrieve fluid from the system or deactivated to stop the movement of fluid.

In some embodiments, the fluidics management channel is substantially duplicated for each catheter configured for use in a particular medical procedure. Different channels may differ in sensors, pumps, and/or valves employed based on the interventional device that is connected to each fluidics channel. For example, a fluidics system for a procedure catheter (e.g., for aspiration) may include an inline vacuum pump and filter. Further for example, a fluidics system for a guide, access, or insert catheter may include an inline drip rate sensor, air bubble sensor, pressure sensor, and/or air bubble filter.

The source and/or sink 12 represents either a fluid source or a fluid sink (e.g., waste canister). For example, a fluid source may include a container adapted to house a fluid (e.g., saline, contrast, pharmaceuticals, blood, plasma, or other fluid) for use with the fluidics management system 10. The container may be configured to release fluid into a fluid delivery line (e.g., fluid delivery tube) using active means (e.g., pumps, vacuums, etc.) or passive (e.g., gravity). The fluid sink may include a container adapted to receive fluids (e.g., aspirate, thrombus, particulate, saline, contrast, pharmaceuticals, blood, or other fluid or combination thereof) from the patient and/or from other fluidics infrastructure within the fluidics management system 10.

The valve 14 represents one or more valves that are coupled to the source and/or sink 12 at a first side of the valve 14 and coupled to the manifold 16 at a second side of the valve 14. The manifold 16 is configured to connect each valve 14 to a particular hub 18. In some embodiments, the valve 14 may instead couple directly to the hub 18 to avoid the use of a separate manifold 16. In some embodiments, the manifold 16 may be integrated into the hub. In some embodiments, a second valve 14 may connect the manifold 16 to the hub 18. For example, the second valve 14 can be coupled to the manifold 16 at a first side and coupled to the hub 18 at the second side.

The hub 18 is configured to releasably or non-releasably couple to an interventional device (i.e., a catheter, guidewire, or other medical device). For example, a catheter 19 has a proximal end attached to a hub 18. In some embodiments, the hub 18 is moveable along a path along the surface of a robotic drive table to advance or retract the catheter 19 (or other medical and/or interventional device). Each hub 18 may also contain mechanisms to rotate or deflect the catheter 19 or guidewire as desired. The hub 18 may be connected to fluid delivery tubes (e.g., source/sink line 17) to provide fluid release or fluid capture. Each hub 18 may be in electrical communication with an electronic control system, either via hard wired connection, RF wireless connection, or a combination of both. Additional details of the hubs, drive table and related systems are found in U.S. patent application Ser. No. 17/816,669, entitled Method of Supra-Aortic Access for a Neurovascular Procedure, filed Aug. 1, 2022, which is hereby expressly incorporated by reference in its entirety herein.

Any of the hubs disclosed herein may further comprise one or more fluid injection ports and/or a wireless RF transceiver for communications and/or power transfer. In some embodiments, the hub 18 may also comprise a wired electrical communications port and a power port.

In some embodiments, the hub 18 or line 17 leading to the hub 18 may include a visual indicator, for indicating the presence of an aspirated clot. The visual indicator may comprise a clot chamber having a transparent window. A filter may be provided in the clot chamber. Additional details of the clot capture filter and related features may be found in U.S. Provisional Patent Application Ser. No. 63/256,743, entitled Device for Clot Retrieval, filed Oct. 18, 2021, which is hereby expressly incorporated by reference in its entirety herein.

Any of the hubs or interventional devices disclosed herein may further comprise a sensor for detecting a parameter of interest such as a location or orientation of a distal tip or a status of the distal tip of an interventional device. The status of the distal tip may include, but not be limited to detection of an interaction between a vessel wall and the distal tip, detection of an interaction between a vessel wall and a clot, or detection of an unobstructed distal tip. The sensor, in some instances, may be positioned on a flexible body of an interventional device. The sensor may comprise a pressure sensor to capture arterial blood pressure waveform at the distal end of the catheter, or an optical sensor to determine captured clot or air bubbles. In some embodiments, the sensor may comprise one or more of: a force sensor, a positioning sensor, a temperature sensor, a torque sensor, a strain sensor, and/or an oxygen sensor. In some embodiments, the sensor may comprise a Fiber Bragg grating sensor. For example, a Fiber Bragg grating sensor (e.g., an optical fiber) may detect strain locally that can facilitate the detection and/or determination of force being applied.

Figure 1B:
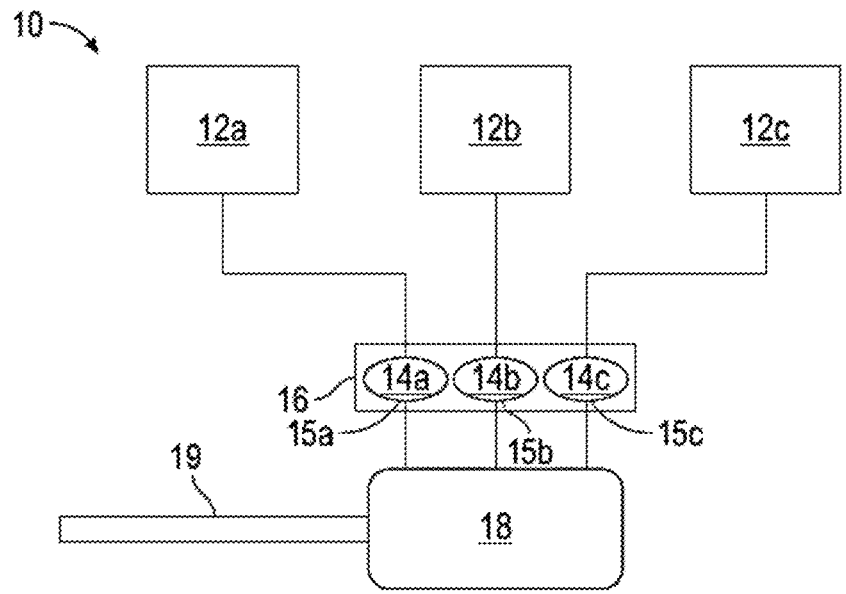
FIG. 1B illustrates one embodiment of a three channel fluidics management system.

FIG. 1B illustrates a schematic view of multi-channel fluidics management system 10 having a first source 12*a*, a second source 12*b*, and a sink 12*c*. The first source 12*a* is coupled to a valve 14*a*. The second source 12*b* is coupled to a valve 14*b*. The sink 12*c* is coupled to a valve 14*c*. The valves 14*a*, 14*b*, 14*c*, (hereinafter "valves 14*a*-14*c*") are part of a valve manifold 16. The valve manifold 16 is coupled to a hub 18. In certain embodiments, the valve manifold 16 is part of or directly connected to the hub 18. In other embodiments, the valve manifold 16 is positioned remotely from the hub 18 and is connected to the hub 18 via one or more fluid lines. In other embodiments, the valve manifold is part of or directly connected to hemostatic valve. In other embodiments, the valve manifold 16 is positioned remotely from the hemostatic valve and is connected to the hemostatic valve via one or more fluid lines. The valves 14*a*-14*c* can be opened and closed to selectively place the first fluid source 12*a*, the second fluid source 12*b*, and the sink 12*c* in communication with a lumen of the catheter 19. For example, the valve manifold 16 can include fluid ports (e.g., a first port 15*a* associated with valve 14*a*, a second fluid port 15*b* associated with valve 14*b*, and a third port 15*c* associated with valve 14c) that can be selectively placed in communication with the lumen of the catheter 19 or blocked from communication with the lumen of the catheter 19. For example, in some embodiments, one of the first port, second port, and third port can be placed into communication with the lumen of the catheter 19 while the other two ports are blocked from communication with the catheter 19.

In certain embodiments, the first source 12a can be a source of heparinized saline. The source 12b can be a source of contrast solution. In certain embodiments, one or more of the source 12a, the source 12b, and the source 12c can couple to a plurality of manifolds 16, each coupled to a unique interventional device 18. The valve manifold 16 as shown herein may be utilized in any of the systems described herein.

FIG. 2 illustrates a schematic view of a three channel fluidics system 100 for use with a fluidics management system 10 including a stack of four concentric interventional devices. The fluidics system 100 shown here includes a fluid management portion 102 and an interventional portion 104. In some embodiments, the interventional portion 104 may comprise a concentric catheter and guidewire stack configured for manual manipulation by the physician. In some embodiments, the interventional portion 104 may comprise a concentric catheter and guidewire stack configured for manipulation by a robotic drive system. In some embodiments, the interventional portion 104 includes a combination of both robotically driven medical devices and manually manipulated medical devices.

The components of fluid management portion 102 may be located outside of the sterile field or within the sterile field. In some embodiments, the fluid management portion 102 is located outside of the sterile field, but is coupled to the interventional portion 104, which is located within the sterile field, by flexible tubing and flexible electrical conductors.

The fluid management portion 102 may include at least two or three or more channels (e.g., parallel channels) of the type shown in FIG. 1A, each for a separate fluid source or fluid sink. In the illustrated embodiment, the fluid management portion 102 includes three channels that each are in communication with each of three catheters via corresponding catheter hubs. Two channels provide for the delivery of two separate fluids to each of the catheters, each at a controllable pressure, volume and delivery rate. The third channel provides for aspiration from each catheter into a sink.

Each of the two or more fluid channels may be primed by completely degassing and filling with a respective fluid in order to be ready for transport into the catheter and into the bodily lumen. In some embodiments, fluid lines, catheters, and/or catheter lumens can be simultaneously flushed and primed with a fluid (e.g., saline).

In some embodiments, the fluidics systems 100, 200 may be configured to backfill each sink connection to each catheter with fluid (e.g., saline) at procedure initialization and/or between fluidics step. This may provide a backfilled column of saline downstream of the sink connection, for example, to ensure that contrast injections flow to a distal tip of a particular catheter rather than to the sink. In some embodiments, the fluidics systems 100, 200 may be configured to provide a backfilled column of saline upstream of a saline valve at the hub, for example, to ensure that contrast injections flow to the distal tip of a particular catheter or the sink rather than through the saline valve.

As shown in FIG. 2, the fluid management portion 102 of the fluidics system 100 includes a first source 110a, a second source 110b, and a sink 112. The first source 110a and the second source 110b may each be configured to hold and distribute at least one fluid (e.g., saline, contrast, pharmaceuticals, blood, or other fluid, or combinations thereof). The sink 112 may be configured to receive waste fluid and/or waste product from a selected aspiration line leading to a corresponding catheter. Although two fluid sources and one fluid sink are shown, any number of fluid sources and/or fluid sinks is possible (e.g., one fluid source and one fluid sink, two fluid sources without a fluid sink, more than two fluid sources, etc.) corresponding to the fluid delivery and/or aspiration needs of a particular procedure.

A number of valves (and/or valve arrays) are provided to stop and start flow of each respective fluid to or through one or more fluid lines, and/or hubs within the fluid management portion 102 and/or interventional portion 104. In the illustrated implementation, a first valve array 116a (e.g., with three valves) is carried by a first manifold 118a, a second valve array 116b (e.g., with three valves) is carried by a second manifold 118b, and a third valve array 116c (e.g., with three valves) is carried by a third manifold 118c. Although valve arrays with three valves are shown, any number of valves are possible and may correspond to the number of catheters and/or fluid sources being used in the procedure or a subset of the interventional devices being used in the procedure. For example, in some situations, each valve array may include at least one valve, two valves, three valves, or four or more valves.

In some embodiments, each valve in a valve array (e.g., first valve array 116a) may be configured to independently control and/or adjust fluid resistance, flow rate, and/or pressure of fluid flowing through the valve and corresponding tubing. In some embodiments, each valve in a valve array can be independently and/or simultaneously adjusted for a respective catheter and/or for more than one catheter.

In the illustrated implementation, the fluidics channel is duplicated for each catheter and will therefore be described only in connection with the first source 110a below. A first outflow valve 117a is in communication with a first catheter 126 by a unique first fluid source line 120a. A second outflow valve 117b is in communication with a second catheter 128 by a unique second fluid source line 120b. A third outflow valve 117c is in communication with a third catheter 130 by a unique third fluid source line 120c. The fluid source lines 120a, 120b, 120c may be hereinafter referred to as the "fluid source lines 120a-120c." Each of the outflow valves 117a, 117b, 117c (hereinafter "outflow valves 117a-117c") is preferably electronically actuated in response to signals from the control system, between a fully closed, fully open, or partially open positions. Any of a variety of valve mechanisms may be utilized, such as a ball valve driven by a stepper motor, solenoid, a stopcock valve (e.g., a rotating stopcock valve), a rotary valve, or other drive mechanism known in the art. The drive mechanisms may provide for automated control and sequencing of the valves. For example, valve actuation may be achieved using stepper motors with in-built encoding to provide consistent switching and sequencing. The drive mechanisms may be controlled using motor controllers of a user control interface (for example, or a computer system). The control system may include modules that read values from sensors (e.g., flow, bubble, pressure, etc.) and display the values to control the behavior of the fluid system.

In some embodiments, a stopcock valve mechanism (e.g., a rotating stopcock valve) may be used in the manifolds described herein. For example, one or more stopcock valves may be placed adjacent to (or integrated into) a hub to avoid management of a column of fluid in particular tubing. Such tubing may be sterile disposable tubing that may offer a one-time use. Placing a manifold with stop cock valves near or integrated into the hub has the advantage of simplicity without the need to manage a column of fluid in the tubing. Having the manifold and stopcock valves away from the hub(s) may allow the manifold and the stopcock valves to both be used outside of a sterile field in conjunction with non-sterile equipment. Such a configuration may provide an advantage of preserving sterility of the components in the sterile field.

In some embodiments, the fluidics control system may further include a drive mechanism configured to adjust the sealing strength of the hemostatic valve in response to a signal from the control system, for example, from a processor of the control system. The control system (e.g., the processor) may be configured to increase the sealing strength of the hemostatic valve in response to the manipulation of the contrast control to introduce contrast into the catheter. The control system (e.g., the processor) may additionally be configured to decrease the sealing strength of the hemostatic valve in response to the manipulation of the contrast control to stop introducing contrast into the catheter. In some embodiments, the control system (e.g., the processor) may be configured to decrease the sealing strength of the hemostatic valve in response to a signal received to drive a catheter or guidewire through the hemostatic valve. Such a feature may provide the advantage of reducing friction between the hemostatic valve and a moving catheter shaft, for example.

In operation, all three outflow valves 117a-117c may be in an open configuration to flow saline through each of the three catheters. Forward flow (in the direction of arrow 122a) of saline may be driven by a pump 114 such as an electronically controlled peristaltic infusion pump or a rotary piston pump. Alternatively, any one of the valves may be open with the other two closed depending upon the desired performance. Alternatively or additionally, other sources of volume and/or pressure (for example, pump 114) can be deactivated or disconnected to prevent flow.

In the concentric catheter stack illustrated in FIG. 2, the first catheter 126 may be a 'large bore' access catheter having a diameter of at least about 0.075 or at least about 0.080 inches in diameter. The second catheter 128 may be an aspiration catheter having a diameter within the range of from about 0.060 to about 0.075 inches. The third catheter 130 may be a steerable catheter with a deflectable distal tip, having a diameter within the range of from about 0.025 to about 0.050 inches. The guidewire 132 may have a diameter within the range of from about 0.014 to about 0.020 inches. In one example, the first catheter may have a diameter of about 0.088 inches, the second catheter about 0.071 inches, the third catheter about 0.035 inches, and the guidewire may have a diameter of about 0.018 inches.

The available lumen in the first catheter 126 is the difference between the inner diameter (ID) of first catheter 126 and the outer diameter (OD) of second catheter 128. That may be different than the available lumen in the second catheter 128 (which may be the difference between the ID of second catheter 128 and the OD of third catheter 130), which may be different than the available lumen of the third catheter 130 (which may be the ID of the third catheter 130 or the difference between the ID of the third catheter 130 and the OD of the guidewire 132). In order to produce the same delivered infusion flow rate through each of the catheters, the control system may be configured to adjust the pump 114 and/or each of the outflow valves 117a-117c to compensate for differences in the effective cross sections of each respective flow-path in order to achieve the same delivered flow rate through each catheter. "Flow-path" as used herein is a broad term that can refer to a path for communication of fluid through one or more channels, lines, tubes, lumens, and other structures (e.g., portions of a valve, pump that communicates fluid) that can communicate blood, saline, contrast, vacuum, or other fluids and gasses. "Flow-path" can also refer to the structures themselves (i.e., one or more channels, lines, tubes, lumens, portions of a valve, pump that communicates fluid, and other structures that communicate fluid and can be considered synonymous and interchangeably with "channel" unless based on context or as explicitly stated. In an example, a saline subsystem can be described as having a saline flow-path that receives saline from a saline source and provides saline to downstream saline communication channels and to mounts/hubs, a contrast subsystem (e.g., for priming the contrast subsystem and downstream communication channels), and a vacuum subsystem (for priming a portion of the saline subsystem), referring to a plurality of branches of a saline flow-path formed by channels, tubes, etc. In an example, a contrast subsystem can be described as having a contrast flow-path that receives contrast from a contrast source and provides contrast to downstream contrast communication channels and to mounts/hubs, and to a vacuum subsystem (for priming the contrast subsystem), referring to one or more branches of a contrast subsystem formed by channels, tubes, etc. In another example, a vacuum subsystem can be described as having a vacuum flow-path that has vacuum from a vacuum source and provides vacuum to the saline and contrast subsystem (for priming the saline and contrast subsystem) and provides vacuum communication channels and to mounts/hubs, referring to one or more branches of a vacuum subsystem formed by channels, tubes, etc.

In one implementation of the invention, the catheters may be assembled into the concentric stack orientation illustrated in FIG. 2 prior to flushing the catheters to remove air by displacing it with a fluid such as saline. This is preferably accomplished in each fluid lumen, such as, for example, the annular lumen between the first catheter 126 and second catheter 128 and in between each of the additional concentric interventional devices in the stack orientation. Infusing saline under pressure may displace substantially all of the air but some small bubbles may remain, adhering, for example, to the inside wall of the first catheter 126, the outside wall of second catheter 128, or both.

While saline is being introduced under pressure into the proximal end of the annular lumen between two interventional devices (for example, the annular lumen between the first catheter 126 and the second catheter 128), the inner catheter may be moved with respect to the outer catheter (for example, the second catheter 128 may be moved with respect to the outer catheter), to disrupt the holding forces between the microbubbles and adjacent wall and allow the bubbles to be carried downstream and out through the distal opening of the lumen. The catheters may be moved axially, rotationally or both with respect to each other. In one implementation, a first catheter is moved reciprocally with respect to the adjacent catheter or guidewire, such as axially through a range of from about 0.5 inches to about 10 inches, or from about 1 inch to about 5 inches at a reciprocation frequency of no more than about 5 cycles per second or two cycles per second or less.

Reciprocation of adjacent catheters to disrupt microbubbles may be accomplished manually by grasping the corresponding catheter hubs and manually moving the catheters axially or rotationally with respect to each other while delivering pressurized saline. Alternatively, such as in a robotically driven system, a processor may be configured to robotically drive at least one hub of two adjacent catheters (for example, at least one of first catheter hub 124a and second catheter hub 124b) to achieve relative movement between the adjacent catheters thereby disrupting and expelling microbubbles, such as in response to user activation of a flush control.

The second source 110b is in fluid communication with the second manifold 118b, allowing fluid to flow as shown by arrow 122b to any number of valves (e.g., three) within the second valve array 116b. Forward flow (in the direction of arrow 122b) of contrast may be driven by a pump 136 such as a syringe pump, high pressure positive displacement pump, contrast injection pump, etc. Any one of the valves of the second valve array 116b may be open with the other two closed depending upon the desired performance. Alternatively or additionally, other sources of volume and/or pressure (for example, pump 136) can be deactivated or disconnected to prevent flow. A proximal opening of each fluid source line 121a, 121b, 121c (hereinafter "fluid source lines 121a-121c") may be coupled to a respective output port on the corresponding valve within the second valve array 116b. A distal opening of each of the fluid source lines 121a-121c may be coupled to each of the respective catheter hubs 124a, 124b, 124c (hereinafter "catheter hubs 124a-124c"), and thus to the corresponding first catheter 126, second catheter 128, and/or third catheter 130. The respective first catheter 126, second catheter 128, third catheter 130, and/or guidewire 132 may be guided into a patient (not shown). Additional hubs and/or catheters may be added to the fluidics system 100 and corresponding fluidics management system components (e.g., system 10) may be added to the fluidics system 100. In other embodiments, the fluidics system 100 may include less hubs and/or catheters, for example two hubs and/or catheters.

The sink 112 is coupled to a third manifold 118c to receive fluid from aspiration lines 123a, 123b, 123c (hereinafter "aspiration lines 123a-123c") in the direction shown by arrow 122c. The aspiration lines are configured to receive fluid and embolic material from one or two or all three respective catheters 126, 128 and 130 depending upon input from the physician into the control system. Once the physician has determined which catheter(s) will be placed into aspiration mode, and actuated the corresponding aspiration control(s) the corresponding valve(s) within the third valve array 116c may be opened to allow the fluid to flow through the corresponding catheter and into the sink 112, in response to the control system activating an aspiration pump 115. Any one of the valves of the third valve array 116c may be open with the other two closed depending upon the desired performance. Alternatively or additionally, other sources of volume and/or pressure (for example, aspiration pump 115) can be deactivated or disconnected to prevent flow.

In an example embodiment, the fluidics system 100 represents an aspiration configuration in which the first source 110a contains heparinized saline and the second source 110b contains contrast solution. The sink 112 in this example may contain waste blood/saline/embolic material that has been aspirated from a patient (not shown). Other additional sources and/or sinks may be used in combination with respective fluids.

Similarly, the contrast solution contained by the second source 110b may flow in the direction of arrow 122b and may flow into the second manifold 118b. In a given procedure, the physician may determine to inject contrast through any of the three catheters, and typically through the most distal catheter at a given injection time. In response to an inject contrast command, the control system will open the valve corresponding to the selected catheter and typically maintain the other two valves closed. In some embodiments, the physician may inject contrast concurrently into two or more catheters. In some embodiments, for example, while driving catheters or guidewires, contrast or aspiration may be applied concurrently.

In some embodiments, each valve (or valve array) can be housed inside or carried by a respective catheter hub 124a-124c. In some embodiments, each valve (or valve array) may be housed adjacent to or remote from a respective hub. In such examples, additional fluid lines (e.g., fluid source lines 120a-120c, fluid source lines 121a-121c, and aspiration lines 123a-123c) may be added between each manifold and a corresponding valve. The fluid source lines 120a-120c, 121a-121c, and the aspiration lines 123a-123c may be tubes. In some embodiments, any of the fluid source lines 120a-120c, 121a-121c, and the aspiration lines 123a-123c may be removably coupled to their respective hubs. Alternatively, any of the fluid source lines 120a-120c, 121a-121c, and aspiration lines 123a-123c may be inseparably connected to the hubs and removably coupled to other components of the fluid management portion 102, such as the valve arrays 116a, 116b, 116c (hereinafter "valve arrays 116a-116c") or manifolds 118a, 118b, 118c (hereinafter "manifolds 118a-118c").

In some embodiments, the fluidics system 100 may also include any number of pressure sensors, volume sensors, flow rate sensors, tubing sets, connectors, bubble sensors/detectors as will be discussed. In the illustrated implementation a pressure transducer 134a is in pressure sensing communication with the first catheter 126 by way of the first catheter hub 124a. Additional pressure transducers 134b, 134c may be placed in communication with their corresponding catheters as illustrated.

The control system may be configured to automatically adjust the various manifold valves, pumps and hemostatic valves (discussed below) in response to commands input by the physician. For example, the physician might input a command to infuse contrast through the third catheter 130. The control system may cause a series of responsive events to automatically occur. At least the saline valve (e.g., the third outflow valve 117c) would close. Outflow valves 117a, 117b may be closed or may remain open to provide positive pressure through the first and second catheters, to prevent backflow of contrast.

A control signal will be sent to a hemostasis valve in each of the first catheter hub 124a and second catheter hub 124b, to clamp down from a low pressure sliding fit to a high pressure clamp around the second catheter 128 and third catheter 130 respectively. This will prevent contrast from escaping proximally through the first catheter 126 and second catheter 128. A control signal will additionally be sent to a valve 119c to place the third catheter 130 in fluid communication with the second source 110b containing contrast solution.

If the space between the OD of the guidewire 132 and the ID of the third catheter 130 is insufficient to allow a desired contrast infusion rate, a further signal will be sent from the control system to the drive system controlling a guidewire hub 124d, to proximally retract the guidewire 132 from the third catheter 130 a distance sufficient to allow the flow of contrast through the third catheter 130. An additional control signal may be sent to a hemostasis valve carried by the third catheter hub 124c to clamp in a high pressure mode around a distal portion of the guidewire 132 or to clamp into a completely closed configuration if the guidewire 132 was fully retracted. A further control signal may be sent to an electronically activated high pressure pump 136 such as a syringe pump, high pressure positive displacement pump, contrast injection pump, etc., to deliver contrast solution through the third catheter 130.

If the physician initiates a command to perform aspiration through, for example, the first catheter 126, the control system may automatically transmit another series of control signals to execute the command. Signals will be sent to each of the hemostasis valves to move them from the high pressure configuration to the low pressure configuration in which there is less friction generated against a shaft of the catheter or guidewire. Such a configuration may permit relative movement of the various devices and proximal retraction of the second catheter 128 and third catheter 130 from first catheter 126 while still inhibiting proximal blood loss through the hemostasis valves. Signals will be sent to the drive system to proximally retract each of the catheter hubs 124a-124c and the guidewire hub 124d. Check valve 113c will be opened to place the first catheter 126 into fluid communication with the sink 112. A signal will be sent to actuate the aspiration pump 115, thereby aspirating blood and thrombus into the sink 112. In some embodiments, when performing aspiration of the first catheter 126, for example, communication between the first catheter 126 and the first source 110a and the second source 110b may be obstructed. For example, the corresponding valves of the valve arrays 116a, 116b may be closed to obstruct the manifolds 118a, 118b. Alternatively, the sources of volume and/or pressure (for example, pump 114 and pump 136) may be deactivated or disconnected.

All of the fluid lines between the first source 110a and second source 110b and each of the catheters, and all of the fluid lines between sink 112 and each of the catheters are preferably completely flushed free of any bubbles and filled with a fluid such as saline during system preparation before the procedure. This allows seamless transition between infusion, aspiration and manipulation of the catheters and guidewire without the need to disconnect and reconnect any fluid lines between the sources, sink and catheters, eliminating the risk of introducing air emboli during such exchanges.

It may also be desirable to enable confirmation of the absence of bubbles in any of the fluid lines. This may be accomplished placing bubble sensors in bubble sensing proximity to each of the fluid lines, such as in or upstream of each of the hubs, or at the manifolds. This may be particularly desirable in a telemedicine application, where the physician is at a remote workstation, and out of direct line of sight from the patient.

This may be accomplished using a non-contact ultrasonic flow sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow-path within the hub, or in a supply line leading to the hub.

For example, to detect the presence of air bubbles in the infusion line (that is formed of ultrasonically or optically transmissive material) the sensor may include a signal source on a first side of the flow-path and a receiver on a second side of the flow-path to measure transmission through the liquid passing through the tube to detect bubbles. Alternatively, a reflected ultrasound signal may be detected from the same side of the flow-path as the source due to the relatively high echogenicity of bubbles.

Alternatively, an optical sensor may be provided to detect changes in optical transmission or reflection due to the presence of bubbles, or to transmit a visual signal to a display at the remote workstation where the physician can visually observe the presence of a bubble moving through the tubing. In a system having a bubble detector, the control system can be configured to automatically shut down all fluid flow in response to the detection of a bubble to give personnel an opportunity to plan next steps.

In one implementation, a bubble removal system is automatically activated upon detection of in line bubbles. A processor may be configured to activate a valve positioned in the flow-path downstream of the bubble detector, upon the detection of bubbles. The valve diverts a column of fluid containing the detected bubble out of the flow-path leading to the patient and instead into a bypass flow-path or reservoir. Once bubbles are no longer detected in the flow-path and after the volume of fluid in the flow-path between the detector and the valve has passed through the valve, the valve may be activated to reconnect the source of fluid with the patient through the flow-path. In some embodiments, the flow-path may include any number of bubble filters and/or traps to remove bubbles from the flow-path.

The interventional portion 104 may include a drive table that is configured to receive (e.g., be coupled to) any number of hubs (e.g., the first catheter hub 124a, the second catheter hub 124b, the third catheter hub 124c, the guidewire hub 124d, etc.). Additional details of the hubs, drive table and related systems are found in U.S. patent application Ser. No. 17/816,669, entitled Method of Supra-Aortic Access for a Neurovascular Procedure, filed Aug. 1, 2022, which is hereby expressly incorporated by reference in its entirety herein. Each hub is configured to be coupled to a catheter, or guidewire, one or more fluidics lines, one or more electrical lines, one or more controls, and/or one or more displays. For example, a drive table may be positioned over or alongside the patient, and configured to support axial advancement, retraction, and in some cases rotation and/or lateral deflection of two or three or more different (e.g., concentrically or side by side oriented) devices (e.g., catheters, guidewires, etc.).

The drive system independently drives movement of each hub independently in a proximal or distal direction across the surface of the table to move the corresponding interventional device (e.g., the first catheter 126, the second catheter 128, the third catheter 130, and/or guidewire 132) proximally or distally within the patient's vasculature.

The respective first catheter 126, second catheter 128, third catheter 130, and/or guidewire 132 may be guided into a bodily lumen (not shown) as a single concentric catheter stack, in response to movement of the respective catheter hubs 124a-124c as discussed elsewhere herein. The fluidics system 100 may also include a guidewire hub 124d for controlling the guidewire 132, which may also be introduced into a bodily lumen along with one or more of first catheter 126, second catheter 128, and/or third catheter 130.

In some embodiments, a driven magnet is provided on each hub. Each driven magnet is configured to cooperate with a drive magnet associated with the table such that the driven magnet(s) move in response to movement of the drive magnet(s). In such examples, the drive magnet(s) may be axially movably carried by the support table.

Because multiple sources and/or sinks are configured to each be coupled (and remain coupled) to each catheter hub (e.g., the first catheter hub 124a, the second catheter hub 124*b*, and the third catheter hub 124*c*), the fluidics system 100 provides the advantage of enabling faster procedures than conventional fluidics systems that utilize manual removal, addition, and/or switching of fluids, catheters, hubs, and the like during the procedure. For example, the fluidics system 100 enables each fluid line/catheter hub to be connected to each source fluid and/or sink before beginning a procedure. When the interventionalist (or other medical practitioner) performing the procedure is ready to use a particular source fluid or sink, the fluidics system 100 is already configured and ready to allow use of the particular source fluid or sink without having to switch between different fluid lines for particular catheters. In some embodiments, the fluidics system 100 may be used to provide a method of treatment in which fluid sources need not be connected to and/or disconnected from a medical device more than once during a procedure.

Thus, the interventionalist can inject any of the fluids contained in fluid sources (e.g., the first source 110*a* and the second source 110*b*) and/or collect aspirate from any of the catheters 126, 128, and/or 130 at any point during the procedure because each catheter hub 124*a*-124*c* is provided access to all fluid lines at all times.

Because the multiple sources that are indicated for a particular procedure are preconfigured to be connected to each catheter/catheter hub, an interventionalist (or other medical practitioner) may be assured that there is no repetitive connecting and disconnecting of syringes or other source fluid containers, fluid lines, etc. during the procedure. This assurance removes the possibility of introducing bubbles into the catheter flow during the procedure because no connecting or disconnecting of fluid sources are needed with the use of the fluidics system 100. Instead, each fluid source and sink are connected and tested before the procedure and are not removed until after the procedure is completed. In some embodiments, the constant connection of fluid sources and sinks to catheter hubs associated with operation of the fluidics system 100 removes the variability and risk in remote procedures where the interventionalist is in a control room rather than the procedure room.

The valves within valve arrays 116*a*-116*c* of the fluidics system 100 are depicted at the respective manifolds 118*a*-118*c*. In such a configuration the valves are near the respective source and/or sinks with about two meters to about three meters (e.g., about six to about ten feet) of fluid line between the valves of valve arrays 116*a*-116*c* and the respective catheter hubs 124*a*-124*c*. In some embodiments, the valves of valve arrays 116*a*-116*c* may instead be located at the sources/sinks (e.g., first source 110*a*, second source 110*b*, and/or sink 112). In some embodiments, the valve arrays 116*a*-116*c* are coupled to the fluid lines at a location between the source/sink and the hubs. In some embodiments, one or more of the valve arrays 116*a*-116*c* may be located at the catheter hubs 124*a*-124*c*. In some embodiments, valves that are located at or near the hubs may be disposable valves. Other components of the fluidics systems 100, 200 may also be disposable and/or re-processable for reuse.

In some embodiments, the fluidics system 200 may additionally include check valves 113*a*, 113*b*, 113*c*, 113*d*, 113*e*, 113*f*, 113*g*, 113*h*, 113*i* (hereinafter "check valves 113*a*-113*i*") between the valve arrays 116*a*-116*c* and the respective catheter hubs 124*a*-124*c*. The check valves 113*a*, 113*b*, 113*c* can be part of a valve manifold (for example, such as the valve manifold 16 of FIG. 1B) that is part of or coupled, directly or indirectly, to the first catheter hub 124*a*. The check valves 113*d*-113*f* can be part of a valve manifold (for example, such as the valve manifold 16 of FIG. 1B) that is part of or coupled, directly or indirectly, to the catheter hub 124*b*. The check valves 113*g*-113*i* can be part of a valve manifold (for example, such as the valve manifold 16 of FIG. 1B) that is part of or coupled, directly or indirectly, to the third catheter hub 124*c*. The check valves 113*a*-113*i* may be one-way check valves. As shown in FIG. 2, the one-way check valves 113*a*-113*i* can allow flow in the direction in which their respective arrows are pointing.

Figure 3:
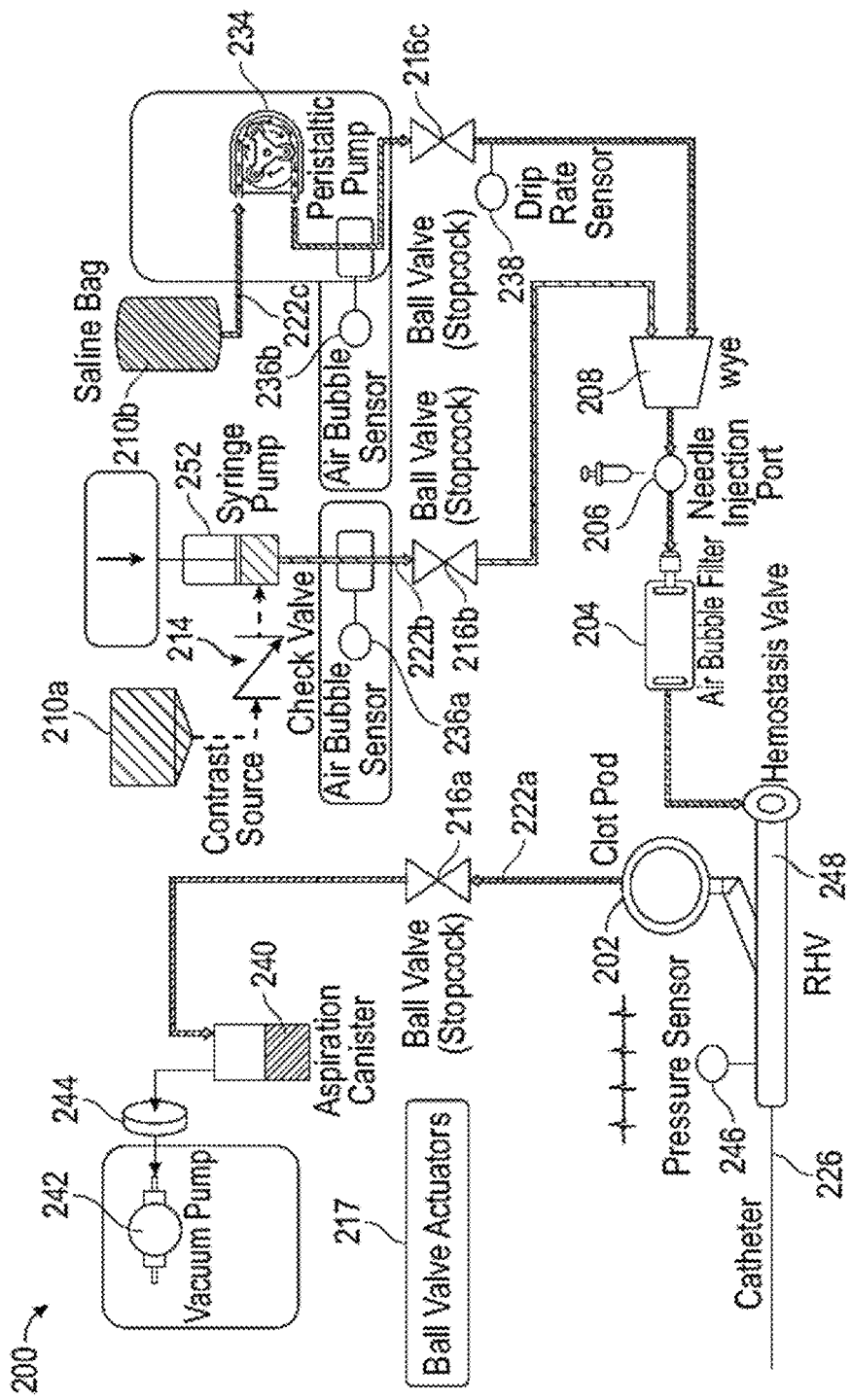
FIG. 3 shows another schematic of a fluidics system.

Each of the catheter hubs 124*a*-124*c* may be provided with a hemostasis valve to accommodate introduction of another device therethrough, as illustrated in FIG. 3. The hemostasis valve includes a variable diameter aperture such as an aperture through a resilient gasket.

The gasket may be actuatable between a first, fully open state; a second partially open state for sealing against low pressure fluid injections from the first fluid source or the second fluid source through a first port (as described herein), for permitting fluid to flow through the first port to the sink, while allowing advancing or retracting an interventional device; and a third tightly closed state for resisting backflow of high pressure fluid (e.g., contrast media) injections from the second fluid source through the first port or for permitting fluid flow through the first port to the sink. The gasket may be manually actuatable or automatically actuatable, for example based on a user input corresponding to manipulation of one or more of the interventional devices of the system.

FIG. 3 illustrates another embodiment of a fluidics system 200 for use with a fluidics management system. In general, the fluidics system 200 includes two or more fluid channels that feed one or more fluid lines configured to interface with a rotating hemostatic valve. The two or more fluid channels may receive fluids from fluid sources with any number of fluid materials. The two or more fluid channels may allow different fluid materials provided by different fluid sources (of various volumes and/or under different pressures) to flow into or from a bodily lumen. Each of the two or more fluid channels may be primed with a respective fluid in order to be ready for transport into the single fluid line and into the body. Valves and/or valve arrays may be employed to switch between usage of the two or more fluid channels.

As shown in FIG. 3, the fluidics system 200 may include a sterile field clot capture container, vacuum chamber, and/or control 202, within the sterile field. The vacuum chamber may have a clot filter with a window for visualizing trapped clot, and a valved vent which when momentarily opened permits entrance of air to allow direct visualization of the clot through the window. To permit inspection by a remote physician, a CCD or CMOS sensor may be mounted such that the upstream surface of the clot filter is within the sensor field of view. This permits viewing the contents of the filter on a remote monitor. Air intake to clear the optical path from the window to the filter may be controlled remotely using an electronically actuated valve.

An air bubble filter 204 may be provided in line between a needle injection port 206 and catheter 226. The fluidics system 200 further includes a line branch point 208 (e.g., a wye) in fluid communication with a first source 210*a* and a second source 210*b*. The line branch point 208 may include luer lock connectors or wye connector that interfaces with multiple fluid sources.

The fluidics system 200 may also include a pump 234 such as a peristaltic pump or rotary piston pump that drives fluid under pressure from the second source 210*b* to the line branch point 208 in the direction of arrow 222*c*.

An air bubble sensor may be provided on an upstream or downstream side of the pump 234. The air bubble sensors 236a, 236b may be non-contact ultrasonic flow sensors that measure an intensity and doppler shift of a reflected ultrasound through a sidewall of fluid tubing to detect bubbles and measure fluid flow rates or fluid levels as has been discussed. In some embodiments, the air bubble sensor 236a may also be a pressure sensor or a separate pressure sensor may be provided.

A third valve 216c such as a ball valve or rotary valve can selectively open or close fluid communication between the second source 210b and the catheter 226. A flow rate detector such as a drip rate sensor 238 enables determination and display of the flow rate from second source 210b.

Fluid flow from the first source 210a is directed through a one way check valve 214 and on to a high pressure pump 252, which may be a syringe pump, high pressure positive displacement pump, contrast injection pump, etc. High pressure fluid (e.g., contrast solution) is directed through an air bubble sensor 236a and on to the line branch point 208 through the second valve 216b. Arrows 222b indicate the direction of fluid flow.

Resistance to fluid flow through different catheters in a concentric catheter stack differs based upon the available lumen cross sectional area. For example, resistance measurements within an inner catheter with a fully open lumen (e.g., with guidewire removed) may be lower than resistance measurements within an outer catheter having a second catheter (or a guidewire) extending therethrough. Therefore, when performing saline flushing steps, the fluidics system 200 may be configured to ensure a similar flow rate or a procedure appropriate flow rate through each inner and outer catheter to avoid clotting or other issues within the catheters. To do so, a valve may be adjusted for each catheter to ensure the flow rate remains constant amongst all catheters during saline flushing. The fluidics system 200 may determine such flow rates in real time based on flow rate sensors, and the control system may be configured to automatically adjust valve settings and/or pump parameters to maintain the desired flow rate through each catheter.

In some embodiments, fluid resistance may be altered by adjusting an insertion length of each shaft into its concentrically adjacent lumen. As described herein, fluid resistance within a lumen may be greater when there is a reduction in cross sectional luminal area for flow, for example, when a second catheter (or a guidewire) extends into the lumen. The amount of fluid resistance can be affected by the length of the cross sectional narrowing, for example, due to placement of the second catheter (or guidewire) within the lumen. A second catheter (or guidewire) extending partially through the lumen of a first catheter will provide a smaller length of cross-sectional narrowing, and accordingly may result in a lower fluid resistance within the lumen of the first catheter, than if the second catheter (or guidewire) were to extend entirely through the lumen of the first catheter. Thus, fluid resistance can be lowered by partially retracting a depth of insertion of a second catheter (or guidewire) into the lumen through which fluid is to be injected.

The fluidics system 200 further includes an aspiration canister 240 coupled to an upstream side of filter 244. A downstream side of the filter 244 is coupled to a vacuum pump 242. The aspiration canister 240 is connected to a first valve 216a, which may be in communication with a sterile field clot capture container, vacuum chamber, and/or control 202 which has been discussed elsewhere herein. Arrow of the fluid lines 222a indicates the direction of fluid flow.

An optional pressure sensor 246 is depicted on a proximal end of a catheter 226 or hub coupled to a hemostatic valve, such as a rotating hemostatic valve (RHV) 248. In other embodiments, different types of hemostatic valves (e.g., non-rotating hemostatic valves) may be used alternatively to the RHV 248.

In this example, the RHV 248 is connected to two different fluid sources. The RHV 248 may be carried by and at least partially disposed in a hub (e.g., the first catheter hub 124a of FIG. 2). The RHV 248 may comprise a first fluid source connection, a second fluid source connection, and a sink connection. For example, the first connection, the second connection, and the third connection may comprise respective valves (e.g., valves 216a, 216b, 216c) connected via fluid lines to RHV 248. In some embodiments, the connection points may be formed as part of the RHV 248 itself and fluid lines may connect directly to the connection points at proximal ends of the fluid lines and connect to sources and/or sinks at the respective distal ends of the fluid lines. In certain embodiments, the valves 216a, 216b, 216c may be arranged in a valve manifold or a valve manifold cassette. In certain embodiments, the pump 234 may also be arranged in the valve manifold or valve manifold cassette. In certain embodiments, any of the valves 216a, 216b, 216c can be a ball valve, a stopcock valve, a rotary valve, a solenoid valve, or any other suitable valve. Any of the valves 216a, 216b, 216c can be controlled by one or more actuators 217.

The RHV 248 may be configured to enable a catheter or other instrument to be introduced into the body of a living being while precluding unintended back bleeding. In some embodiments, each RHV described herein may be configured with at least a fully closed configuration, a low sealing force state in which devices may be advanced therethrough without leaking, and a high sealing force state (e.g., mode) which prevents escape of fluids under high pressure and may prevent axial movement of devices therethrough.

The RHV 248 is configured to be concurrently and fluidly connected to a first fluid source (e.g., the first source 210a) via the first fluid source connection (e.g., the second valve 216b). The RHV 248 is further configured to be concurrently and fluidly connected to a second fluid source (e.g., the second source 210b) via the second fluid source connection (e.g., the third valve 216c). In addition, the RHV 248 is further configured to be concurrently and fluidly connected to the sink (e.g., aspiration canister 240) via the sink connection (e.g., the first valve 216a).

In operation, the fluidics system 200 is configured to automatically switch between introducing fluid into a lumen of the elongate body (e.g., catheter 226) through the RHV 248 from the first fluid source (e.g., the first source 210a) or from the second fluid source (e.g., the second source 210b) or to permit fluid removal from the lumen to be collected in the sink (e.g., aspiration canister 240).

In some embodiments, the optional pressure sensor 246 is located at either the upstream side or downstream side of the RHV 248 (as shown in FIG. 3). In some embodiments, the optional pressure sensor 246 is located in the catheter (e.g., in a sidewall of the catheter) to measure arterial pressure at the catheter distal end. The pressure may be assessed by the interventionalist to verify that the catheter is not misaligned within the vessel and/or the thrombus.

For example, if the catheter is misaligned against a vessel wall, then the detected pressure (e.g., waveform) may be blunted. Such a detection may be provided to an algorithm performed by a processor associated with the fluidics system 200, for example, to determine the patency of the lumen of the catheter of the patency of the catheter distal tip. Such a pressure sensor and algorithm may provide an improved alternative to conventional determinations of pressure where manual operation of fluidics is occurring and an interventionalist may retract (e.g., pull back) on a syringe coupled to the catheter to verify that blood capture occurs and to assess tactile feedback of the catheter.

Such blood capture and tactile feedback assessments may indicate patency of the lumen or distal tip before an injection or aspiration is performed. However, the pressure sensor 246 may provide for an automated and improved way to assess lumen or distal tip patency. That is, the addition of a pressure sensor 246 (e.g., a blood pressure sensor) on the proximal end of a catheter may capture an arterial pressure waveform. The waveform can be used to determine whether the catheter distal tip is pressed against a vessel wall, the catheter tip is pressed against a thrombus, the catheter tip has full patency, or the catheter lumen is in a clogged or fully patent state, without having direct visual or tactile feedback. In some embodiments, the waveform can be used to determine a state of engagement of the catheter distal tip against the clot and/or a consistency of the clot.

In some embodiments, the fluidics systems (e.g., fluidics system 100, fluidics system 200) described herein include a hemostasis valve (e.g., RHV 248) that includes a first three-way connector having a first fluid source connection (e.g., first valve array 116a, or second valve 216b), a second fluid source connection (e.g., second valve array 116b, or third valve 216c) and a sink connection (e.g., the first valve 216a).

In some embodiments, the fluidics systems described herein (e.g., fluidics system 100, fluidics system 200) utilize a first fluid source that comprises one of saline, heparinized saline, or a pharmaceutical. In some embodiments, the second fluid source (e.g., second source 110b, 210b) comprises contrast.

The fluidics systems 100, 200 may further include a second hemostasis valve that is in communication with and may be at least partially disposed in the second hub (e.g., the second catheter hub 124b). The second hemostasis valve may include a third fluid source connection (e.g., second valve array 116b), a fourth fluid source connection (second valve array 116b), and a second sink connection (e.g., third valve array 116c). In this example, the first manifold 118a may include a second output line that is configured to connect to a third fluid source connection (not shown).

Figure 4:
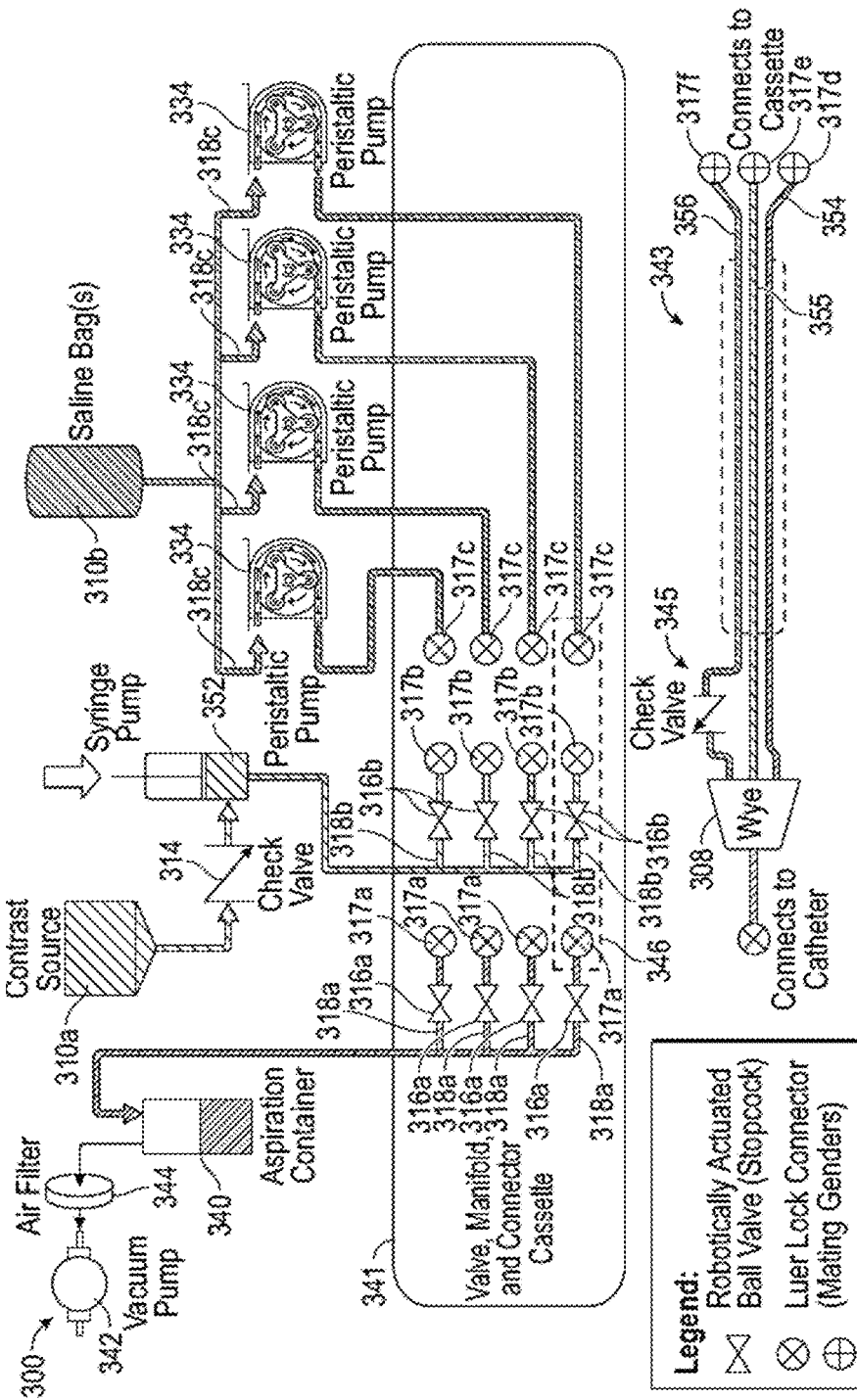
FIG. 4 shows another schematic of a fluidics system.

FIG. 4 illustrates another embodiment of a fluidics system 300 for use with a fluidics management system. In general, the fluidics system 300 includes a cassette that can couple a plurality of fluid sources and/or sinks to a plurality of interventional devices. A plurality of fluid lines may extend between a source or sink and the cassette for coupling to different interventional devices. For other sources and sinks, a single fluid line may extend between the source or sink and the cassette and may split within the cassette to connect to different interventional devices. In certain embodiments, the cassette can include connection arrays formed of connections from a plurality of fluid sources and/or sinks for coupling to a single interventional device (for example, in a row or column). Each connection array can couple to a tubing set having a tube corresponding to each connection in the connection array.

The cassette 341 may be a self-contained unit comprising a housing having a plurality of valves, tubing and connectors as described below. A first connector array comprises a plurality of releasable connectors such as luer connectors, for placing the cassette in fluid communication with complementary connectors in fluid communication with sources of aspiration and at least one or two or more fluids. A second connector array is configured for releasable connection to a tubing set configured to extend between the cassette and at least one or two or three interventional devices.

The cassette 341 thus forms a bridge module that when assembled resides between the various fluid and vacuum sources, and the corresponding interventional devices. The cassette 341 may be configured for a single use, or may be re-sterilizable and reusable.

As shown in FIG. 4, the fluidics system 300 may include a first fluid source 310a and a second fluid source 310b. Fluid flow from the first fluid source 310a is directed through a one way check valve 314 and on to a high pressure pump 352, which may be a syringe pump, high pressure positive displacement pump, contrast injection pump, etc. The fluid from the first fluid source 310a may be a contrast solution which is preferably injected under high pressure.

Fluid flow from the syringe pump is directed into a cassette 341, which may include a plurality of valves, manifolds, and/or connectors. Within the cassette 341, the fluid flow may split along a plurality of branches 318b to a plurality of connectors 317b (for example, four connectors 317b as shown in FIG. 4.) for coupling with different interventional devices. The cassette may include a valve 316b (e.g., a ball valve) with each branch 318b upstream of the connector 317b. In certain embodiments, any of the unique valves 316a, 316b can be a ball valve, a stopcock valve, a rotary valve, a solenoid valve, or any other suitable valve.

Fluid flow from the second fluid source 310b may be directed into a plurality of branches 318c to a plurality of pumps 334 (for example, four pumps 334 as shown in FIG. 4), such as peristaltic pumps or rotary piston pumps. Each of the plurality of pumps 334 can drive the fluid (for example, saline) under pressure from the second fluid source 310b to a unique connector 317c for each interventional device within the cassette 341.

The system further includes an aspiration canister 340 in communication with an upstream side of a filter 344. A downstream side of the filter 344 is in communication with a vacuum pump 342. The aspiration canister receives fluid from the cassette 341 which includes a plurality of connectors 317a each being configured to couple to a unique interventional device. A unique valve 316a (at least two, and four in the illustrated example) may be positioned upstream of each of the plurality of connectors 317a. Each unique valve 316a may be positioned along a branch 318a.

In certain embodiments, one or more connector arrays 346 may be arranged, each connector array 346 configured to couple an interventional device. For example, a connector array 346 is indicated by dashed lines in FIG. 4. As shown in FIG. 4, the connector array 346 can include one of the plurality of connectors 317a, one of the plurality of connectors 317b, and a connector 317c. As shown in FIG. 4, the connector array 346 may be organized with all connectors facing in the same direction on a common plane, such as a linear row.

The connector array 346 can releasably couple to a tubing set 343 including an aspiration tube 354, a first fluid tube 355, and a second fluid tube 356. In some embodiments, the plurality of connectors 317a, 317b, and 317b can be luer lock connectors. The aspiration tube 354 can couple to one of a plurality of connector 317a of the connector array 346 by way of a complementary connector 317d for aspiration from the interventional device to the aspiration container. The first fluid tube 355 can couple to one or a plurality of connectors 317b of the connector array 346 by way of a complementary connector 317e to provide fluid flow from the first fluid source 310a to the interventional device. The second fluid tube 356 can couple to the connector 317c of the connector array 346 by way of a complementary connector 317f to provide fluid flow from the second fluid source 310b to the interventional device. The tubes 354, 355, 356 may be joined together over a majority of their lengths. The tubes 354, 355, 356 can each have a length of at least about three or four feet, and in certain embodiments between about 6 feet and about 8 feet.

As shown in FIG. 4, the tubing set 343 includes a line branch point 308 (e.g., a two to one or a three to one wye) that can provide fluid communication between the interventional device and the aspiration tube 354, the first fluid tube 355, and second fluid tube 356. The line branch point 308 may include luer lock connectors or wye connectors that interface with complementary connectors on the tubing set. In certain embodiments, a one way valve 345 may be positioned upstream of the line branch point 308 and downstream of the cassette 341 along the flow-path of the second fluid.

In certain embodiments, the fluidics system 300 (or other systems described herein) can direct the flow of the second fluid (for example, saline) using two different flow modes. In a low flow drip mode, a flow rate of about 1-2 drips per second or 3-6 mL/min may be provided, for example, by the plurality of pumps 334. In some embodiments, a low flow mode rate of 1-8 mL/min may be provided. Each catheter coupled to the system may experience a different fluid resistance as described herein.

The pumps, for example the plurality of pumps 334, can be operated to provide the same flow rate in each catheter. In certain embodiments the fluid pressure within the catheter can be at least about 330 mmHg or 6.5 psi. This pressure may be enough to overcome arterial pressure while delivering the desired drip rate. In certain embodiments, the pressure within the catheter can be greater than 330 mmHg. In certain embodiments, the delivered fluid volume can be at least about 1 liter over the length of a procedure. In some embodiments, the fluid volume can be up to 2 liters.

In a high flow flush mode, all of the fluid lines may be flushed to remove air. The flow rate can be between 100-1000 mL/min. The fluid pressure may be between 5-10 psi. The volume delivered can be between 0.5-1 liters per procedure. Volume may depend on tubing length and diameter. In some embodiments, the high flush flow rate is at least about 20 times and in some cases between 30 to 150 times the low flow drip mode flow rate.

In certain embodiments, the first fluid (for example, contrast solution) can be provided at a flow rate of between 3-8 L/s (for example, about 4 mL/s), for example, by the pump 352. In certain embodiments, the flow rate can be up to about 8 mL/s. In other embodiments, the flow rate can be up to about 20 mL/s. In certain embodiments, the first fluid can be provided with a pressure of about 400 psi for a flow rate of about 4 mL/s. The amount of pressure needed may depend on flow rate and flow restriction of the fluid path. The pressure may increase proportionally with the flow rate for higher flow rates. In certain embodiments, the pressure may be up to 1200 psi.

In certain embodiments, the high pressure pump, such as pump 352, can provide a delivered volume of between 5-15 mL per high pressure injection. In certain embodiments, the pump can provide the 5-15 mL per high pressure injection in increments of about 1 mL per puff. In certain embodiments, the second fluid source can provide a total volume of about 200 mL per procedure. In certain embodiments, the syringe pump is sized to hold at least about 150 mL or 200 mL so as to provide uninterrupted flow throughout the procedure without the need to add additional contrast solution. In other embodiments, the second fluid source can provide a total volume of between 150-250 mL per procedure.

In certain embodiments, the flow rate may vary depending upon the anatomical location at the distal end of the catheter. For example, within the aortic arch, the flow rate may be about 20 mL/s. A total delivered volume of about 25 mL may be infused in the aortic arch. Within the common carotid artery, the flow rate may be about 20 mL/s. A total delivered volume of 12 mL may be infused in the common carotid artery. Within the subclavian artery, the flow rate may be about 6 mL/s. A total delivered volume of about 15 mL may be infused in the subclavian artery. Within the internal carotid artery, the flow rate may be about 6 mL/s. A total delivered volume of about 8 mL may be infused in the internal carotid artery. Within the external carotid artery, the flow rate may be about 3 mL/s. A total delivered volume of about 6 mL may be infused in the external carotid artery. Within the vertebral artery, the flow rate may be about 6 mL/s. A total delivered volume of 8 mL may be infused in the vertebral artery.

In certain embodiments, a motor may be provided to drive the high pressure pump, such as pump 352, which can be controlled with a position and velocity control loop using a potentiometer as a measurement to close the loop. In certain embodiments, current control may be applied to provide approximate pressure limiting. In certain embodiments, the second fluid can be a contrast solution such as Omnipaque 300, Omnipaque 350, or Visipaque 320.

In certain embodiments, a vacuum pump, such as vacuum pump 342, can provide a pressure of about −29.5 inHg or up to −29.5 inHg (−999 mbar). In certain embodiments, tubing used for aspiration can have an inner diameter of 0.11 inches (about 2.8 mm). In certain embodiments, the volume of the aspiration canister 340 can be at least about 0.5 L. In certain embodiments, the volume of the aspiration container can include about 0.5 L for blood and additional volume for a saline flush. In certain embodiments, the aspiration container can have a volume between 0.25-0.75 L. In certain embodiments, the vacuum pump can be configured to operate to additionally provide a low pressure/flow setting to assist a flushing process as it may be desirable that an aspiration line is full of saline at all times (except when aspirating a clot). In certain embodiments, a separate pump may be provided for the low pressure/flow setting.

Figure 5A:
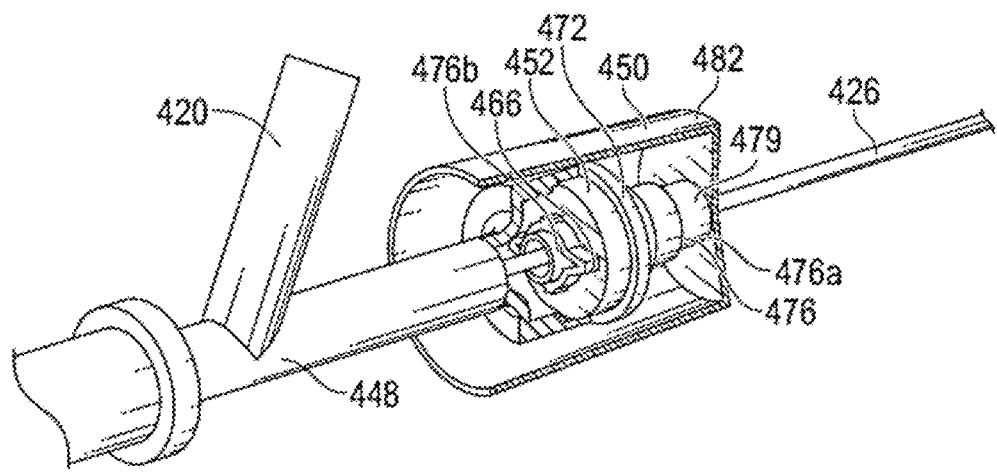
FIGS. 5A and 5B illustrate cross-sectional views of an exemplary rotating hemostatic valve with a gasket configured in an open position.
Figure 5B:
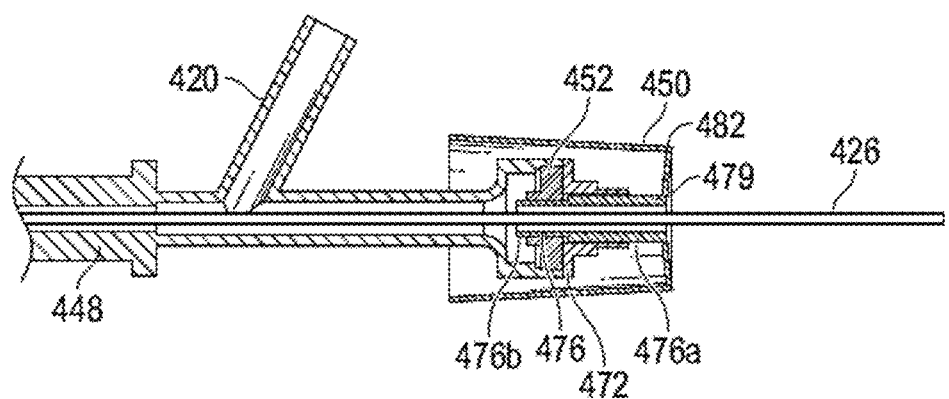

FIGS. 5A and 5B illustrate perspective and cross-sectional views of an example rotating hemostatic valve (RHV) 448 with a dual membrane gasket configured in an open position. That is, both a distal and a proximal membrane are provided with a slit, and a support tube is positioned through both membranes to hold the slits in an open, constrained configuration (e.g., see FIG. 8B). The RHV 448 may represent the RHV 248 in the fluidics system 200, or a hemostasis valve in any of the catheter hubs 124a-124c may be configured for use with a manual procedure and fluidics system, a robotic procedure and fluidics system, or a combination thereof.

The RHV 448 includes a side port 420, a dual membrane gasket 452, and a plunger 476 having a housing 482 and a support tube 479 configured to reversibly advance distally through the gasket to maintain patency therethrough. The RHV 448 is coupled to a proximal end of a first interventional device and is adapted to receive a second interventional device (e.g., a catheter 426) therethrough. The plunger includes a proximal end 476a and a distal end 476b.

The second interventional device is disposed in a lumen defined by the first interventional device. As shown, the catheter 426 is advanced through the support tube 479 of the RHV 448. A proximal end 450 of the RHV 448 includes a housing coupled to the plunger 476. The gasket 452 is configured to be coupled to a gasket housing 472 that surrounds a circumference of the plunger.

The gasket 452 may be actuatable between a first fully open state, a second low sealing force state for sealing around a catheter but permitting sliding movement of the catheter, a third state for sealing around a catheter for high pressure management and a fourth, completely closed state in the absence of any secondary devices extending therethrough.

The first open state represents a back bleed position or an interventional device loading or unloading position that configures the RHV 448 to allow the gasket 452 to be fully open. The second partially open state represents a position that configures the RHV 448 to allow the gasket 452 to close around the catheter 426 within the RHV 448 with sufficient sealing that blood or saline solution pumped at relatively low pressure does not leak while the catheter 426 is advanced or retracted through the RHV 448 with low resistance. The third state represents a tightly scaled configuration for enabling high pressure fluid (contrast) injection from a fluid source. In certain embodiments, a control system can be configured to determine a sealing force of the hemostasis valve around the catheter 426 (for example, in response to a human input). The control system can be configured to change the sealing force if it is determined that the sealing force is too high or too low. For example, the control system can increase the sealing force if the sealing force is too low.

As shown in FIG. 5B, the gasket 452 is restrained by the support tube in the first open state. The first open state ensures that the gasket 452 is configured in a back bleed position or an interventional device loading or unloading position. The open position configures the RHV 448 to open the gasket 452 by moving a tubular support portion of the plunger 476 through the gasket 452 such that the tubular support forcibly opens and restrains the gasket providing an open central lumen. The movement may allow arterial blood pressure to push blood proximally through the catheter 426 until the blood is viewable at the RHV 448. Moving the gasket into the open position, which enables back bleeding, allows visual and/or tactile confirmation that there are no air bubbles in the RHV 448 and/or that the distal tip of the catheter is not against a vessel wall and/or that a lumen defined by the catheter is unobstructed.

In some embodiments, the RHV 448 may include a side port 420. The side port 420 may be releasably connected to a three-way connector that is configured to be fluidly connected to a first fluid source (e.g., first source 110a), a second fluid source (e.g., second source 110b), and a sink (e.g., sink 112). Alternatively, or additionally, the RHV 448 may further include one or more additional ports for connection with fluid sources and/or sinks. See, for example, FIG. 11 which will be described in further detail elsewhere herein.

Figure 6A:
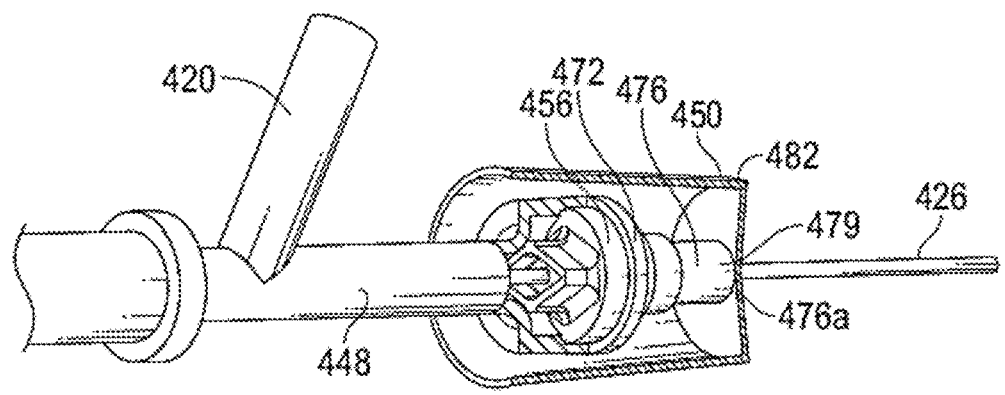
FIGS. 6A and 6B illustrate cross-sectional views of a rotating hemostatic valve with a gasket configured in a low pressure position.
Figure 6B:
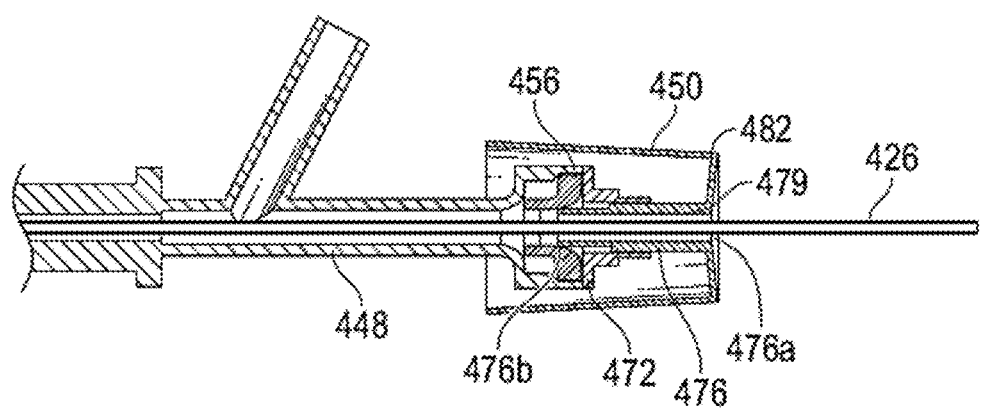

FIGS. 6A and 6B illustrate cross-sectional and zoomed in cross-sectional views of a rotating hemostatic valve with a gasket (e.g., gasket 456) configured in a partially open or low scaling pressure position. In this position, the distal end 476b of plunger 476 has been retracted proximally such that the distal slit 464 of the gasket 456 (see FIG. 8B) is in sliding contact with catheter 426 but the proximal slit 468, 470 (see FIG. 8C) remain restrained in the open configuration by the support tube. The low pressure state of the gasket 456 enables saline (e.g., from second source 110b) to be burst injected through the RHV 448 side port 420 at a pressure of up to about 276 kPa (i.e., about 40 psi).

As shown in FIG. 6B, the gasket 456 is in the partially open state with the plunger 476 advanced partially into the gasket 456. This position represents a low pressure position in which blood or saline solution does not leak while the catheter 426 is advanced or retracted through the RHV 448 with low resistance. The second partially open state configures the RHV 448 for receiving low pressure fluid injections from a first fluid source (e.g., first source 110a) or a second fluid source (e.g., second source 110b) through a first port or for permitting fluid to flow through the first port to a sink (e.g., sink 112).

Figure 7A:
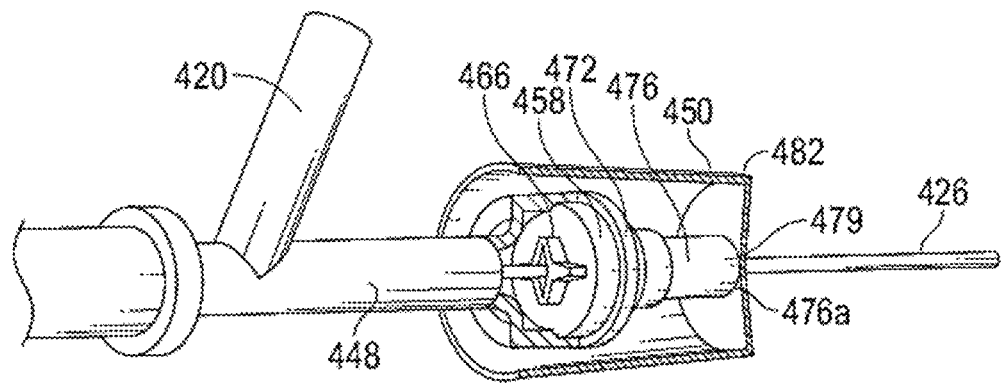
FIGS. 7A and 7B illustrate cross-sectional views of an exemplary rotating hemostatic valve with a gasket configured in a high-pressure position.
Figure 7B:
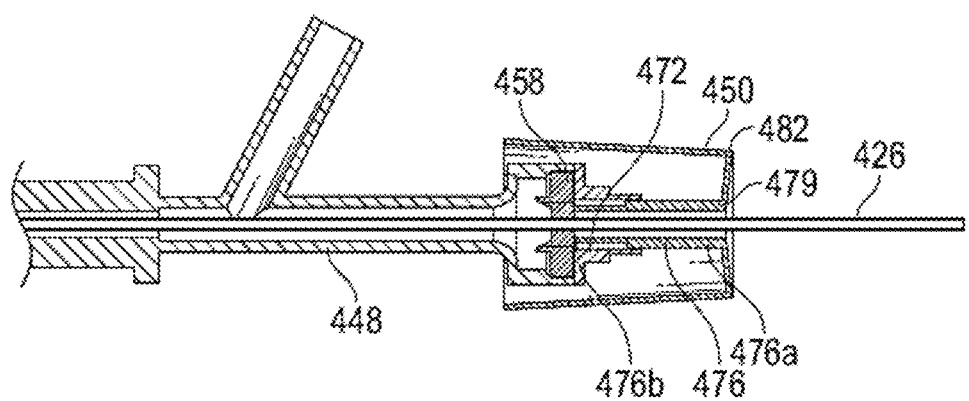

FIGS. 7A and 7B illustrate cross-sectional views of an example rotating hemostatic valve with a gasket configured in a high sealing force (mode) or high-pressure position. As shown in FIG. 7A, a distal membrane 460 includes a thickened sidewall in the form of a cross of material 466 which aligns with the transverse slits of the proximal membrane 462. The cross of material 466 provides additional gasket contact around the catheter 426 in the tightly closed (e.g., high-pressure) state.

The tightly closed state represents a configuration for high-pressure fluid transfer from a fluid source (e.g., contrast/second source 110b). The closed state of the gasket 458 enables contrast medium (e.g., from second source 110b) to be injected through the RHV 448 side port 420 at a pressure of up to about 2.76 MPa (i.e., about 400 psi). As shown in FIG. 7B, in the closed state, the plunger 476 is retracted proximally so that both the distal slits 464 and proximal slits are no longer supported by the support tube and are able to provide a seal against the catheter 426. In other words, both the proximal end 476a and the distal end 476b of the plunger 476 are clear of the gasket 458 to achieve the closed state of the gasket 458.

Figure 8A:
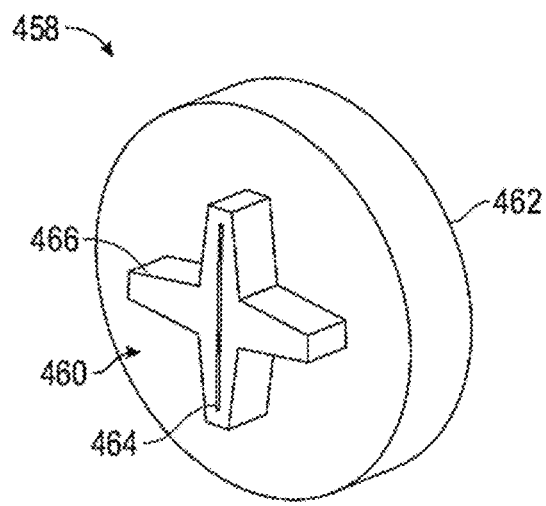
FIGS. 8A-8C illustrate various views of an exemplary gasket for use in the hemostatic valve described herein.
Figures 8B, 8C:
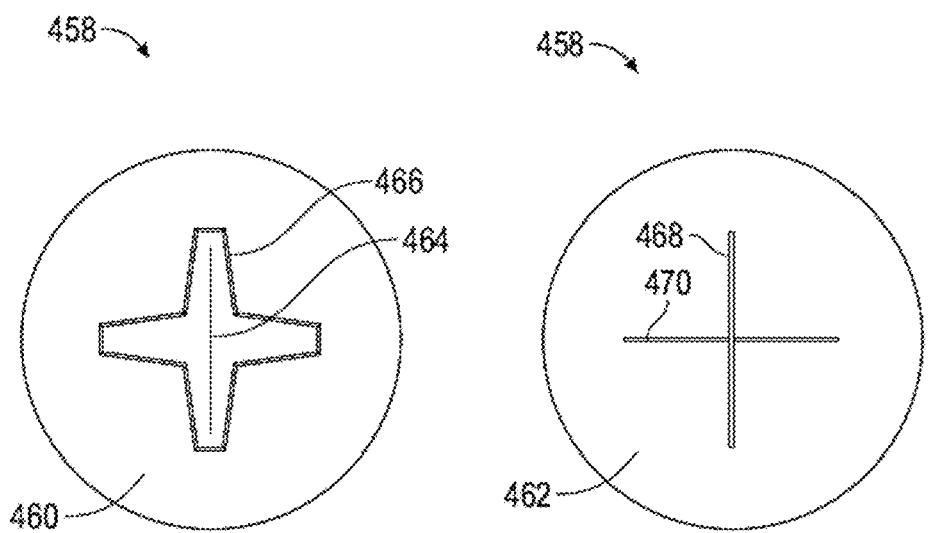

FIGS. 8A-8C illustrate various views of an example gasket for use in the fluidics systems described herein. FIG. 8A illustrates a perspective view of the gasket 458. The gasket 458 includes a distal membrane 460 and a proximal membrane 462. A cross slit (substantially horizontal slit 470 intersecting substantially vertical slit 468) on the proximal membrane 462 of the gasket 458 may be allowed to compress against the catheter for high-pressure sealing or a closed position of gasket 458. A distal slit 464 vertically oriented on a distal membrane 460 of gasket 458 may be allowed to compress against the catheter for low-pressure sealing or a closed position of gasket 458.

FIG. 8B illustrates a distal end view of the gasket 458. The distal membrane 460 of the gasket 458 includes the distal slit 464 vertically oriented in a center of a gasket portion having the thickened sidewall which may be configured as a cross of material 466.

FIG. 8C illustrates a proximal end view of the gasket 458. A vertical slit 468 of the gasket 458 is substantially perpendicular to a horizontal slit 470 on the proximal membrane 462 of the gasket 458.

In some embodiments, the rotating hemostatic valves described herein may be configured with an open setting during which catheters can be freely inserted or removed from the lumen manually. In addition, in the open setting, free flushing of the system with saline may be performed to purge the system of air bubbles. In some embodiments, the open setting may additionally allow for retrograde back bleeding of blood to purge the system of air bubbles.

Figure 9:
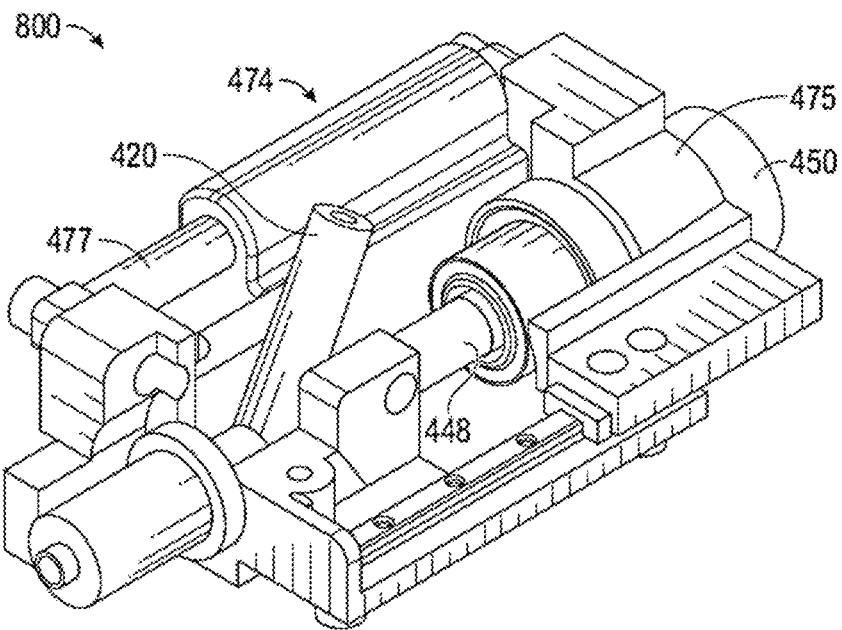
FIG. 9 illustrates a perspective view of an actuation mechanism for use with the rotating hemostatic valves described herein.

FIG. 9 illustrates a perspective view of an actuation mechanism 800 for use with the rotating hemostatic valves described herein. The actuation mechanism 800 comprises at least a linear actuator 474 connected coaxially about a tubular drive shaft 477, which couples to the proximal end 450 of the RHV 448 to drive one or more gears to rotate the RHV 448. To manipulate the catheter (e.g., catheter 226), the linear actuator 474 drives a tang (not shown) which may engage with a circular flange fixed to an outer shaft of a catheter. In some embodiments, the RHV 448 is coupled to a hub (e.g., the first catheter hub 124*a*) capable of rotation, translation, and/or deflection of a catheter (or wire).

Figure 10A:
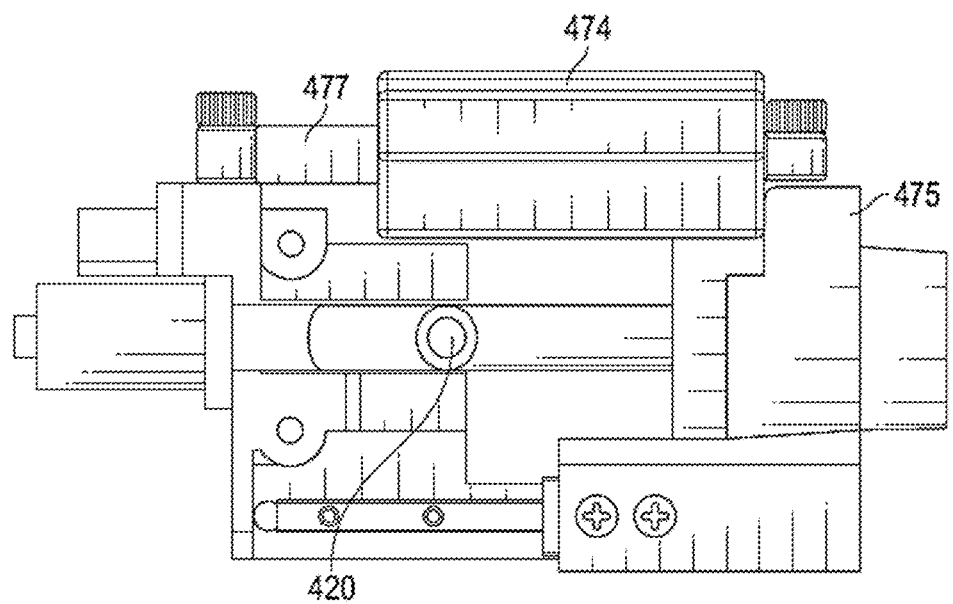
FIGS. 10A-10B illustrate two different positions of the actuation mechanism of FIG. 9.
Figure 10B:
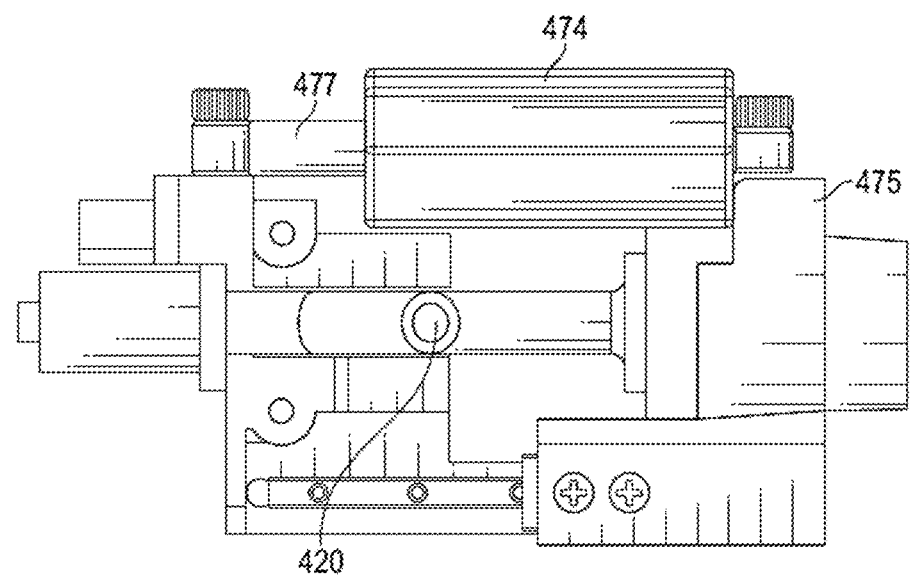

FIG. 10A illustrates the RHV drive mechanism restraining the valve in the open position as illustrated in FIG. 5B. The linear actuator 474 has driven the drive shaft 475 to a proximal limit of travel, at which the support tube extends across the gaskets, holding them open. In FIG. 10B, the support tube has been advanced out of the gaskets, allowing them to close tightly around any inner catheter extending therethrough in the high pressure position.

Figure 10C:
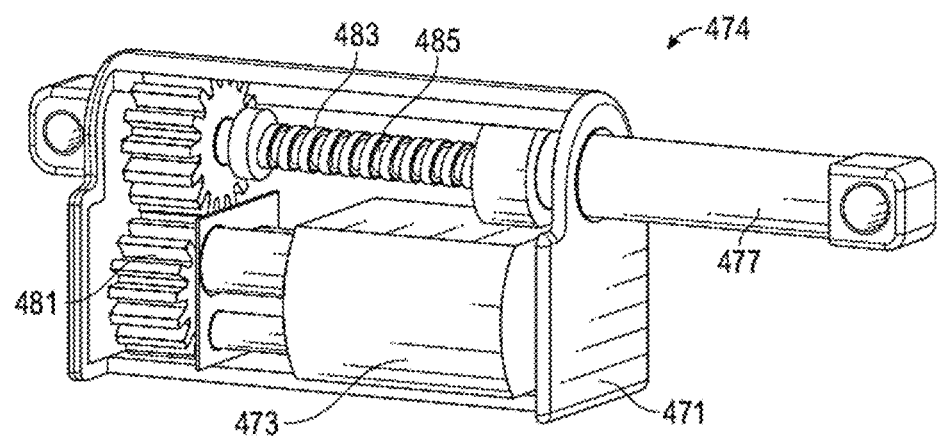
FIG. 10C illustrates a linear actuator assembly.

FIG. 10C is a schematic representation of one implementation of a linear actuator 474. A housing 471 supports a motor 473 which rotates a gear train 481 which in turn rotates a lead screw 483. A helical thread 485 on lead screw 483 slidably engages a complementary projection on an inside surface of a tubular drive shaft 477, causing axial reciprocation of the drive shaft 477 and corresponding axial displacement of the support tube relative to the gaskets.

The sterile field clot capture container, filter, RHV, pressure sensor, etc. could all be part of the hub and move with the catheter. If capturing the clot with the clot pod close to the hub, then the tubing between the hub and the fluidics management tower does not need to be as large of a diameter (would inject saline at higher pressure than arterial pressure and then aspirate back through clot pod to make the clot more visible). The valve manifold may be configured without regard to design details for handling large pieces of clot going through the manifold. In some embodiments, the valve manifold may be carried by the hub. In some embodiments, the valve manifold may be integrated into the hub. Alternatively, the valve manifold may be remote from the hub, and in communication with the hub by way of a tubing set having vacuum, saline, and contrast lines.

If the first catheter 126 is left in place, pulling out second catheter 128 creates a pressure gradient from outside to inside, creating a risk of sucking in air if the valve isn't tight enough, but the valve can't be so tight that it inhibits pulling out the second catheter 128, so the saline delivery flow rate may be set so that it is creating a positive pressure so that no air bubbles are introduced.

Figure 11:
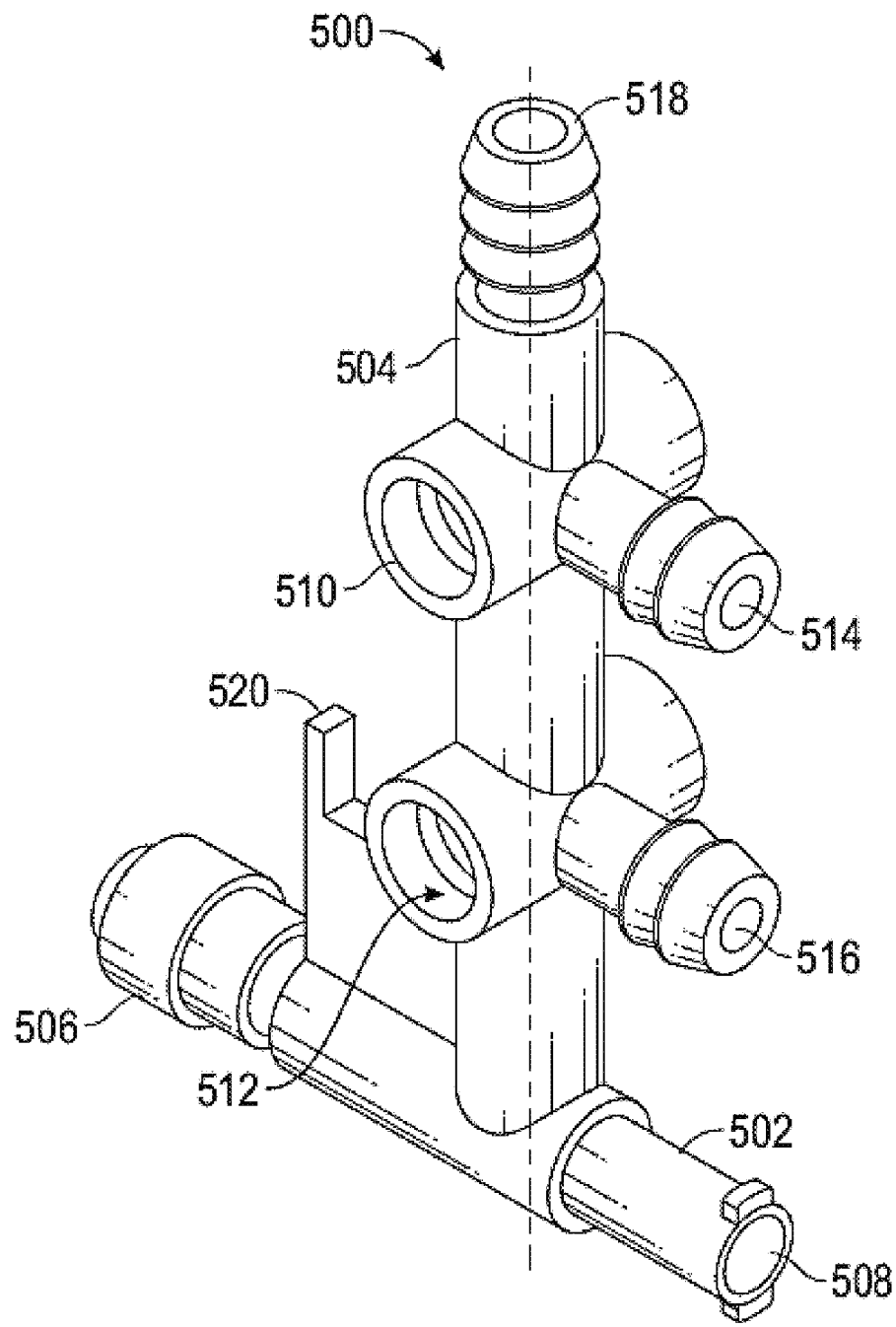
FIG. 11 illustrates a perspective view of an example assembly with a rotating hemostatic valve integrated with a manifold.

FIG. 11 illustrates a perspective view of an example assembly 500 that includes a rotating hemostatic valve (RHV) 502 integrated with a manifold 504. The example shown in FIG. 11 depicts an embodiment with a manifold located adjacent to or within a particular RHV associated with a hub. Such an embodiment may replace the separate manifolds 118*a*-118*c* in the fluidics system 100.

The RHV 502 is depicted as a tapered tube with a rotating portion 506 and a port 508 for receiving one or more catheters (not shown) threaded therethrough. One or more catheters may be attached to a portion of RHV 502 adjacent to port 508. The portion may include a luer lock rotating nut or another valve or introducer valve.

The RHV 502 may be fixedly attached to the manifold 504. In some embodiments, the RHV 502 is removably attached to the manifold 504. The manifold 504 is configured with any number of ports for receiving fluid lines attached into hubs. For example, the manifold 504 includes at least a first port 510 for receiving one or more fluid source lines 120*a*, 120*b*, 120*c* from at least one manifold valve (e.g., at least one valve in the first valve array 116*a*). The manifold 504 includes at least a second port 512 for receiving one or more fluid source lines 121*a*, 121*b*, 121*c* from at least one manifold valve (e.g., at least one valve in the second valve array 116*b*).

The manifold 504 is further configured with any number of ports for receiving fluid lines connected to particular fluid sources. For example, the manifold 504 includes a port 514 for receiving contrast fluid via fluid lines connected to a contrast source (e.g., second source 110*b*). The manifold 504 also includes a port 516 for receiving saline fluid via fluid lines connected to a saline source (e.g., first source 110*a*). The manifold 504 additionally includes a port 518 for receiving (e.g., evacuating) waste via fluid lines connected to a sink (e.g., sink 112). The manifold 504 may include an optional clip 520 for attaching the RHV 502 to a hub.

Although two source ports and a sink port are depicted in FIG. 11, any number of source ports or sink ports may be possible on the assembly 500. Further, any number of valve ports may also be provided and may correspond to a number of catheter hubs configured to function in a particular fluidics system.

Figure 12:
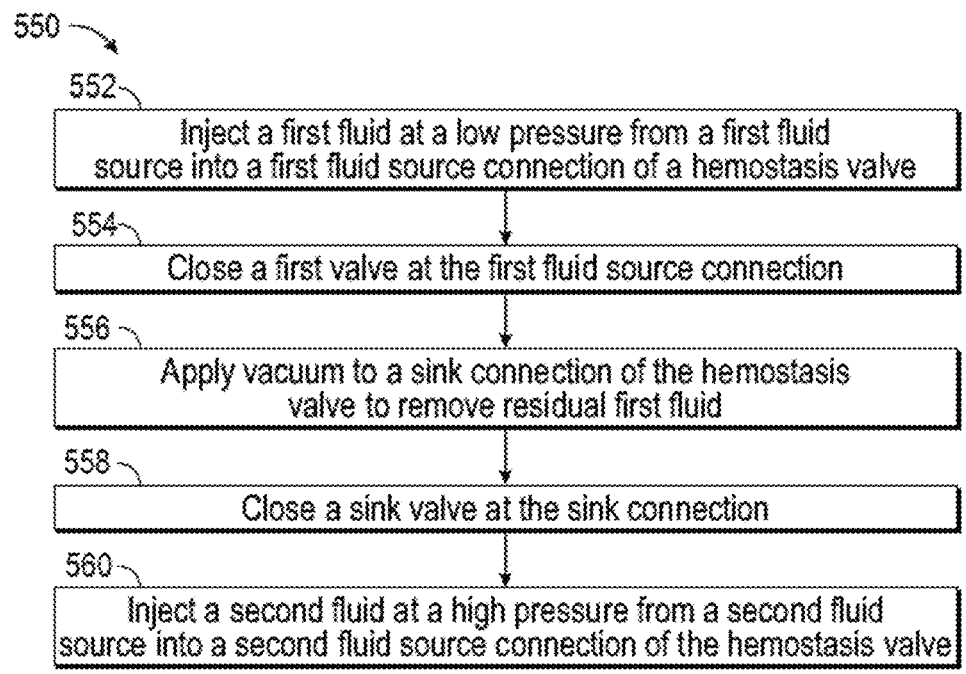
FIG. 12 is a flow diagram of a method for degassing a fluid management system of a robotically driven medical device.

FIG. 12 depicts an example of a method 550 for degassing a fluid management system of a robotically driven medical device. Embodiments of the method for degassing a fluid management system may remove gases from a lumen of robotically driven medical device (e.g., a catheter as described herein), one or more fluid lines of the fluid management system, and/or or one of more fluids (for example, removing dissolved gases from one or more fluids). In certain embodiments, the method for degassing may be used to build a wall or column of fluid within one or more sections of the fluid management system (e.g., one or more fluid lines) by removing gases therefrom.

Thus, in certain embodiments, the method for degassing may be referred to as a method for forming a fluid column or a method of arranging fluid within a fluid management system. For example, a first fluid, such as saline, from a first fluid source can be driven through a first fluid line into a first fluid source connection of a hemostasis valve coupled to the medical device. A first valve at the first fluid source connection can be closed, resulting in a column of fluid in the first fluid line connection without gas or with a relatively low amount of gas.

Aspiration can then be applied to a sink connection of the hemostasis valve to remove the residual first fluid from the hemostasis valve. This may result in an empty hemostasis valve while a column of fluid is maintained in the first fluid line. The hemostasis valve may then be ready to receive a second fluid, such as contrast media, which may be injected at high pressure. When the second fluid is injected, for example, through a second fluid connection of the hemostasis valve, the column of fluid in the first fluid line may prevent or inhibit the second fluid from flowing into the first fluid line. The second fluid can traverse a path of least resistance, for example, through the lumen of the medical device, instead of through first fluid line.

In certain embodiments, a column or wall of fluid can be formed in a sink line extending from the sink connection to a sink. For example, while aspirating fluid, such as the first fluid, through the sink line via the sink connection, a sink valve at the sink connection can be closed and aspiration can be stopped so that at least some fluid is retained in the sink line instead of flowing to the sink, resulting in a column or wall of fluid in the sink line at the location of the sink connection. In some embodiments, the first fluid may be driven into the hemostasis valve during aspiration in order to form the wall or column of fluid in the sink line. The wall or column of fluid in the sink line may prevent or inhibit a fluid, such as the first fluid or second fluid, from flowing into the sink line. For example, a column or wall of fluid may be formed in both the first fluid line and the sink line, as described herein. The second fluid (e.g., contrast media) can then be injected into the hemostasis valve, and the second fluid can flow through the lumen of the medical device instead of into the first fluid line or the sink line. By preventing undesired flow of fluid into the first fluid line and/or the sink line, fluid waste can be prevented and an amount of fluid flowing to a patient can be known and controlled.

In certain embodiments in which a wall or column of fluid is desired in the sink line, various methods may be employed to prevent or inhibit the retrograde drawing of air through the lumen of the medical device (e.g., a catheter) while building the wall or column of the fluid in the sink line. In certain embodiments, the medical device can be inserted into a patient before aspiration so that blood is drawn through the lumen of the medical device and into the sink line. The column of fluid in the sink line may be formed of blood and/or the first fluid.

In certain embodiments, if the medical device is positioned outside of the body, a tip of the medical device can be placed into a container of fluid, such as saline, which can then be aspirated into the sink line. In other embodiments, the tip of the medical device may be blocked (for example, using a plug) so that air is not aspirated from the distal end while aspirating the first fluid to build a column of fluid in the sink line. In other embodiments, a valve (for example, in a valve manifold as described herein), may be closed to obstruct a connection between the lumen and the hemostasis valve or between the lumen and the sink connection to prevent retrograde air from entering the sink line while building a column of fluid.

In one embodiment, the method includes injecting a first fluid at a low pressure from a first fluid source into a first fluid source connection of a hemostasis valve, closing a first valve at the first fluid source connection, applying vacuum to a sink connection of the hemostasis valve to remove residual first fluid, closing a sink valve at the sink connection, and injecting a second fluid at a high pressure from a second fluid source into a second fluid source connection of the hemostasis valve. The method 550 functions to remove dissolved gases from fluids and fluid lines of the fluid management system. The method is used for catheter and fluid preparation but can additionally or alternatively be used for any suitable applications, clinical or otherwise. The method 550 can be configured and/or adapted to function for any suitable fluid degassing technique.

In some embodiments, instead of injecting first fluid at a low pressure from a first fluid source into a first fluid source connection of a hemostasis valve and closing a first valve at the first fluid source connection, the method may instead evacuate particular ports and/or fluid lines and subsequently inject the first fluid from the first fluid source into a first fluid source connection of the hemostasis valve. In certain embodiments, evacuating particular ports and/or fluid lines prior to fluid injection may provide a negative pressure with may assist subsequent flow of fluid through the fluid management system.

In operation of fluidics system 100, an interventionalist may access fluid management portion 102 and interventional portion 104 to perform a method 550. The method 550 may be a degassing method part of an initial configuration for the fluidics system 100. For example, the method 550 may be performed for all or a portion of a fluid management system of a manually driven medical device, a robotically driven medical device, or a combination thereof.

In some embodiments, the degassing method includes injecting a first fluid from a first fluid source into a first fluid source connection of a hemostasis valve, and closing a first valve at the first fluid source connection. In some embodiments, the degassing method includes injecting the first fluid at a low pressure. Vacuum is applied to a sink connection of the hemostasis valve to remove residual first fluid into the sink. A sink valve is closed and a second fluid is injected from a second fluid source into a second fluid source connection of the hemostatic valve. In some embodiments, the first fluid source connection of the hemostatic valve may not be integrated with the hemostatic valve, but may instead be integrated via a wye adapter to integrate the fluid connection with the hemostatic valve. In other embodiments, the first fluid connection may be otherwise separately integrated with the hub.

In some embodiments, the degassing methods described herein may be a scheduled function that can be accomplished in several ways. In a first example, the degassing function may be accomplished using positive pressure in which the system 10 can inject saline into the fluid port that connects with the catheter lumen. In such an example, the saline may then fill the luminal space in the antegrade direction (i.e., distally toward the catheter tip) and also in the retrograde direction (i.e., through an open proximally situated hemostatic valve). In a second example, the degassing function may be accomplished prior to performing the first example and may include closing the hemostatic valve and applying suction through the fluid port or through a fixture that temporarily connects to the distal end of the catheter. In either example, the distal end of the catheter may be temporarily sealed. After purging the luminal air using suction, the system 10 can close a vacuum valve and then open a saline valve to fill the channel with, possibly degassed, saline. Optionally, the distal tip seal may be removed and the first example may be repeated to complete the degassing function. While a method of degassing is described with respect to FIG. 12, the methods described herein may generally be used to clear a fluid (including gasses, liquids, and/or combinations of gasses and liquids) prior to introduction of another fluid.

As shown in FIG. 12, one embodiment of degassing a fluid management system of a robotically driven medical device includes block 552, which recites injecting a first fluid at a low pressure from a first fluid source into a first fluid source connection of a hemostasis valve. For example, fluid from the second source 210b (e.g., saline) may be injected at a low pressure into a first fluid line of the line branch point 208 that is coupled to RHV 248 and/or one or more catheters associated with RHV 248. In some embodiments, the first fluid source includes heparinized saline.

At block 554, the method 550 includes closing a first valve at the first fluid source connection. For example, the third valve 216c may be closed to stop the first fluid from flowing. In some embodiments, the fluid source connection is a fluid line connected to a fluid source via a ball valve. In some embodiments, the third valve 216c is placed adjacent to or within a manifold, which may function as the first fluid source connection.

At block 556, the method 550 includes applying vacuum (e.g., pump) to a sink connection of the hemostasis valve to remove residual first fluid. For example, a sterile field clot capture container, vacuum chamber, and/or control 202 may be triggered to remove the residual first fluid to the aspiration canister 240 through a connection to the RHV 248, such as the first valve 216a.

At block 558, the method 550 includes closing a sink valve at the sink connection. For example, the first valve 216a may function as a sink valve that may close off fluid flow within fluid lines 222a.

At block 560, the method 550 includes injecting a second fluid at a high pressure from a second fluid source into a second fluid source connection of the hemostasis valve. For example, fluid from the first source 210a (e.g., contrast) may be injected at a high pressure from the first source 210a and into a second fluid line of the line branch point 208 that is coupled to RHV 248 and/or one or more catheters associated with RHV 248. In some embodiments, the second fluid is contrast. In some embodiments, the second fluid source connection may not be integrated directly with the hemostatic valve, but may instead be integrated via a wye adapter to integrate the fluid connection with the hemostatic valve. In other embodiments, the second fluid source connection may be otherwise separately integrated with the hub.

In some embodiments, the method 550 further includes actuating a gasket of the hemostasis valve to a high pressure position before injecting the second fluid or before applying the vacuum. For example, a gasket 458 (FIG. 7A) may be part of RHV 248, 448. The gasket 458 may be actuated to open to a high pressure position before injecting the contrast or before applying the vacuum at the RHV 248, 448.

In some embodiments, the method 550 may further include actuating a gasket of the hemostasis valve to a low pressure position before injecting the first fluid. For example, the gasket 456 (FIG. 6A) may be part of RHV 248, 448. The gasket 456 may be actuated to open to a low pressure position before injecting the saline.

Figure 13:
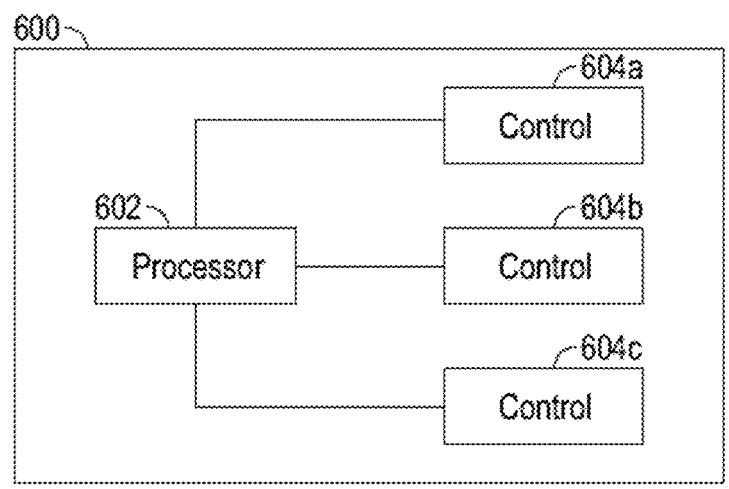
FIG. 13 illustrates a schematic of a control system.

FIG. 13 illustrates a schematic view of an example of a fluidics control system 600 that may be used to electronically control the fluidics systems or components described herein and/or perform the methods described herein. The fluidics control system 600 may be configured to automatically adjust the various manifold valves, pumps, hemostatic valves, hubs, and/or catheters described herein in response to commands input by an operator, such as a physician. In response to command inputs by an operator, the fluidics control system 600 may cause a series of responsive events to automatically occur.

In certain embodiments, the fluidics control system 600 can include one or more processors 602. The one or more processors 602 can be configured to automatically adjust the various manifold valves, pumps, hemostatic valves, hubs, and/or catheters described herein in response to commands input by an operator, for example, using one or more controls of the fluidics control system 600. In certain embodiments, the fluidics control system 600 includes a first control 604a, a second control 604b, and a third control 604c, though any suitable number of controls may be provided to correspond to various functions of the fluidics systems described herein.

For example, in certain embodiments, the first control 604a may be a contrast control that can be operated by a user to initiate the introduction of contrast media into a catheter. The second control 604b may be a saline control that can be operated by a user to initiate the introduction of saline into a catheter. The third control 604c can be a vacuum control configured to initiate the application of vacuum to the catheter. In some embodiments, each unique catheter may have its own unique first control 604a, second control 604b, and/or third control 604c. Alternatively, each of the controls 604a, 604b, 604c (hereinafter "controls 604a-604c") may be actuated to cause a particular response in a plurality of catheters of the fluidics system.

The processor 602 may receive signals from the controls 604a-604c, and in response, initiate corresponding actions in the components of the fluidics system. For example, the processor 602 may be configured to generate output signals that cause responsive actions to be performed by the components of the fluidics system. For example, in certain embodiments, in response to initiation of the first control 604a by a user, the processor 602 can be configured to open a first contrast valve, close a first saline valve, and close a first vacuum valve associated with a unique catheter. In certain embodiments, the processor 602 may also actuate a first contrast media pump in response to actuation of the first control 604a or a separate unique control.

In certain embodiments, the processor 602 may also adjust a hemostasis valve of the unique catheter to a high compression state as discussed herein in response to actuation of a control, such as the first control 604a or a separate unique control. Although one processor 602 is shown in FIG. 13, in other embodiments, a plurality of processors 602 may be used to control the fluidics systems described herein. For example, each of the controls 604a-604c may communicate with a unique processor.

As described herein, for example with reference to FIG. 1B, in certain embodiments, a catheter system may have a valve manifold in communication with a hub of a catheter. The valve manifold may include a first port configured for connection with a source of vacuum, a second port configured for connection with a source of saline, and a third port configured for connection with a source of contrast media. The fluidics control system 600 (e.g., via the processor 602) can be configured to adjust the valve manifold (for example, in response to operation of one or more controls, such as controls 604a-604c) into an aspiration mode in which the first port is in communication with a lumen of the catheter, and communication between the second port and the lumen and the third port and the lumen is obstructed. In certain embodiments, the fluidics control system 600 (e.g., via the processor 602) can be configured to adjust the valve manifold into a contrast injection mode in which the third port is in communication with the lumen, and communication between the first port and the lumen and between the second port and the lumen is obstructed. The fluidics control system 600 (e.g., via the processor 602) can be configured to control a volume of delivered contrast media.

In certain embodiments, the fluidics control system 600 (e.g., via the processor 602) can be configured to adjust a hemostasis valve of a first catheter between a low sealing force mode or low compression mode and a high sealing force mode or high compression mode. In certain embodiments, the fluidics control system 600 (e.g., via the processor 602) can be configured to adjust the hemostasis valve into the high sealing force mode or high compression mode, and to adjust the valve manifold to selectively place the third port into communication with the lumen while simultaneously blocking the first port and the second port from communicating with the lumen (for example, in response to a human input such as operation of such as operation of one of the controls of the control system).

In certain embodiments, the fluidics control system 600 (e.g., via the processor 602) can be configured to determine a sealing force of the hemostasis valve around a second catheter or a guidewire extending through the hemostasis valve (for example, in response to a human input such as operation of one of the controls of the control system). In certain embodiments, the fluidics control system 600 (e.g., via the processor 602) can be configured to increase the sealing force of the hemostasis valve if the fluidics control system 600 determines that the sealing force of the hemostasis valve around the second catheter or guidewire is low.

In certain embodiments, the processor 602 can be configured to send a first control signal to place the hemostasis valve into the high sealing force mode or high compression mode (for example, in response to human input, such as operation of one of the controls of the control system). In certain embodiments, the processor 602 can be configured to send a second control signal to open the contrast valve (for example, in response to human input, such as operation of one of the controls of the control system). In certain embodiments, the processor 602 can be configured to send a third control signal to place the hemostasis valve into the low sealing force mode or low compression mode (for example, in response to human input, such as operation of one of the controls of the control system).

In certain embodiments, the processor 602 can be configured to send a fourth control signal to a robotic catheter drive system to axially adjust the second catheter with respect to the first catheter (for example, in response to human input, such as operation of one of the controls of the control system). In certain embodiments, the processor 602 can be configured to send a fifth control signal to the robotic catheter drive system to axially proximally withdraw a guidewire from the second catheter prior to opening the contrast valve (for example, in response to human input, such as operation of one of the controls of the control system). One or more of the first control signal, second control signal, third control signal, fourth control signal, or fifth control signal can be sent in response to a single human input. Any of the first control signal, second control signal, third control signal, fourth control signal, or fifth control can be sent in response to a unique human input.

FIGS. 14-63 disclose embodiments of systems, components, and methods for managing fluidics systems that administer and remove fluids during medical procedures. These systems and methods also may include a programmable and/or automated (or semi-automated) fluid injection and removal system to perform procedures, and may be coupled to robotically driven interventional devices, manually driven interventional devices, or any combination thereof. A controller in the system can be configured to control the fluid administration equipment of a robotic catheter system to ensure proper diagnostics and/or treatment is provided. Such a controller can include or more hardware processors that are capable of executing instructions for controlling fluid administration equipment (e.g., actuating valves and pumps). When used herein, a "controller" can refer to one controller or one or more controllers. In referring to a controller or controllers, for ease of reference, a "controller" or "one or more controllers" may be referred to herein simply as "a controller" or "the controller" unless otherwise indicated by context or explicitly, and accordingly reference to "a controller" or "the controller" should be understood to include disclosing one controller or one or more controllers.

Figure 14:
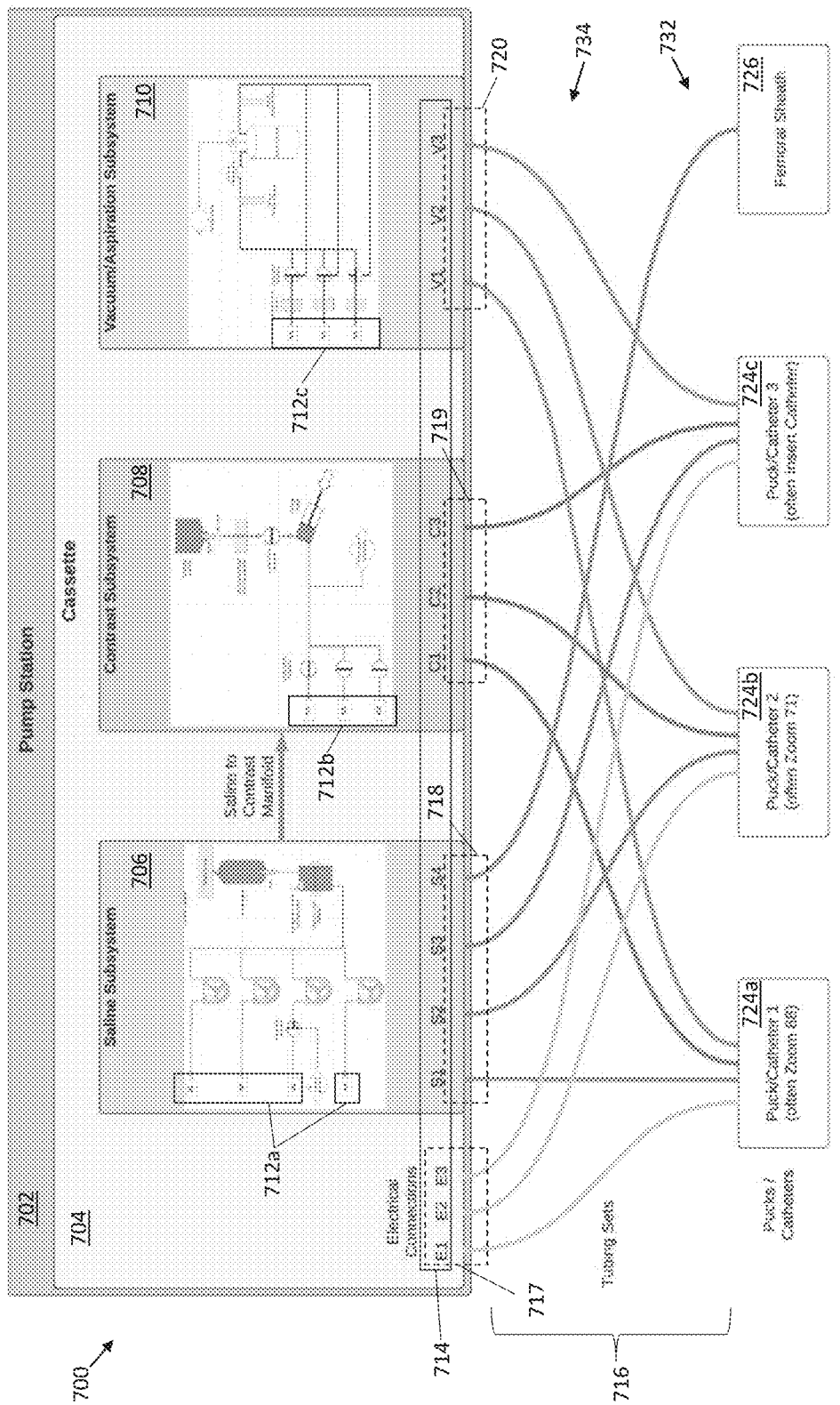
FIG. 14 illustrates an example of a fluidics system.

FIG. 14 illustrates certain aspects of an example of a portion of a robotic catheter system that includes an embodiment of a system 700 for managing fluidics. As described further below, in some embodiments system 700 can include a pump station 702 and a cassette 704. The cassette 704 can include components and fluid communication channels of a saline subsystem 706, a contrast subsystem 708, and a vacuum subsystem 710. For example, cassette 704 can include connections/ports to connect to a tubing set and sources of saline, contrast, and vacuum, one or more peristaltic pumps, one or more valves, one or more sensors, one or more contrast pumps, one or more vacuum canisters, one or more clot pods, and fluid communication channels for communicating saline, contrast, and vacuum from the saline, contrast, and vacuum sources to the hubs and catheters. The pump station 702 can include components that interact with the subsystems in the cassette when the cassette 704 is coupled to the pump station 702. In an example, the pump station 702 can include one or more valve actuators, one or more peristaltic pump drive mechanisms, one or more contrast pump drive mechanisms, configured to actuate and drive valves and pumps in the cassette that are part of the saline, contrast, and vacuum subsystems. The pump station 702 can also include one or more sensors that are configured to sense fluid flowing in certain fluid communication channels of the cassette 704.

In some embodiments, the cassette 704 and the pump station 702 include corresponding electrical contacts or connections (both referred to as "contacts") that are connected when the cassette 704 is coupled to the pump station 702 to connect electrical components (e.g., sensors) in the cassette 704 to the pump station 702. The electrical contacts may include contacts for providing information from a component in the cassette (or the hub coupled to the cassette) to a controller in the pump station or a controller in communication with the pump station that is configured to operate the fluidics system, or another system that utilizes such information. The electrical contacts may include contacts for providing power to a component in the cassette. In some embodiments, the electrical contacts can also electrically connect the pump station 702 to one or more hubs 724 via the cassette 704. Accordingly, the electrical contacts can provide power to a component in a one or more hubs via the cassette (and via electrical connections between the cassette and the one or more hubs). Certain components of the system 700 can be configured to be disposable and certain components can be configured to be reusable. For example, the one or more hubs 724 and catheters coupled to the hubs, a tubing set 716, and/or cassette 704 can be configured to be disposable. Valves related to controlling providing fluids and providing vacuum in system 700 can be referred to collectively as a "valve assembly" for ease of reference. The valve assembly can include, but is not limited to, valves in a saline subsystem 706, contrast subsystem 708, and vacuum subsystem 710 that are located in a pump station 702, cassette 704, and/or the one or more hubs 724. As described in examples below, the system 700 provides saline, contrast, and vacuum, from saline, contrast, and vacuum sources (respectively) through fluid communication channels to the one or more hubs 724 and catheters coupled to the hubs 724. The fluid communication channels can include channels, tubes, ports, lines connectors, and other structure to communicate fluid and provide vacuum. Unless otherwise indicated explicitly or by context "channels," "tubes," "lines," molded apertures and structures, and other structures or portions of components through which a fluid or gas flows may be used synonymously herein as referring to a fluid communication channel, or simply a "channel" for ease of reference. For example, the fluid communication channels can include channels in the cassette 704, one or more tubes that are part of tubing set 716, and tubes and/or channels located in a hub 724, and the fluid communication channels can be collectively referred to as a fluid communication system.

Figure 15:
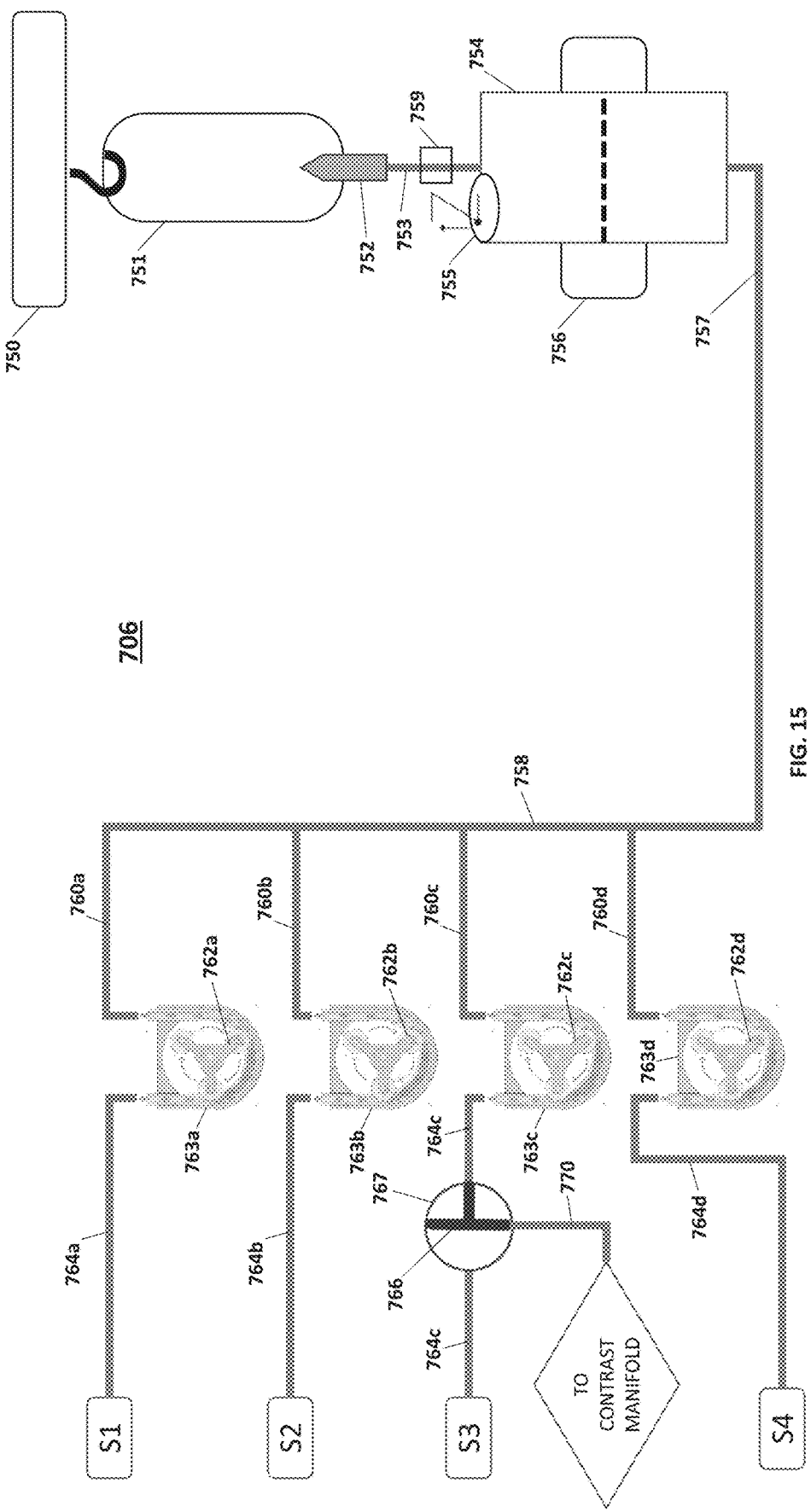
FIG. 15 illustrates an example of an embodiment of a saline subsystem.
Figure 16A:
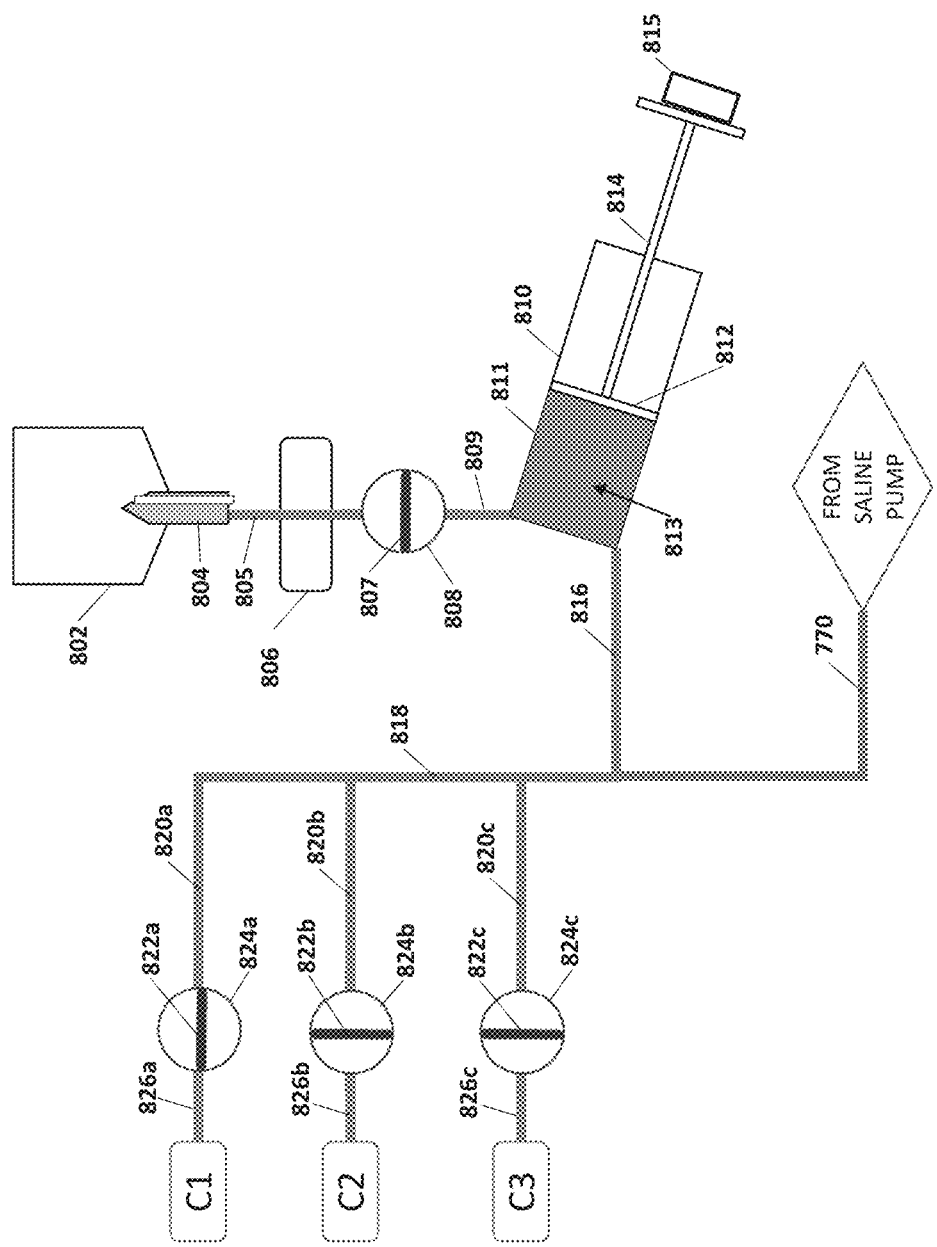
FIG. 16A illustrates an example of an embodiment of a contrast subsystem.
Figure 16B:
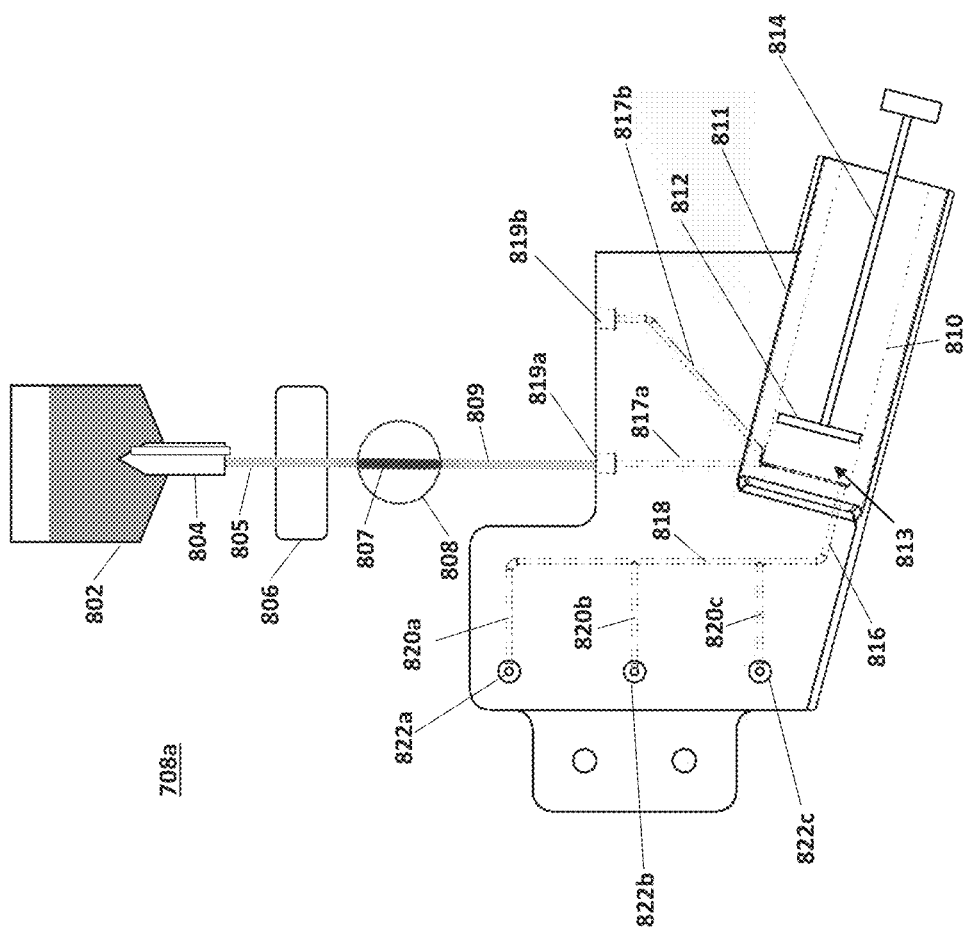
FIG. 16B illustrates another example of an embodiment of a contrast subsystem.
Figure 17:
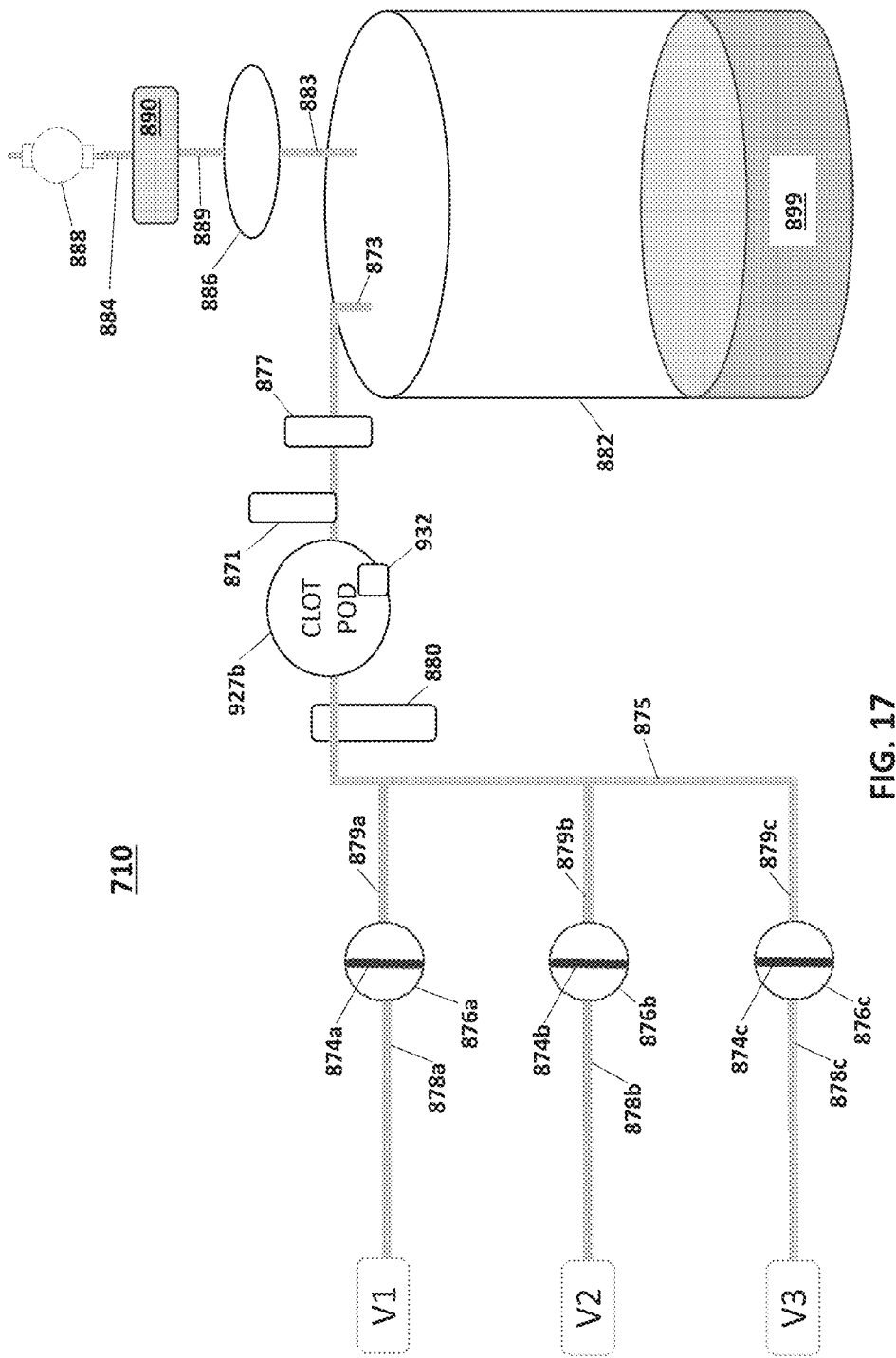
FIG. 17 illustrates an example of an embodiment of a vacuum/aspiration ("V/A") subsystem ("vacuum subsystem").
Figure 19:
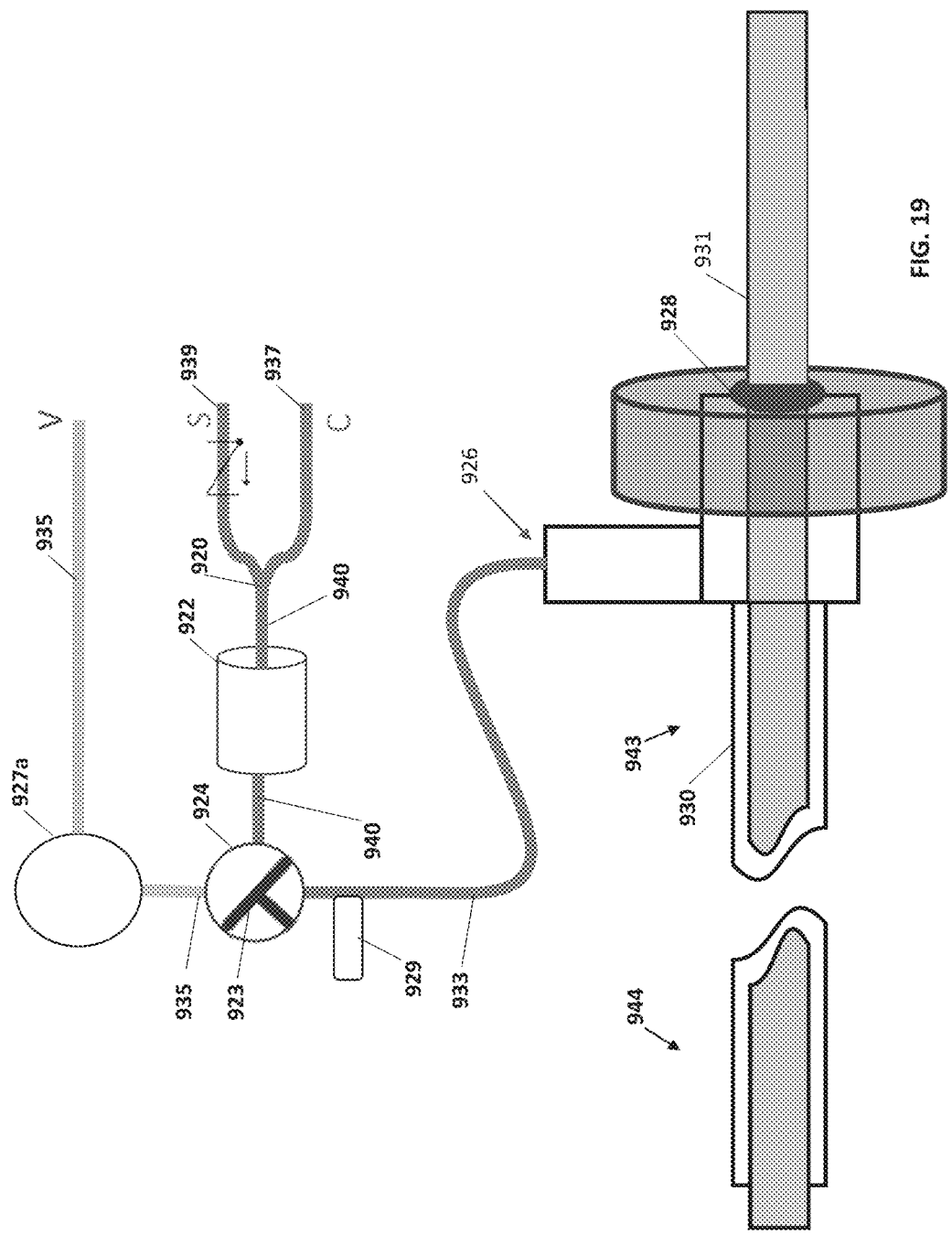
FIG. 19 illustrates another example of a catheter coupled to an embodiment of a hub.
Figure 20:
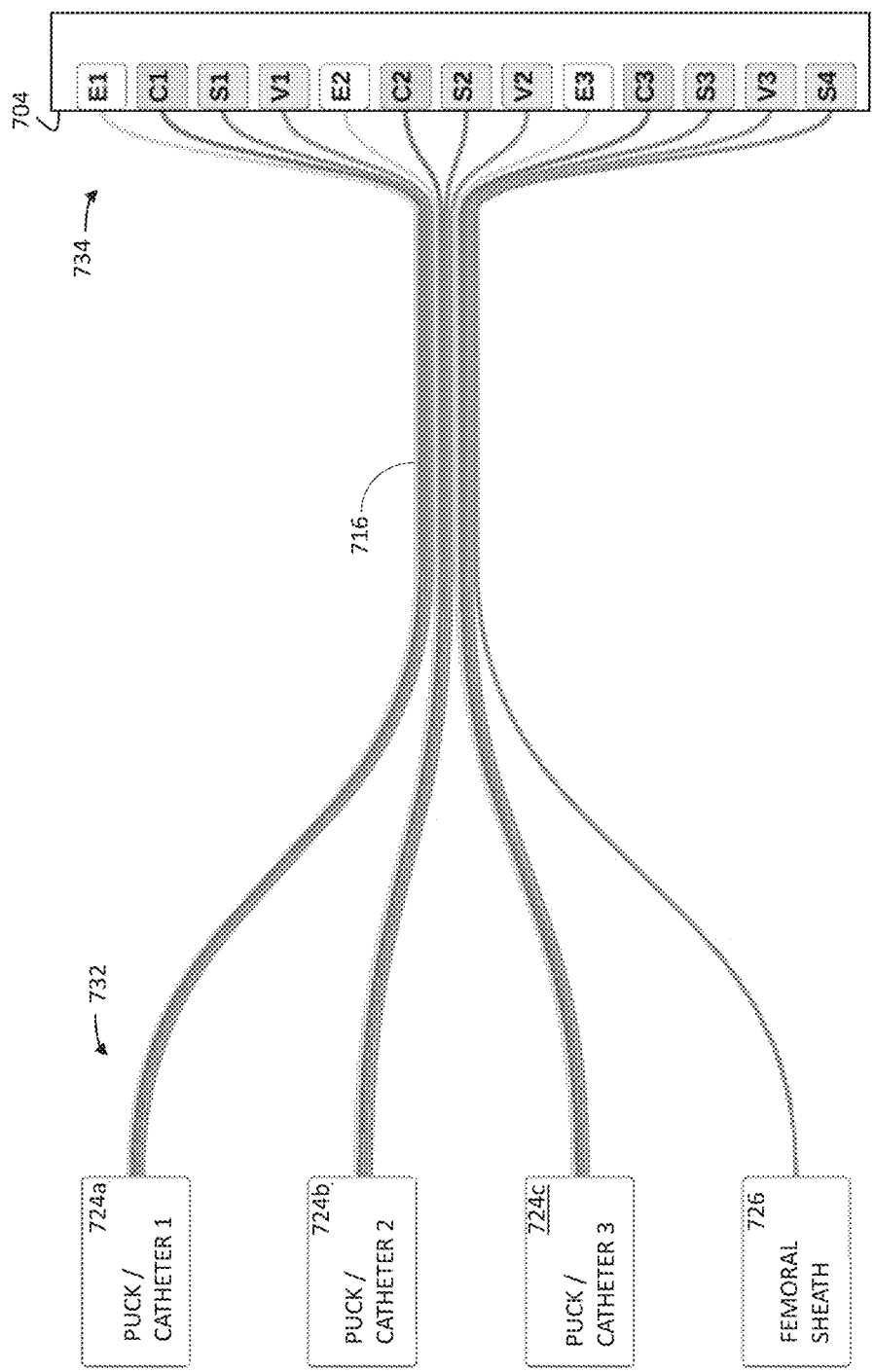
FIG. 20 illustrates an example of a tubing set that is a portion of a fluid communication system that provides channels for communicating substances (e.g., air, fluids, and/or materials) between a plurality of catheters and a saline subsystem, a contrast subsystem, and a vacuum subsystem, the tubing set coupled, on a proximal end of the tubing set, to a cassette and coupled, on a distal end of the tubing set, to a plurality of hubs, and in this example the tubing set also includes electrical connections between the cassette and the plurality of hubs.
Figure 21:
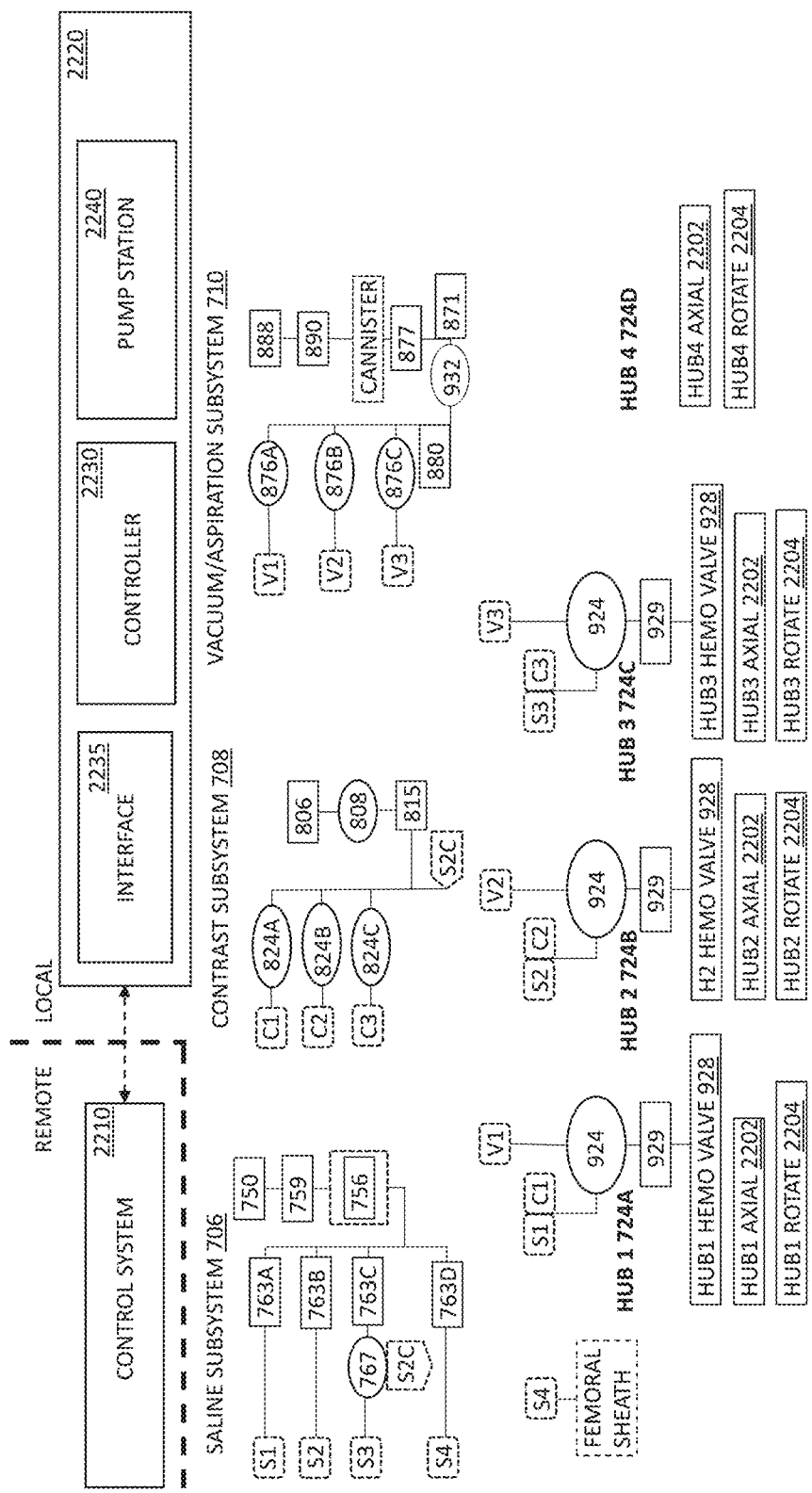
FIG. 21 illustrates a schematic of an example of a robotic catheter system that includes a remotely located system ("remote system") and a locally located system ("local system"), and illustrates an example of certain components of the local system that includes certain components of a fluidic management system ("fluidics system") including actuatable components that are actuated by a controller and sensors that provide information to a controller for the controller to control the fluidics systems and other aspects of the robotic catheter system, according to some embodiments.
Figure 22:
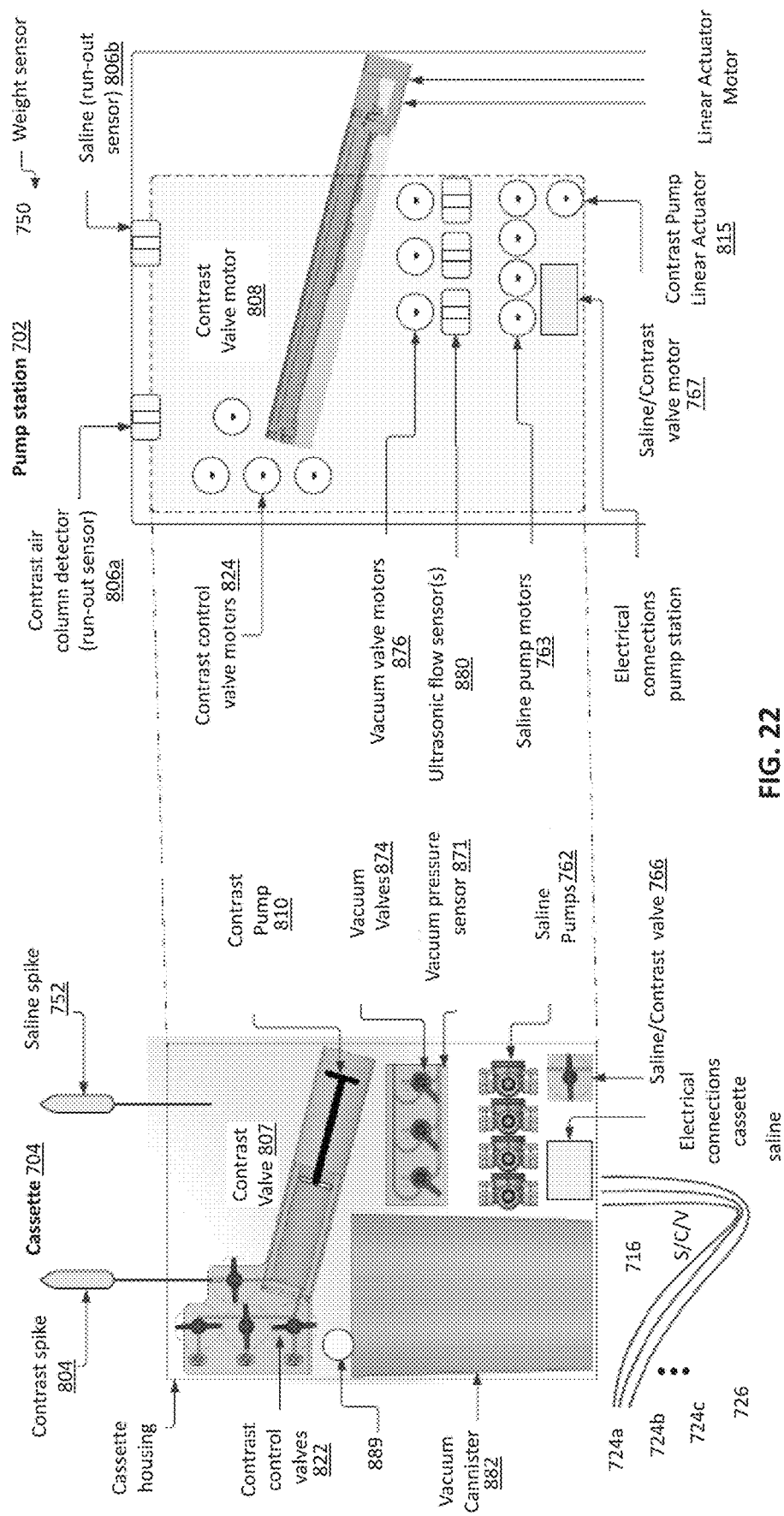
FIG. 22 illustrates an example of an embodiment of a cassette and a pump station illustrating certain components of the cassette (e.g., valves, electrical connections) and corresponding components (e.g., motors, electrical connections) of the pump station.

Embodiments of a saline subsystem 706, a contrast subsystem 708, and a vacuum subsystem 710 that can be used to perform methods for controlling fluid administration equipment are illustrated in FIGS. 15, 16, and 17, respectively. FIGS. 18 and 19 illustrate examples of configurations portions of a fluidic system relating to a hub. FIG. 20 illustrates an example of a tubing set 716 coupled to a cassette 704 on one end, and one or more hubs 724 and a femoral sheath 726 on the other end. FIG. 21 illustrates certain components of a robotic catheter system that are part of, or related to, a fluidics system, that are actuatable by a controller or provide information to a controller, and the controller perform methods for controlling fluid administration equipment by actuating such components and based on (at least in part) such information. FIGS. 23-63 illustrate examples of flow diagrams and configurations of fluidic subsystems and components that can be controlled for performing fluidic methods on the robotic catheter system including, for example, priming the saline subsystem, priming the contrast subsystem, injecting contrast, aspirating a clot, and back-bleeding a hemostasis valve. Such processes are controlled at least in part by a controller, for example, system controller 2220 (FIG. 22). Valves, pumps and other actuatable (or movable) components can be driven to be in a certain state or position by a controller. In some embodiments, the state or position of actuatable components can be determined by sensing mechanism on the component such that the controller can determine the current position of the component before, during, or after a process. In some examples, the sensing mechanism can include a switch, encoder, and the like. In some embodiments, the current state or position of the components can be electronically stored information (e.g., in a table or file) and the controller is configured to determine the position of one or more components by accessing the stored information. In an example, before contrast is injected using a selected catheter in a system having multiple catheters, a valve coupling the selected catheter to a contrast subsystem can be determined to be aligned in an open position to provide contrast to the selected catheter, and one or more valves coupling non-selected catheters to the contrast subsystem can be determined to be aligned in a closed position to de-couple the non-selected catheters from the contrast subsystem. Such determinations may be made using the stored information or by using information from a sensing mechanism. The processes described herein are examples of some of the processes a controller can be configured to perform by controlling fluidic equipment, either automatically or semi-automatically, based on one or more user inputs, sensed information, and/other information.

As indicated above, an example of a fluidics system 700 configured to provide saline, contrast, and vacuum to the one or more hubs 724 and provide saline to a femoral sheath 726 is illustrated in FIG. 14. The one or more hubs 724 may comprise a first hub 724a, a second hub 724b, and a third hub 724c, collectively hereinafter "hubs 724a-724c". As shown in FIG. 14, a catheter is coupled to each of the one or more hubs, and each of the hubs 724a-724c is configured to provide saline, contrast, and vacuum from the fluidic system 700 to the lumen of the catheter coupled to the hub (for example, as shown in FIGS. 18 and 19). For simplicity of disclosure, unless otherwise specified indicated by context, providing saline, contrast, or vacuum to a hub also refers to providing saline, contrast, or vacuum to the catheter coupled to the hub. The example in FIG. 14 is a multi-channel fluidics system that is configured to provide separately controllable amounts of saline, contrast, and vacuum to each of the one or more hubs 724a-724c and femoral sheath 726 as needed during a medical procedure. Being able to separately control the saline, contrast, and vacuum to each hub is advantageous because each catheter has a different sized lumen due to the catheter having a different inside diameter, and the amounts of saline, contrast, and/or vacuum needed during their use may be different based on the lumen size. Each catheter can also have a different effective lumen size which may change at certain times during the procedure based on its lumen containing another catheter or guidewire nested inside its lumen. Being able to separately control the saline, contrast, and vacuum to each hub can also be advantageous because during a medical procedure different amounts of saline, contrast, or vacuum at each catheter may be desired based on what a particular catheter is being used for. In other embodiments, such a fluidics system can be configured as a one-channel fluidics system that provides controlled amounts of saline, contrast, and vacuum to one hub, or a multi-channel fluidics system configured to provide controlled amounts of saline, contrast, and vacuum to two hubs, or four or more hubs.

In various embodiments, the fluidics system 700 can have similar or the same features as other fluidic systems described herein. In this example, fluidics system 700 includes a pump station 702 and a cassette 704 which is releasably couplable to the pump station. The pump station 702 can include components that may be capital equipment. The cassette 704 can include components that may be designed for a one-time use and the cassette is disposable. In an example of use, the cassette 704 is a sterilized disposable component that is coupled to the pump station 702 prior to performing a procedure, and the cassette 704 is removed and disposed of after the procedure is completed. The fluidic system 700 can include numerous valves that control saline, contrast, or vacuum, located in a cassette, pump station, or hub (as illustrated in, for example, FIGS. 2-4, 14-19, 21) and can be referred to collectively as a valve assembly. In various embodiments, portions of the valve assembly can be located in the pump station 702 or in the cassette 704. Various embodiments of the valve assembly can include additional valves, fewer valves, or different valves, than illustrated in the figures. The fluidic system 700 can also include sensors in the saline, contrast, and vacuum subsystem, and these senses can be collectively referred to as a sensor assembly. In various embodiments, portions of the sensor assembly can be located in the pump station 702 or in the cassette 704. Various embodiments of the sensor assembly can include additional sensors, fewer sensors, or different sensors, than illustrated in the figures.

In this example, the fluidics system 700 includes a saline subsystem 706, a contrast subsystem 708, and a vacuum subsystem 710. In some embodiments, the vacuum subsystem 710 may be a vacuum/aspiration ("V/A" or simply "vacuum") subsystem. An example of a saline subsystem 706 is illustrated in FIG. 15. An example of an embodiment of a contrast subsystem 708 is illustrated in FIG. 16A. FIG. 16B illustrates another example of an embodiment of a contrast subsystem. An example of an embodiment of a vacuum subsystem 710 is illustrated in FIG. 17. The embodiments illustrated in FIGS. 15, 16, and 17 can have additional components (e.g., valves, fluid channels/tubing, connectors, etc.) that are not shown for clarity of the figures (e.g., check valves). In various embodiments, certain components of the fluidics system 700 can be part of the pump station 702 and other components can be part of the cassette 704. For example, a portion of the saline subsystem 706 can be in the cassette 704 and a portion of the saline subsystem can be in the pump station 702. As a specific example, a portion of a peristaltic saline pump that controls saline flow can be in the cassette 704, and a drive mechanism of the peristaltic saline pump (e.g., an actuator/drive motor, a drive member) can be in the pump station 702. When a cassette is coupled to the pump station 702, a drive mechanism is coupled to the portion of the peristaltic pump in the cassette such that controlling the drive mechanism controls the flow of saline through the peristaltic pump. In another example, the cassette 704 may include a saline port to receive saline from a saline bag positioned outside of the cassette, and a weight sensor that senses the weight of the saline bag may be part of the pump station.

Also, the contrast subsystem 708, or a portion thereof, can be in the cassette 704. For example, a contrast syringe pump, or a portion thereof, can be located in the cassette 704, and the cassette 704 may include a contrast port to receive contrast from a contrast container positioned outside of the cassette 704. Pump station 702 may include an air column detector configured to detect air in a fluid communication channel (e.g., a tube) between the contrast container and the syringe pump.

Further, the vacuum subsystem 710, or a portion thereof, can be included in the cassette 704, and a portion of the vacuum subsystem can be included in the pump station. For example, a vacuum canister and vacuum control valves can be in the cassette 704, and a vacuum pump and actuators for the vacuum control valves can be located in the pump station 702. As another example, the cassette 704 may also include a vacuum port for coupling to a vacuum source of the pump station. Other configurations where certain components of the saline subsystem 706, the contrast subsystem 708, and the vacuum subsystem 710 are located in the pump station 702, and other components of the saline subsystem 706, the contrast subsystem 708, and the vacuum subsystem 710 are located in the cassette 704, are also possible.

The saline, contrast, and vacuum ports are part of a fluid communication system which includes fluid communication channels (e.g., channels, tubes, lines, etc.) to couple the catheters to the saline source, contrast source, and vacuum source. The cassette 704 includes a portion of the fluid communication system that is couplable to the saline, contrast, and vacuum source, and valves in the cassette partially control fluid flowing through channels of the fluid communication system in the cassette. The fluid communication system also includes a tubing set 716. The tubing set 716 can include fluid communication channels for communicating saline, contrast, and/or vacuum to hubs 724a-724c and/or saline to the femoral sheath 726. In this example, the tubing set 716 includes saline tubes 718, contrast tubes 719, and vacuum tubes 720. In preferred embodiments, the tubing set includes flexible tubes for providing saline, contrast and vacuum to the hubs. For example, tubes that may be 4' to 10' long, according to some embodiments. As illustrated in the embodiment of FIG. 14, the saline subsystem 706 includes a first connector array 712a, a second connector array 712b, and a third connector array 712c that represent where the saline, contrast, or vacuum is provided. Depending on the configuration of the cassette 704, in some embodiment, the first connector array 712a, a second connector array 712b, and a third connector array 712c can be arranged in a second connector array 714 where the tubing set 716 can be coupled to. Electrical channels 717 can connect the first hub 724a, the second hub 724b, and the third hub 724c to the cassette 704 or to the pump station 702, and can be used to provide control signals to the hubs or to receive information from the hubs. Although the illustrated electrical channels 717 are physical communication channels (e.g., include wires, cables, or fiber optic), in some embodiments where the electrical channels 717 are configured to provide control signals to the hubs 724a-724c or provide information from the hubs 724a-724c, the electrical channels 717 can be wireless communication channels.

Each of the hubs 724a-724c may include a plurality of components related to providing saline, contrast, and vacuum to a catheter, and components related to moving the hub and an interventional device attached thereto in an axial direction and rotating the catheter. The tubing set 716 can also include electrical connections to communicate control information to the one or more hubs 724 and/or receive information from components of the hubs 724a-724c (e.g., sensor information). A proximal end 734 of the tubing set 716 may be coupled to the cassette 704, and a distal end 732 of the tubing set 716 may be coupled to the hubs 724a-724c and the femoral sheath 726. In the illustrated example, each of the hubs 724a-724c is coupled to the cassette 704 by an electrical channel 717, a saline tube 718, a contrast tube 719, and a vacuum tube 720. An example of fluidic components in an embodiment of a hub is illustrated in FIG. 18. In some embodiments, the hubs 724a-724c may include additional components. For example, a hub can include components associated with coupling an interventional device to the hub, moving the hub and the interventional device in an axial direction, and rotating the interventional device. An example of a tubing set 716 is further illustrated in FIG. 20.

FIG. 15 illustrates certain components and connections of an example of a saline subsystem 706, which can be the saline subsystem 706 illustrated in FIG. 14. In this embodiment, the saline subsystem 706 includes a saline weight sensor 750 that is coupled to a saline bag 751. A contrast spike 752 is used to puncture the saline bag 751 and allow saline to flow through a saline tube 753 into a saline chamber 754. An air vent 755 on the chamber allows air to escape the saline chamber 754 when it is being filled with saline. A chamber level detector 756 is positioned to sense the saline level in the chamber. A line 757 communicates saline from the saline chamber 754 to the saline manifold 758. Four peristaltic pumps 762a, 762b, 762c, 762d (hereinafter "peristaltic pumps 762a-762d") receive saline from the saline manifold 758 via lines 760a, 760b, 760c, 760d (hereinafter "lines 760a-760d"). Each peristaltic pump 762a-762d is driven by an actuator 763a, 763b, 763c, 763d (hereinafter "actuator 763a-763d"). In some embodiments including the example in FIG. 15, the peristaltic pumps are located in the cassette 704 and the actuators 763a-763d are located in the pump station 702. When the peristaltic pumps 762a-762d are driven by the actuators 763a-763d, saline flows through lines 764a, 764b, 764c, 764d (hereinafter "lines 764a-764d") to ports S1-S4, respectively, which can be at a connector array which is couplable to the tubing set 716.

In the illustrated embodiment, a saline/contrast valve 766 is included in line 764c. The saline/contrast valve 766 can be moved to be in a first position of a second position by a saline/contrast valve actuator 767, which may be in the pump station 702. The saline/contrast valve 766 is configured such that when it is placed in a first position (shown in FIG. 15), the saline/contrast valve 766 connects line 764c to line 770 to route saline from peristaltic pump 762c to the contrast manifold 818 (FIGS. 16A, 16B) for priming the contrast subsystem 708. When the saline/contrast valve 766 is placed in a second position (shown in FIG. 25), the saline/contrast valve 766 connects line 764c to line 768 and to port S3.

FIG. 16A illustrates certain components and connections of an embodiment of a contrast subsystem 708. In this embodiment, contrast subsystem 708 includes the contrast container 802, a connection 804 to the contrast container (e.g., a "contrast spike"), and a line 805 coupled to the connection 804 and to a contrast intake valve 807. The contrast intake valve 807 is opened and closed by a contrast intake valve actuator 808. A line 809 is coupled to the contrast intake valve 807 and also coupled to a contrast pump 810, such that line 809, contrast intake valve 807, line 805, and connection 804 form a fluid communication channel between the contrast pump 810 and the contrast container 802, where the contrast intake valve 807 is configured to open or close this fluid communication channel. An air column detector 806 is positioned to detect air in line 805 and generate a corresponding information (e.g., a signal) which the system controller 2220 can use as input for performing a process.

The contrast pump 810 includes a housing 811 that encloses a contrast chamber 813 which receives contrast from the contrast container 802. The contrast pump 810 includes a wall or movable portion 812 that can be moved to increase or decrease the size of the contrast chamber 813. The movable portion 812 is coupled to a movable member 814, which can be moved by a linear contrast pump actuator 815 which includes a motor. In some embodiments, the contrast intake valve actuator 808, the contrast pump actuator 815, and the air column detector 806 (run-out sensor) can be located in the pump station 702, and the contrast intake valve 807 (between the connection 804 and the contrast pump 810), the contrast pump 810, contrast control valves 822a, 822b, 822c (hereinafter "contrast control valves 822a-822c"), and the lines and components that communicate contrast to ports C1, C2, C3 can be located in the cassette 704, as shown in FIG. 22.

Contrast is provided from the contrast pump 810 to a contrast manifold 818 by line 816. The contrast manifold 818 provides a fluid communication channel to contrast ports C1, C2, and C3 via lines 820a, 820b, 820c (hereinafter "lines 820a-820c"), contrast control valves 822a-822c, and lines 826a, 826b, 826c (hereinafter "lines 826a-826c"). Contrast valve actuators 824a, 824b, 824c (hereinafter "actuators 824a-824c") are coupled to the contrast control valves 822a-822c when the cassette 704 is coupled to the pump station 702, and are controlled by the system controller 2220 to open and close the contrast control valves 822a-822c for performing preparation processes (e.g., priming) or for performing a medical procedure (e.g., injecting contrast). Line 770 is a fluid communication channel connected to the saline subsystem 706 connection and allows saline to flow from the saline subsystem 706 to the contrast manifold 818 as controlled by the saline/contrast valve 766.

FIG. 16B illustrates another example of an embodiment of a contrast subsystem 708a. In this embodiment, contrast subsystem 708a includes certain similar structure as the contrast subsystem illustrated in FIG. 16A. For example, this embodiment may include a contrast container 802, a connection 804 to the contrast container (e.g., a "contrast spike"), and a line 805 coupled to the connection 804 and to a contrast intake valve 807. The contrast intake valve 807 may be opened and closed by a contrast intake valve actuator 808. A line 809 can be coupled to the contrast intake valve 807 and also coupled to a contrast pump 810 via a connector 819a and a contrast intake line 817a, such that line 817a, connector 819a, line 809, contrast intake valve 807, line 805, and connection 804 form a fluid communication channel between the contrast pump 810 and the contrast container 802, where the contrast intake valve 807 is configured to open or close this fluid communication channel. An air column detector 806 can be positioned in line 805 to detect air and generate a corresponding information (e.g., a signal) which the system controller 2220 can use as input for performing a process. In this embodiment, the contrast subsystem 708a includes two fluid communication channels, lines 817a, 817b, coupled to the contrast pump 810 at an upper portion of the contrast pump 810 (i.e., when oriented as shown in FIG. 16B) such that lines 817a and 817b are in fluid communication with the contrast chamber 813. Line 817b can be coupled to connector 819b which can vent to atmosphere or can be coupled to a vacuum source. In operation, contrast flows from the contrast container 802 and through line 817a into the contrast chamber 813, for example, when the movable member 814 is moved to increase the size of the contrast chamber 813. The contrast intake valve 807 can be closed, and the moveable member ("plunger") 814 can be moved to decrease the size of the contrast chamber 813 which forces any air or other gas in the contrast chamber 813 into line 817b and out through the connector 819b. In some embodiments, a vacuum source is coupled to connector 819b and a vacuum is applied. The vacuum can be applied when the plunger 814 is moved to decrease the size of the contrast chamber, to remove any air or other gases in the movable chamber 813 out through line 817b and connector 819b. A valve (not shown) can be coupled to the connector 819b to close the line when the contrast pump 810 is in use.

The contrast pump 810 includes a housing 811 that encloses a contrast chamber 813 which receives contrast from the contrast container 802. The contrast pump 810 includes a wall or movable portion 812 that can be moved to increase or decrease the size of the contrast chamber 813. The movable portion 812 is coupled to a movable member 814, which can be moved by a linear contrast pump actuator. In some embodiments, the contrast intake valve actuator 808, the contrast pump actuator 815, and the air column detector 806 (run-out sensor) can be located in the pump station 702, and the contrast intake valve 807 (between the connection 804 and the contrast pump 810), the contrast pump 810, contrast control valves 822a, 822b, 822c (hereinafter "contrast control valves 822a-822c"), and the lines and components that communicate contrast to ports C1, C2, C3 can be located in the cassette 704, as shown in FIG. 22.

Contrast is provided from the contrast pump 810 to a contrast manifold 818 by line 816 and line 817a. The contrast manifold 818 provides a fluid communication channel to contrast ports C1, C2, and C3 via lines 820a, 820b, 820c (hereinafter "lines 820a-820c"), contrast control valves 822a-822c, and other downstream lines. This embodiment may include contrast valve actuators are coupled to the contrast control valves 822a-822c when the cassette is coupled to the pump station 702, and are controlled by the system controller 2220 to open and close the contrast control valves 822a-822c for performing preparation processes (e.g., priming) or for performing a medical procedure (e.g., injecting contrast). In some embodiments, the contrast subsystem 708a can have a fluid communication channel in fluid communication with the contrast manifold 818 connected to the saline subsystem 706 connection and allows saline to flow from the saline subsystem 706 to the contrast manifold 818 as controlled by the saline/contrast valve, similar to the configuration illustrated in FIG. 16A.

FIG. 17 illustrates an example of an embodiment of vacuum subsystem 710 that includes a vacuum source (vacuum pump 888), a communication channels that can be aligned to provide vacuum from the vacuum source to a catheter, and components to control providing the vacuum to the catheter. Various configuration of vacuum subsystems are possible to be able to selectively provide vacuum to portions of a fluidic system and a catheter at varying amounts of vacuum, for example, at a first level (e.g., a lower level) and at a second (e.g., a higher level). In the embodiment illustrated in FIG. 17, a vacuum pump 888 is coupled to lines 885, 889, and 883 which provide a channel to vacuum canister 882. Specifically in this example, vacuum pump 888 is coupled to line 885, which is coupled to a vacuum regulator 890 that can be controlled by a controller to provide a desired level of vacuum. Line 889 is coupled to the vacuum regulator 890 and also to a sterility filter 886. Line 883 is coupled to the sterility filter and to the vacuum canister 882 which provides a reservoir to collect aspirated material 899. Line 873 is also coupled to the vacuum canister 882 and is coupled to a vacuum manifold 875 which is further coupled to channels that provide vacuum to multiple hubs/catheters of the robotic catheter system, for example, as illustrated in FIGS. 18 and 19. In this example, line 873 is coupled to a vacuum regulator valve 877 that can be controlled by a controller to provide a desired level of vacuum to the downstream vacuum subsystem (e.g., the vacuum manifold 875, ports V1-V3, etc.). A vacuum pressure sensor 871 can be positioned between the vacuum regulator valve 877 and the ports V1-V3 to measure vacuum provided to hubs and catheters. In this example, the vacuum pressure sensor 871 is positioned on line 873 between the vacuum regulator valve 877 and a clot pod 927b, which is positioned on line 873 between the vacuum manifold 875 and the vacuum regulator valve 877 to receive a clot aspirated by any one of a plurality of catheters connected to the vacuum subsystem 710. In some embodiments, the clot pod 927 includes a clot pod sensor 932 that is in communication with a controller to provide information of the contents of the clot pod 927 (e.g., when it contains a clot). In some embodiments, the clot pod sensor 932 includes one or more imaging devices. For example, an embodiment can include a video camera. Images generated by the one or more imaging devices can be displayed on a display of the remote control station and/or on a display in local operating room. The A flow sensor 880 (e.g., an ultrasonic flow sensor) is positioned between the clot pod 927 and the vacuum manifold 875 to sense the flow of material through line 873 and provide flow information to a controller.

The vacuum manifold 875 can be coupled to lines 879a, 879b, 879c (hereinafter "lines 879a-879c") and lines 878a, 878b, 878c (hereinafter "lines 878a-878c") which provide a vacuum channel to hubs/catheters via ports V1-V3. Vacuum control valves 874a, 874b, 874c (hereinafter "vacuum control valves 874a-874c") may be one-way valves and are coupled between lines 879a-879c and lines 878a-878c to control providing vacuum to ports V1-V3, and the vacuum control valves 874a-874c are opened and closed by vacuum control valve actuators 876a, 876b, 876c (hereinafter "vacuum control valve actuators 876a-876c") of the pump station 702, vacuum control valve actuators 876a-876c being controlled by a controller. To provide vacuum to one or more of the ports V1-V3, and hubs and catheters coupled to ports V1-V3, a controller opens the vacuum control valve 874a-874c corresponding to the desired port, actuates the vacuum pump 888, and controls the vacuum regulator 890 and vacuum regulator valve 877 to produce the desired vacuum and monitors the vacuum being provided by using the vacuum pressure sensor 871. Some embodiments can include a flow sensor 880 that is associated with each port V1-V3 and/or a vacuum pressure sensor 871 that is associated with each port V1-V3. However, in most procedures, vacuum is provided to one catheter at a time and in such cases multiple flow sensors and pressure sensors do not provide any operational advantage, and having a single flow sensor 880 and a single vacuum pressure sensor 871 positioned upstream of the vacuum manifold 875, as shown in FIG. 17, reduces cost. In some embodiments, the vacuum pump 888, the vacuum regulator 890, vacuum control valve actuators 876a-876c, and the flow sensor 880 are part of the pump station 702, and the sterility filter 886, the vacuum canister 882, the vacuum regulator valve 877, the vacuum pressure sensor 871, the clot pod 927 and vacuum control valves 874a-874c are located in the cassette 704.

FIG. 18 illustrates an example of a catheter 730 coupled to an embodiment of a tubing set 716 in a hub portion 910 of a fluidics management system. The distal end 732 of the tubing set 716 is coupled to the hub 724 and to the catheter 930, and the proximal end 734 of the tubing set 716 can be connected to a cassette 704, which can include all or part of a saline subsystem, all or part of a contrast subsystem, and/or all or part of a vacuum subsystem of the fluidics management system. Certain components illustrated in FIG. 18 may be described as being part of the tubing set 716, even though they may be in the hub 724 or in a portion of a sterile adapter, because they operate to perform part of the fluid and vacuum communication functionality facilitated by the configuration of the tubing set. Means for providing fluid and electrical connections to the catheter can include one or more of the saline subsystem, the contrast subsystem, the vacuum subsystem, and/or electrical connections that are described herein.

As illustrated in FIG. 18, the catheter 930 can be coupled to a portion of the tubing set 716 of the fluidics management system via a luer connection 926. In this example, the portion of the tubing set 716 includes a contrast tube 937 connected to port/connection point C1, a saline tube 939 S1 connected to port/connection point, and an aspiration tube 935 connected to port/connection point V1. One or more electrical channels 717 are connected to port/connection point E1 which can be on the cassette 704 or on the pump station 702. In some embodiments, the electrical channels 717 are part of the tubing set 716, such that the tubing set 716 includes tubes for communicating saline, contrast, and vacuum tubes from the cassette to the hubs, and electrical connections to the hubs, and such embodiments may be advantageous for wire/tube management. The tubing set 716 can include a branch point in the form of a two-to-one wye connector 920 that couples upstream of the contrast tube 937 and the saline tube 939 of the tubing set 716 to a single downstream saline/contrast tube 940. The tubing set can further include a three-way valve 923 that can be actuated by a three-way valve actuator 924 to selectively place the catheter 930 in communication with the single downstream saline/contrast tube 940 or the aspiration tube 935. In some embodiments, the tubing set 716 can further include a catheter coupling tube 933 downstream of the three-way valve 923 to couple the three-way valve 923 with the catheter 930. The three-way valve actuator 924 can be actuated by a controller. In some embodiments, the three-way valve actuator 924 comprises a drive assembly configured to move the three-way valve 723. In some embodiments, the three-way valve actuator 924 comprises electromechanical means for moving the three-way valve 923, the electromechanical means controlled by a controller.

In some embodiments, the three-way valve actuator 924 comprises a motor controlled by a controller.

In some embodiments, the three-way valve 923 can be a three-way stopcock. The three-way valve 923 may be actuated (e.g., rotated) to selectively provide or prevent fluid communication between ports coupled to the saline/contrast tube 940, the aspiration tube 935, and the catheter coupling tube 933. The three-way valve 923 can be actuated to a first position to open a fluid communication channel between the aspiration tube 935 and the catheter coupling tube 933 and a second position to open a fluid communication channel between the saline/contrast tube 940 and the catheter coupling tube 933. In some embodiments, the three-way valve 923 can be actuated to third position in which the aspiration tube 935, the saline/contrast tube 940, and the catheter coupling tube 933 are all in fluid communication. In some embodiments, the three-way valve can be actuated to a fourth position in which the vacuum tube 935 and the saline/contrast tube 940 are in fluid communication. In some embodiments, the three-way valve 723 can be actuated to a fifth position in which none of the aspiration tube 935, the saline/contrast tube 940, and the catheter coupling tube 933 are in fluid communication.

While a three-way valve 923 is shown in FIG. 18, other valve arrangements for selectively placing the catheter 930 in communication with the saline/contrast tube 940 or the aspiration tube 935 may be used.

As shown in FIG. 18, an air bubble filter 922 may be positioned between the wye connector 920 and the three-way valve 923. In some embodiments, a clot pod 927 may be positioned along the aspiration tube 935 upstream of the three-way valve 923. A clot pod sensor 932 (in communication to a controller) can be positioned to detect material on the clot pod 927. In some embodiments, a clot pod 927 may be positioned in the hub 724 along the aspiration tube 935 upstream of the three-way valve 923. In some implementations, the wye connector 920, three-way valve 923, three-way valve actuator 924, clot pod 927a, and/or portions of the tubing set can be housed within a magnetic sterile adapter that may couple with the hub 724 (also referred to as a mount) and can be considered to be part of a hub assembly. In some embodiments, a clot pod 927b can be positioned. A clot pod 927a may be positioned along the aspiration tube 935 closer to the vacuum canister 882, for example, between the vacuum manifold 875 and the vacuum canister 882 as illustrated in the embodiment in FIG. 17

A hemodynamic pressure sensor 929 may be positioned between the three-way valve 923 and the catheter 930, for example, on the catheter coupling tube 933. The hemodynamic pressure sensor 929 is configured to sense a hemodynamic pressure of a patient in which the catheter 930 is inserted, and provide information relating to the sensed pressure to a controller. FIG. 19 illustrates another embodiment of components and fluid communication channels that can be coupled to and/or positioned in a hub, and also illustrates an example of another interventional device 931 (e.g., a catheter, a guidewire) which can be coupled to another hub and positioned to extend through the hemostasis valve 928 and at least partially into the lumen of the catheter 930.

FIG. 20 illustrates an example of an embodiment of a tubing set 716 that can provide communication channels from a cassette to one or more hubs and a femoral sheath. The tubing set 716 has a distal end 732 and a proximal end 734. In this example, different portions of the distal end 732 is coupled to a first hub 724a, a second hub 724b, a third hub 724c, and a femoral sheath 726. Different portions of the proximal end 734 are coupled to contrast, saline, vacuum, and electrical connections on the cassette. In this example, different portions of the proximal end 734 are coupled to contrast ports (C1, C2, C3) of a contrast subsystem, saline ports (S1, S2, S3, S4) of a saline subsystem, vacuum ports (V1, V2, V3) or a vacuum subsystem to provide fluid communication channels from a contrast, saline, and vacuum source to the hubs, and provide a fluid communication channel from the saline subsystem to the femoral sheath. In this example, the tubing set 716 also includes electrical communication channels that are connected to hubs 724a-724c and connectors E1, E2, E3 on the cassette 704. The electrical communication channels can provide power to the hub to operate components of the hub, and/or can provide signals/information from the hub to the cassette, for example, from a hemodynamic sensor positioned in or on a hub. The cassette can include electrical connections which are coupled to corresponding electrical connections on the pump station when the cassette is attached to the pump station, such that the pump station can provide power to the hubs via the cassette and the electrical communication channels of the tubing set, and/or receive signals/information from the hubs via the electrical communication channels of the tubing set and the cassette.

Figure 63:
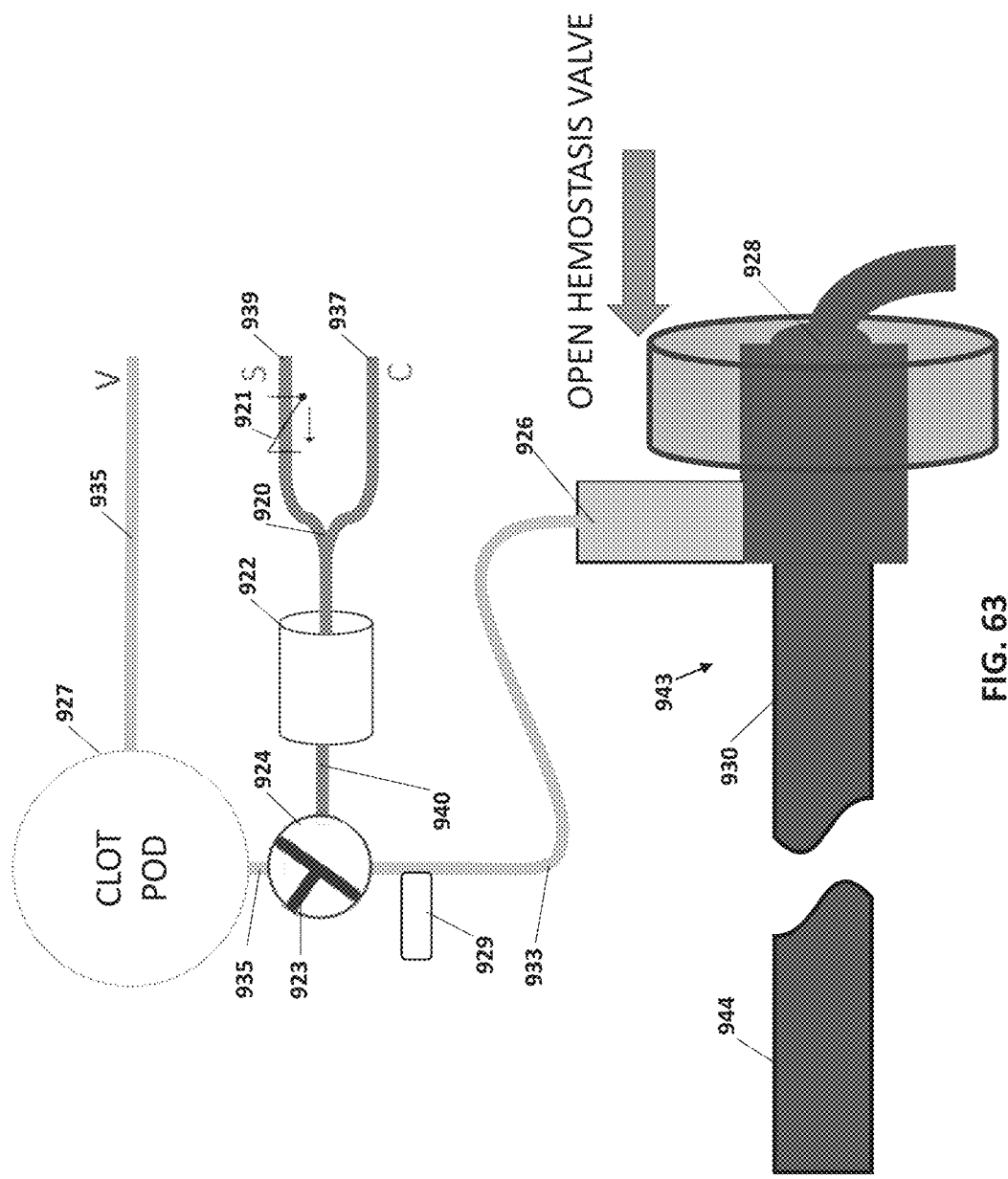
FIG. 63 further illustrates a configuration of a hub for backbleeding a catheter out of a hemostasis valve.
Figure 64:
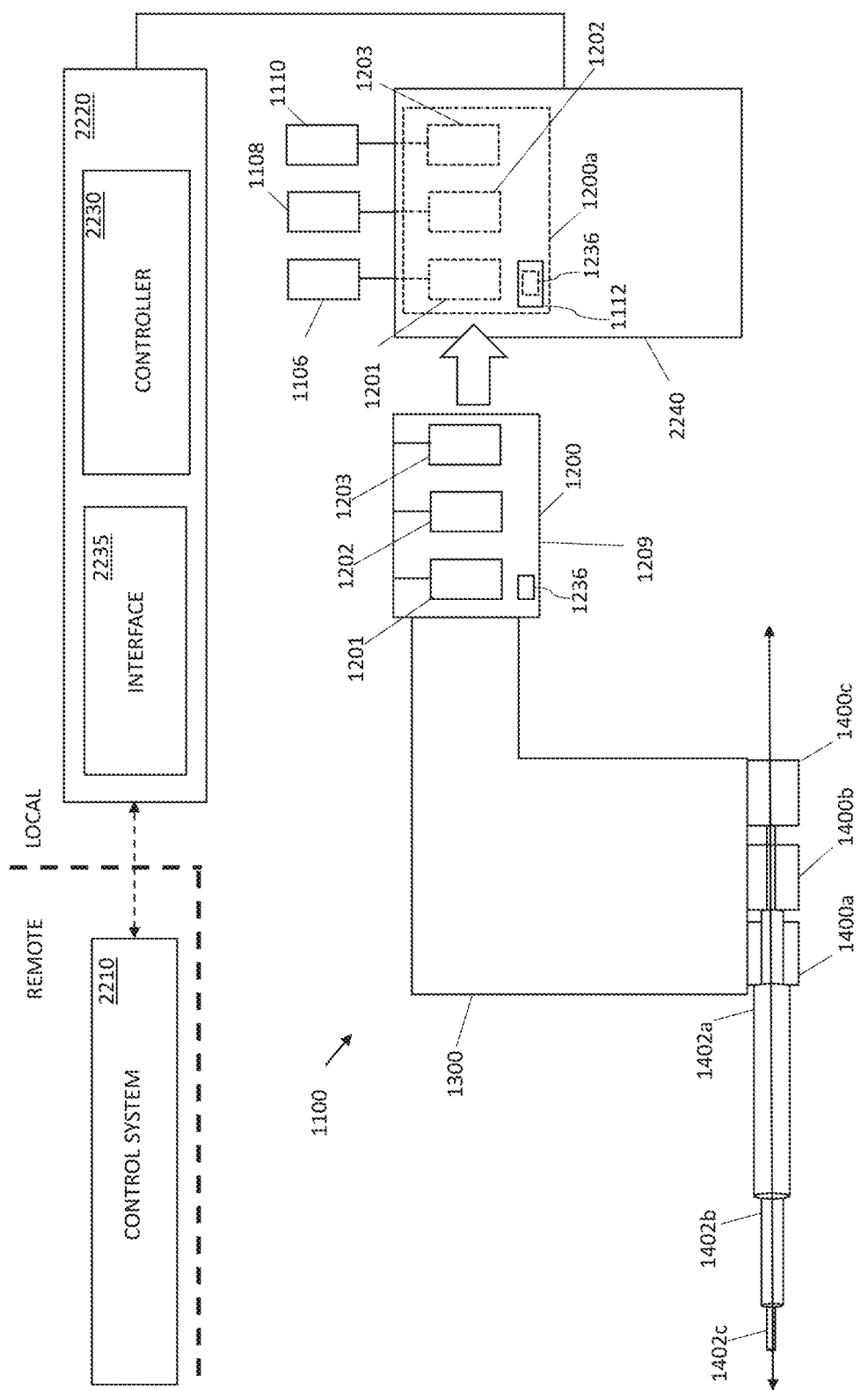
FIG. 64 is a schematic illustrating an example of a robotic catheter system that includes another embodiment of a fluidics system.

FIGS. 21 and 64 illustrate schematics of examples of a robotic catheter system that includes a remotely located system ("remote system") and a locally located system (which may be referred to a "local system," "bedside system," or a "near-patient system"). FIG. 21 generally relates to examples of embodiments and processes in FIGS. 22-63, but aspects of these embodiments may also relate to the embodiments of FIGS. 64-87. FIG. 64 generally relates to examples of embodiments and processes in FIGS. 65-87, but aspects may also relate to other embodiments described herein. FIGS. 21 and 64 also illustrate examples of certain components of the local system that includes certain components of a fluidic management system ("fluidics system") including actuatable components that are actuated by a controller and sensors that provide information to a controller for the controller to control the fluidics systems and other aspects of the robotic catheter system, according to some embodiments. The remote portion includes a control system 2210 located remotely from the patient. "Local" or "bedside" or "local location" as used herein are broad terms that refer to the location where the "local" portion of the robotic catheter system is located, that is, at the actual location where the patient is receiving medical treatment using the robotic catheter system. "Remote" or "remote location" or "remote portion" as used herein is a broad term and generally refers to a location other than where the patient/local system is located when the patient undergoes a medical procedure using the robotic catheter system. In some circumstances, the remote location is within the same building as the patient. For example, in a different portion of a room where the patient is, e.g., on the other side of a barrier or positioned bedside, in the same building but in a room next door to the patient, in the same building but in a different room from the patient, in a different building from the patient, or in a different town or city or state. In some embodiments the remote portion is located several feet away, or hundreds or thousands of miles away from the local portion. The control system 2210 is configured to be in communication with a system controller 2220 which is part of the local portion of the system. The system controller 2220 may include multiple controllers each having one or more processors. In this example, the system controller 2220 includes an interface 2235. The interface 2235 can include multiple interfaces and may be a user interface. The interface 2235 can be configured for communicating with the remotely located control system 2210. For example, the interface 2235 can be configured to receive control signals from the control system 2210 and communicate corresponding signals to a controller (e.g., controller 2230 or pump station 2240) to perform a fluidic action (e.g., inject contrast from a catheter, provide aspiration from a catheter), or to move one or more of the hubs (724, FIG. 21), (1400, FIG. 64) axially to correspondingly move an attached elongated devices (e.g., a catheter, a guidewire) axially, or to cause one or more hubs to move an attached elongated device rotationally around its longitudinal axis. The interface 2235 can also be configured to receive control information from a user located locally (e.g., for a fluidic action or to control movement of the hubs and coupled to interventional devices, and to provide information (status, images, etc.) to a local user. The interface 2235 can include multiple interfaces. For example, one or more displays and displaying information relating to the robotic catheter system, the medical procedure, and/or the patient. The interface 2235 can also include one or more user input devices, for example, switches, buttons, touchscreen controls, etc.

The interface 2235 can also be configured to communicate information to the remotely located control system 2210. The communicated information can be related to a received control action, fluidic information, catheter position information, status information, images or video, audio and other communications from the robotic system or users located locally with the patient, and any other information that may be needed to control the robotic catheter system from the control system 2210. The interface 2235 can also be configured to receive inputs from users of the robotic catheter system located with the patient.

The system controller 2220 can include pump station 2240 for performing fluidic-related actions, and a controller 2230 configured for processing user inputs received locally or from the control system 2210, and processing sensor information, and controlling the pump station 2240 and other portion of the robotic control system to perform medical procedures based on the user inputs and the sensed information, including providing saline, contrast, and vacuum to the hubs. In some embodiments, the system controller 2220 can also control providing saline to a femoral sheath.

The robotic catheter system illustrated in FIG. 21 can include actuatable components of a fluidics management system that are movable, as controlled by a controller, to align fluid communication channels to provide saline, contrast, and vacuum from a saline, contrast, and vacuum source (respectively) to hubs 724a-724c, and including certain sensors that are configured to sense a condition related to providing provide saline, contrast, and vacuum to the hubs 724a-724c and provide the sensed information to a controller. The controller can be configured to use the sensed information, user inputs, and/or stored information to control actions of the fluidics system to perform a medical procedure. In various embodiments, a pump station 2240 may include a controller to control actuators of the pump station 2240 to perform fluidic-related actions (e.g., provide saline, contrast, and vacuum to the hubs 724a-724c). In other embodiments, controller 2230 and/or system controller 2220 can be configured to control actuators and other components of the pump station 2240 to perform fluidic-related actions. Many components and systems of the robotic catheter system may not be illustrated in FIG. 21 for clarity of this illustration (for example, a hub axial drive system, check valves, a catheter rotational system, controllers of the remote control system 2210, etc.).

A cassette configured to be releasably attached to the pump station can include all or part of the saline subsystem 706, the contrast subsystem 708, and the vacuum subsystem 710. A determination of what is disposable may be based on contact or near contact with patient materials (cells, blood, removed clots, etc.). In some embodiments, the cassette and its components are disposable, and the pump station 702 and its components are non-disposable (e.g., capital equipment). In an example of a saline subsystem 706, a pump station 702 can include saline weight sensor 750 and a saline drip rate sensor 759, peristaltic pumps actuators 763a-763d, and a saline/contrast valve actuator 767, and a cassette 704 can include a saline level detector 745, peristaltic pumps 762a-762d, and a saline/contrast valve 766 (FIG. 15). In an example of a contrast subsystem 708, a pump station 702 can include contrast intake valve actuator 808, contrast pump actuator 815, contrast valve actuators 824a-824c, and air column detector 806, and the cassette 704 can include contrast valves 822a-822c, contrast pump 810, and contrast intake valve 807 (e.g., FIG. 16A, 16B). In an example of a vacuum subsystem 710, a pump station 702 can include vacuum pump 888, vacuum regulator 890, vacuum control valve actuators 876a-876c, and flow sensor 880 (e.g., an ultrasonic flow sensor), and a cassette 704 can include a vacuum regulator valve 877, a vacuum pressure sensor 871, a clot pod sensor 932, and vacuum control valves 874a-874c. In various embodiments, pump station 702 and the cassette 704 can include additional components or fewer components. Also, in some embodiments, certain components illustrated and/or described herein as being part of a cassette can be located in a pump station, and certain components illustrated and described herein as being a part of, or supported by a cassette, can be located in a pump station.

In FIG. 21, the components shown in solid lines represent actuatable components and sensors, where the actuatable components can be controlled directly or indirectly by a controller, and the sensors provide information to a controller. Components shown in dashed lines are not sensors and not actuatable components (e.g., ports S1-S4, C1-C3, V1-V3; a saline chamber, a vacuum canister, a femoral sheath). In this embodiment, actuatable components of saline subsystem 706 can include peristaltic pump actuators 763a-763d and a saline/contrast valve actuator 767 that can be operated to position saline/contrast valve 766 (FIG. 15) in an first or second position to open or close a fluid communication channel between the saline subsystem 706 and the contrast subsystem 708; and sensors of the saline subsystem 706 can include saline weight sensor 750, saline level detector 745 that senses saline level in saline chamber 754, and saline drip rate sensor 759. In this embodiment, actuatable components of the contrast subsystem 708 can include contrast intake valve actuator 808, contrast pump actuator 815, and contrast valve actuators 824a-824c; sensors of the contrast subsystem can include air column detector 806. In some embodiments, the contrast subsystem may comprise a plurality of air column detectors 806a, 806b. In this embodiment, actuatable components of the vacuum subsystem 710 can include vacuum pump 888, vacuum regulator 890, vacuum regulator valve 877, and vacuum control valve actuators 876a-876c; sensors of the vacuum subsystem can include vacuum pressure sensor 871, clot pod sensor 932, and flow sensor 880 (e.g., an ultrasonic flow sensor).

The fluidics system also can include channels and components in the one or more hubs 724. For example, as illustrated in the embodiments of FIGS. 18 and 19. Examples of actuatable components related to a hub that can be actuated by a controller for administering fluids or providing vacuum are also illustrated in FIG. 21. In this embodiment, a robotic catheter system includes three hubs 724a-724c that have catheters coupled thereto, and a fourth hub 724d that has a guidewire coupled thereto. In some embodiments, the guidewire is releasably coupled to the fourth hub 724d. Hubs 724a-724c include a hemostasis valve 928 and a valve 923 (e.g., a three-way valve) that is used to couple a catheter lumen to a fluid or vacuum. Hubs 724a-724d have driving mechanisms 2202 that can function to move the hubs (and an interventional device coupled thereto) forward and back along a common line ("axially"). Hubs 724a-724d also have driving mechanisms 2204 that can rotate an interventional device coupled to the hub, around its longitudinal axis. In various embodiments, the driving mechanisms in a hub 724 can couple with a driving mechanism outside of the hub (e.g., magnetically, mechanically, etc.) such that the drive mechanisms interact to move the hub axially and rotate the interventional device.

FIG. 22 illustrates a representation of an embodiment of a cassette 704 and a pump station 702 illustrating certain components of the cassette (e.g., valves, electrical connections, etc.) and corresponding components (e.g., motors, electrical connections, etc.) of the pump station. The illustrated components in the cassette and pump station illustrated in FIG. 22 can correspond to the components described here in and illustrated in, for example, FIGS. 2-4, 14-17, 20, and 21, and many of the other figures.

Figure 23:
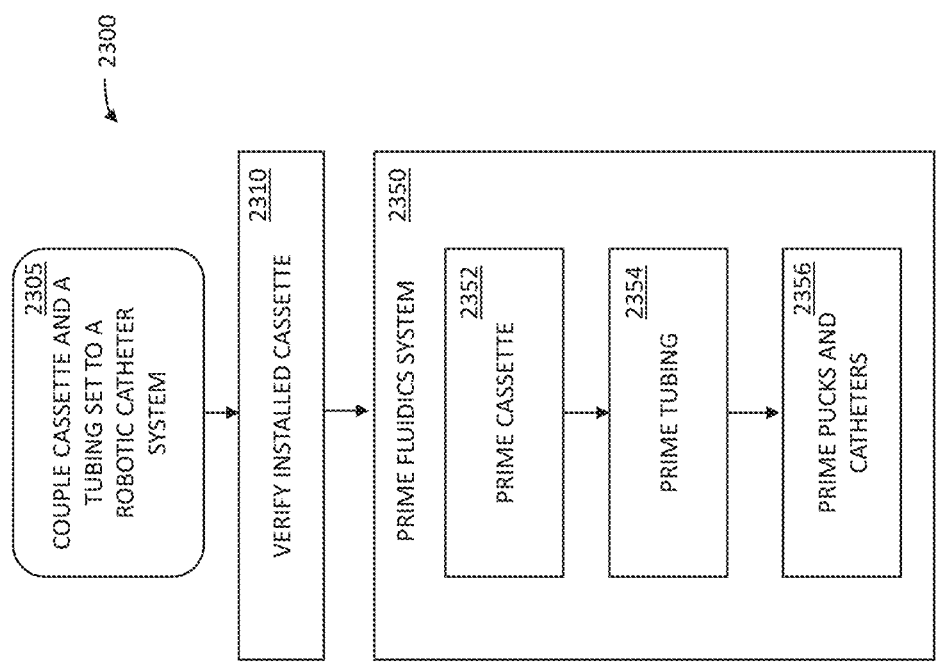
FIG. 23 illustrates a process for priming a fluid communication system including priming fluid communication channels in a cassette, a tubing set, and hubs and catheters coupled to the hubs.
Figure 24:
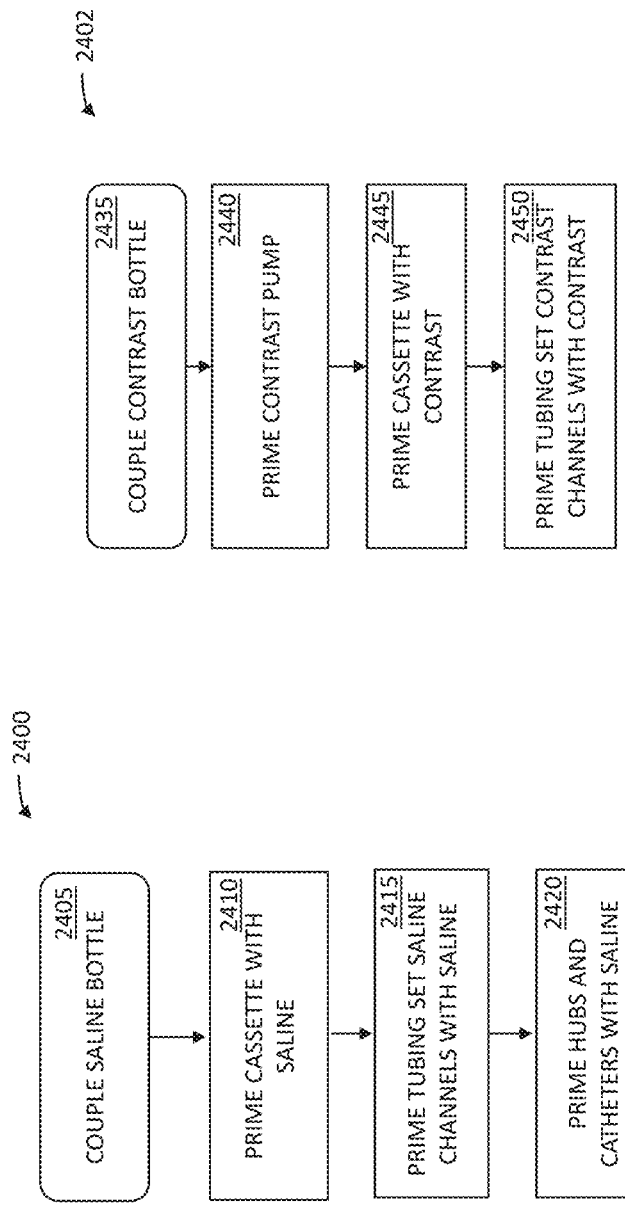
FIG. 24A illustrates a process for priming a portion of a fluid communication system including priming fluid communication channels in a cassette, tubing/tubing set, hubs, and catheters coupled to the hubs, with saline.
FIG. 24B illustrates a process for priming a portion of a fluid communication system including priming fluid communication channels in a cassette and a tubing set with contrast.

FIG. 23 is a flow diagram illustrating a fluidics process 2300 which can be performed using the robotic catheter system. At block 2305, a cassette and a tubing set is coupled to the robotic catheter system. In some embodiments, the cassette can be the cassette 704 illustrated in FIG. 22, and the tubing set can be the tubing set 716 illustrated in FIG. 20. Although the embodiments herein generally describe the cassette being coupled to a pump station, in alternate embodiments the cassette can be coupled to any such system configured to provide actuation of actuatable components of the cassette. For ease of reference, herein, the phrase "pump station" is used to indicate a system or a pump station that is configured to receive a cassette and provide actuation of actuatable components of the cassette and connect with sensors of the cassette, as needed. For example, a pump station or other system configured with actuators illustrated in FIG. 22. Coupling a cassette and a tubing set to a pump station can be done automatically in certain embodiments, coupling the cassette to the pump station can also be done manually.

At block 2310, the process verifies the cassette is installed. Verification can include verifying the cassette is installed properly such that actuators of the pump station are coupled to actuatable components in the cassette and sensors are coupled to connectors (e.g., electrical connectors) of the pump station configured to receive signals from the sensors. Verification can include verifying information about the cassette. For example, the type of cassette, that the cassette is compatible with the pump station, that the cassette is a genuine cassette from a certain manufacturer, etc. In an example, verification can be performed by a user. In another example, verification can be performed by a controller that receives information relating to the cassette and verifies the cassette based on stored information. For example, through a mechanical or electrical component of the cassette (e.g., an RF ID tag, a chip, a transducer, an electrical or electronic circuit, a mechanical key, and the like).

At block 2350, the fluidics process 2300 primes the fluidic system for preparing the fluidic system to operate during a medical procedure. In some embodiments, a user can prime the cassette, the tubing set, and the hubs and catheters using the robotic catheter system. For example, by providing user input controls to the interface 2235. In some embodiments, the robotic catheter system can perform fluidic operations automatically based on stored executed instructions for performing fluidic processes and input from the components of the robotic catheter system, for examples, sensors, feedback signals from actuators, and the like. Priming the fluidics system can include filling fluid communication channels of the fluidics system with saline and/or contrast to remove air in the fluid communication channels. A fluidics process 2300 may be a priming process which can include, priming a cassette 2352, priming a tubing set 2354, and priming hubs and catheters 2356. Examples of certain priming processes are described in reference to flowcharts in FIGS. 24A and 24B, and schematics of priming processes in FIGS. 25-43, which schematically illustrate processes for priming a fluid communication system that provides saline, contrast, and aspiration to one or more hubs and to the lumens of catheters coupled to the one or more hubs.

The fluid communication system (or fluidics system) can include fluid communication channels ("channels") in a cassette, one or more tubing sets, a splitter, a manifold, and/or one or more mounts and hubs to provide saline, contrast, and vacuum, from one or more saline sources, one or more contrast sources, and/or one or more vacuum sources, to one or more hubs. Portions of the fluidics system can be incorporated in other system components, for example, in mounts that are coupled to catheters. The fluid communication channels can include tubes, channels, subchannels, manifolds, valves, and other components, through which saline and contrast flow, and through which vacuum is provided, in a cassette, splitter, tubing set(s), mounts, hubs, and catheters.

For ease of reference herein, providing a fluid (saline, contrast) to a hub is used synonymously with providing a fluid to a catheter coupled to the hub, unless otherwise specifically indicated or indicated by context. Also, for case of reference herein, technology related to providing vacuum or aspiration to a mount/hub/catheter may also be described as providing a fluid to a mount/hub/catheter, unless otherwise specifically indicated or indicated by context. For example, fluid communication channels, lines, subchannels etc. may be described as providing saline, contrast, and/or vacuum to a mount/hub/catheter.

Although the embodiments herein are described with having one saline source, one contrast source, and one vacuum source, as a person of skill in the art will appreciate other embodiments may include other embodiments can include a plurality of saline sources, a plurality of contrast sources, and/or a plurality of vacuum sources. In an example, in some embodiments a saline subsystem can include multiple saline sources feeding into a single fluid communication channel to provide saline to a saline chamber. In an example, in some embodiments a contrast subsystem can include multiple contrast sources feeding into a single fluid communication channel to provide contrast to a contrast pump. Embodiments of the fluidic systems that provide saline to multiple hubs (e.g., three) and a femoral sheath and provide contrast to multiple hubs (e.g., three) may have a need for higher volumes of saline and contrast than a fluidic system that provides saline and/or contrast to a single catheter. Accordingly, having a plurality of saline sources, a plurality of contrast sources, and/or a plurality of vacuum sources may be advantageous for redundancy purposes to increase the safety of medical procedures (e.g., a vacuum pump becoming inoperative), and also obviate changing to a new contrast or saline source during a long medical procedure.

FIGS. 24A and 24B illustrate processes for priming channels in a cassette, tubing set, and hubs with saline and contrast. As illustrated herein, operations for priming channels with saline and contrast can be interrelated, for example, contrast channels may first be primed with saline to remove air and then the contrast channels are primed with contrast. FIG. 24A illustrates a process 2400 for priming a portion of a fluid communication system that provides saline to one or more hubs. At block 2405 a container (e.g., bag, bottle, or other container) containing saline is coupled to a saline subsystem to be in fluid communication with the saline subsystem. Although block 2405 may be done manually, in some embodiments a controller controls a fluidic system to perform this operation. At block 2410, the process 2400 primes a cassette with saline. At block 2415, the process 2400 primes a tubing set with saline. At block 2420, the process 2400 primes hubs and catheters with saline. In process 2402, at block 2435 a container (e.g., bag, bottle, or other container) containing contrast is coupled to a contrast subsystem to be in fluid communication with the contrast subsystem. Although block 2435 may be done manually, in some embodiments a controller controls a fluidic system to perform this operation. At block 2440, the process 2402 primes a contrast pump with contrast. At block 2445, the process 2402 primes a cassette with contrast. At block 2450, the process 2402 primes a tubing set contrast channels hubs with contrast. Examples of these operations are illustrated in FIGS. 25-43.

Figure 25:
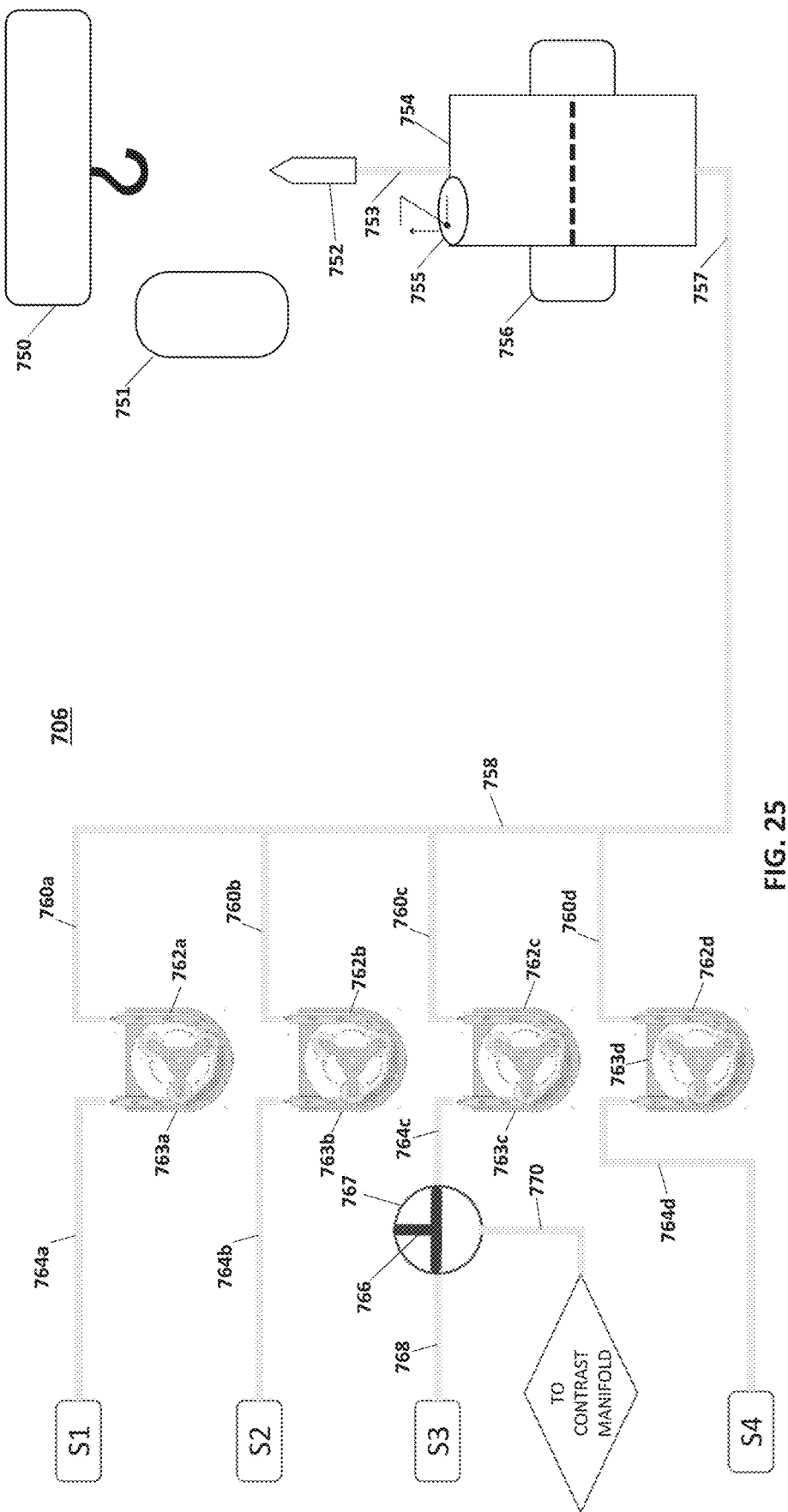
FIG. 25 illustrates an example of a saline subsystem 706 in a dry configuration where a saline bag 751 is not yet coupled to the saline subsystem 706.

FIG. 25 illustrates an example of a saline subsystem 706 in a dry configuration where a saline bag 751 is not yet coupled to the saline subsystem 706. The saline subsystem 706 illustrated in FIG. 25 has the same components as the saline subsystem 706 described in FIG. 15. In the fully dry (per-prime) configuration, the channels and components of the saline subsystem 706 do not contain saline, instead containing, for example, air or an inert gas. The positioning of these components, and other components of the saline subsystem 706 can be determined by the controller to ensure they are correctly aligned prior to beginning the priming operation.

FIG. 26 illustrates a configuration of the saline subsystem 706 after saline bag 751 has been coupled to saline subsystem 706 by the contrast spike 752 such that saline from the saline bag 751 begins to flow into the saline chamber 754 via saline tube 753. Saline flows into the saline chamber 754, air escapes from the chamber through air vent 755 which includes a check valve configured so that there passes through the air vent 755 in one direction. Saline level in the saline chamber 754 is sensed by chamber level detector 756 which provides this information to a controller. In this configuration, the peristaltic pumps 762a-762d have not yet been activated and the saline/contrast valve 766 is positioned to connect line 764c to port S3.

Figure 27:
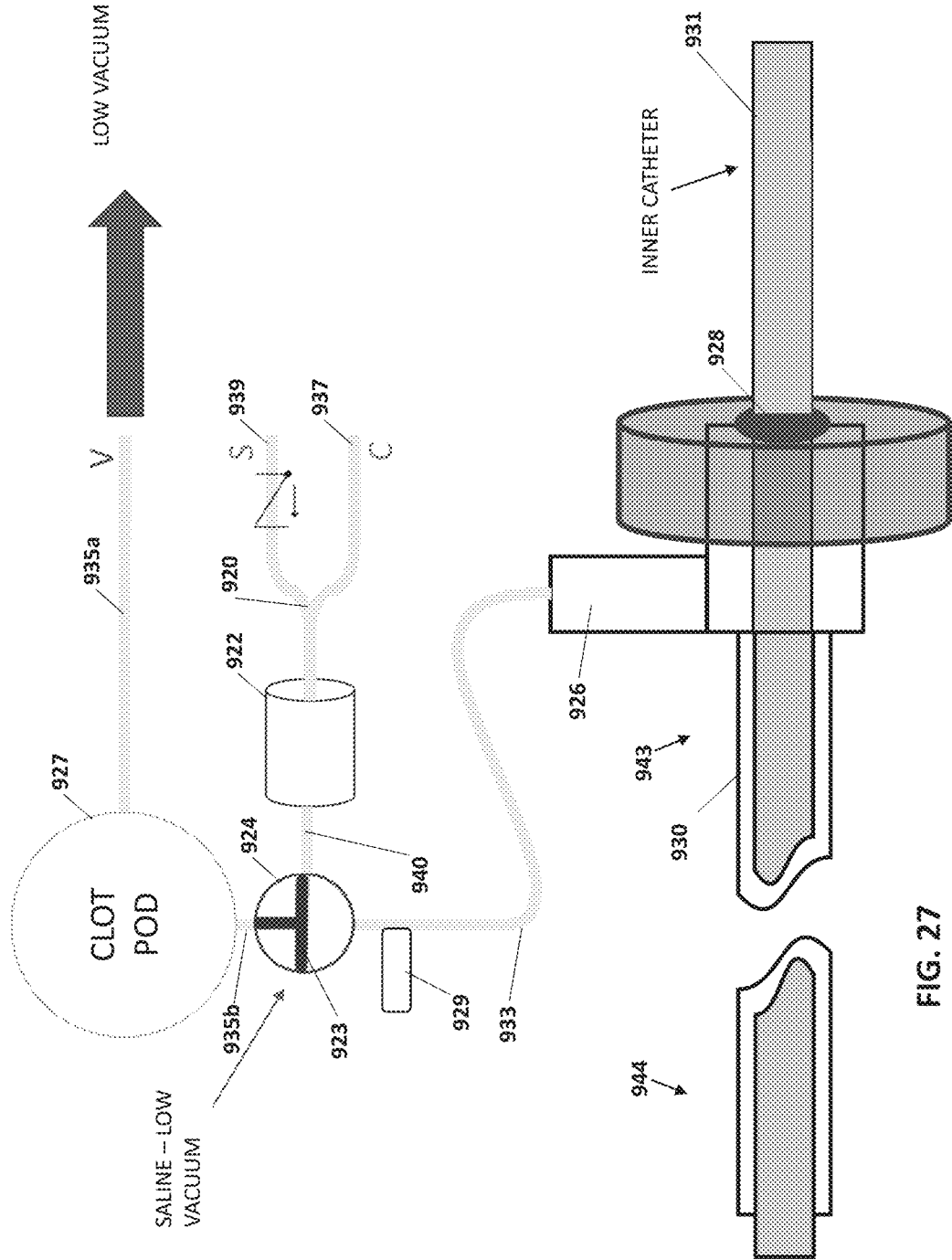
FIG. 27 illustrates an example of a hub, according to some embodiments.

FIG. 27 illustrates an example of a hub (similar to FIG. 19). As part of the saline priming process, the three-way valve actuator 924 positions three-way valve 923 to connect saline tube 939 to the aspiration tube 935, and the vacuum subsystem is controlled to provide vacuum on the aspiration tube 935. Connecting the saline tube 939 to the aspiration tube 935 facilitates priming the cassette and tubing set with saline as it provides for the flow of saline through the cassette and tubing set. FIG. 27 illustrates this configuration for a single. In configurations of systems having multiple hubs, a similar configuration can be arranged at each hub such that all the hubs have their saline minds in fluid communication with a vacuum line.

Figure 28:
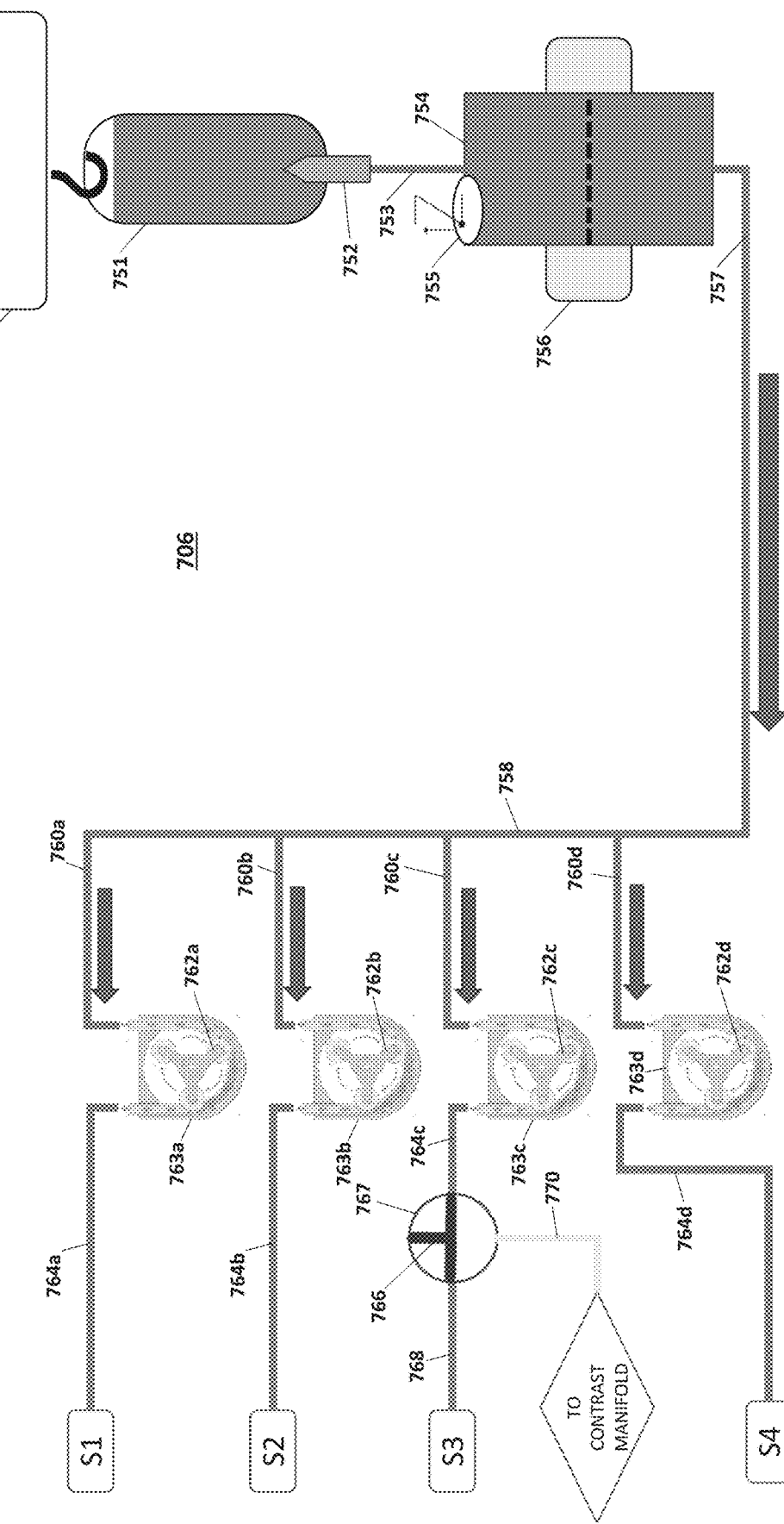
FIG. 28 illustrates a configuration where a controller actuates peristaltic pumps to prime channels of the saline subsystem in the cassette with saline after the fluid communication system has been configured with an exhaust path for saline.

After the fluid communication system has been configured with an exhaust path for saline, the controller actuates peristaltic pumps 762a-762d to prime channels of the saline subsystem in the cassette with saline, as illustrated in FIG. 28. The saline/contrast valve 766 is still positioned to connect line 764c to port S3. In this example, actuation of the peristaltic pumps 762a-762d provides saline to flow out of the saline chamber 754 through line 757 to the saline manifold 758, and then to lines 760a-760d, through the peristaltic pumps 762a-762d, through lines 764a-764d to ports S1-S4 (which are coupled to a tubing set and hubs) such that the saline manifold 758 and lines 757, 760a-760d, 764a-764d, and 768 fill with saline. The controller continues to actuate the peristaltic pumps 762a-762d to provide a continuous flow of saline through these lines.

Figure 29:
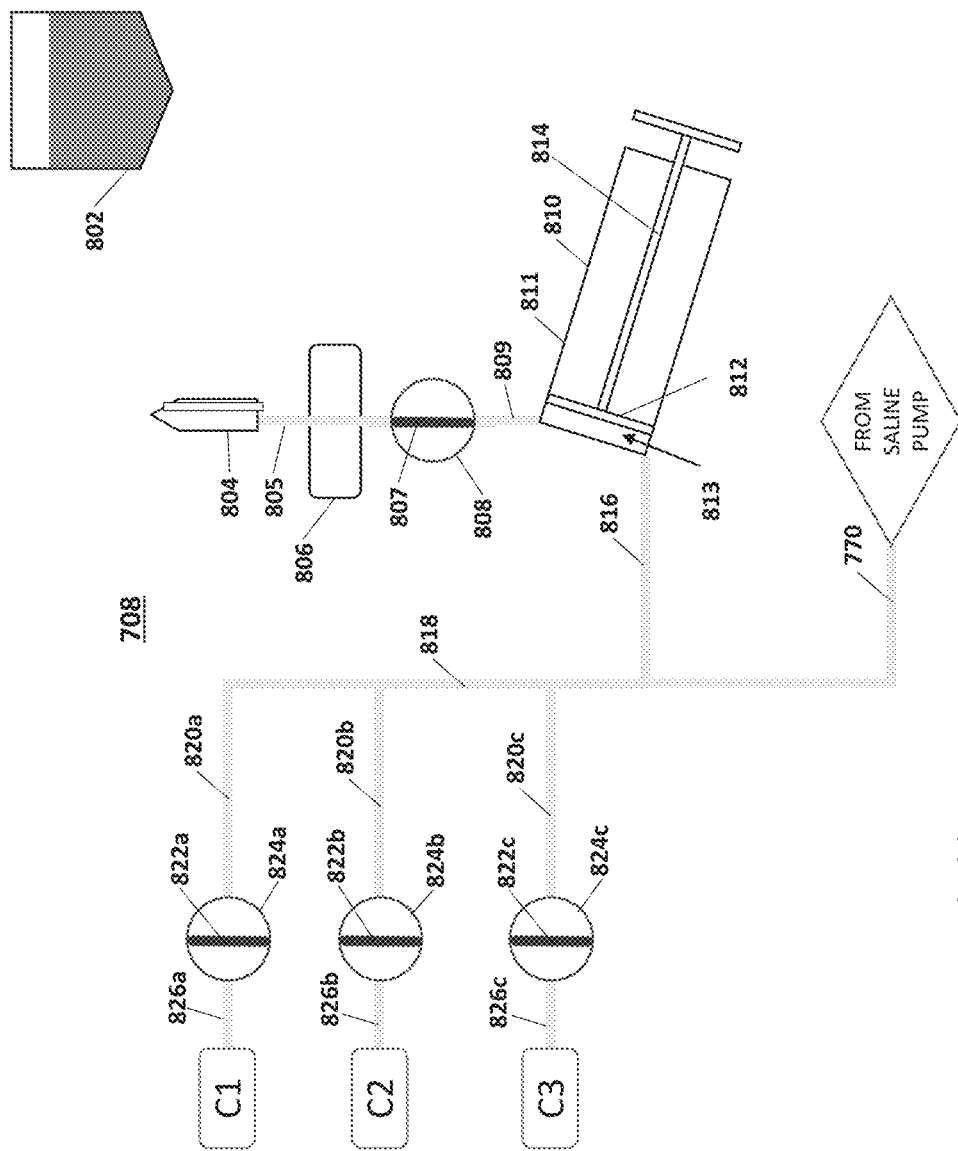
FIG. 29 illustrates an example of a contrast subsystem in a configuration before a contrast container is coupled to the contrast subsystem.

FIG. 29 illustrates an example of a contrast subsystem 708 in a configuration before a contrast container 802 is coupled to the contrast subsystem 708. In the fully dry (per-prime) configuration, the channels and components of the contrast subsystem 708 do not contain contrast, instead containing, for example, air or an inert gas. In this configuration, contrast control valves 822a-822c are in the closed position and a contrast intake valve 807 positioned upstream from the contrast pump 810 is in an open position. The positioning of these components, and other components of the contrast subsystem 708 can be determined by the controller to ensure they are correctly aligned prior to beginning the priming operation.

Figure 30:
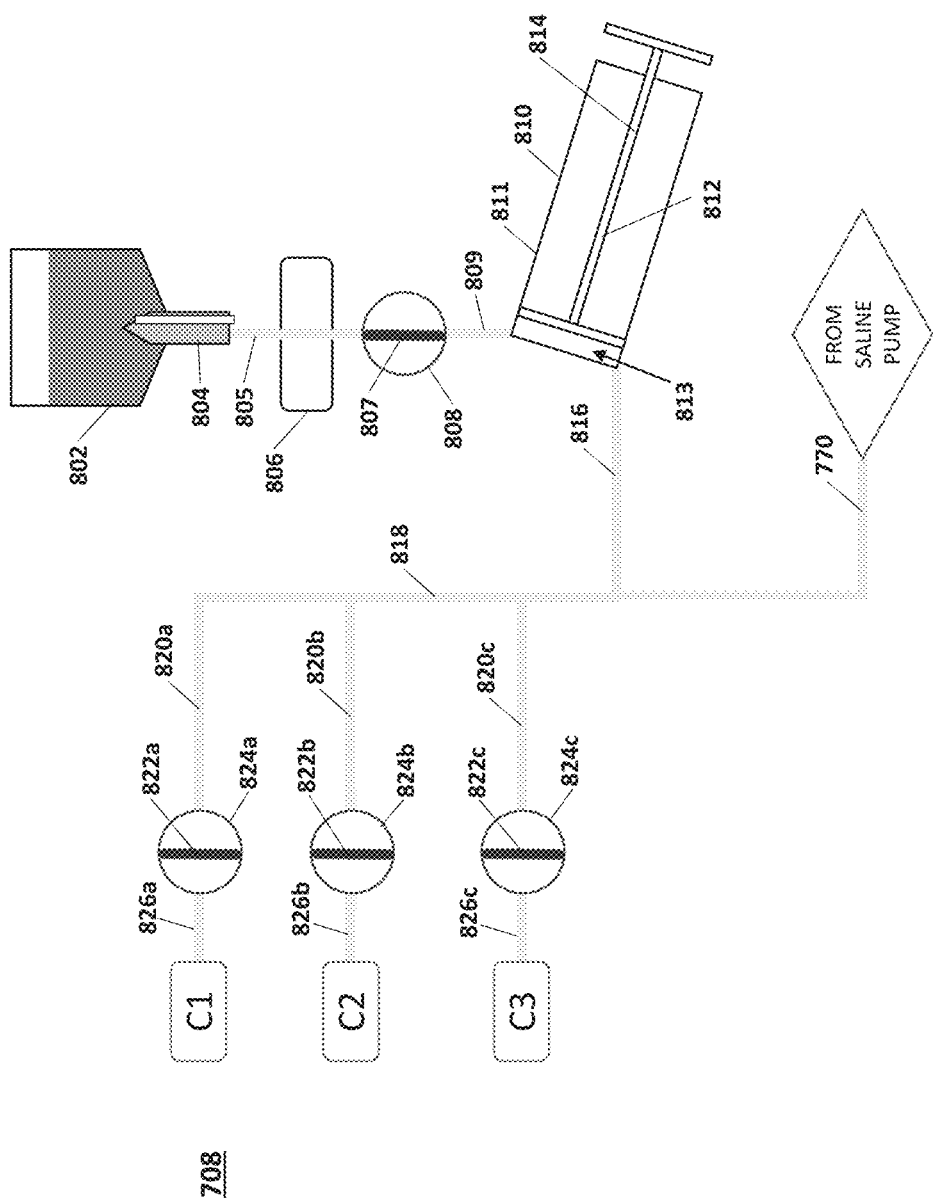
FIG. 30 illustrates a contrast subsystem, illustrated in FIG. 29, now coupled to the contrast container.

FIG. 30 illustrates the contrast subsystem 708 of FIG. 29 now coupled to the contrast container 802. In some embodiments, the user can perform the operation of coupling the contrast container 802 to the contrast subsystem 708. In other embodiments, a controller can control to couple the contrast container 802 to the contrast subsystem 708. For example, the contrast container 802 can be positioned in proximity to the pump station (e.g., attached to the pump station, positioned in a compartment of the pump station, etc.), and a controller can operate the pump station to couple line 805 to the contrast container 802 ("spike" the contrast container 802).

Figure 31:
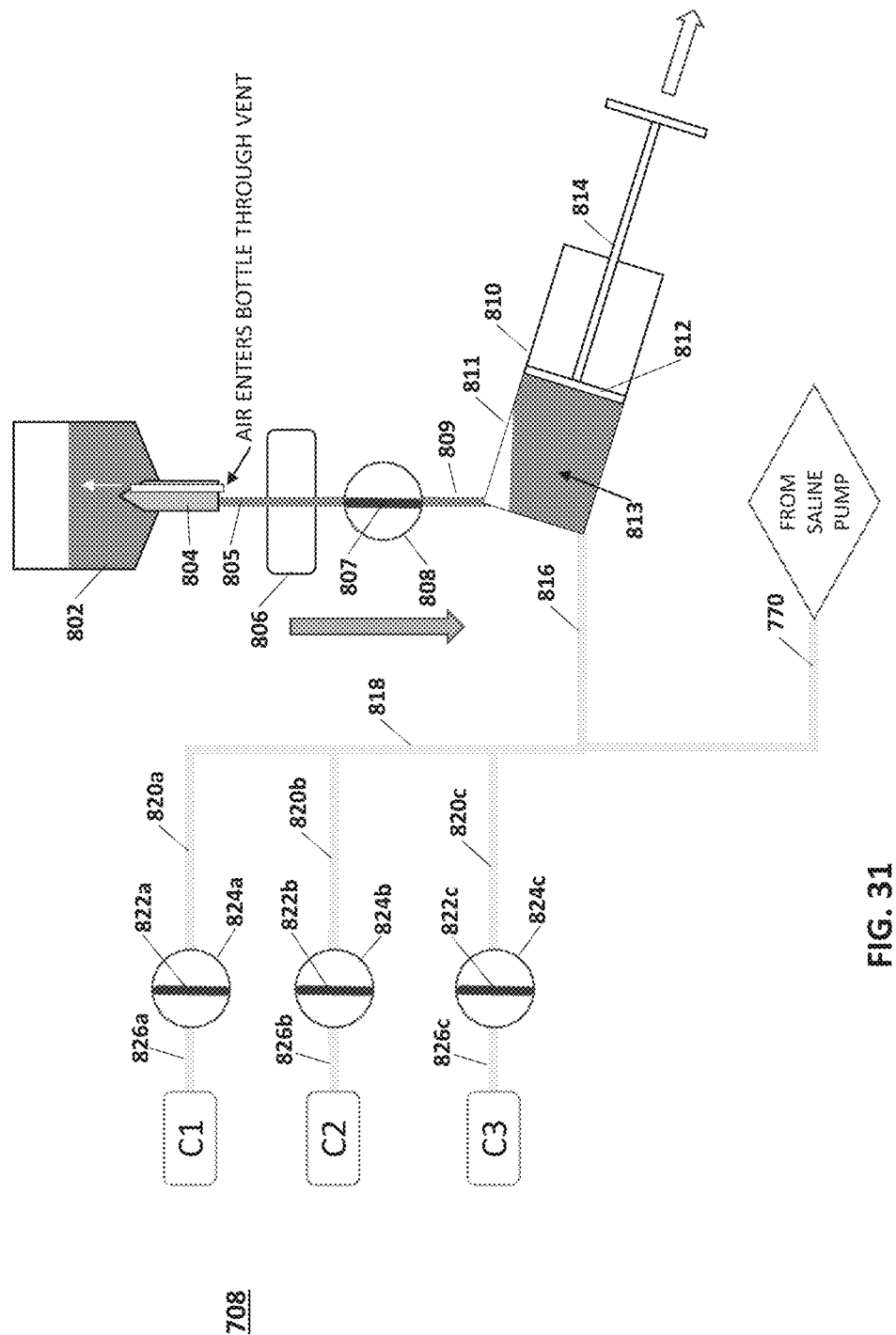
FIG. 31 illustrates an example of a contrast pump being actuated to fill a portion a chamber in the contrast pump with contrast.

Referring now to FIG. 31, the contrast pump 810 is actuated to fill a portion of the contrast chamber 13 with contrast. In this example, an actuator of the pump station is coupled to and moves the movable member 814 to correspondingly move a movable portion 812 to increase the volume of the contrast chamber 813 and causing contrast to flow from the contrast container 802 through line 805, though a contrast intake valve 807 through line 809 and into the contrast chamber 813. In some examples, the contrast chamber 813 can be filled with contrast to about 50% of its capacity in this portion of the process. In some examples, the contrast chamber 813 can be filled with contrast to between about 20% and 80% of its capacity. Still in other examples, the contrast chamber 813 can be filled with contrast to between about 5% and 95% of its capacity. During this part of the priming process, the contrast chamber 813 may contain air and contrast. In this configuration, contrast control valves 822a-822c are closed and the saline/contrast valve 766 (FIG. 28) is also aligned such that the saline subsystem 706 and the contrast subsystem 708 are not connected.

Figure 32:
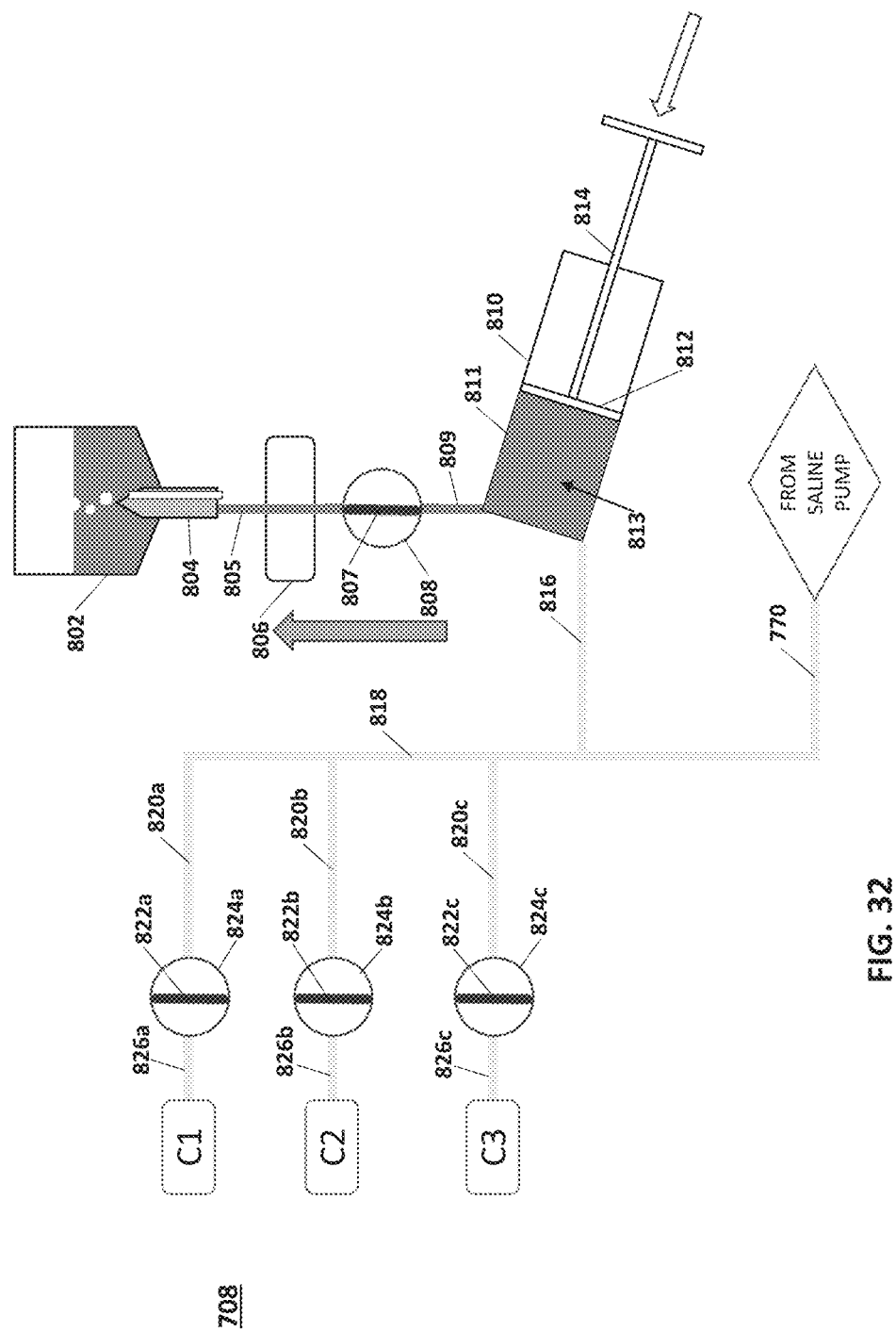
FIG. 32 illustrates an example of a contrast pump being actuated to push contrast and air out of the contrast chamber.

As illustrated in FIG. 32, next the contrast pump 810 can be actuated to move movable portion 812 to decrease the size (volume) of the contrast chamber 813 to push contrast and air out of the contrast chamber 813 through line 809 (a first line), contrast intake valve 807, line 805 and back into the contrast container 802 to remove all the air from the contrast chamber 813. Line 809 is coupled to the contrast chamber 813 at an upper portion of the contrast chamber 813 such that any air in the contrast chamber 813 flows out through line 809. The mixture of air and contrast flowing out of the contrast pump 810 can flow past air column detector 806 which is configured to sense air bubbles and provide information to a controller such that the controller can determine when all the air has been removed from the contrast chamber 813. In this configuration, contrast control valves 822a-822c are closed and the saline/contrast valve 766 (FIG. 28) is also aligned such that the saline subsystem 706 and the contrast subsystem 708 are not connected.

Figure 33:
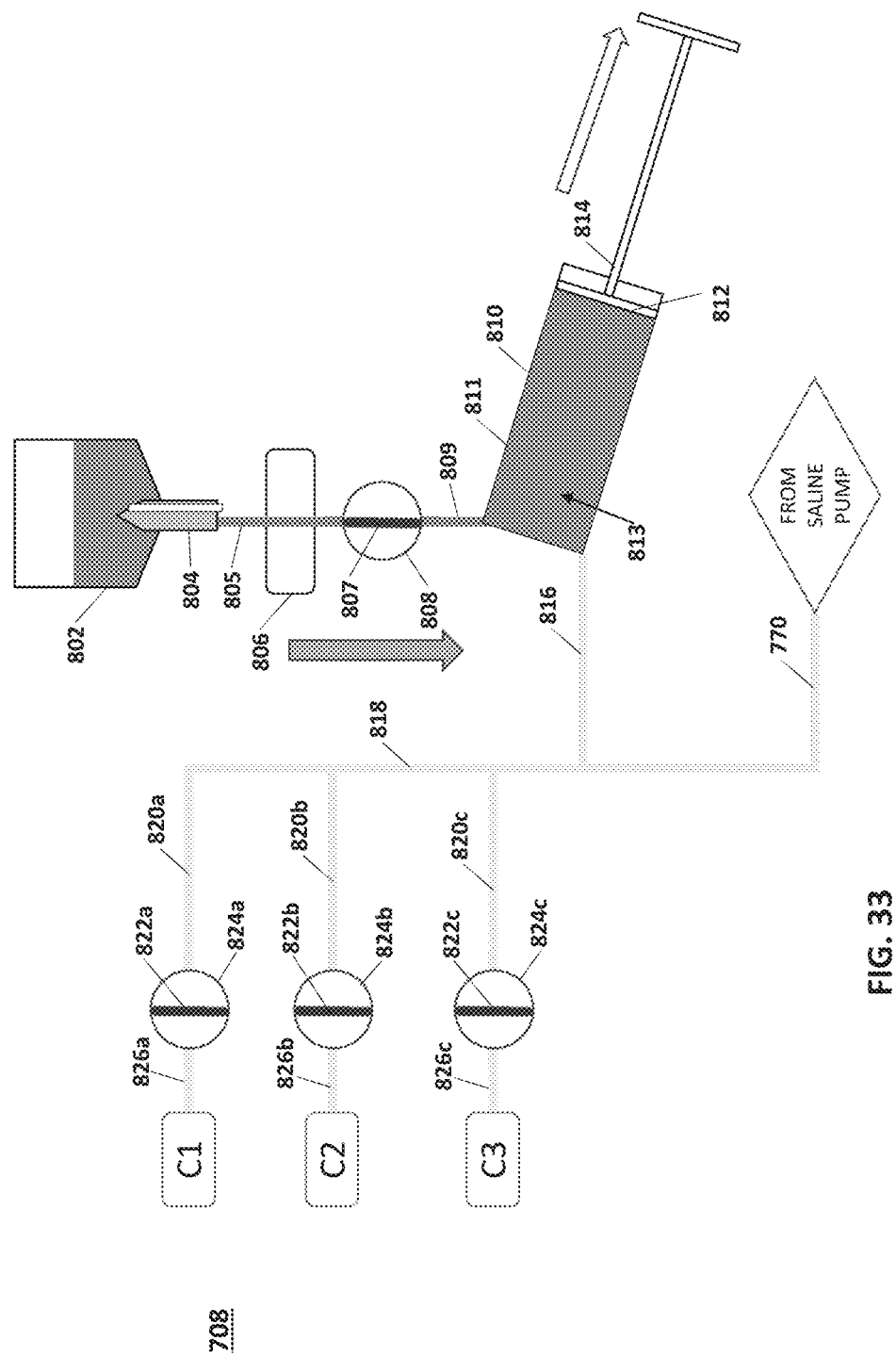
FIG. 33 illustrates an example of a contrast pump being actuated to draw contrast into a contrast chamber.

As illustrated in FIG. 33, next the contrast pump 810 can be actuated to move movable portion 812 to increase the size of the contrast chamber 813 to draw contrast through line 809 (a first line), contrast intake valve 807, line 805 into contrast chamber 813. In some examples, the contrast chamber 813 can be filled with contrast to, for example, 90% to 100% of its capacity in this portion of the process. In this configuration, contrast control valves 822a-822c are closed and the saline/contrast valve 766 (FIG. 28) is also aligned such that the saline subsystem 706 and the contrast subsystem 708 are not connected.

Figure 34:
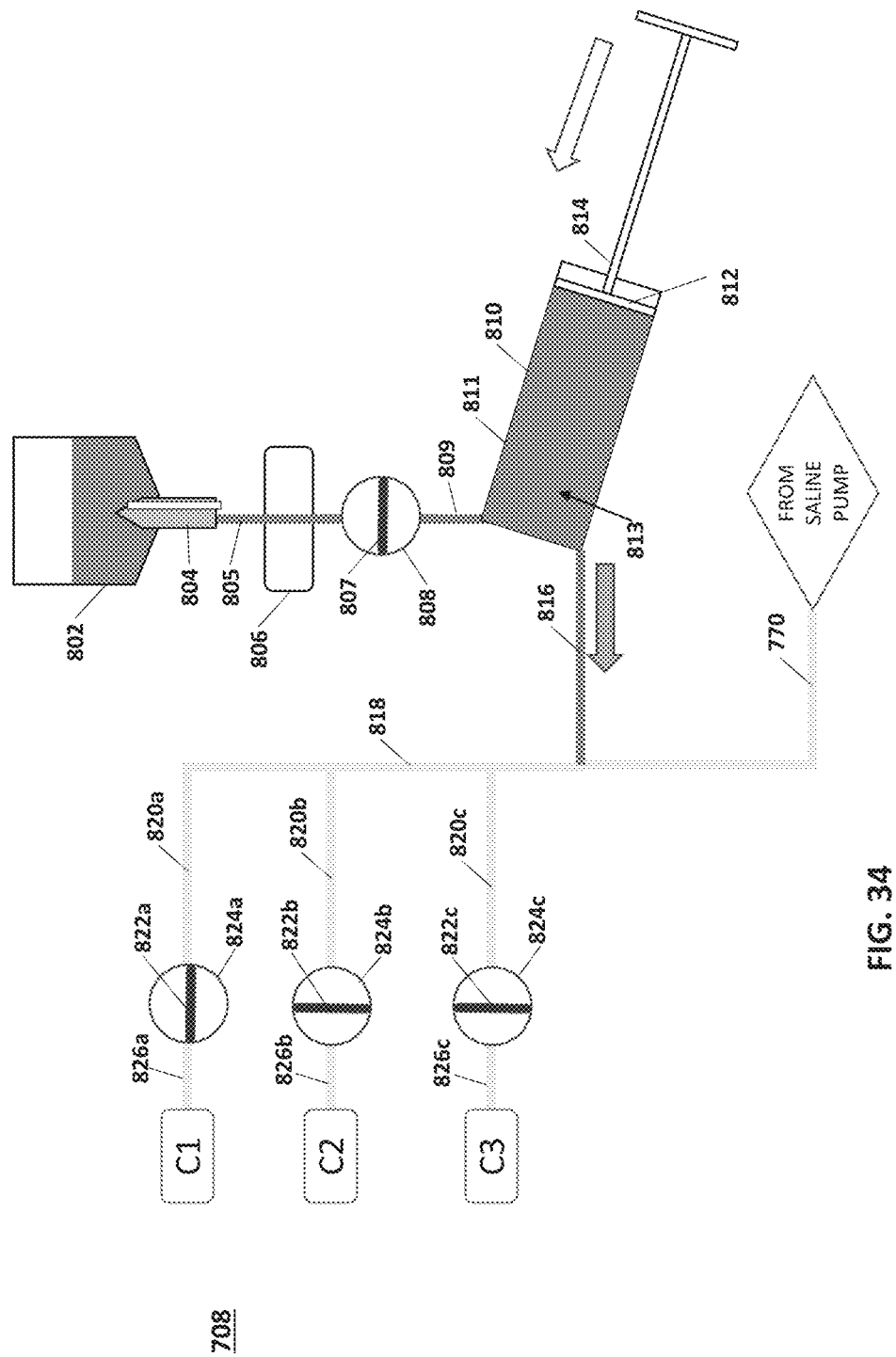
FIG. 34 illustrates an example of a contrast pump being actuated to begin to prime fluid communication channels of the contrast subsystem in the cassette.

Referring now to FIG. 34, to begin to prime the fluid communication channels of the contrast subsystem 708, contrast intake valve 807 is closed to prevent contrast flow between the contrast container 802 and the contrast pump 810, and a first contrast control valve 822a is opened to provide a fluid communication channel from the contrast pump 810 to port C1. The contrast pump 810 is then actuated to push contrast into line 816 to the contrast manifold 818. In this configuration, the saline/contrast valve 766 (FIG. 28) is still aligned such that the saline subsystem 706 and the contrast subsystem 708 are not connected.

Figure 35:
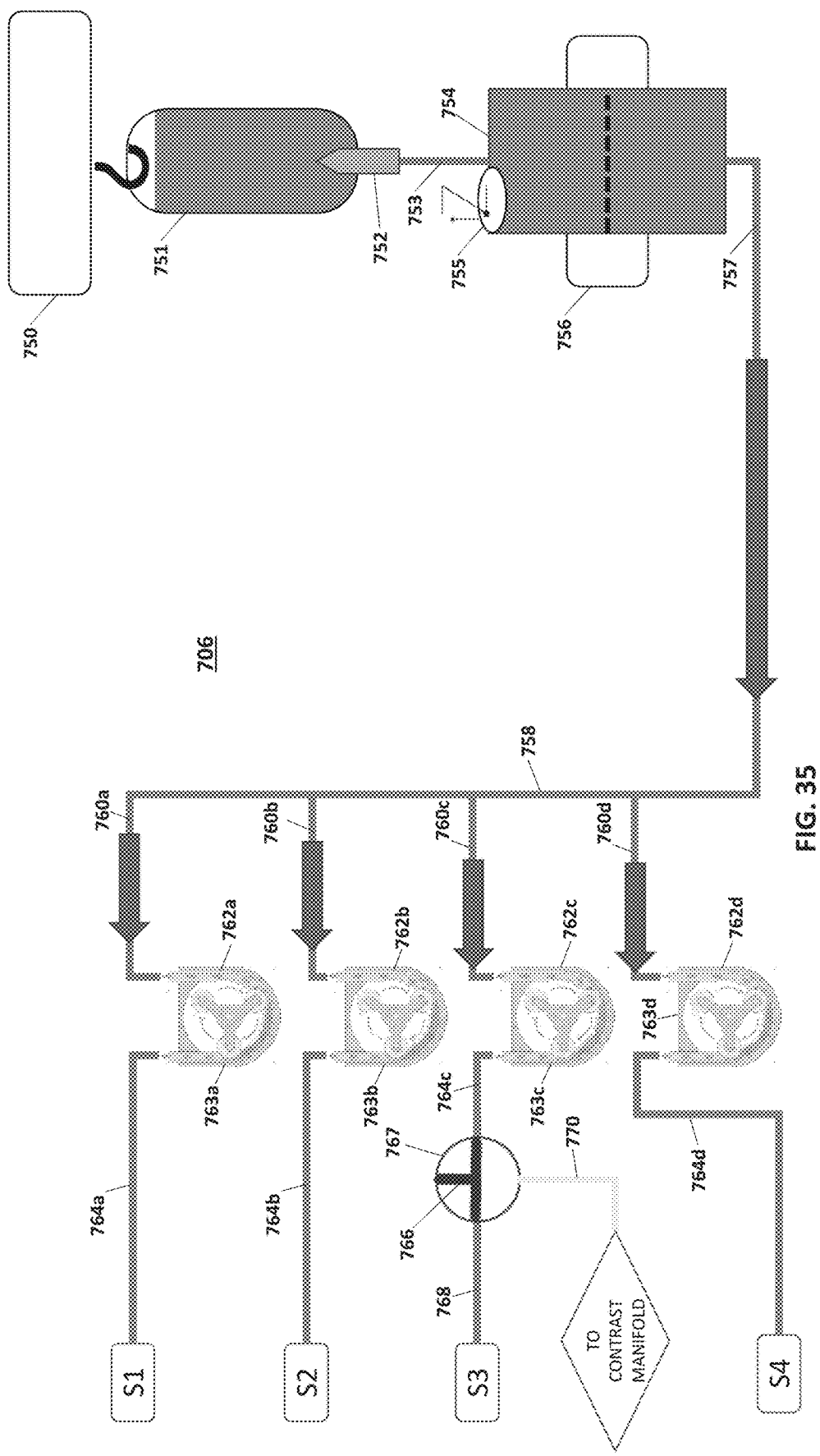
FIG. 35 and FIG. 36 illustrate another portion of a priming process where a plurality of peristaltic pumps of a saline subsystem are actuated to prime a saline communication channel between a cassette and a hub.
Figure 36:
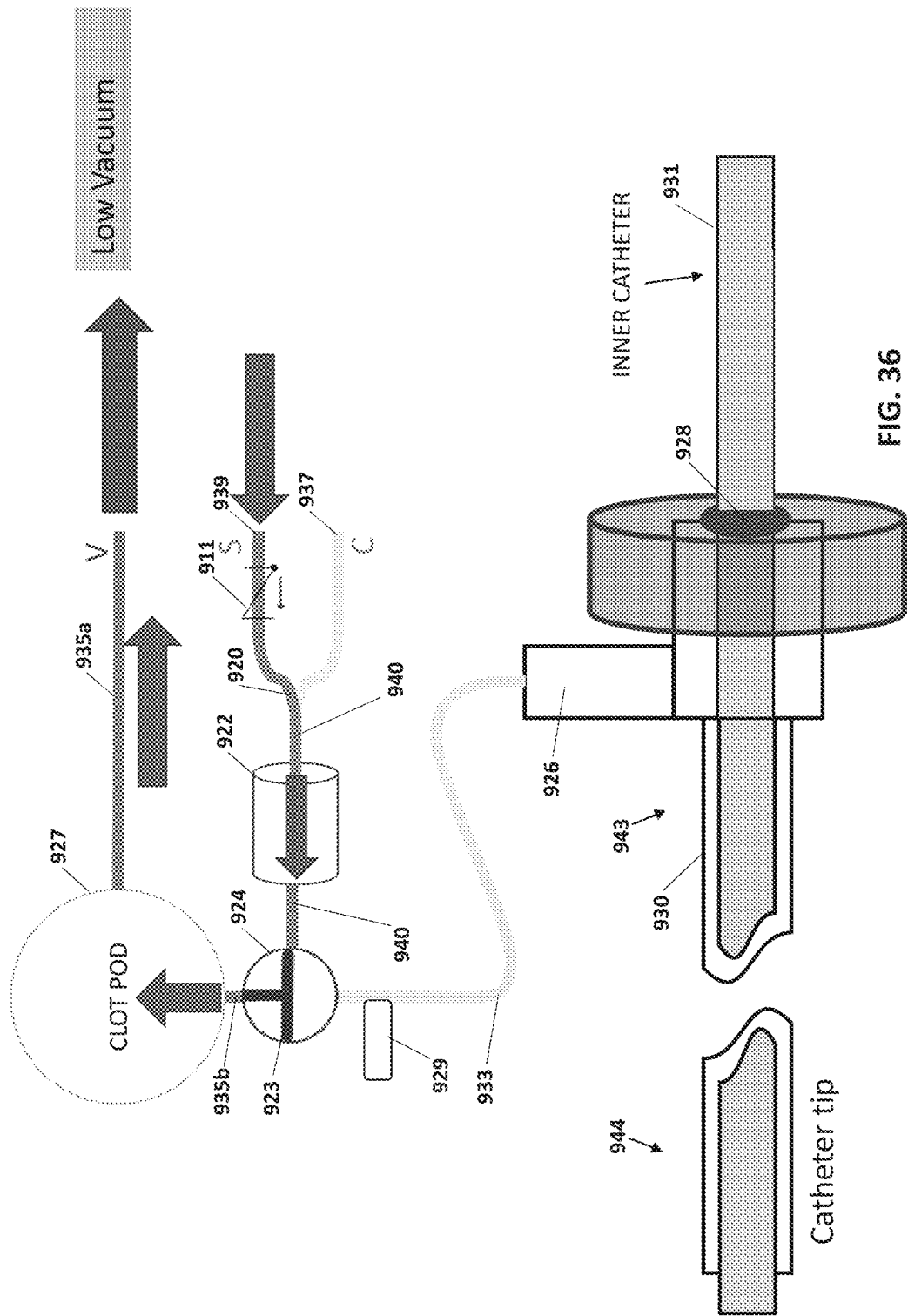
Figure 53:
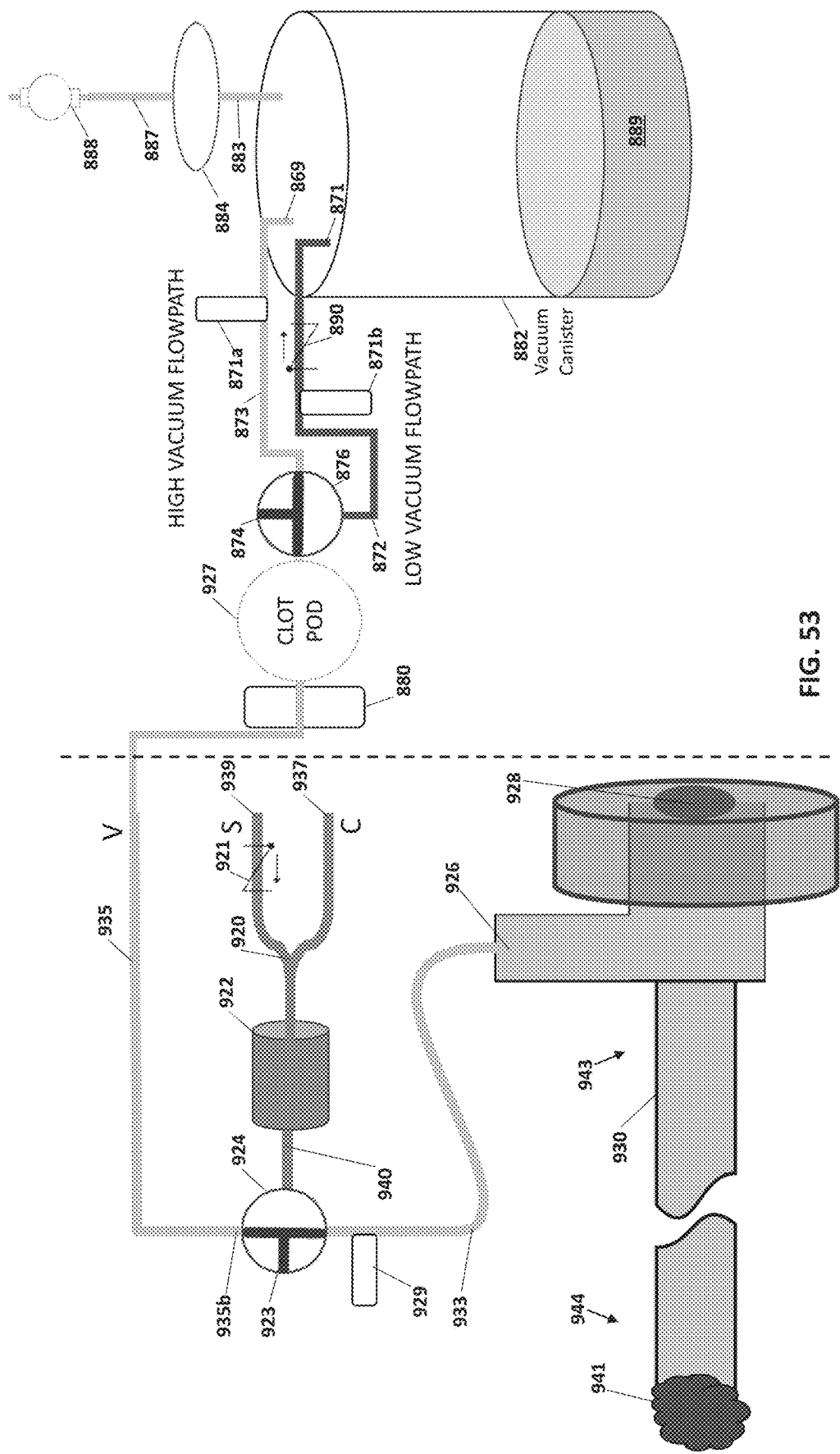
FIG. 53 illustrates an alternative embodiment from the one shown in FIG. 53, where the clot pod is positioned closer to the vacuum canister than in the configuration illustrated in FIG. 52 (e.g., the clot pod positioned in the cassette or in a portion of the tubing set).

FIGS. 35 and 36 illustrate another portion of the priming process where all the peristaltic pumps 762a-762d are running, priming a saline communication channel between the cassette and a hub. FIG. 35 illustrates a configuration to provide saline flow from the saline chamber 754 through line 757, the saline manifold 758, through lines 760a-760d, the peristaltic pumps 762a-762d, and lines 764a-764d and line 768 to ports S1-S4. In the configuration shown in FIG. 35, the saline/contrast valve 766 (FIG. 28) is aligned such that the saline subsystem 706 and the contrast subsystem 708 are not connected. As illustrated in FIG. 36, in an example of a hub configuration, three-way valve 923 is aligned to connect saline tube 939 to an aspiration tube 935 which is providing a low vacuum. In this configuration, saline flows through a saline tube 939 of the tubing set, the check valve 921, the wye connector 920, the air bubble filter 922, the saline/contrast tube 940, the three-way valve 923, the line 936, to the aspiration tube 935. In this example, the saline also flows through clot pod 927 that is positioned between line 936 and the aspiration tube 935. In other examples, the clot pod 927 can be positioned further upstream closer to a vacuum canister, or positioned at another location. In some embodiments, as shown in FIG. 53 for example, the line 936 may be part of the aspiration tube 935.

Figure 38:
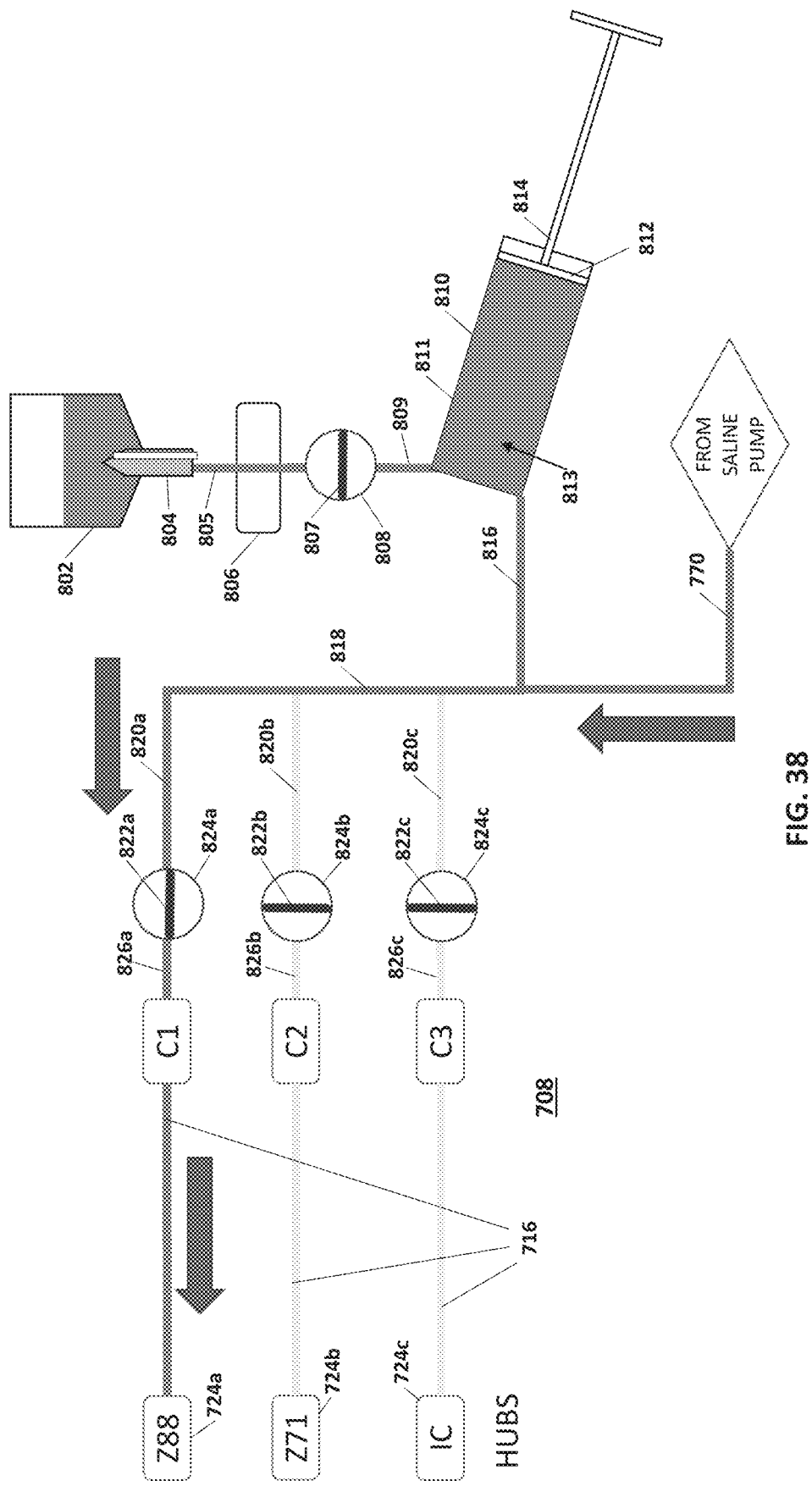
FIG. 38 illustrates an example of a configuration for priming fluid communication channels that provide contrast to the hubs.
Figure 39:
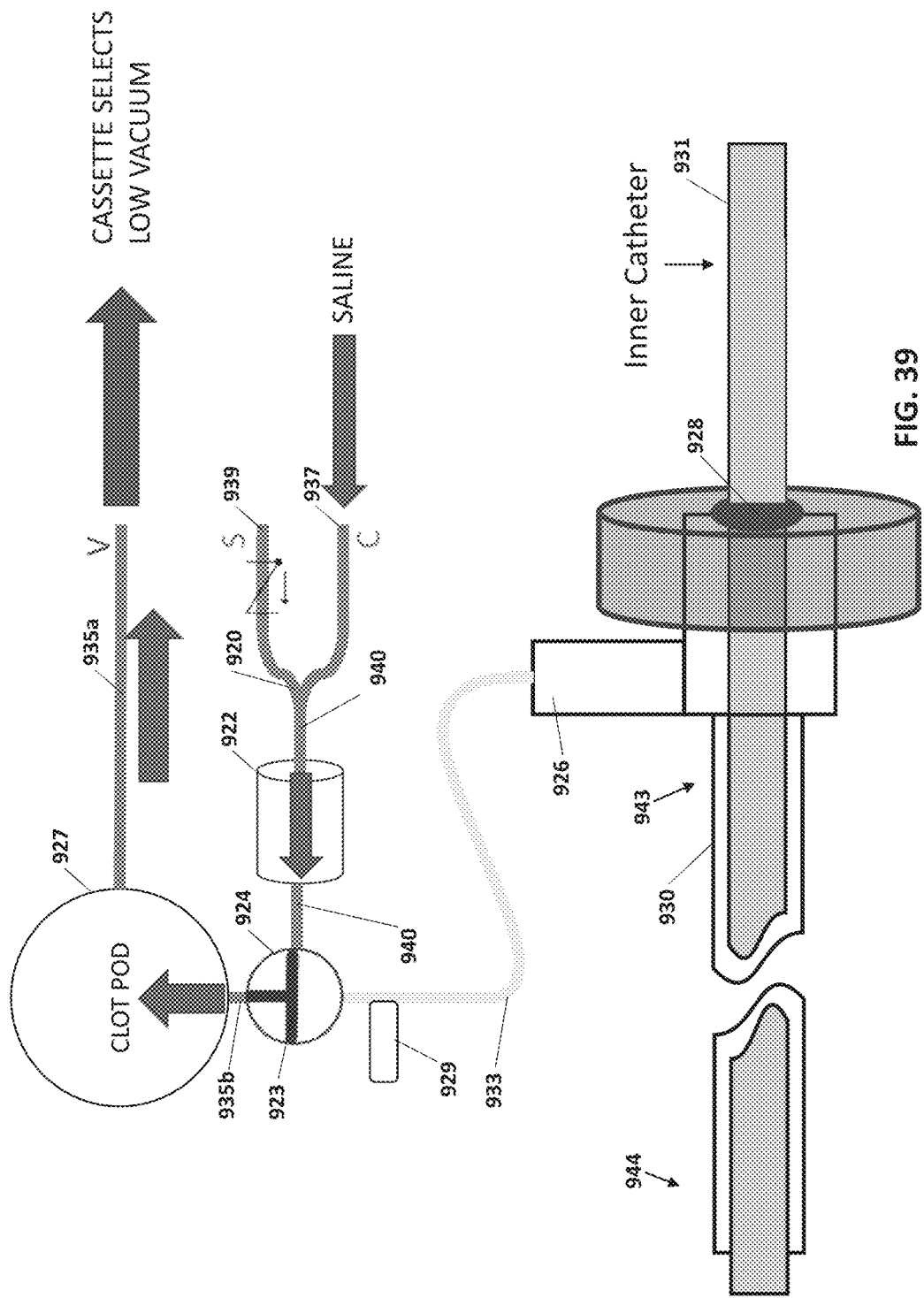
FIG. 39 illustrates priming fluid communication channels that provide contrast to a catheter from a contrast subsystem with saline.

As shown in FIG. 37, while all the peristaltic pumps 762a-762d are running, the saline/contrast valve 766 can be actuated to connect the saline subsystem 706 to the contrast subsystem 708 to prime fluid communication channels in the contrast subsystem 708 with saline. In this example, the saline/contrast valve 766 can be positioned to connect line 764c to line 770, which is connected to the contrast manifold 818, as illustrated in FIG. 38. As illustrated in FIG. 38, the contrast lines are primed with saline. In this example, the contrast lines are primed with saline one at a time. In this example configuration, the saline provide to the contrast manifold 818 comes from a single peristaltic pump 762c and the volume of saline provided by the single pump is not likely to be sufficient to flush multiple contrast lines at the same time. In other implementations, if the peristaltic pump output is sufficient, or in a configuration with multiple peristaltic pumps each being able to be placed in fluid communication with the contrast manifold 818, more than one contrast line can be primed at the same time. In the configuration in FIG. 38, the first contrast control valve 822a is opened to prime the contrast communication channel to the first hub 724a. The contrast control valves 822a-822c are opened, one at a time, while saline/contrast valve 766 remains open to provide saline to flow through from line 770, through the contrast manifold 818, through lines 820a-820c, contrast control valves 822a-822c, lines 826a-826c, ports C1-C3, the tubing set 716, to the one or more hubs 724, to prime contrast lines in the cassette and the tubing set with saline. In this example, a Zoom 88 catheter is coupled to a first hub 724a, a Zoom 71 catheter is coupled to a second hub 724b, and an insert catheter is coupled to a third hub 724c. FIG. 39 illustrates a hub and further illustrates priming the fluid communication channels of the contrast subsystem 708 with saline. As illustrated in FIG. 39, the fluidic system is configured such that saline is provided through a contrast tube 937, and through the wye connector 920, the air bubble filter 922, the saline/contrast tube 940, the three-way valve 923, to the aspiration tube 935, while a vacuum pump provides a vacuum on the aspiration tube 935 to facilitate the saline flow through these lines and components.

Figure 40:
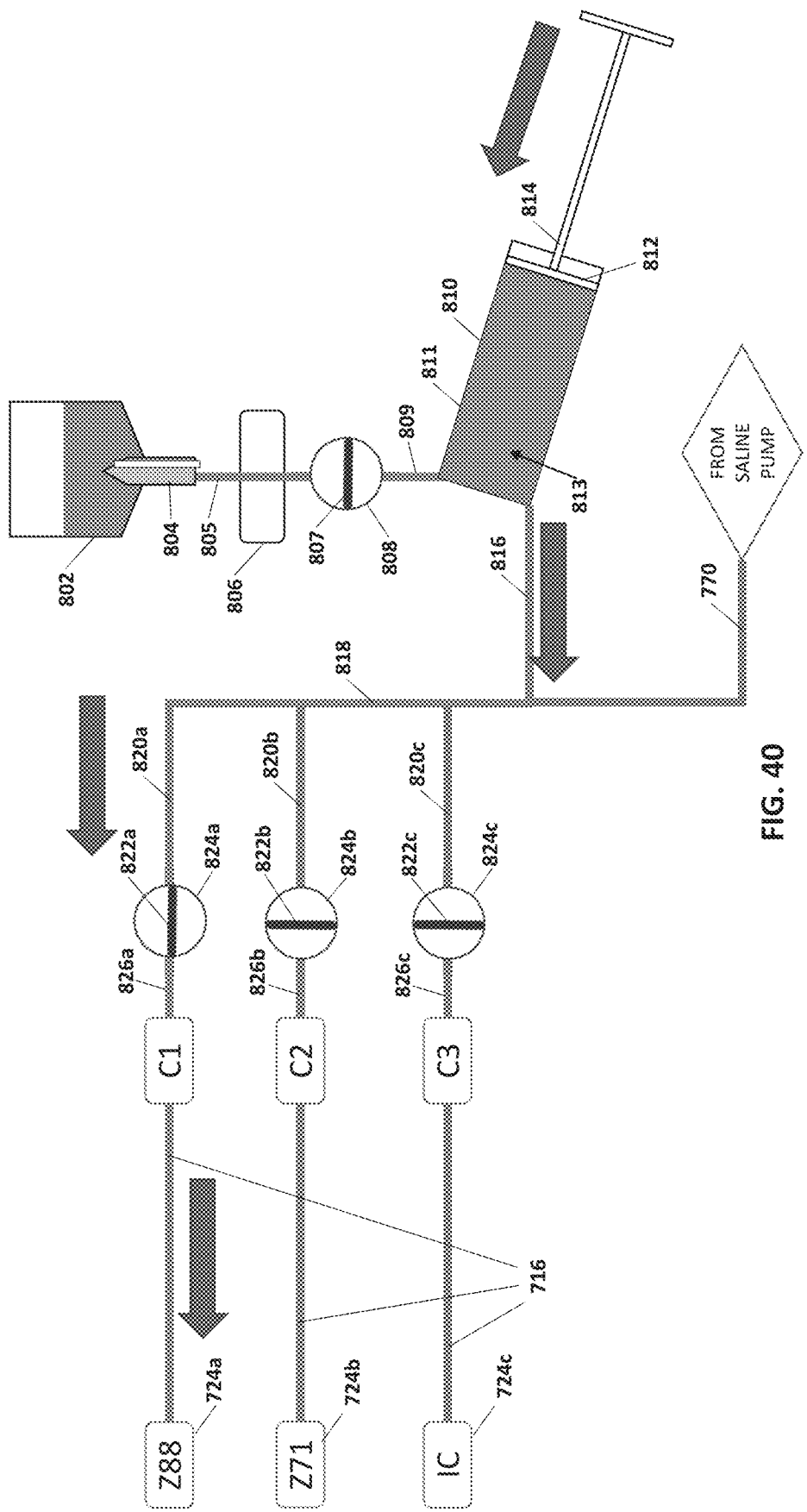
FIG. 40 illustrates an example of a configuration for priming fluid communication channels that provide contrast to a catheter from a contrast subsystem with contrast.
Figure 41:
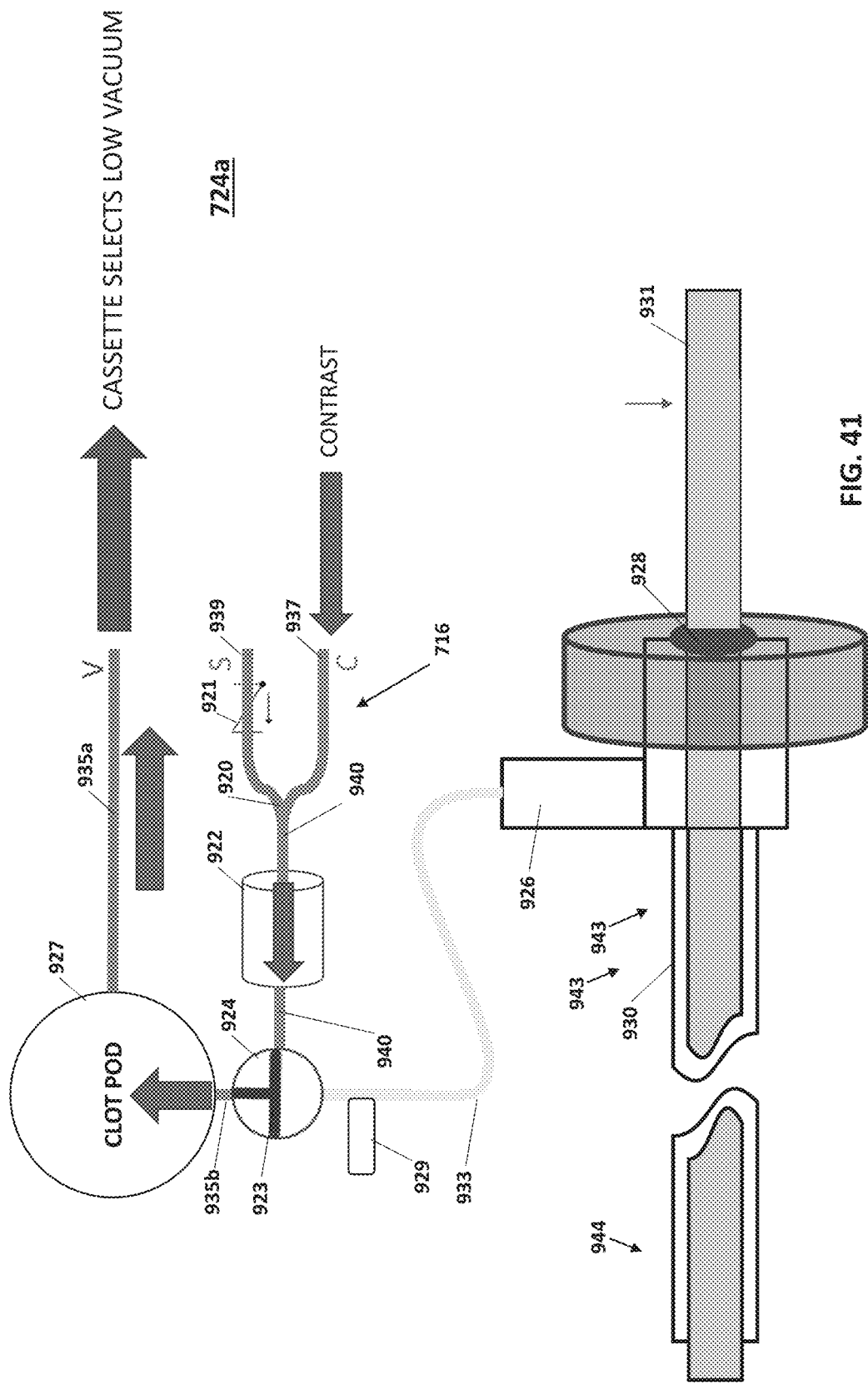
FIG. 41 further illustrates an example of a configuration for priming fluid communication channels that provide contrast to a catheter from a contrast subsystem with contrast.

Once the contrast fluid communication channels (or "contrast channels") in the cassette and tubing set are primed with saline, a controller can operate the fluidic system to prime each of the contrast channels in the cassette and tubing set with contrast to remove air from the contrast channels. For example, as illustrated in FIG. 40, with the contrast intake valve 807 closed and one of the contrast control valves 822a-822c (e.g., the first contrast control valve 822a) open such that contrast can flow from lines 820a and 826a, and the three-way valve 923 (FIG. 39) connecting the saline/contrast tube 940 to the aspiration tube 935, the contrast pump 810 is actuated and pushes contrast out of the contrast chamber 813 and through line 816, the contrast manifold 818, line 820a, the first contrast control valve 822a, line 826a to port C1 and then through a contrast tube if tubing set 716 to the first hub 724a. As shown in FIG. 41 (which depicts an example of the first hub 724a), contrast is received through the tubing set 716 through a contrast tube 937, and it flows through the wye connector 920, through the air bubble filter 922, through the saline/contrast tube 940, and is routed by the three-way valve 923 to the aspiration tube 935 (a vacuum channel of tubing set 716) where it is exhausted into the vacuum canister 882 (FIG. 17). The saline tube 939 remains filled with saline, check valve 921 preventing saline and contrast from being pushed back from the wye connector 920 into the saline tube 939. In the example illustrated in FIG. 41, the catheter 930 can be a Zoom 88 catheter and interventional device 931 can be a Zoom 71 catheter.

As illustrated in FIG. 41, interventional device 931 is an inner catheter relative to catheter 930. That is, interventional device 931 can be positioned within the lumen of catheter 930. To continue priming the contrast channels of the cassette 704 and the tubing set 716, after the contrast channels associated with the first hub 724a are primed with contrast, the first contrast control valve 822a is closed and a second contrast control valve (e.g., the second contrast control valve 822b) can be opened to similarly prime the contrast channels associated with the third hub 724c. After the contrast channels associated with the second hub 724b are primed with contrast, the second contrast control valve 822b is closed and a third contrast control valve (e.g., the third contrast control valve 822c) can be opened to similarly prime the contrast channels associated with hub 724c. This order of priming the contrast channels is an example, the contrast channels can be primed in any order. After the contrast channels of the cassette 704 and the tubing set 716 are primed, the contrast control valves 822a-822c can be moved to a closed position. Also, after the contrast channels of the cassette 704 and the tubing set 716 are primed, the saline/contrast valve 766 can be moved to a closed position.

Figure 42:
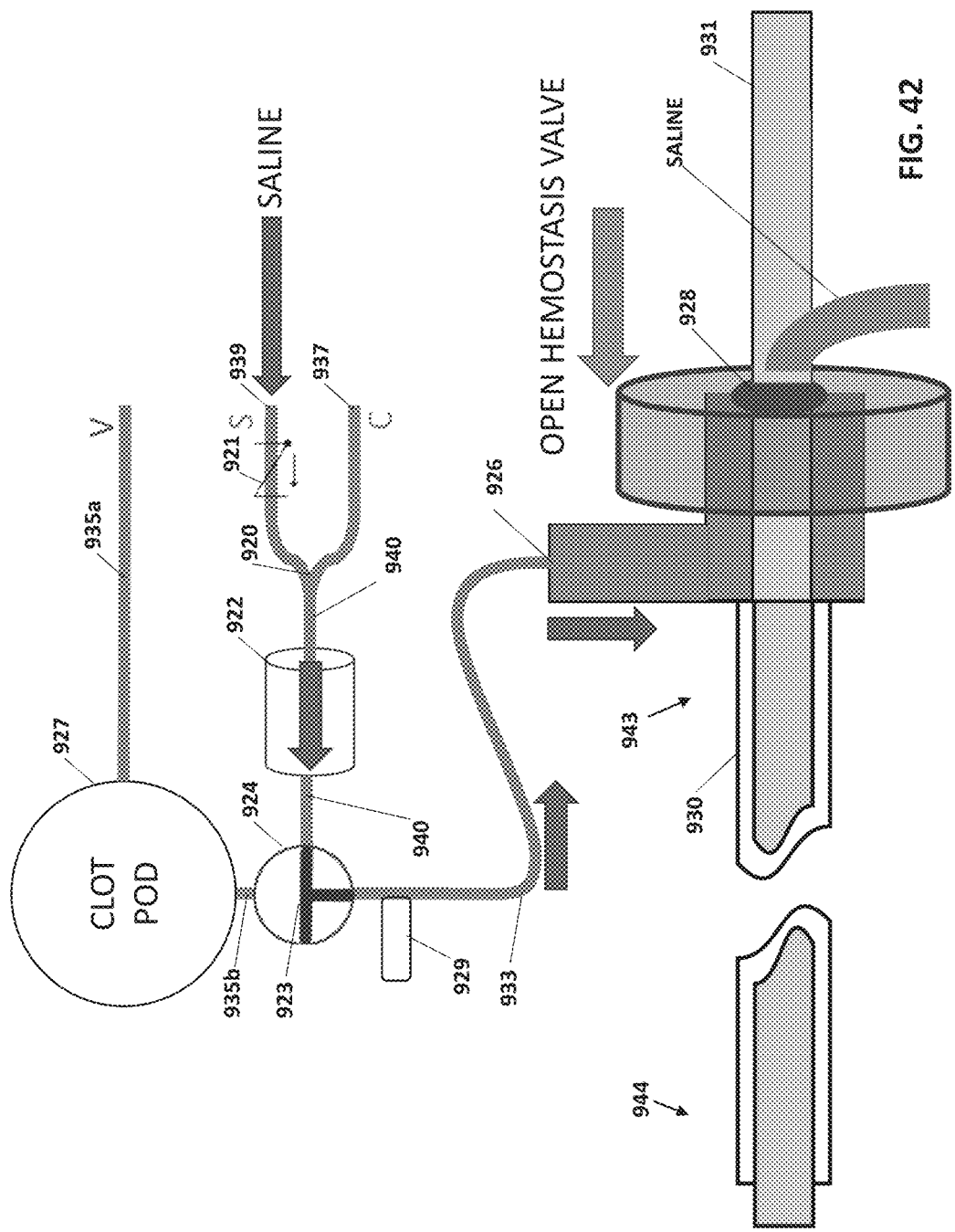
FIG. 42 and FIG. 43 illustrate configurations for priming a hub, and the catheter coupled to the hub with saline.
Figure 43:
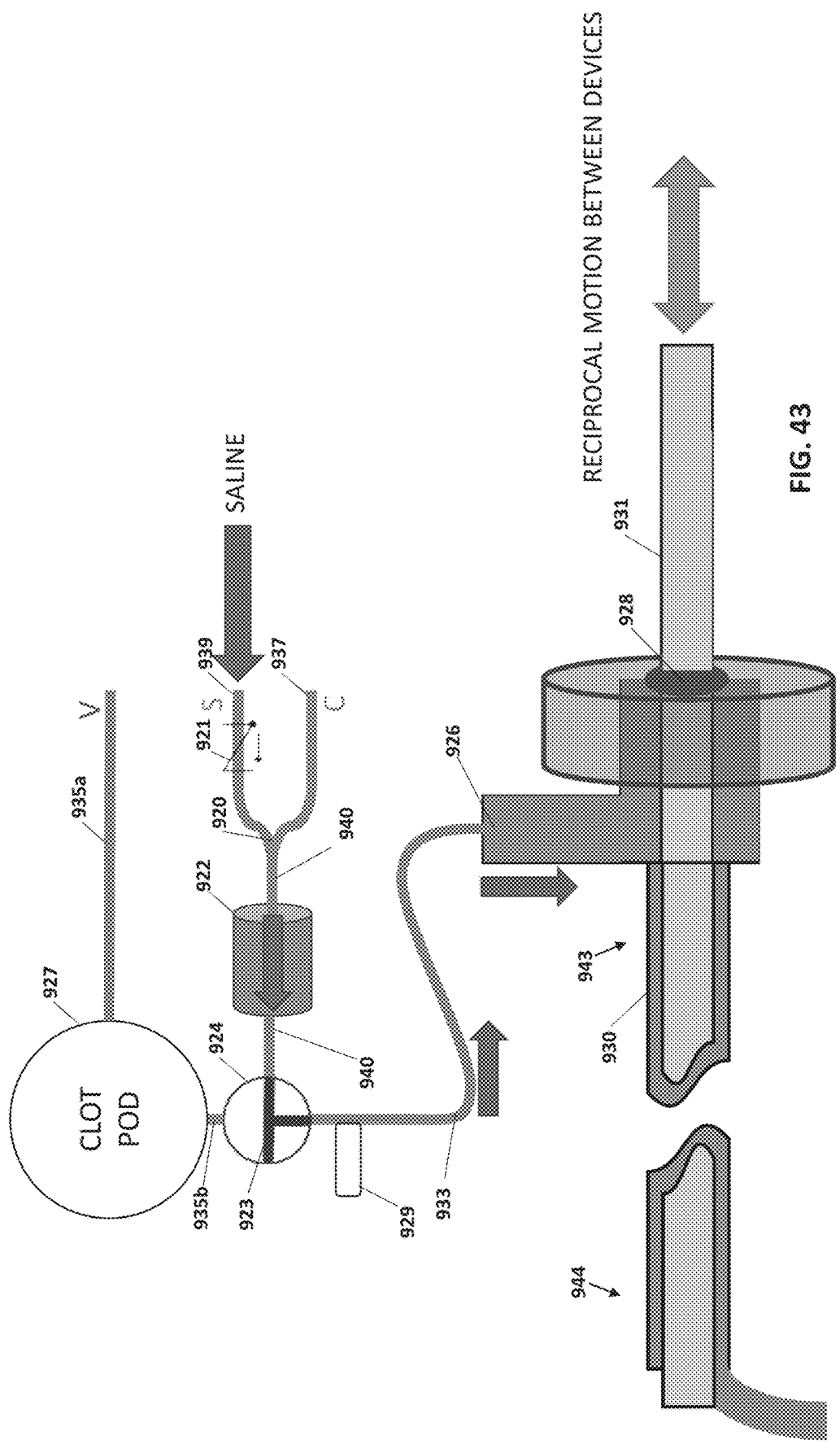

FIGS. 42 and 43 illustrate configurations for priming a hub, and the catheter coupled to the hub (a "hub/catheter"), with saline. The controller can be configured to prime hubs/catheters with saline one at a time, or prime two or more of the hubs/catheters with saline at the same time. After the contrast channels and the saline channels cassette 704 and tubing set 716 have been primed, the peristaltic pumps can be continuously operated to provide a continuous flow of saline. As illustrated in FIG. 42, the three-way valve 923 is positioned such that the saline/contrast tube 940, which receives contrast and saline, is connected to the catheter coupling tube 933. In this configuration, a peristaltic pump 762a-762d can provide saline into the saline tube 939, through the wye connector 920, through the air bubble filter 922, through the three-way valve 923, to the catheter coupling tube 933 and through a luer connection 926 to a hemostasis valve 928. In this configuration, the hemostasis valve 928 can be opened to allow saline to flow out of the hemostasis valve 928 to remove air that was in the catheter coupling tube 933, the luer connection 926, and the hemostasis valve 928, flushing out the catheter coupling tube 933, the luer connection 926, and the hemostasis valve 928. In this embodiment, an interventional device 931 extends through the hemostasis valve 928 and into the catheter 930. The catheter 930 may be an outer catheter and the interventional device 931 may be an inner catheter. The interventional device 931 may be positioned within the catheter 930. The saline flows out of the hemostasis valve 928 through a portion of the lumen of the catheter 930, through a space between the outer surface of the interventional device 931 and an inner surface (a surface of the lumen) of the catheter 930.

In the configuration illustrated in FIG. 43, three-way valve 923 is still aligned to route saline received in the saline/contrast tube 940 to the catheter coupling tube 933 and to the hemostasis valve 928, but the hemostasis valve 928 is now closed. In this configuration, saline is prevented from exhausting through the hemostasis valve 928 and instead flows through the catheter 930, from a proximal portion of the catheter 930 to the catheter tip and exhausts out of the tip, thus removing air from the catheter 930. To help remove smaller air bubble that may be in the lumen of the catheter 930 between the interventional device 931 and the catheter 930, the interventional device 931 and the catheter 930 can be moved, for example, in reciprocal motion. In an example, a first hub that the outer catheter 930 is coupled to and a second hub that the interventional device 931 is coupled to can both be moved towards and away from each other. In another example, a first hub the catheter 930 is coupled to can be held stationary and a second hub that the interventional device 931 is coupled to can both be moved towards and away from the first hub. In another example, a first hub the catheter 930 is coupled to can both be moved towards and away from a second hub that the interventional device 931 is coupled which remains stationary.

Figure 44:
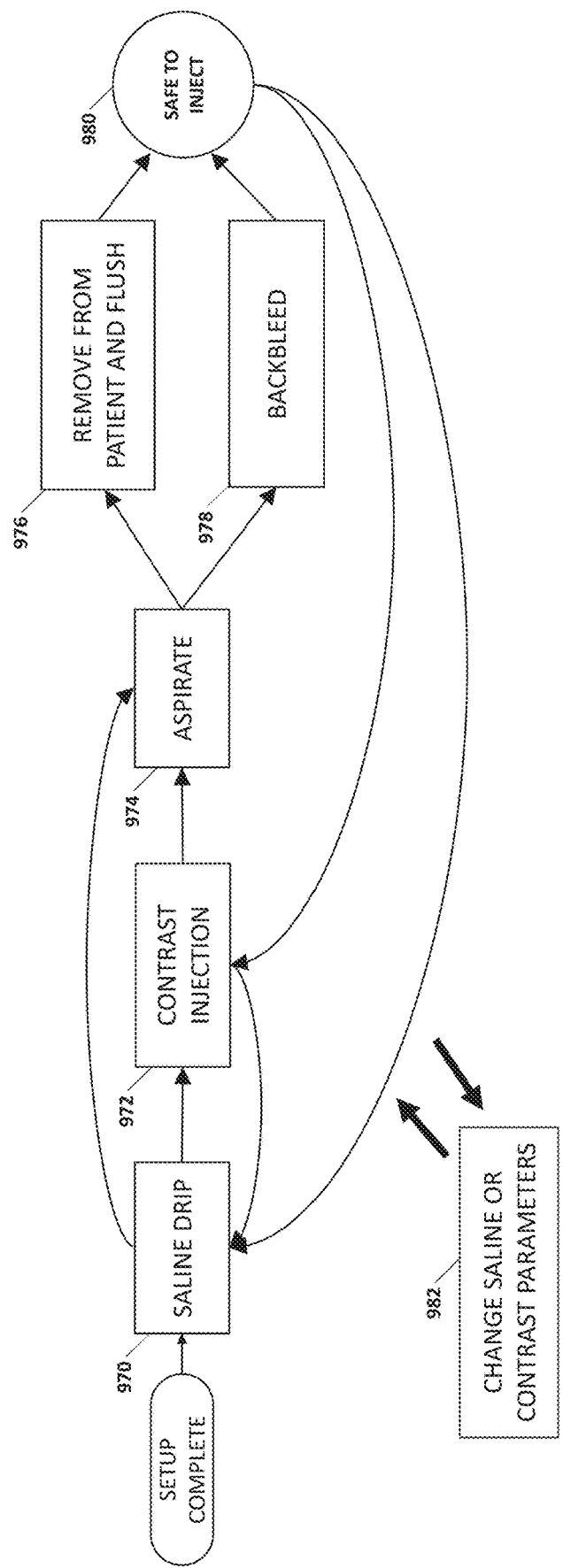
FIG. 44 illustrates an example of a state diagram of a robotic catheter system illustrating different operational states in which a controller can operate a fluidic system after setup is completed, according to some embodiments.

FIG. 44 illustrates an example of a state diagram of a robotic catheter system illustrating different operational states in which a controller can operate a fluidic system after setup is completed, according to some embodiments. A controller can operate a fluidic system based on system information. As used herein, system information can include, but is not limited to, user input from a local control interface, a user input from a remotely located control system, information received from one or more sensors, and/or previously stored information including processes that can be executed by a controller. These states represent examples of operations of the fluidic system during a medical procedure. Setup can be "complete," for example, after a cassette is attached to a robotic catheter system (e.g., to a pump station) and after priming the contrast subsystem and the saline subsystem, including components and fluid communication channels of the cassette 704, the tubing set 716, and the hubs. In this example, the states may be represented by one or more distinct blocks. For example, a first block 970, a second block 972, a third block 974, a fourth block 976, a fifth block 978, and a sixth block 980. The first block 970 may represent a saline drip state. The second block 972 may represent a contrast injection state. The third block 974 may represent an aspirate state. The fourth block 976 may represent a state to remove from patient and flush. The fifth block 978 may represent a backbleed state. The sixth block 980 may represent a safe to inject contrast state. For ease of reference, these blocks may be referred to as their states, e.g., as "saline drip," "contrast injection," "aspirate," "remove from patient and flush," "backbleed," and/or "safe to inject"). The state diagram also includes a seventh block 982 representing a change saline or contrast parameters state. For ease of reference, the seventh block 982 may be referred to as its state e.g., as "change saline or contrast parameters." This can be, for example, a state where saline or contrast parameters are changed such that a controller uses the changed parameters to affect the flow of saline or contrast through the fluidic system. In an example, during the change saline and contrast parameters state shown in the seventh block 982, a saline and/or contrast parameter can be changed based on a system information. The previously stored information can be information that is used during any of the states shown in FIG. 44 and/or during a certain portion of a medical procedure (e.g., relating to catheter insertion, removal, movement through specific portions of a patient's vasculature, aspiration, etc.). During a medical procedure, the fluidic system state can transition from state-to-state. In the example illustrated in FIG. 44, when the fluidic system is in the first block 970, the fluidic system can transition from a saline drip state to contrast injection state or the aspirate state represented by the second block 972 and third block 974, respectively. When the fluidic system is in second block 972, the fluidics system can transition from the contrast injection state to saline drip state or the aspirate state represented by the first block 970 and the third block 974, respectively. When the fluidic system is in the third block 974, the fluidics system can transition from the aspirate state to the state to remove from patient and flush or the backbleed state represented by the fourth block 976 and the fifth block 978, respectively. The goal of the backbleed state represented in the fifth block 978 is to clear the catheter lumen for subsequent injection while the catheter is in the body, thus replicating a procedure of pulling back on a syringe in a non-robotic catheter system process, and is described below in reference to FIGS. 58-63. When the fluidic system is in the fourth block 976, the fluidic system transitions from the remove from patient and flush state to a safe to inject state represented by the seventh block 980. When the fluidic system is in the fifth block 978, the fluidic system transitions from the backbleed state to the safe to inject state represented by the seventh block 980. And when the fluidic system is in the seventh block 980, the fluidics system can transition from the safe to inject state to the saline drip state or contrast injection state represented by the first block 970 and the second block 972, respectively. Each of the states corresponds to a configuration of the fluidic system. For example, a configuration of a saline subsystem 706, a contrast subsystem 708, and a vacuum subsystem 710, in cassette 704 or hub 724. When the fluidic system enters a certain state, a controller can control a pump station and/or a hub to actuate valves and components to align the fluid communication channels into a configuration for that state such that the robotic catheter system can perform saline drip, contrast injection, aspiration, or other desired actions. These various states are described further in reference to FIGS. 45-63.

Figure 45:
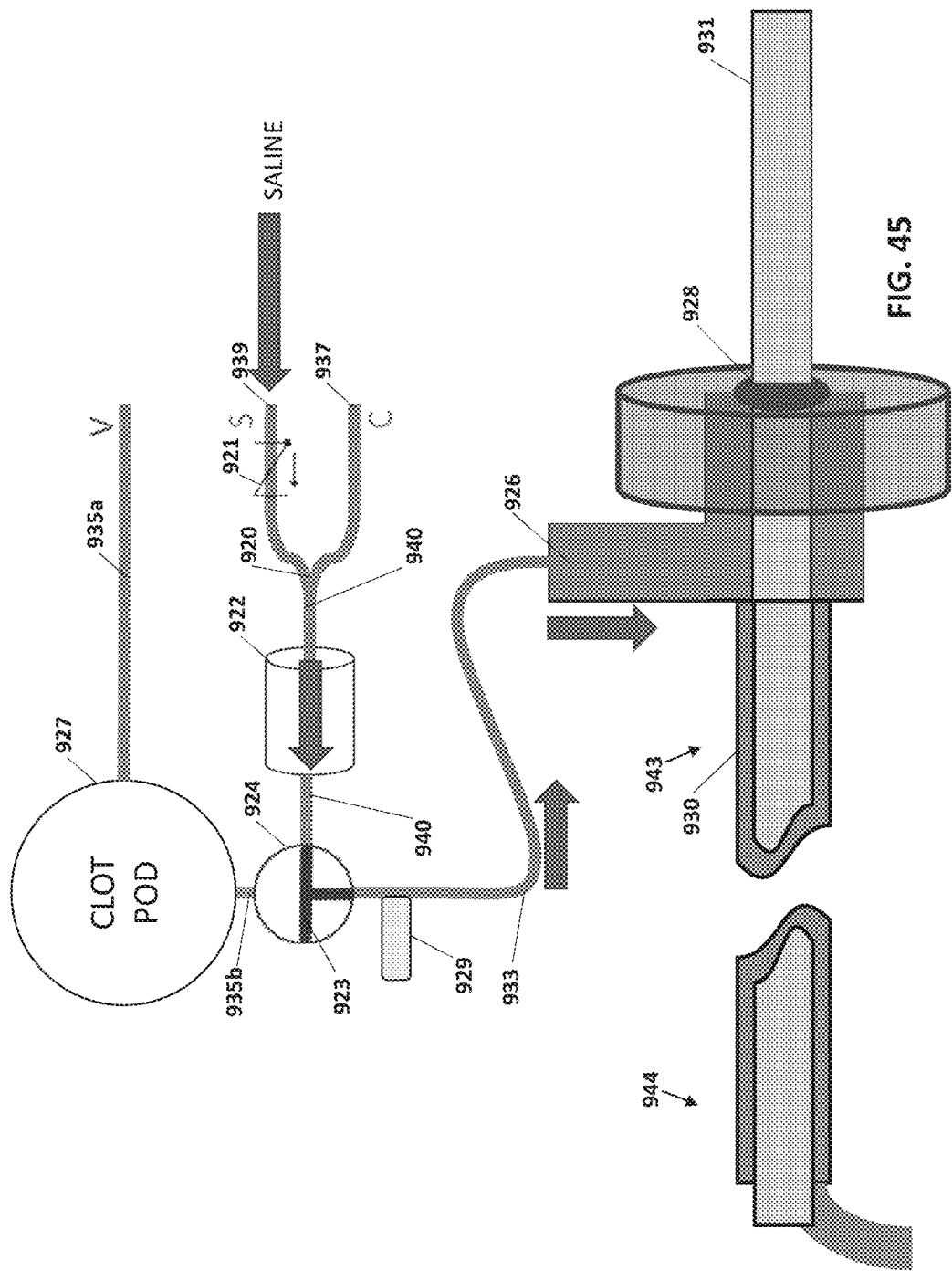
FIG. 45 illustrates an example of a configuration of hub of a fluidic system in the state saline drip, according to some embodiments.

FIG. 45 illustrates an example of a configuration of hub of a fluidic system in the saline drip state represented by the first block 970, according to some embodiments. In an example, the hub can be one of the one or more hubs 724a-724c (FIG. 14). While FIG. 45 illustrates one hub, and the saline drip state is described in reference to a hub, in systems with multiple hubs one or more of the hubs can be placed in this configuration during the saline drip state when the fluidics system is in the first block 970. In this configuration, hemostasis valve 928 is closed, and a peristaltic pump 762a-762d corresponding to this hub is actuated to provide a continuous flow of saline to the hub via the saline tube 939. The three-way valve 923 is positioned to connect the saline/contrast tube 940 and the catheter coupling tube 933 providing a channel for saline to flow through the catheter 930 and exhausts out of the catheter tip. The saline flows through the air bubble filter 922, which filters out air bubbles in the saline flow.

Figure 46:
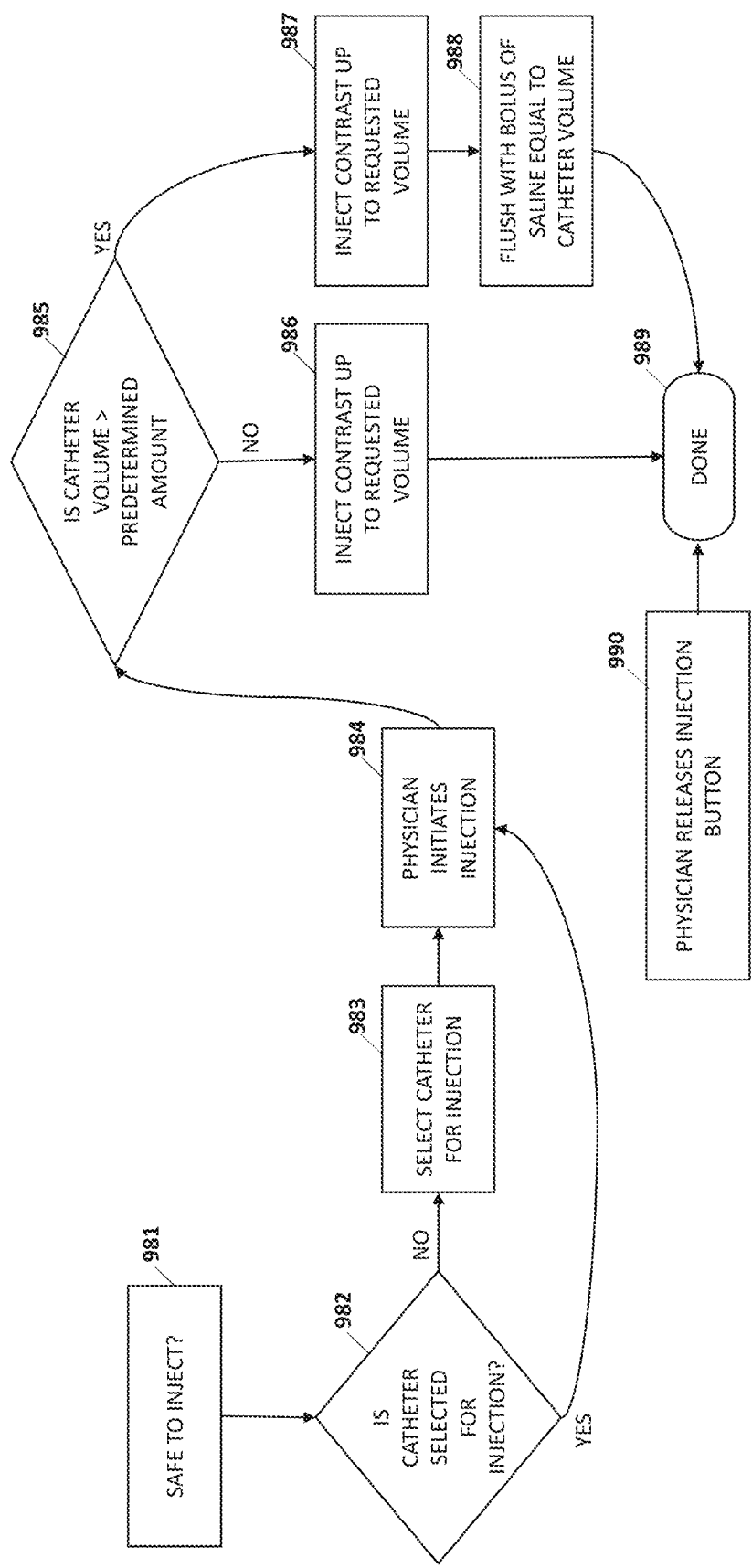
FIG. 46 illustrates an example of a contrast injection process that can be performed when the fluidic system is in state contrast injection.

FIG. 46 illustrates an example of a process, can include subprocesses, that can occur when the fluidic system is in the contrast injection state represented by the second block contrast injection 972 (FIG. 44), according to some embodiments. This process includes actions that can be determined or performed using the robotic catheter system (or "system") and the description of the actions relates to using the robotic catheter system to perform the actions. For example, these actions can be controlled by a controller based at partially on, for example, system information (e.g., user input from a local control interface, a user input from a remotely located control system, information received from one or more sensors, previously stored information, and/or previously stored processes that can be executed by the controller).

Figure 47:
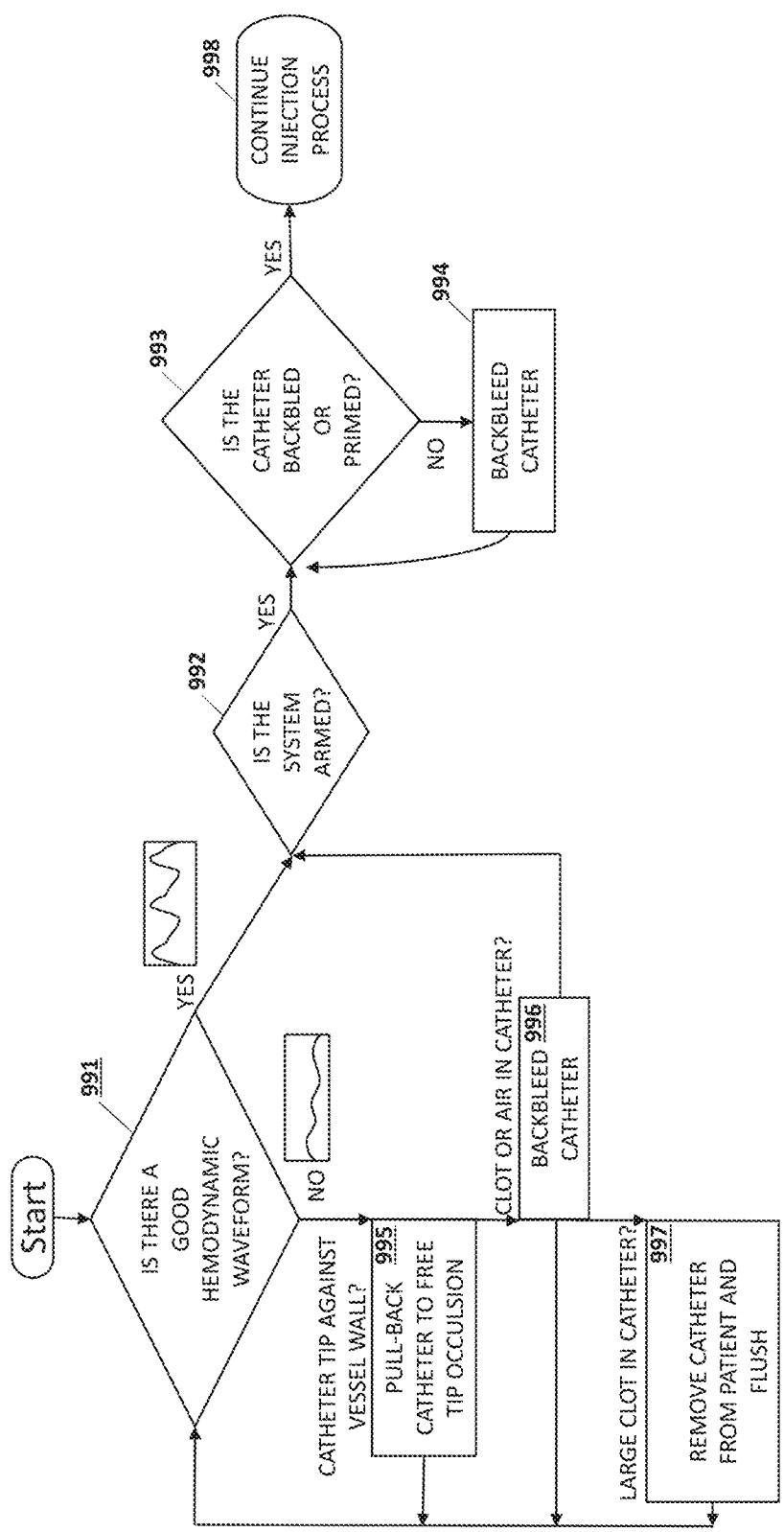
FIG. 47 illustrates a process for determining if it's safe for the system to inject contrast.

In FIG. 46, the system determines if it is safe to inject contrast at block 981. FIG. 47 illustrates a process for determining if it's safe for the system to inject contrast. In this example, the system cannot proceed with contrast injection until it has been determined that it is safe to inject contrast. Referring to FIG. 47, the system determines if there is a good hemodynamic waveform at block 991. The system can determine if there is a "good" hemodynamic waveform based on information received from a pressure sensor in the mount. For example, hemodynamic pressure sensor 929 (e.g., FIGS. 46 and 69) corresponding to the selected catheter (e.g., positioned in a hub that the selected catheter is coupled onto). The system can determine if there is a "good" hemodynamic waveform by comparing received information from the hemodynamic pressure sensor 92 to predetermined hemodynamic pressure information (e.g., waveforms) that indicate an expected hemodynamic waveform. Using the hemodynamic pressure sensor information, the system can determine if the tip of the selected catheter is occluded making it unsafe to inject contrast. The predetermined mode dynamic pressure information can be stored on the robotic catheter system or stored at another storage location that is accessible by the robotic catheter system. If the system determines a good hemodynamic wave does not exist, the system can initiate other actions represented in blocks 995, 996, 997 to clear the occluded catheter tip. For example, the process can proceed to block 995 and where the system moves the selected catheter to free the catheter tip in instances with the catheter tip is against a vessel wall. The process can also proceed to block 996 where the system backbleeds the catheter to remove a clot or error in the catheter. The process can also proceed from block 991 to block 997 where the catheter is removed from the patient flushed in order to, for example, remove a large clot in the selected catheter.

Figure 58:
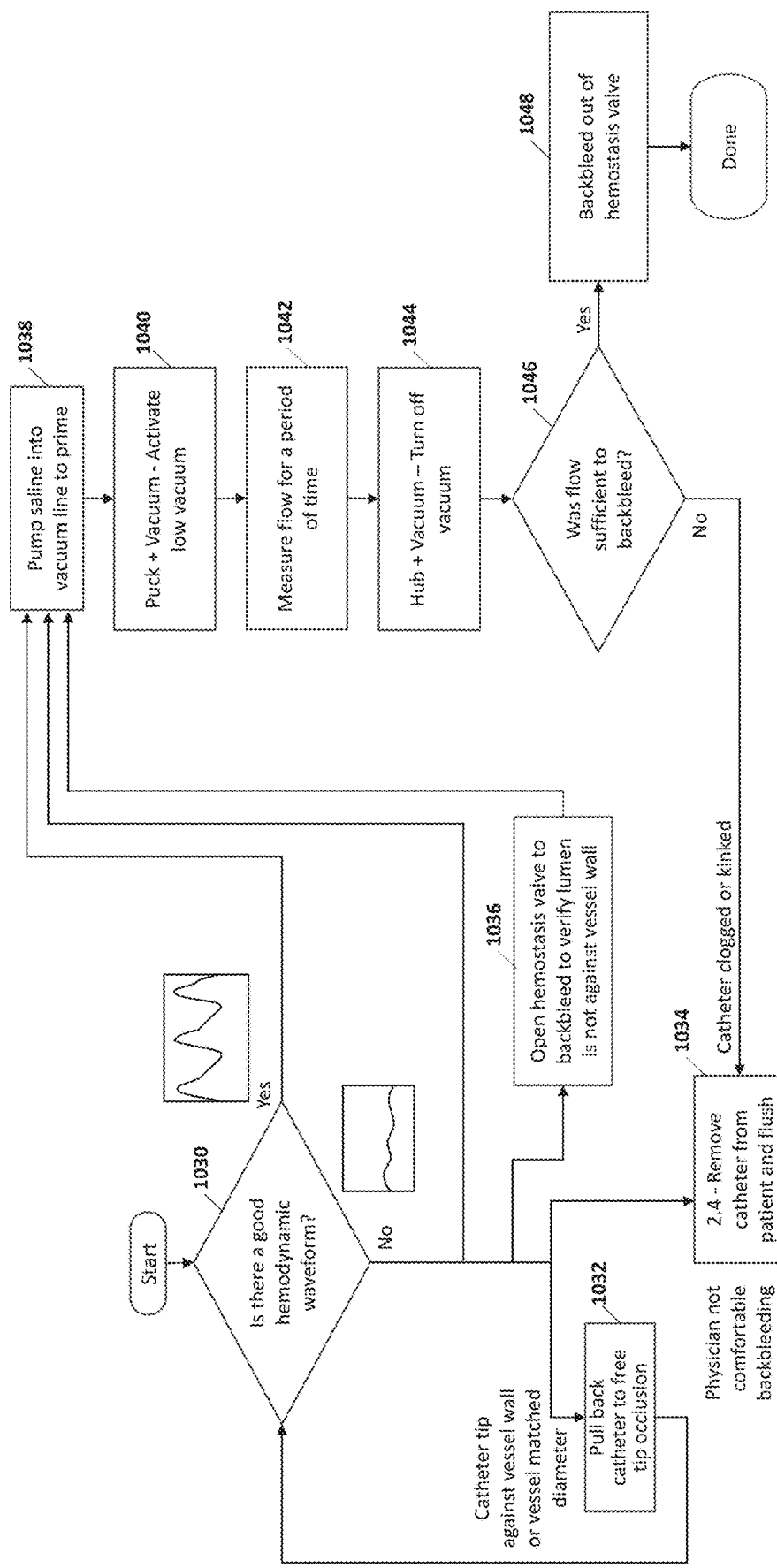
FIG. 58 illustrates an example of a process flow for back bleeding a catheter that can be performed by the robotic catheter system.

After executing any of actions represented in blocks 995, 996, 997, the process can proceed back to block 991 where the system determines if a good hemodynamic waveform exists. If after the system performs one of the actions represented in blocks 995, 996, 997, and a good hemodynamic waveform still does not exist, the system can proceed to another of actions represented in blocks 995, 996, 997, perform that action to proceed back to block 991 and again determine if a good hemodynamic waveform exists. During this process, the system can provide status, to a remotely located control system 2210 and/or on an interface of the local system controller 2220, indicating an action that has taken. In some embodiments, the system receives input from a user indicating which of the actions represented in blocks 995, 996, 997, or another action, to perform in order to ensure the catheter tip is clear. In some embodiments, the system determines which of the actions represented in blocks 995, 996, 997, or another action, to perform, for example, based on historical data, system information, physician's preference, patient information, or other information. After the system determines a good hemodynamic waveform exists, the process can move to block 992 with the system determine/verify if it is armed and ready to inject contrast. For example, if the contrast pump 810 is ready to inject contrast. After the system determines it is armed, the process proceeds to block 993 where it determines if the catheter is backbled and/or primed. If not, the process proceeds to block 994 with the system backbleeds the selected catheter, which is illustrated in FIG. 58. After the system determines that the catheter has been backbled or primed, the process proceeds to block 998 where contrast injection can continue, and the process proceeds to the seventh block 982 in FIG. 46.

Figure 48:
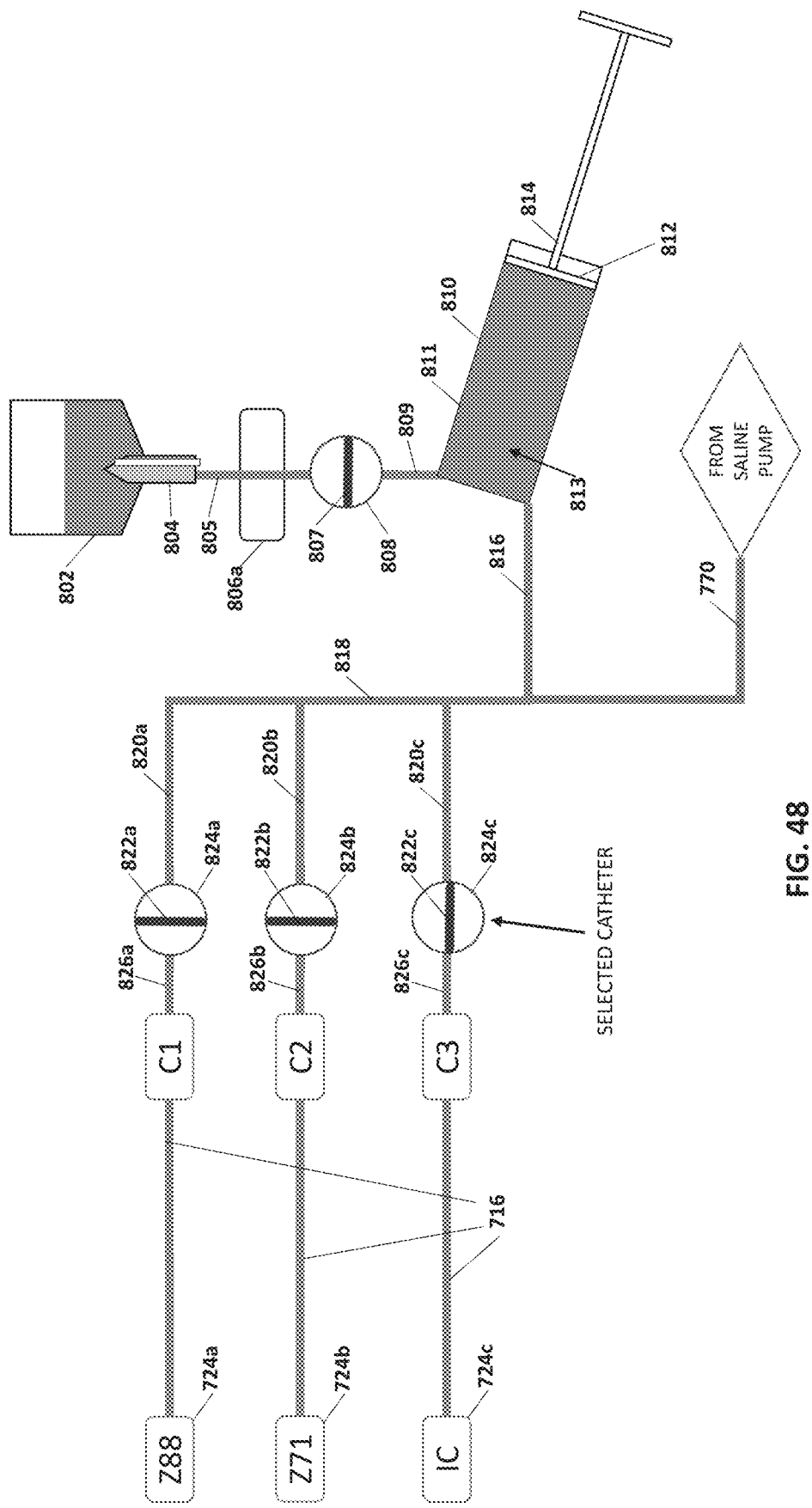
FIG. 48 illustrates an example of the contrast subsystem configuration where an insert catheter coupled to mount has been selected for injecting contrast.

At the seventh block 982 the system determines if a catheter has been selected for injecting contrast. If a catheter has been selected, the process proceeds to block 984 where a user (e.g., physician) initiates contrast injection. If a catheter has not been selected, the process proceeds to block 983 where a catheter is selected for injecting contrast, for example, based on a user input. FIG. 48 illustrates an example of the contrast subsystem 708 configuration where an insert catheter coupled to hub 724*c* has been selected for injecting contrast. When the insert catheter has been selected, the system moves the third contrast control valve 822*c* to an open position connecting lines 826*c* and 820*c* to provide the contrast communication path from the contrast pump 810 to the insert catheter. The system also moves the first and second contrast control valves 822*a*, 822*b* and the contrast intake valve 807 to a closed position, if they are not already closed. The system can perform other actions to prepare for injecting contrast. After a catheter is selected, the process proceeds to block 984 where a user initiates contrast injection by providing an input to the system to inject contrast, for example, from the remotely located control system 2210.

The contrast injection process proceeds to block 985 where the system can determine if the selected catheter volume is greater than a certain predetermined amount (for example, if the volume of the catheter is greater than 2 ml) based on system information. In some instances, the system determines the volume of the selected catheter based at least partially on whether the lumen of selected catheter contains another catheter, or a guidewire, which the system may determine based on information relating to the position of the hubs when contrast injection is being performed. If the volume of the selected catheter is not greater than the predetermined amount, at block 986 the system injects contrast, for example, up to a requested volume.

Figure 49:
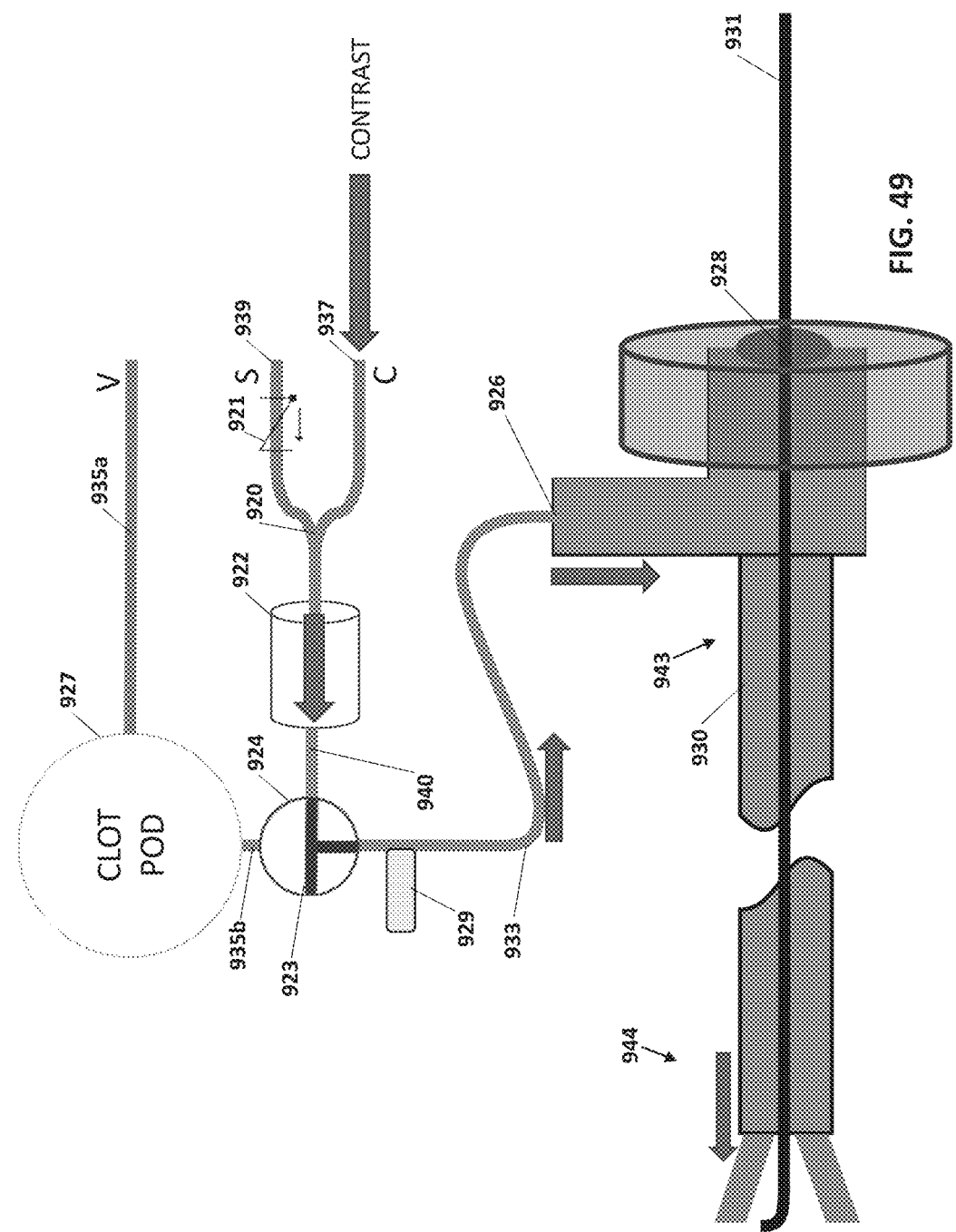
FIG. 49 illustrates an example of a configuration of the mount corresponding to the selected catheter when contrast is injected.

If the catheter volume is greater than the predetermined amount, at block 987 the system injects contrast, for example, up to a requested amount. FIG. 49 illustrates an example of a configuration of the hub corresponding to the selected catheter when contrast is injected. The system actuates contrast pump 810 to provide contrast to the hub via the contrast tube 937. The three-way valve 923 is positioned to connect the saline/contrast tube 940 and the catheter coupling tube 933 so the provided contrast flows through the catheter coupling tube 933, through the luer connection 926, though the catheter 930 and exhausts at the catheter tip. In some embodiments, the system closes hemostasis valve 928 around the interventional device 931 a more forceful level than during saline drip to prevent contrast from leaking out of the hemostasis valve 928.

Figure 50:
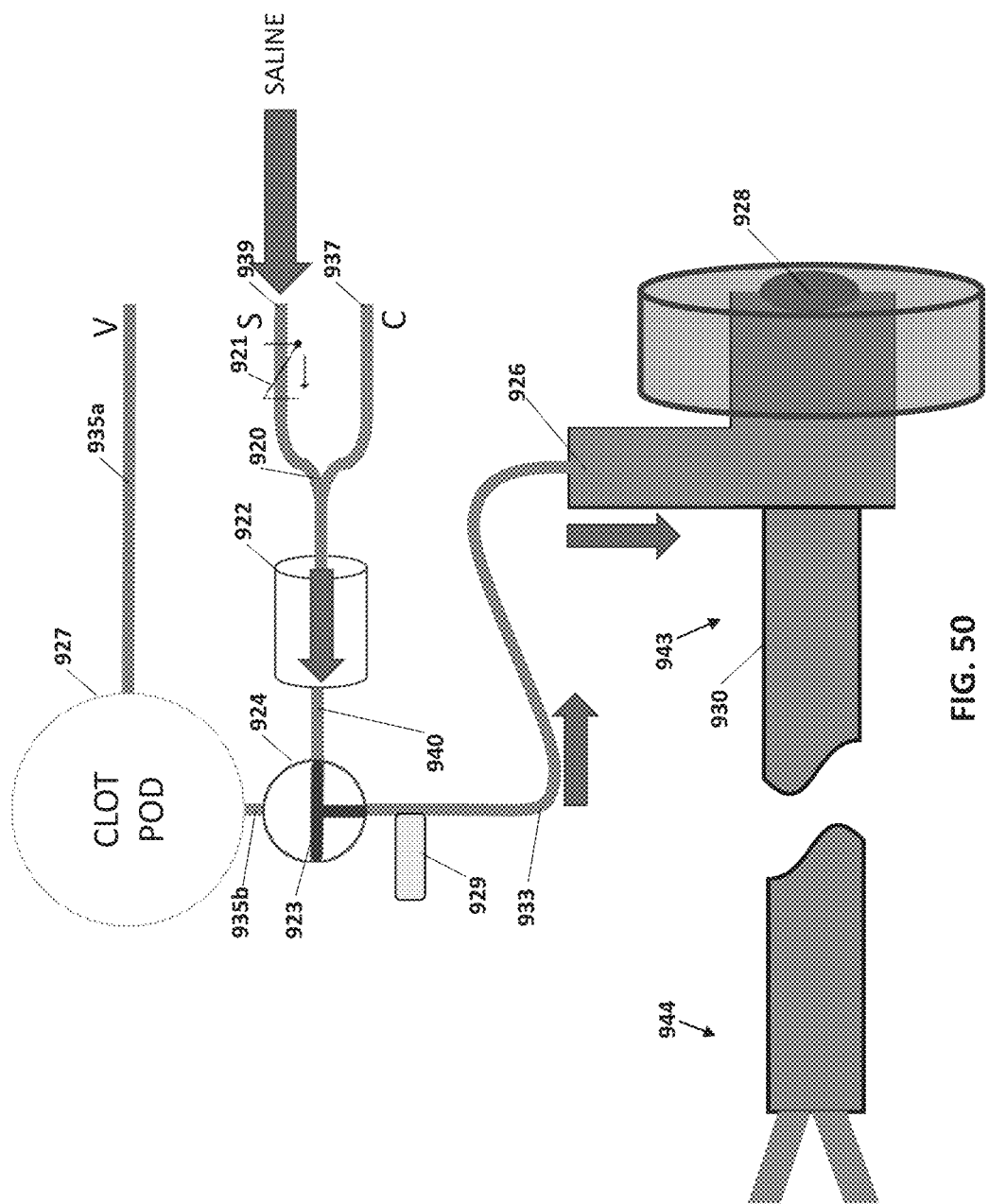
FIG. 50 illustrates an example of a configuration of the mount of a selected catheter configured to inject a saline bolus.

Referring again to FIG. 46, the process then proceeds to block 988 where the system flushes the hub and the catheter with a bolus of saline equal to the catheter volume to exhaust the contrast solution of the catheter. FIG. 50 illustrates an example of a configuration of the hub of the selected catheter configured to inject a saline bolus. The peristaltic pump 763*a*-763*d* associated provides a certain amount of saline to the hub via the contrast tube 937. The amount of saline provided to the hub can be based on the volume of the selected catheter (which can be part of the system information). The three-way valve 923 is the lines to connect the saline/contrast tube 940 to the catheter coupling tube 933 such that the saline flows through catheter coupling tube 933, through the luer connection 926, through the catheter 930 and pushes out contrast that is left in the catheter 930 as a result of the contrast injection. Referring again to FIG. 46, after the contrast is injected to the requested volume and block 986, in after the catheter is flushed with a bolus of saline, if needed, in block 988, the process can indicate this particular injection process is done at block 989. In this example, the process then proceeds to block 990 with a physician can release the contrast injection button indicating the contrast injection is complete.

Figure 51:
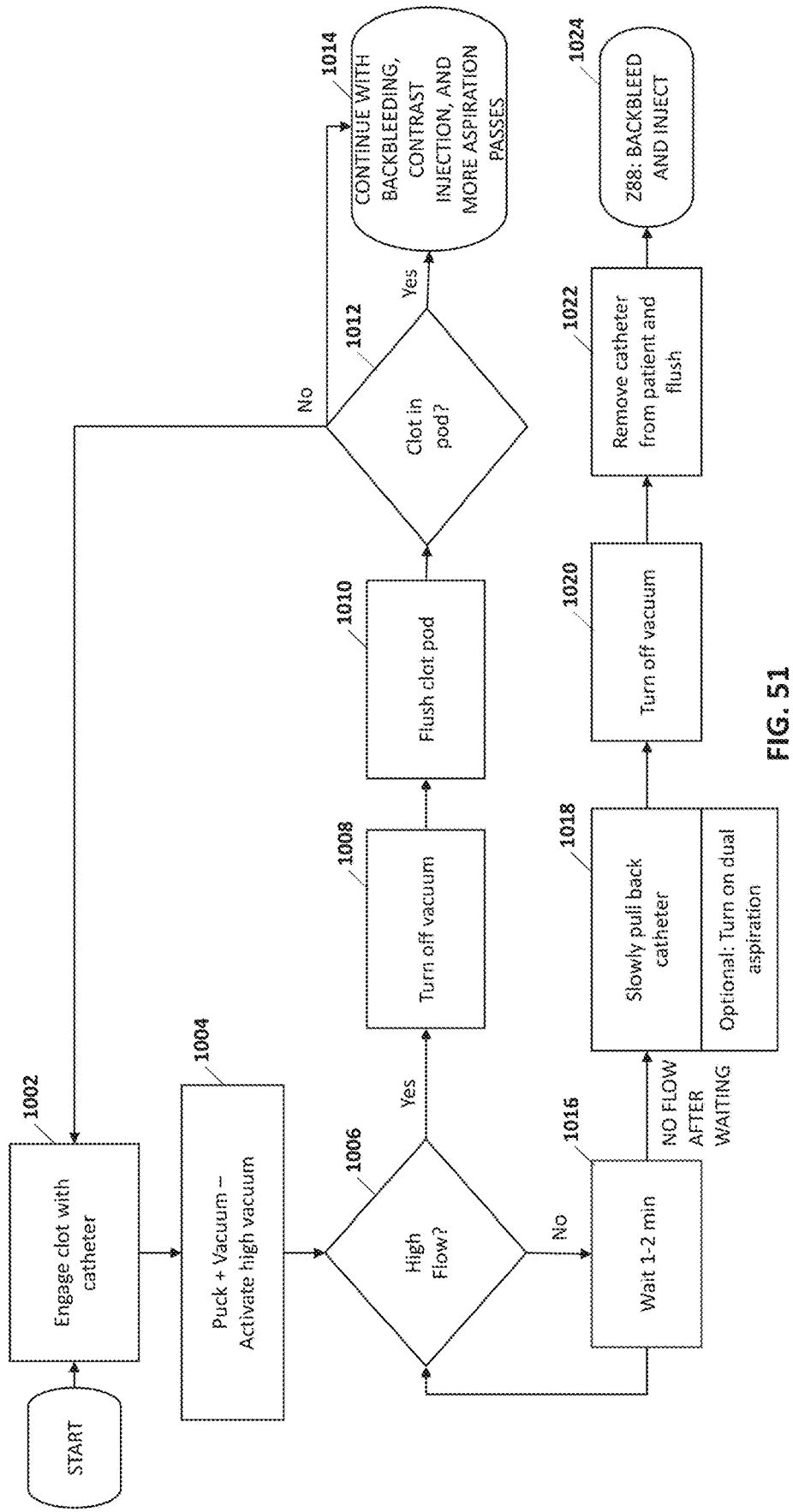
FIG. 51 illustrates an example of an aspiration process that the robotic catheter system can perform when the system is an aspirate state.
Figure 52:
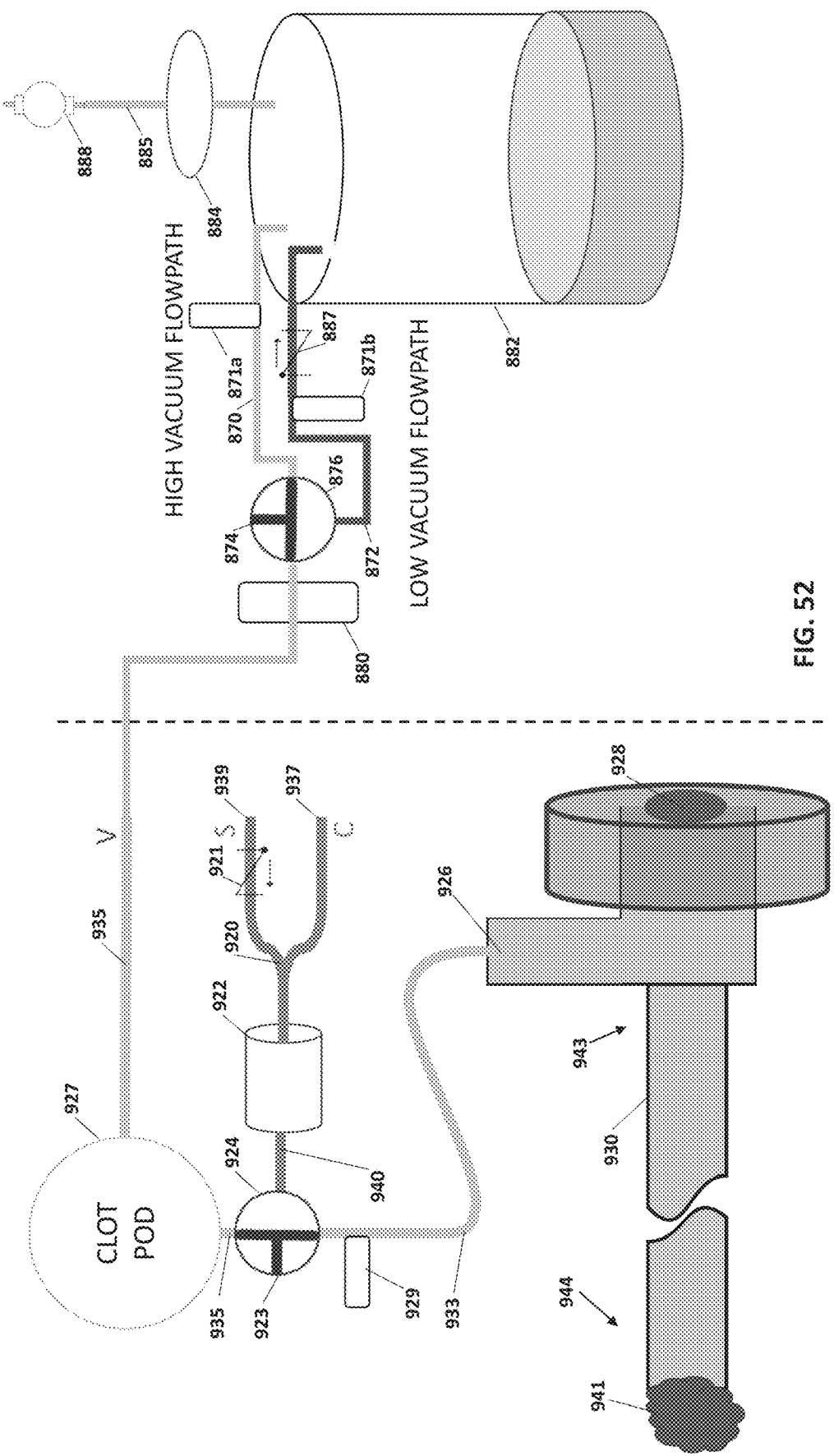
FIG. 52 illustrates an example of a configuration of a hub in a configuration during an aspirate state, where a tip of the catheter is positioned adjacent to a clot, and a three-way valve is positioned to connect line a hub fluidic channel to a vacuum line of the fluidic communication system.

FIG. 51 illustrates an example of an aspiration process that the system can perform when the system is an aspirate state represented by the third block 974 (FIG. 44). At block 1002, the system can engage a clot with a catheter. For example, the system is used to move a particular hub and its corresponding catheter (now referred to as an "aspiration catheter") such that the aspiration catheter tip is positioned adjacent to, or in the proximity of, a clot. At block 1004, the system configures the hub to connect the lumen of the aspiration catheter to a vacuum line. For example, the system configures the hub and the vacuum subsystem including the vacuum pump to provide high vacuum to the hub. FIG. 52 illustrates an example of a configuration of a hub coupled to catheter 930 having distal end 944 and a proximal end 943. The proximal end 943 is coupled to a hemostasis valve 928, and the catheter tip 944 is positioned adjacent to a clot 941, and the three-way valve 923 positioned to connect the catheter coupling tube 933 to an aspiration tube 935. The catheter 930 may be used for aspiration. FIG. 52 also illustrates a first embodiment of a vacuum subsystem that is configured to provide high vacuum to the hub. In this embodiment, the vacuum subsystem includes a vacuum pump 888, a vacuum canister 882, a line 885 connecting the vacuum pump 888, the vacuum canister 882, and a sterility filter 884 in the line 885. In this embodiment, desperation subsystem includes a low vacuum line 872 and a high vacuum line 870 which are connected between the vacuum canister 882 and a three-way vacuum control valve 874. A first vacuum pressure sensor 871*a* is positioned to sense pressure on the high vacuum line 870, and a second vacuum pressure sensor 871*b* is positioned to sense pressure on low vacuum line 872. The low vacuum line 872 also includes a check valve 887 allowing material in the low vacuum line 872 to only flow towards the vacuum canister 882. The aspiration tube 935 is connected to three-way vacuum control valve 874 and clot pod 927, and a flow sensor 880 (e.g., an ultrasonic flow sensor) is positioned along the aspiration tube 935 to sense the flow or material through the aspiration tube 935. The three-way vacuum control valve 874 aligned to connect the high vacuum line 870 and the aspiration tube 935 to provide high vacuum to the aspiration tube 935. FIG. 53 illustrates an alternative embodiment from the one shown in FIG. 52, where the clot pod 927 is not positioned in the hub but instead is positioned closer to the vacuum canister 882 (e.g., in the cassette or in a portion of the tubing set 716).

Figure 54:
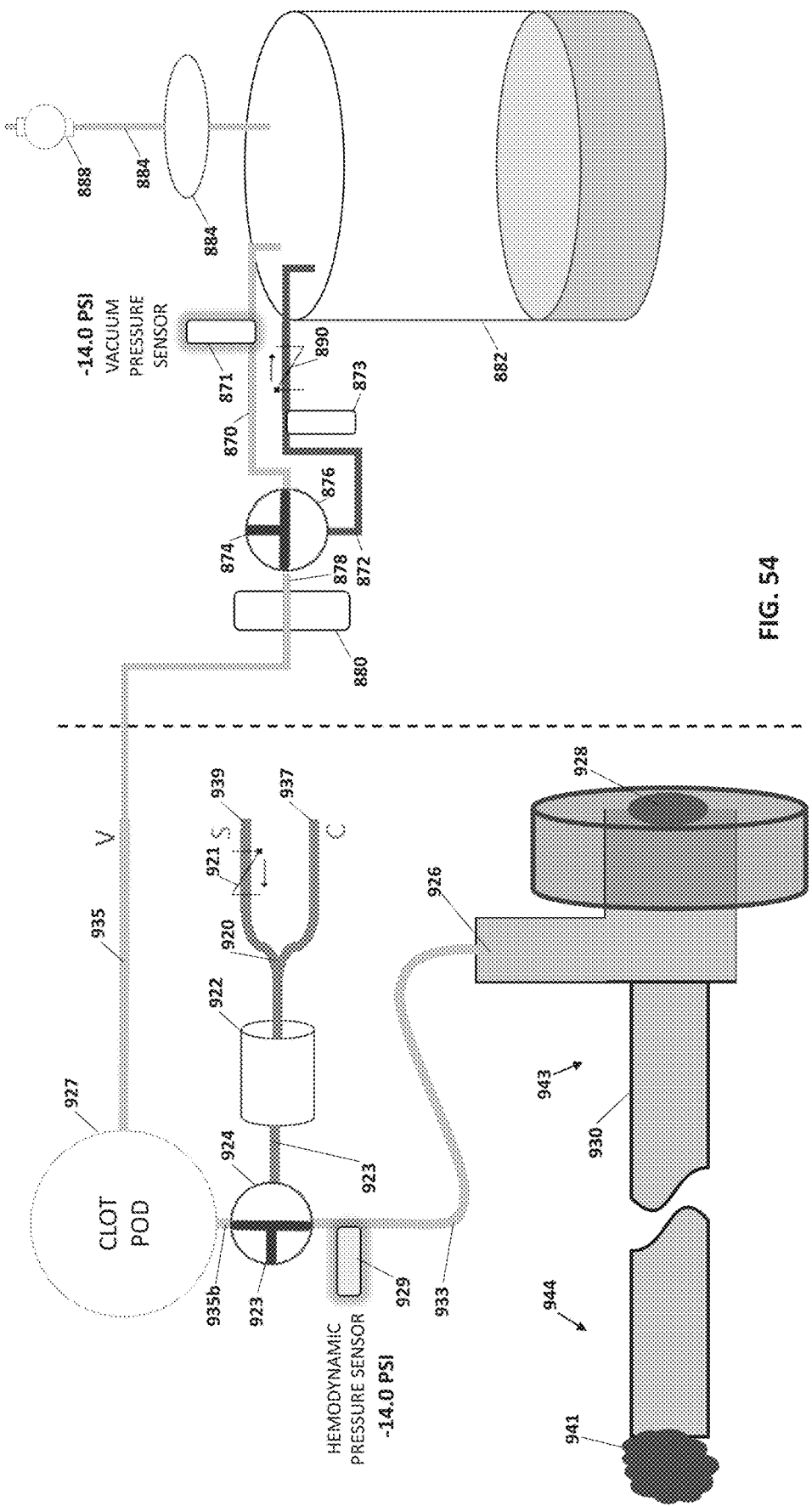
FIG. 54 illustrates a configuration of a hub and a vacuum system during clot aspiration.
Figure 55:
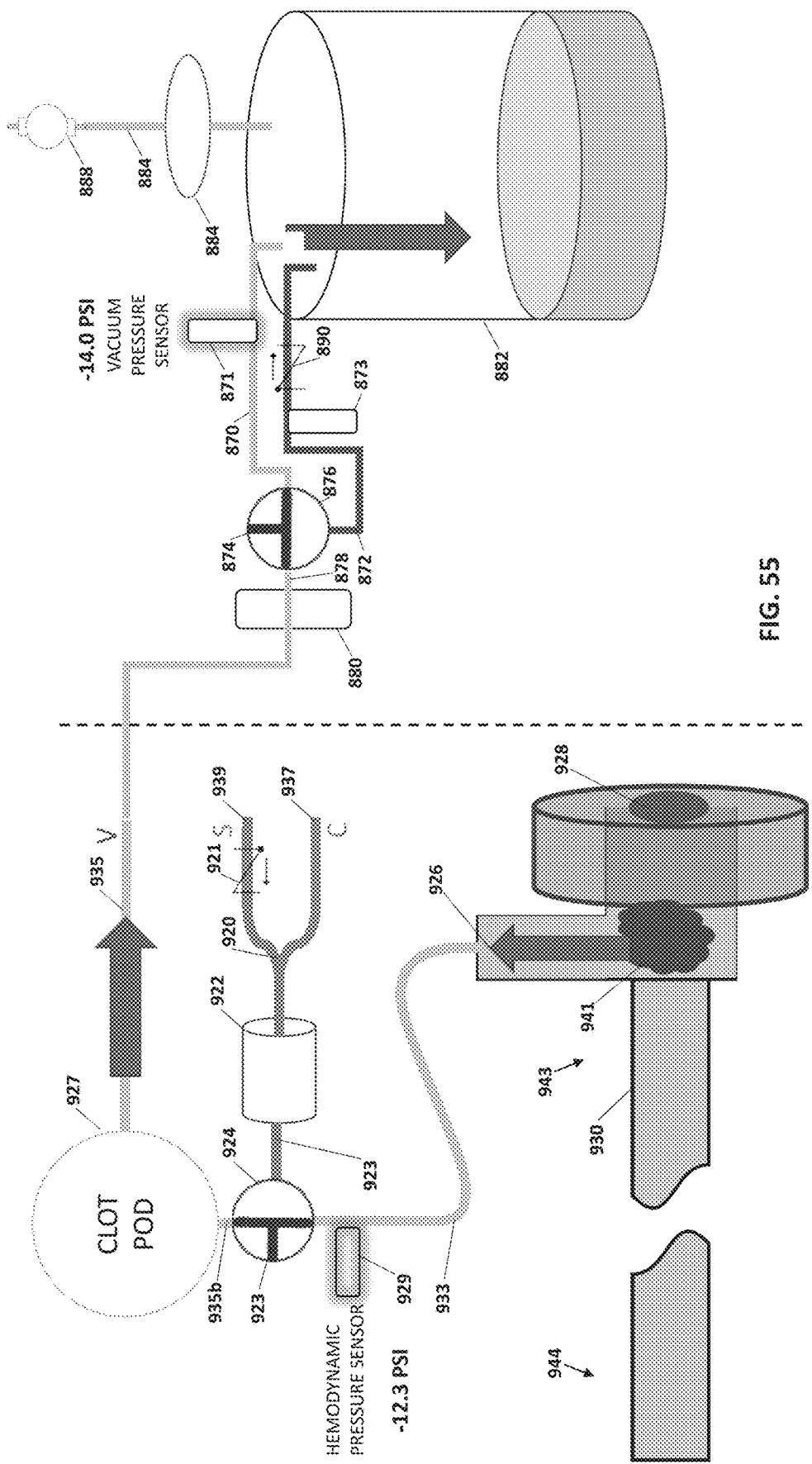
FIG. 55 illustrates another configuration of a hub and a vacuum system during clot aspiration.

Referring back to FIG. 51, process can proceed to block 1006 where the process determines if there is a high flow of material (e.g., blood, clot, saline, etc.) in the vacuum line. The high flow condition indicates that successful aspiration of material through the catheter. If there is not a high flow, the process proceeds to block 1016 where it can wait for a period of time (e.g., 1-2 minutes) while the high vacuum provided. The system can constantly check to see if a high flow condition has started to occur. FIGS. 54 and 55 represent an example of monitoring the vacuum and the aspiration tube 935 for the high flow condition. The system can monitor vacuum in the high vacuum line 870 and the aspiration tube 935 using vacuum pressure sensor 871, and the system can further monitor the flow of material through clot pod 927 and through the aspiration tube 935 to the vacuum canister 882 using flow sensor 880 (e.g., an ultrasonic flow sensor). In FIG. 54, vacuum pump 888 is actuated and the high vacuum line 870, near the vacuum canister 882, has a (high) vacuum of −14.0 psi (as sensed by vacuum pressure sensor 871), and catheter coupling tube 933, near the hemostasis valve 928 and the catheter 930, has a (high) vacuum of −14.0 psi (as sensed by hemodynamic pressure sensor 929). The catheter tip 944 is positioned near clot 941. In this configuration, there is not a high flow, and this can be sensed by the flow sensor 880. In FIG. 55, the clot 941 has passed through catheter 930 and is moving towards the luer connection 926, high vacuum line 870, near the vacuum canister 882, has a (high) vacuum of −14.0 psi, but now the catheter coupling tube 933, near the hemostasis valve 928 and the catheter 930 has a vacuum of −12.3 psi which can indicate clot 941 is being aspirated. This indicates high flow of materials is occurring, and this flow can also be sensed by the flow sensor 880.

Figure 56:
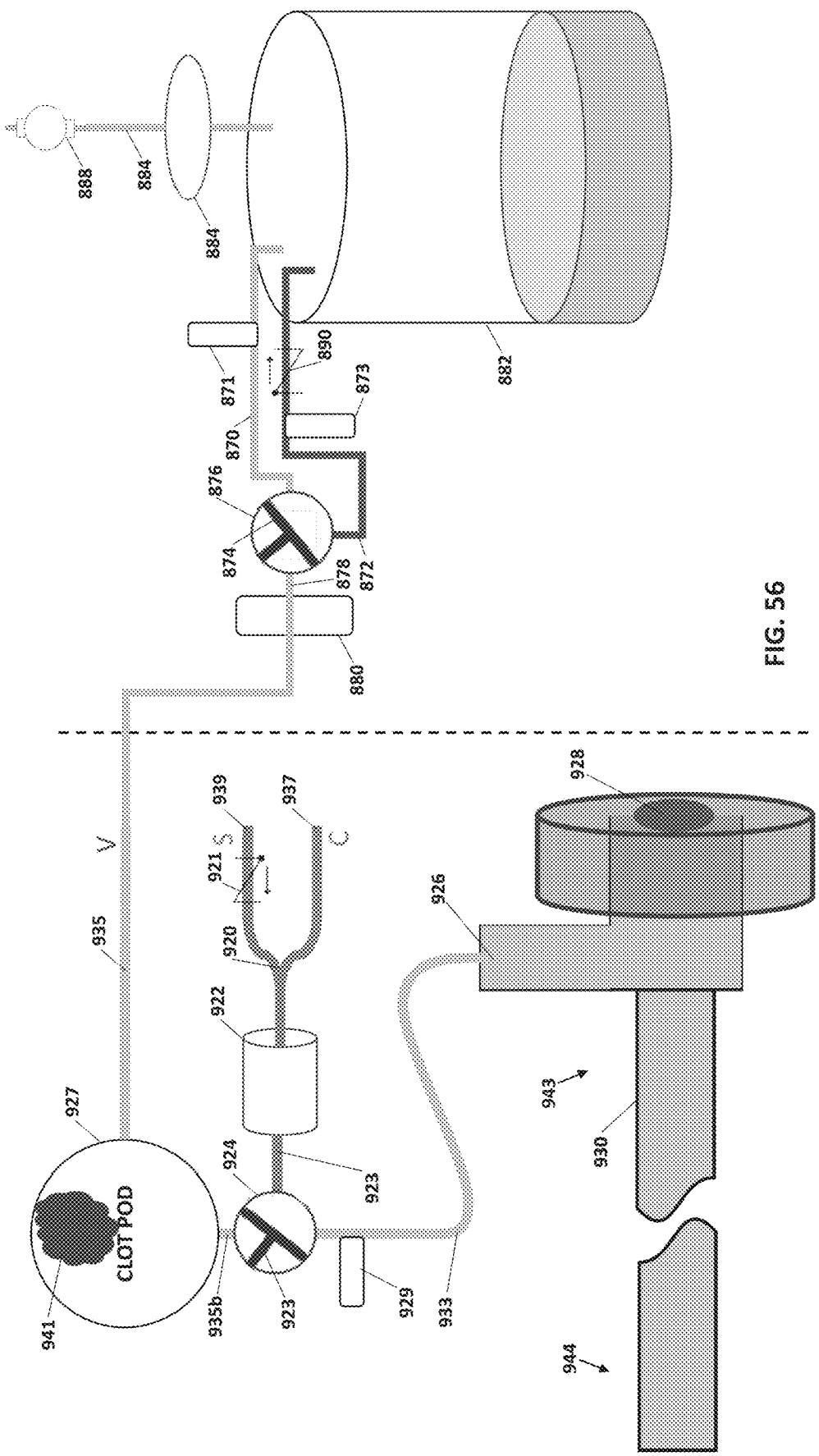
FIG. 56 illustrates a configuration of a hub and a vacuum system during clot aspiration.
Figure 57:
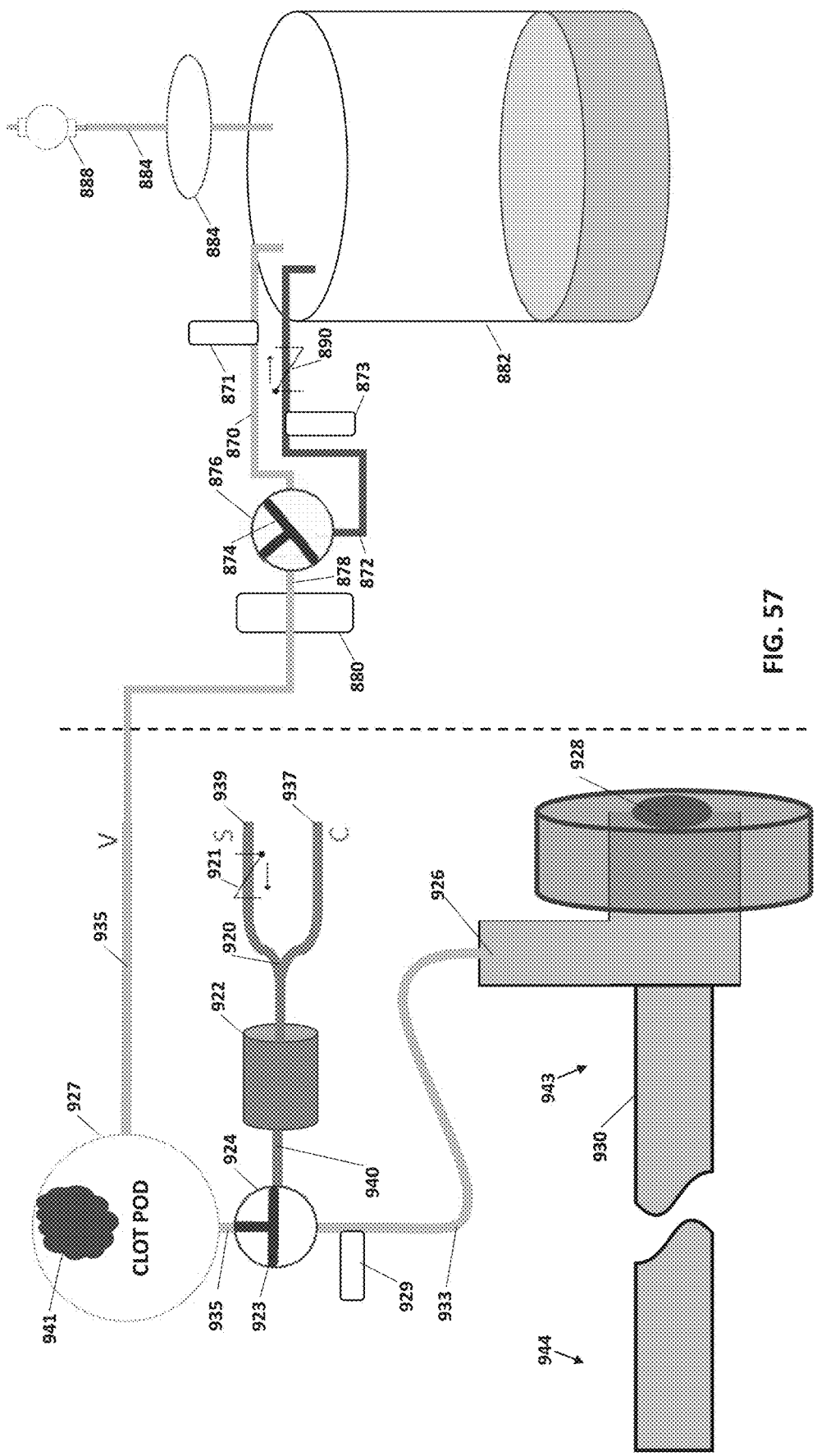
FIG. 57 illustrates a configuration of a hub and a vacuum system during clot aspiration.

Once the system determines that high flow has occurred the process can proceed to block 1008 and turn off the vacuum to the catheter 930. At this point, the clot 941 can be captured in clot pod 927, as illustrated in FIGS. 56 and 57. FIG. 56 also illustrates the system positioning three-way valves 923 and vacuum control valve 874 to stop providing high vacuum to the catheter 930. At block 1010, the process can flush the clot pod 927 which can be done by positioning three-way valve 923 to connect the saline/contrast tube 940 to the aspiration tube 935 which causes saline to be provided to the clot pod 927 to flush the clot pod 927, as illustrated in FIG. 57. Then the process can proceed to block 1012 with the system determines if the clot pod 927 contains the clot 941. In some embodiments, the system sense the presence of the clot 941 in the clot pod 927 using clot pod sensor 932 (FIG. 21). An example, clot pod sensor 932 is an optical sensor. In some embodiments, a user can visually check the clot pod to see if it contains the clot. If at block 1012 the process determines a clot is not in the clot pod 927, the process proceeds to block 1002 where the system is used to once again engage a clot with a catheter. If the system determines a clot is in clot pod 927, the process proceeds to block 1014 where additional backbleeding, contrast injections, and aspiration passes can be performed.

Referring again to FIG. 51, if at block 1016 the process determines that a flow is not occurring, the process proceeds to block 1018 where it can slowly pull back the (first) catheter away from the clot. Optionally, aspiration from a second catheter, either nested inside the first catheter or containing the first catheter in its lumen, can be provided (e.g., dual aspiration). The process can then proceed to block 1020 where the vacuum is turned off, and then to block 1022 where the catheter is removed from the patient and flushed, and then can proceed to block 1024 where the catheter is once again backbled, primed and inserted to continue a procedure.

As indicated above, the goal of backbleed is to clear the catheter lumen for subsequent injection while the catheter is in the body to replicate a procedure of pulling back on a syringe in a manual process of clearing a catheter lumen. FIGS. 58-63 illustrate actions that the system can be used to perform in a backbleed state represented by the fifth block 978 (FIG. 44). FIG. 58 illustrates an example of a process flow for backbleeding a catheter. At block 1030, the process determines if there is a good hemodynamic waveform at the catheter designated for backbleeding. This can be done, for example, using a hemodynamic pressure sensor 929 (FIG. 59) positioned on the catheter coupling tube 933 between luer connection 926 and the three-way valve 923. If there is not a good hemodynamic waveform, the process can proceed to block 1032 where the system can be used to pull back the catheter to free the tip the catheter from occlusion, for example, when the catheter tip is against the vessel wall or with the vessel has a diameter that matches or nearly matches diameter of the catheter. The process can return to block 1030 where it again determines if a good hemodynamic waveform exists. If the physician is not comfortable backbleeding the catheter, if a good hemodynamic waveform does not exist, the process can also proceed to block 1032 where the catheter is removed from the patient and flushed. The process can also proceed to block 1036 where the hemostasis valve can be opened to backbleed the catheter to verify the lumen is not against the vessel wall, and then proceed to block 1038 where saline is pumped into a vacuum line to prime the vacuum line. If a good hemodynamic waveform does exist, and even in some answers when a good hemodynamic waveform does not exist, the process continues to block 1038 from saline into the vacuum line to prime the back.

Figure 59:
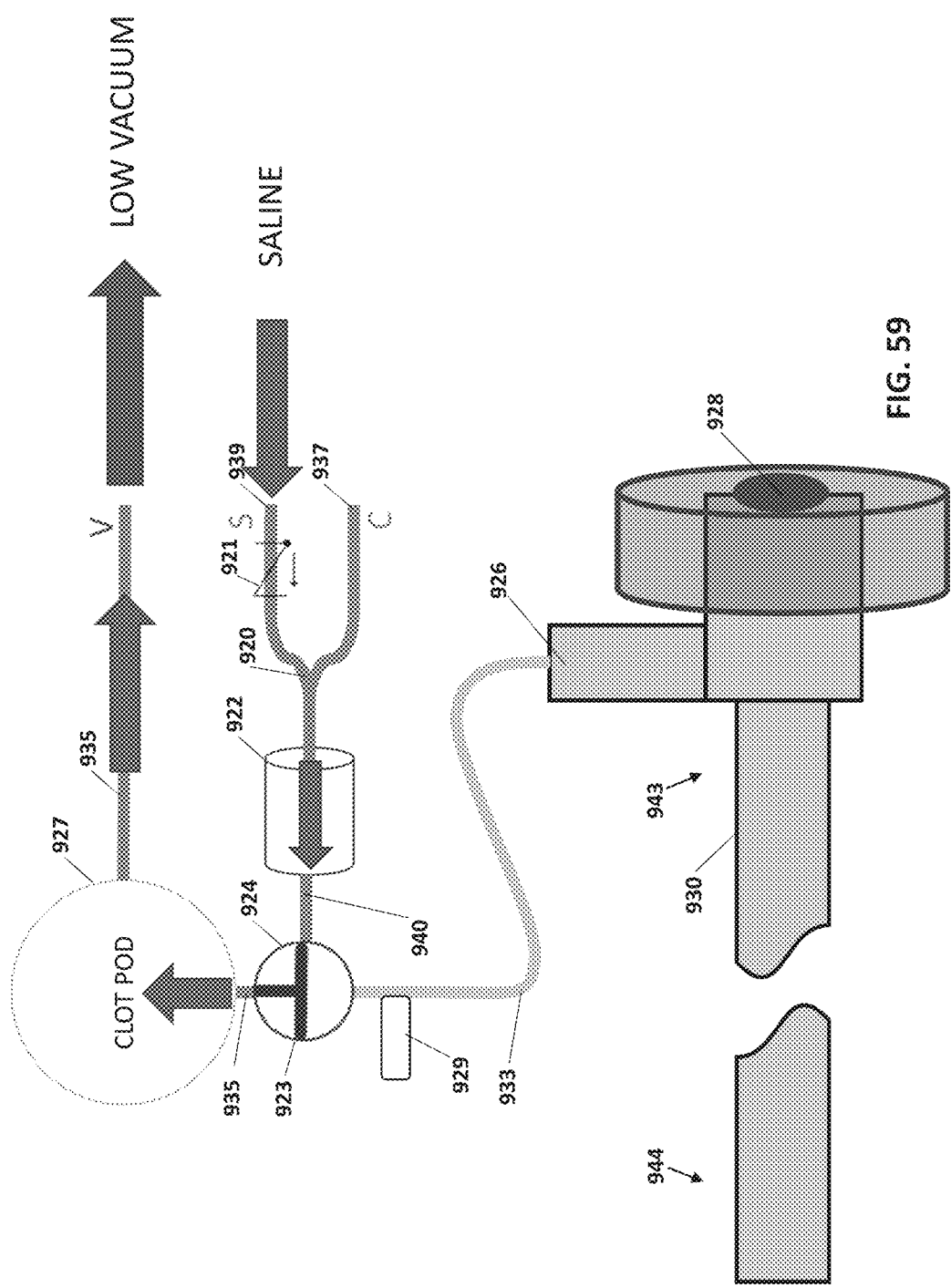
FIG. 59 illustrates an example of a hub in a configuration where saline is used to flush the clot pod.
Figure 60:
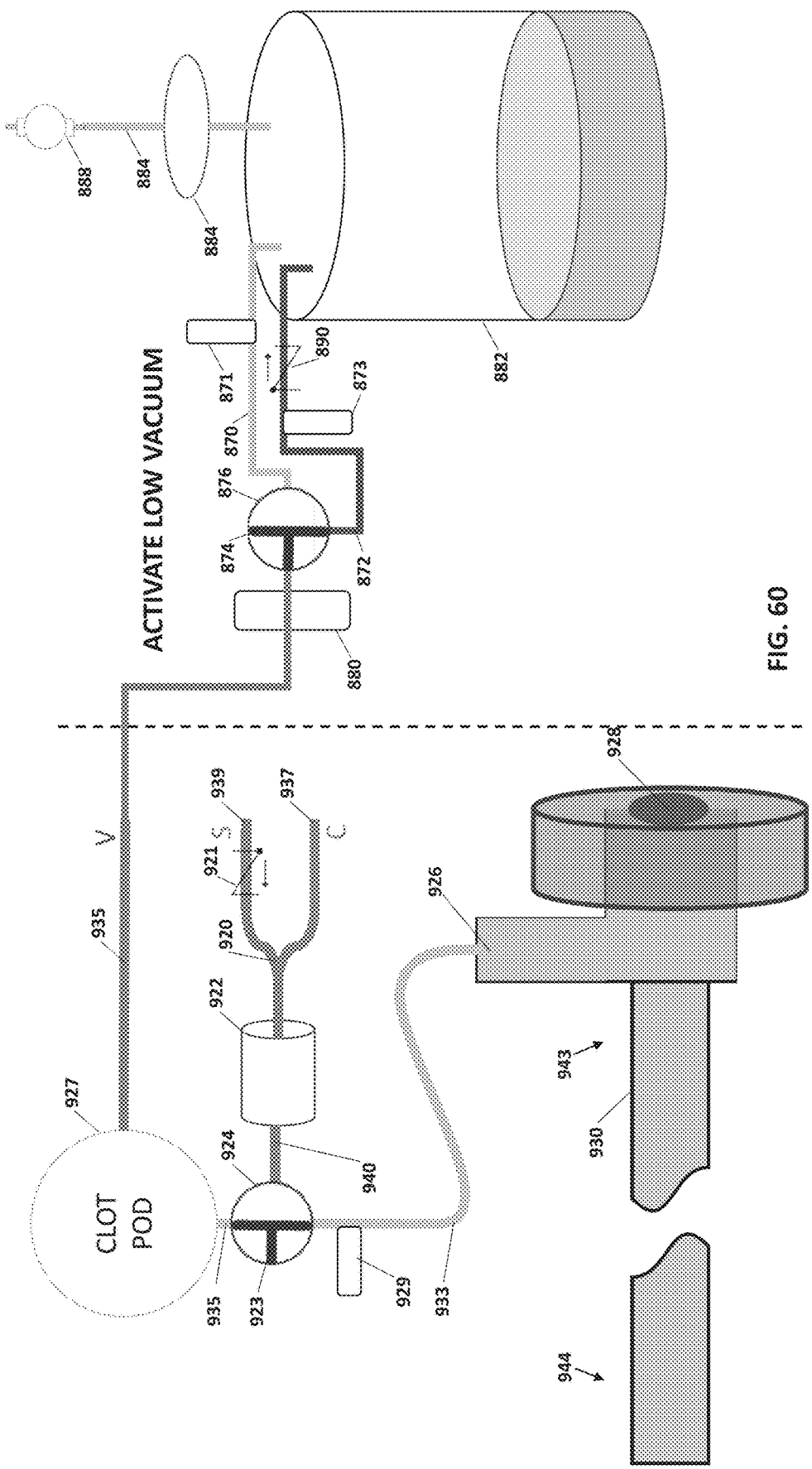
FIG. 60 shows an example of a configuration with a vacuum pump actuated and fluid communication channels are aligned to connect the lumen of a catheter to low vacuum provided by the vacuum subsystem.

Still referring to FIG. 58, at block 1038 saline is pumped into a vacuum line to prime the vacuum line. FIG. 59 illustrates an example of a hub in a configuration where saline is provided to the saline tube 939 from an actuated peristaltic pump 762*a*-762*d* (e.g., FIG. 15) and flows through the check valve 921, the wye connector 920, the air bubble filter 922, and the saline/contrast tube 940 to the three-way valve 923, which is positioned to align the saline/contrast tube 940 with the aspiration tube 935. A vacuum subsystem connected to the aspiration tube 935 can be actuated to provide a low vacuum such that the saline flows through the three-way valve 923, through the aspiration tube 935 and clot pod 927 back to a vacuum canister 882 to prime the aspiration tube 935 with saline. Referring to FIG. 58, the process can proceed from block 1038 to block 1040 and activate a vacuum pump 888 of the vacuum subsystem 710 to provide low vacuum in the aspiration tube 935. FIG. 60 shows a system configuration with vacuum pump 888 actuated, the three-way vacuum control valve 874 positioned to connect low vacuum line 872 to the aspiration tube 935, and the three-way valve 923 positioned to connect the aspiration tube 935 and the catheter coupling tube 933 thus connecting the lumen of catheter 930 to low vacuum.

Referring to FIG. 58, the process can proceed to block 1042 where it measures flow in the aspiration tube 935 for an amount of time. In some embodiments, the amount of time is a predetermined amount of time which can be part of the system information. The amount of time you can be a relatively short amount of time, for example, approximately one second, two seconds, three seconds, four seconds, five seconds, six seconds, seven seconds, eight seconds, nine seconds, or 10 seconds, plus or minus half a second. In some embodiments, the amount of time can be between 10 seconds and 30 seconds.

Figure 61:
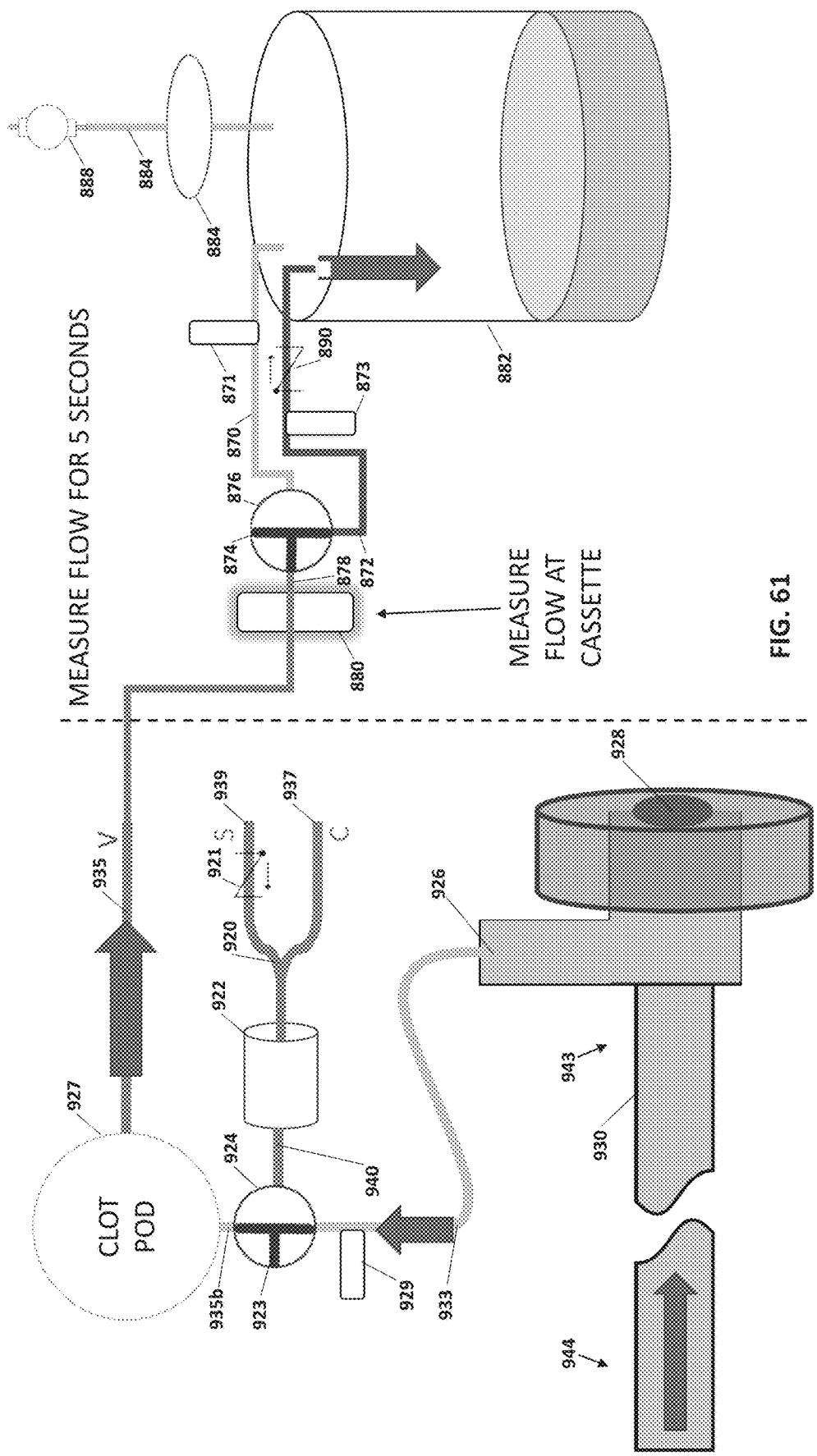
FIG. 61 illustrates a configuration of part of an embodiment of a fluidics system having a flow sensor (e.g., an ultrasonic flow sensor) positioned to sense the flow of substances, in a line in a cassette, exhausting into a vacuum canister in the cassette.
Figure 62:
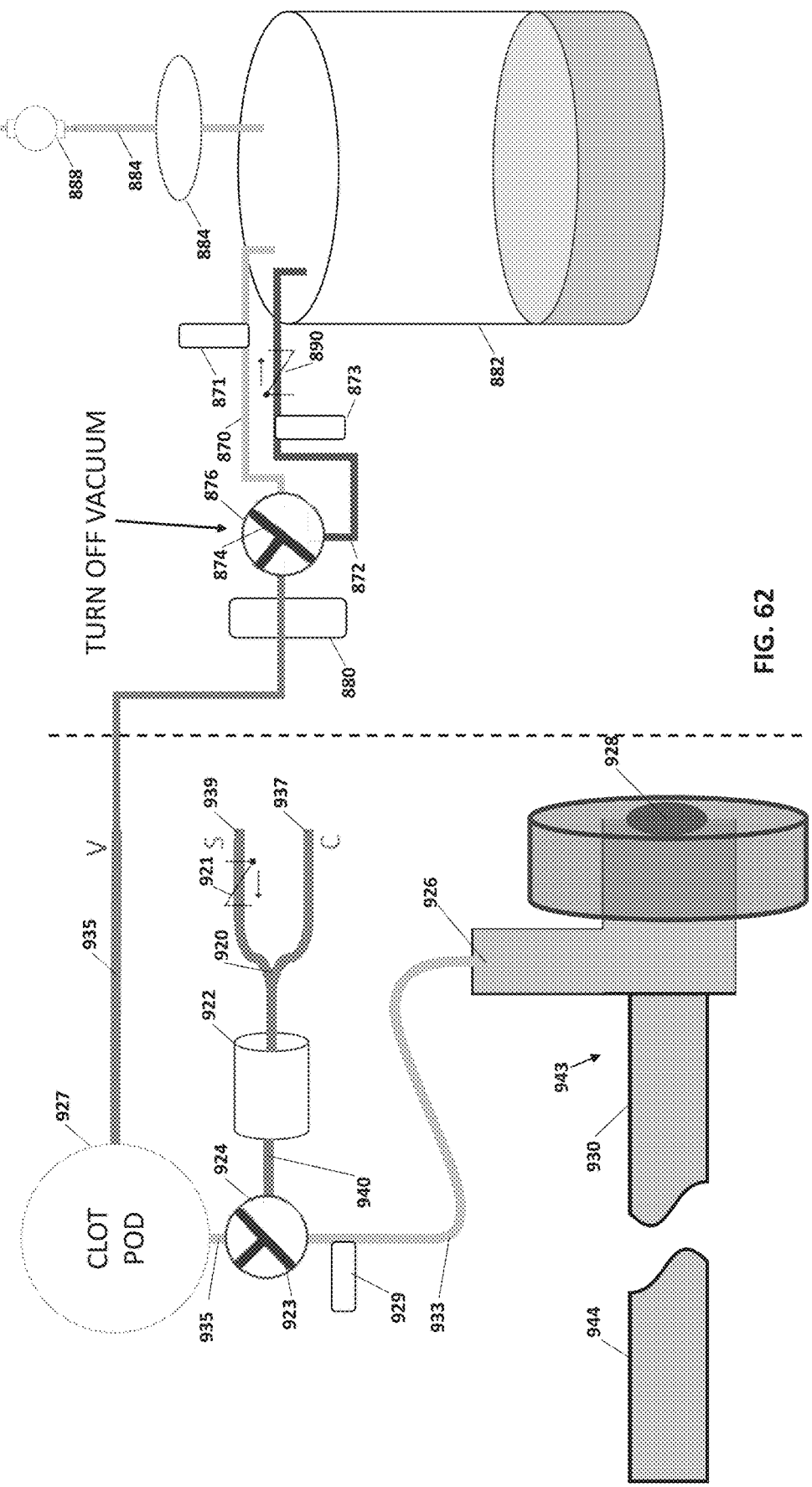
FIG. 62 illustrates an example of a configuration of the hub and a vacuum subsystem where vacuum provided to the hub has been turned off, e.g., in preparation for backbleeding a catheter through a hemostasis valve.

FIG. 61 illustrates a configuration of part of an embodiment of a fluidics system having a flow sensor (e.g., an ultrasonic flow sensor) positioned to sense the flow of substances, in a line in a cassette, exhausting into a vacuum canister in the cassette, where the cassette can be disposable and configured to be releasably coupled to a portion of the robotic catheter system (e.g., a pump station) and the flow sensor can be a component of the cassette or the flow sensor can be a component of the pump station. As illustrated in FIG. 61, a flow sensor 880 (e.g., ultrasonic flow sensor) positioned at the cassette 704 between the three-way valve 923 and three-way valve 84 to sense the flow of substances moving through the aspiration tube 935 and exhausting into the vacuum canister 882. In some embodiments, the cassette 704 includes an aperture into which the flow sensor 880 is positioned to measure the flow of substances through a portion of the aspiration tube 935 that is in the cassette. In some embodiments, flow sensor 880 is positioned to measure the flow of substances through a portion of the aspiration tube 935 that is outside of the cassette 704, between the cassette 704 and the hub 724. After the flows been measured for the period of time at block 1042, vacuum to the hub is turned off at block 1044. FIG. 62 illustrates an example of a configuration of one of the one or more hubs 724 and the vacuum subsystem 710 where vacuum provided to the hub 724 has been turned off by moving the three-way valve 923 to a position where it no longer connects the aspiration tube 935 and the catheter coupling tube 933, and by moving three-way valve 723 to a position where it no longer connects the aspiration tube 935 to low vacuum line 872.

FIG. 63 further illustrates a configuration of a hub for backbleeding a catheter 930 out of a hemostasis valve 928, for example, for performing a backbleeding in a process described herein. This may be done, for example, to clear blood foam or material from the lumen of the catheter 930. In some examples, signals from the hemodynamic pressure sensor 929 indicate that a normal blood pressure waveform is not present in the catheter coupling tube 933, which alerts a controller which provides an indication to a medical practitioner, e.g., on a user interface on a display of the remote system and/or on a local display. In this configuration, the three-way actuating valve 923 is robotically actuated to have an alignment that blocks the catheter coupling tube 933 from being in fluid communication with the aspiration tub 935 and blocks the catheter coupling tube 933 from being in fluid communication with the saline/contrast tube 940. The hemostasis valve 928 is robotically controlled to open such that the lumen of the catheter 930 is exposed to atmospheric pressure which causes and material including fluid (e.g., blood foam) to flow out of the catheter lumen through the hemostasis valve. In some examples, when blood flowing out of the hemostasis valve 928 is consistent and appears to contain no blood foam indicating the catheter lumen is cleared of material and blood foam, the hemostasis valve 928 can be robotically actuated to close.

FIGS. 64-87 illustrate examples of configurations, schematics, and flow diagrams of fluidic subsystems and components that can be controlled for performing fluidic processes on a robotic catheter system including, for example, priming the saline subsystem, priming the contrast subsystem, operating a hemostasis valve, injecting contrast, aspirating a clot, and back-bleeding. Processes performed by the robotic catheter system are controlled at least in part by a controller (FIG. 22, FIG. 78) and can be controlled based on a user input, predetermined programmed processes, parameter information, and/or based on conditions sensed by the system. FIGS. 64-70E illustrate examples of configurations of a fluidics system that can be used in a remotely controllable robotic catheter system to perform such processes. For example, to perform such processes valves, pumps, and other actuatable (or movable) components can be driven to be in a certain state or position by a controller. In some embodiments, the state or position of actuatable components can be determined by a position sensing mechanism on the component such that the controller can determine the current position of the component before, during, or after a process. In some embodiments, the positioning sensing mechanism can include a switch, encoder, etc. The sensing mechanism can be incorporated in the cassette or the mount to determine a position of a movable component (e.g., valve, pump) or on an actuator that drives the movable component. In some embodiments, a current state or position of the components can be electronically stored (e.g., in a table or file) and the controller is configured to determine the position of one or more components by accessing the stored information. In an example, before contrast is injected using a selected catheter in a system having multiple catheters, a valve coupling a selected catheter to a contrast subsystem can be determined to be aligned in an open position to provide a flow-path for contrast to the selected catheter, and one or more valves coupling non-selected catheters to the contrast subsystem can be determined to be aligned in a closed position to shutoff a flow-path of contrast to non-selected catheters. Such determinations may be made using the stored information and/or by using information from a sensing mechanism. The processes described herein are some of the processes a controller can be configured to perform by controlling fluidic equipment, either automatically or semi-automatically, based on one or more user inputs, sensed information, and/other information. An example of processes that can be partially or completely controlled by a controller using embodiments described herein include, but are not limited to:

providing a continuous "low" saline flow to each of one or more catheters, for example, at about 1 mL/minute of saline;

providing a "high" saline flow to flush a single one of the one or more catheters during a procedure, for example, at about 6 mL/second;

providing a contrast injection in any selected catheter of the system (for example, in any of three catheters of the system), the contrast injection provided with minimum delay after receiving a signal from a medical practitioner to inject contrast and being at, for example, up to about 4 mL/second at up to 500 psi;

determining catheter patency, of any of the one or more catheters at a medical practitioner's request;

providing aspiration at high (e.g., full) vacuum on one or more catheters;

backbleeding a selected one of the one or more catheters with low vacuum;

priming the saline subsystem without user interaction;

priming the contrast subsystem without user interaction;

priming fluid communication channels between the cassette and the plurality of mounts priming the saline flow-path in the plurality of mounts priming the contrast flow-path in the plurality of mounts sensing air bubbles in the saline subsystem and/or a mount and performing corrective actions;

sensing air bubbles in the contrast subsystem and/or a mount and performing corrective actions; and performing actions related to refills of fluids (e.g., contrast, saline).

The robotic catheter system illustrated in FIG. 64 can include actuatable components of a fluidics management system that are movable, as controlled by a controller, to align fluid communication channels to provide saline, contrast, and vacuum from a saline, contrast, and vacuum source (respectively) to hub assemblies 1400a-1400c. As indicated above, in some examples the hub assemblies 1400 can include a hub (first subassembly) and a mount (second subassembly). Although some of the examples described herein refer to mounts and components of mounts, this description is not limited to embodiments of hub assemblies that include a hub and a mount, rather the components and processes disclosed can also be implemented in both hub assemblies that do not include a first subassembly and a second hub assembly but instead are housed as a one-part hub assembly. Accordingly, reference to a mount(s) should be understood as also referring to either a multi-part hub assembly (e.g., two-part hub assembly having a hub and a mount) or part of a one-part hub assembly and unless specifically indicated or indicated by context. Correspondingly, reference to a hub assembly should be understood as referring to either a multi-part hub assembly (e.g., two-part hub assembly having a hub and a mount) or a one-part hub assembly.

The robotic catheter system can include certain sensors that are configured to sense a condition related to providing provide saline, contrast, and vacuum to the mounts 1400a-1400c and provide the sensed information to a controller. For example, the position of a valve, information from a pressure sensor, information from an air bubble sensor, etc. The controller can be configured to use the sensed information, user inputs, and/or stored information to control actions of the fluidics system to perform a medical procedure. In various embodiments, a pump station 2240 may include a controller to control actuators of the pump station 2240 to perform fluidic-related actions (e.g., provide saline, contrast, and vacuum to the mounts 1400a-1400c). In other embodiments, controller 2230 and/or system controller 2220 can be configured to control actuators and other components of the pump station 2240 to perform fluidic-related actions. Certain components and systems of the robotic catheter system may not be illustrated in FIG. 64 for clarity of this illustration (for example, a hub axial drive system, check valves, a catheter rotational system, controllers of the remote control system 2210, etc.).

In the embodiment illustrated in FIG. 64, robotic catheter system includes a fluidics assembly 1100 that includes a cassette 1200 which is configured to be releasably attached to a pump station 2240. The cassette 1200 includes a housing 1209 that supports a saline subsystem 1201, a contrast subsystem 1202, and a vacuum subsystem 1203. The saline subsystem 1201, contrast subsystem 1202, and vacuum subsystem 1203 can be all or partially enclosed within the housing 1209. Portions of the saline subsystem 1201, contrast subsystem 1202, and vacuum subsystem 1203 that interface with the components on the pump station 2240 can be positioned on the surface of the housing 1209. For example, an interface for an actuator to mechanically couple to a valve in the cassette, an interface for a portion of a contrast pump or saline pump in the cassette to mechanically couple to a portion of a contrast or saline pump in the pump station 2240 (e.g., a pump driver). The cassette 1200 can be placed on the pump station 2240 in position 1200a such that components of the cassette 1200 align with corresponding components of the pump station 2240. In an example, to align valves in the cassette 1200 with valve actuators of the pump station 2240, to align a portion of a peristaltic pump in the cassette 1200 with a portion of a peristaltic pump in the pump station 2240, and/or to align contrast pump in the cassette 1200 with a contrast pump drive mechanism in the pump station 2240. In another example, an electrical interface 1236 having a plurality of electrical connections on the cassette 1200 can be aligned with a corresponding electrical interface 1112 on the pump station 2240. The saline subsystem 1201, contrast subsystem 1202, and vacuum subsystem 1203 are further described in reference to FIG. 67. The cassette 1200 also includes an electrical interface 1236 which can be coupled to pump station electrical interface 1112 using various corresponding mechanical-electrical connectors can be used. For example, using a socket and a plurality of extended connectors built into the cassette and the pump station, using an electrical pigtail on one or both of the cassette and the pump station, using corresponding pogo pins connectors, etc. In operation, after the cassette 1200 is coupled to the pump station 2240, one or more saline source 1106 can be coupled to the saline subsystem 1201, one or more contrast source 1108 can be coupled to the contrast subsystem 1202, and one or more vacuum source 1110 is coupled to the vacuum subsystem 1203.

Figure 67:
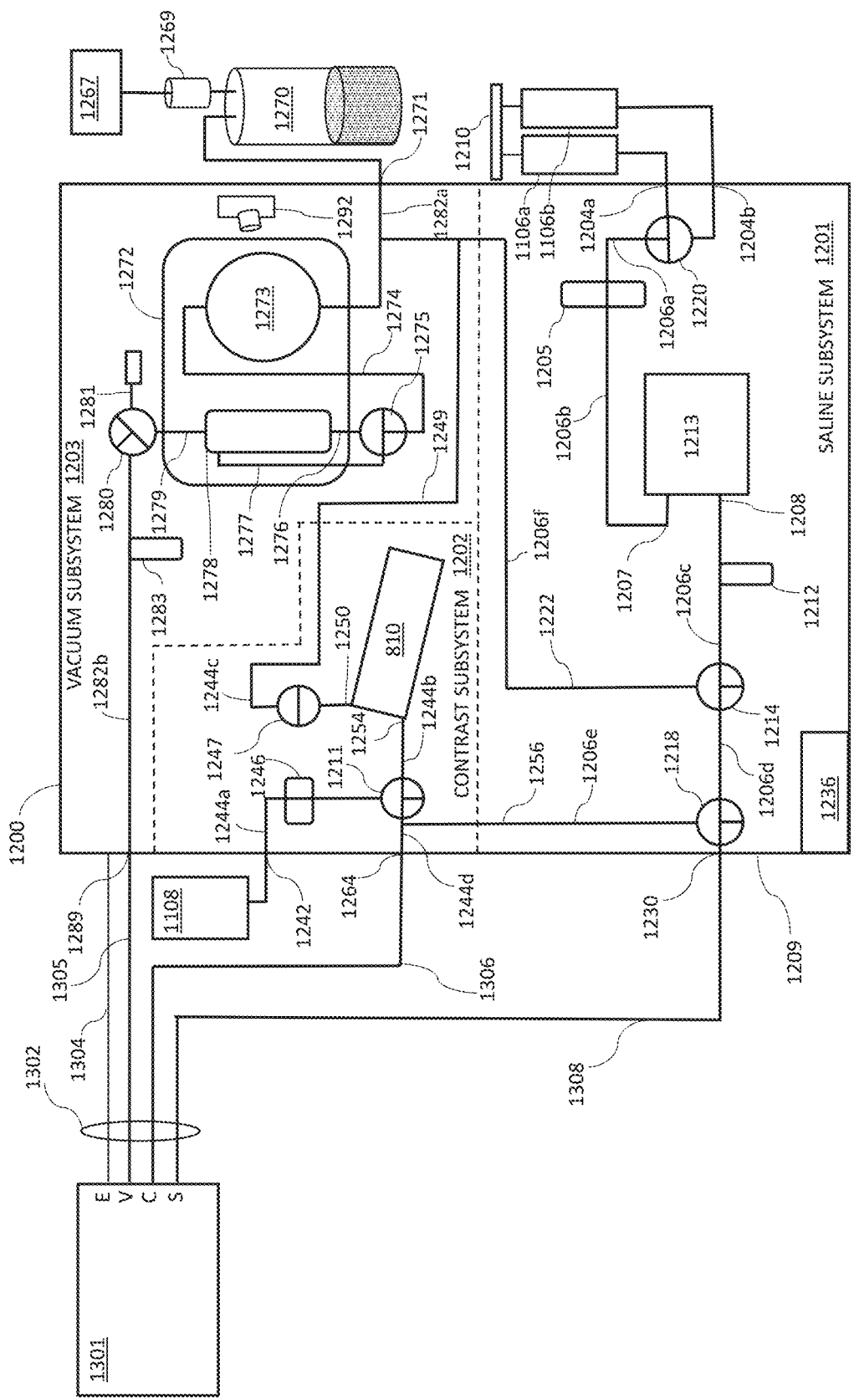
FIG. 67 is a schematic illustrating an example of a cassette of the fluidics assembly, the cassette including a housing that can support, all or part of a saline subsystem, a contrast subsystem, and a vacuum subsystem.

The fluidics assembly 1100 also can include one or more mounts 1400a-c, and communication channels 1300 coupled to the cassette 1200 and to each of the mounts 1400a-c, the communication channels 1300 structured to separately communicate saline, contrast, and vacuum from the cassette 1200 to the mounts 1400. As indicated above, the terms "channels," "tubes," "lines," molded apertures and structures, valves, and other structures or portions of components through which a fluid or a gas flows may be referred to herein generally as a fluid communication channel, or a "communication channel," or a "channel." The vacuum communication channel provides a path for aspirating material from any of the catheters 1402a-c coupled to the mounts 1400a-c, respectively, to a clot pod or vacuum canister (for example, as illustrated in FIG. 67). In the embodiment illustrated in FIG. 64, a guide catheter 1402a is coupled to a guide catheter mount 1400a, a procedure catheter 1402b is coupled to a procedure catheter mount 1400b, and an access catheter (or insert catheter) 1402c is coupled to an access catheter mount 1400c. In this example, the mounts 1400a-c are part of two-part hubs, the mounts 1400a-c being the first hub assemblies. The catheters 1402a-c are attached to second hub assemblies that mechanically couple to respective mounts 1400a-c and are configured to fluidically couple to mounts 1400a-c as well, for example, via connector (port) 1434a-c (FIG. 69). The mounts 1400 are controllable to move in the same axial direction and the catheters are sized and configured to be positioned in a nested configuration, that is, the access catheter 1402c can be positioned in part of or in the entire lumen of the procedure catheter 1402b, and both the access catheter 1402c and the procedure catheter 1402b can be positioned in part of or in the entire the lumen of the guide catheter 1402a, based on the positioning of the mounts 1400.

In some embodiments, all or part of the fluidics system that is attached to the pump station is made to be disposable. In some embodiments, part of the fluidics system that is attached to the pump station is made recyclable. In either case, the system fluidics system can be advantageously designed to be as lowest cost as feasible. For example, valves in the fluidics system can be positioned in the cassette 1200 while their corresponding valve actuators can be positioned in the pump station. The contrast pump can be positioned in the cassette and the corresponding contrast pump driver can be positioned in the pump station. A clot pod can be positioned in the cassette and a vacuum pump and a vacuum regulator can be positioned external to the cassette, as illustrated in FIG. 67. In some embodiments, a camera 1292 (FIG. 67) is used to generate an image of a clot pod assembly 1272 (FIG. 67) for viewing on a local or remotely located display, where the camera 1292 (capital equipment) can be positioned in the pump station 2240 or somewhere bedside (locally) and the clot pod assembly 1272 (disposable) can be positioned in the cassette. As imaging technology continues to become less expensive, in other embodiments a relatively inexpensive camera or sensor can be positioned in the cassette to generate an image of the clot pod to determine if it contains an aspirated clot.

Figure 65:
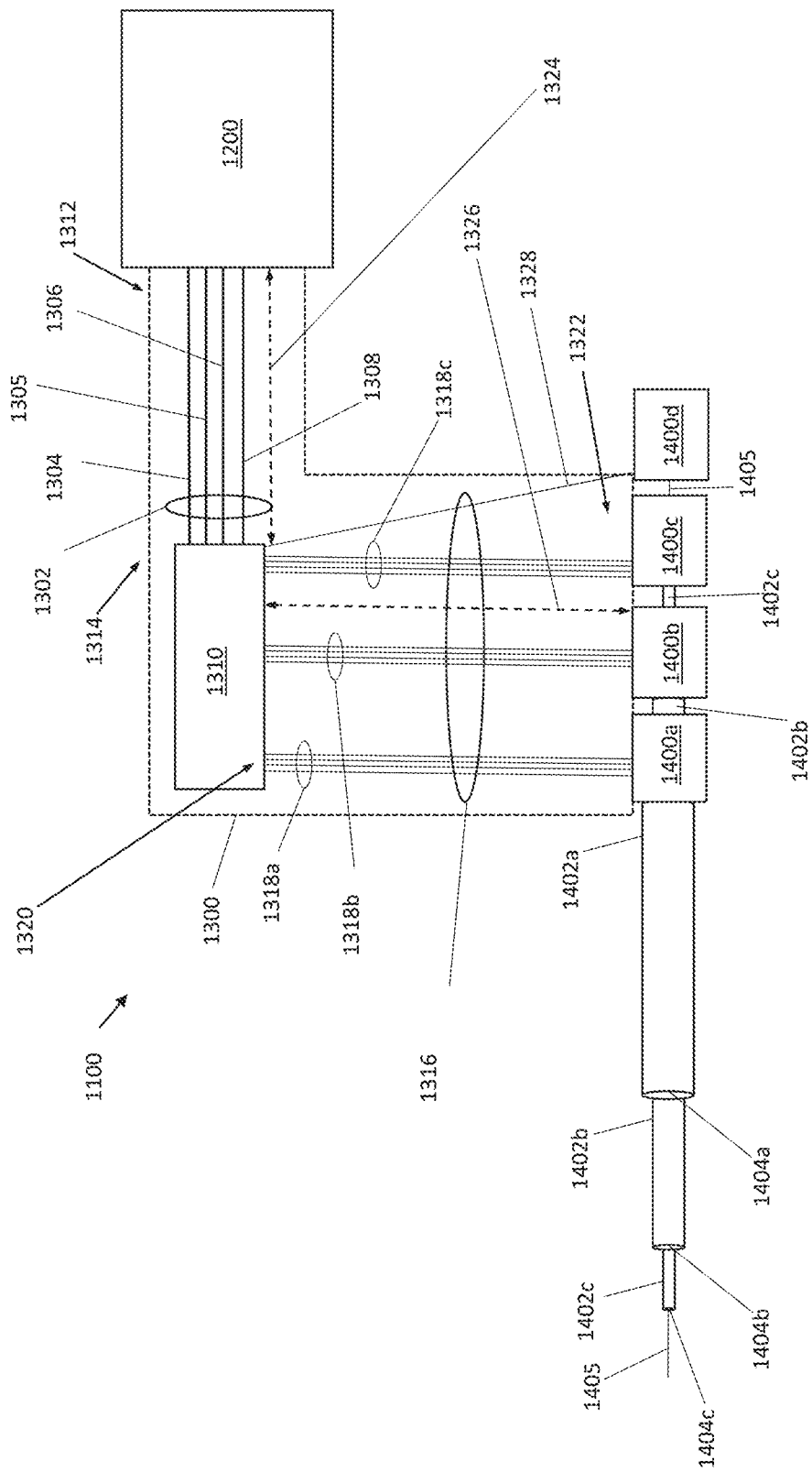
FIG. 65 is a schematic illustrating an example of a fluidics assembly (e.g., a disposable or recyclable fluidics assembly) that includes a cassette that couples to a pump station and couples to a saline source, a contrast source, and a vacuum source, the fluidics assembly also including a plurality of fluid communication channels to provide saline, contrast, and vacuum to mounts and catheters coupled to the mounts.

FIG. 65 is a schematic of the example of the fluidics assembly 1100 of FIG. 64, illustrating some components in further detail. In FIG. 65, the fluidics assembly 1100 includes a cassette 1200 that couples to the pump station and to a saline source, a contrast source, and a vacuum source, for example as described in reference to FIG. 64 and further in reference to FIG. 67. The fluidics assembly 1100 also includes a plurality of fluid communication channels 1300 to provide saline, contrast, and vacuum to one or more mounts 1400*a-c* and to the hubs (not shown) and catheters 1402*a-c* coupled to the mounts 1400*a-c*. The fluid communication channels 1300 also can include a plurality of electrical leads that connect components in the mounts (e.g., bubble sensors, pressure sensors, etc.) to the electrical interface 1236 of the cassette to provide signals to the control system 2220 when the cassette 1200 is coupled to the pump station 2240 (FIG. 64). In systems that include a plurality of hub assemblies, different hub assemblies may be configured differently or may have different fluids communicated to them, which are provided to a catheter. For example, in a system with a plurality of hub assemblies, one hub assembly may only provide saline to a catheter, and/or one hub assembly may provide saline and contrast to a catheter, and/or one hub assembly may provide saline and vacuum to a catheter, and/or one hub assembly may provide saline, contrast, and vacuum to a catheter.

One challenge of a fluidics system that provides fluids (e.g., saline and contrast) that enter a patient via a catheter is to provide such fluids in air-free (that is, bubble-free) fluid flows. As described in detail above and further below, typically when the cassette, fluid communication channels, hubs/mounts, and catheters are provided for use in an operating room they are not filled with fluid, and thus require priming to remove air from the saline and contrast flow-paths to prevent air bubbles entering a patient during a medical procedure. Once primed, air bubble detectors in the cassette and the mounts (illustrated in FIGS. 67 and 69) can help mitigate risks associated with air bubbles within saline and contrast flow-paths. However, because of the dangerous consequences of air entering a patient's bloodstream, where it is possible the fluid communication channels are visually inspected for air bubbles by a medical partitioner after the saline and contrast flow-paths are primed. Because of flexibility and mobility requirements for providing fluids from static saline and contrast fluid sources across a certain distance to moving mounts/catheters, at least a portion of the fluid communication channels between the cassette and the mounts can include flexible clear tubing. During the visual inspection, each centimeter of all the clear tubing supplying saline or contrast from the cassette 1300 to the mounts 1400 is carefully inspected to determine if air bubbles are present, and if so the lines can be re-primed. The length of time it takes to inspect the clear tubing for air bubbles directly relates to the total length of the contrast and saline tubing between the cassette and the mounts. In some examples (e.g., FIG. 64), the pump station is located several feet away from the set of mounts 1400 to provide room around the patient, and the saline and contrast fluid communication channels 1300 between the cassette 1200 and mounts 1400 may be about 14 feet long. If, as illustrated in FIG. 65, there are three mounts 1400*a-c* coupled to the communication channels 1300 and the communication channels include individual tubes for saline and contrast for each of three mounts 1400, this results in 84 linear feet of saline and contrast tubing to inspect. To make inspection of the tubing easier, the communication channels can be configured in a "flat" ribbon-like design with the saline and contrast communication channels next to each other such that the contrast and saline tubing can be inspected at the same time, which effectively reduces the length of tubing to be inspected to 42 feet (14' per mount). During the inspection, as the lines are each handled from end-to-end the medical practitioner typically will change gloves for each line (e.g., three glove changes). Such an inspection can take between 7 and 10 minutes, which is a long delay before proceeding with the operation when every minute of delay of performing a thrombectomy can result in further harm to the patient.

The first tubing set 1302 includes a one saline tube (channel) 1308 in fluid communication with a first saline flow-path in the cassette 1200 and a second saline flow-path in the splitter 1310, one contrast tube (channel) 1306 in fluid communication with a first contrast flow-path in the cassette 1200 and a contrast flow-path in the splitter 1310, and one vacuum tube (channel) 1305 in fluid communication with a first vacuum flow-path in the cassette 1200 and a second vacuum flow-path in the splitter 1310. An example first saline flow-path, first contrast flow-path, and first vacuum flow-path, in the cassette, are illustrated by the saline subsystem 1201, the contrast subsystem 1202, and the vacuum subsystem 1203 in FIG. 67. The splitter 1310 provides saline, contrast, and vacuum from the first tubing set 1302 to the second tubing set 1316, and includes channels forming a second saline flow-path, a second contrast flow-path, and a second vacuum flow-path, where the second saline flow-path, the second contrast flow-path, and the second vacuum flow-path each having a plurality of branches structured to provide outputs of saline, contrast, and vacuum to each mount 1400 from the single inputs of saline, contrast, and vacuum from the first tubing set 1302. The first tubing set 1302 can be configured in a ribbon-like design. In some embodiments, the length 1324 of the first tubing set can be between about 5 feet and about 17 feet in length based on the specific embodiment. In some examples, the ratio of the first length to the second length is greater than about 1:2 (e.g., about 1:3, 1:4, 1:5, 1:6, of 1:7) to minimize the amount of tubing that needs to be visually inspected. In a specific embodiment, the length of the first tubing set is about 12 feet in length. The tubes in the first tubing set have inner diameters to suitably provide saline, contrast and vacuum to the catheters. As a nonlimiting examples, the inner diameter of saline and contrast tubes (channels) in the first tubing set and the second tubing set can be about 0.071 inches. As a nonlimiting example, the inner diameter of vacuum tubes in the first tubing set and the second tubing set can be about 0.110 inches. The first tubing set 1302 can also include an electrical channel 1304. The electrical channel includes multiple electrical leads to communicate electrical signals between the mounts 1400 and the cassette 1200, and can be coupled to the electrical interface 1236. Sensors and electrical components in the cassette 1200 can also be coupled to the electrical interface 1236.

The second tubing set 1316 includes one or more tube groups 1318, each tube subgroup configured to provide a mount 1400 with saline, contrast, and vacuum. Each tube group 1318 can also provide each mount 1400 with one or more electrical leads. In the example in FIG. 65, each tube group 1318*a-c* includes a proximal end 1320 coupled to the splitter 1310 and a distal end 1322 coupled to one of the one or more mounts 1400*a-c*. Each tube group 1318*a-c* includes a saline subchannel in communication with the second saline flow-path in the splitter 1310, a contrast subchannel in communication with the second contrast flow-path in the splitter 1310, and a vacuum subchannel in communication with the second vacuum flow-path in the splitter 1310. Each tube group 1318 can be configured in a ribbon-like design. In some embodiments, the length 1326 of the second tubing set can be between about 1 foot and about 4 feet. In a specific embodiment, the length 1326 of the second tubing set is about 2 feet. In this embodiment, the length of tubing in the first tubing set and the second tubing set needed to be inspected is significantly reduced from 42 feet to 18 feet, which correspondingly drastically reduces the inspection time to about 3-4.5 minutes, advantageously reduces set-up time such that the medical procedure (e.g., a thrombectomy) can begin much sooner, which increases the patient's likelihood of a more successful recovery. In addition, this significant reduction in the amount of tubing to inspect also minimizes glove changes by the medical practitioner inspecting the tubing set from three glove changes to one glove change. The second tubing set 1316 can also provide one or more electrical leads 1328 to another mount that does not require fluids, for example, a guide wire mount 1400*d* configured to axially move and rotate a guide wire 1405 coupled to the guide wire mount 1400*d*, the guide wire 1405 configured to be positioned partially or fully in the lumen of access catheter 1402*c*. In some embodiments, connectors may be used to couple the second tubing set 1306 to the cassette 1200 and/or the splitter 1310. However, use of connectors in fluidic systems can cause air bubbles to be formed and/or trapped in a portion of the connector. In this embodiment, advantageously connectors are not used, rather the second tubing set 1316 is coupled to the splitter 1310 and the mounts 1400 such that the second tubing set 1316 is not meant to be decoupled prior to or during a medical procedure (for example, permanently, semi-permanently).

Figure 66:
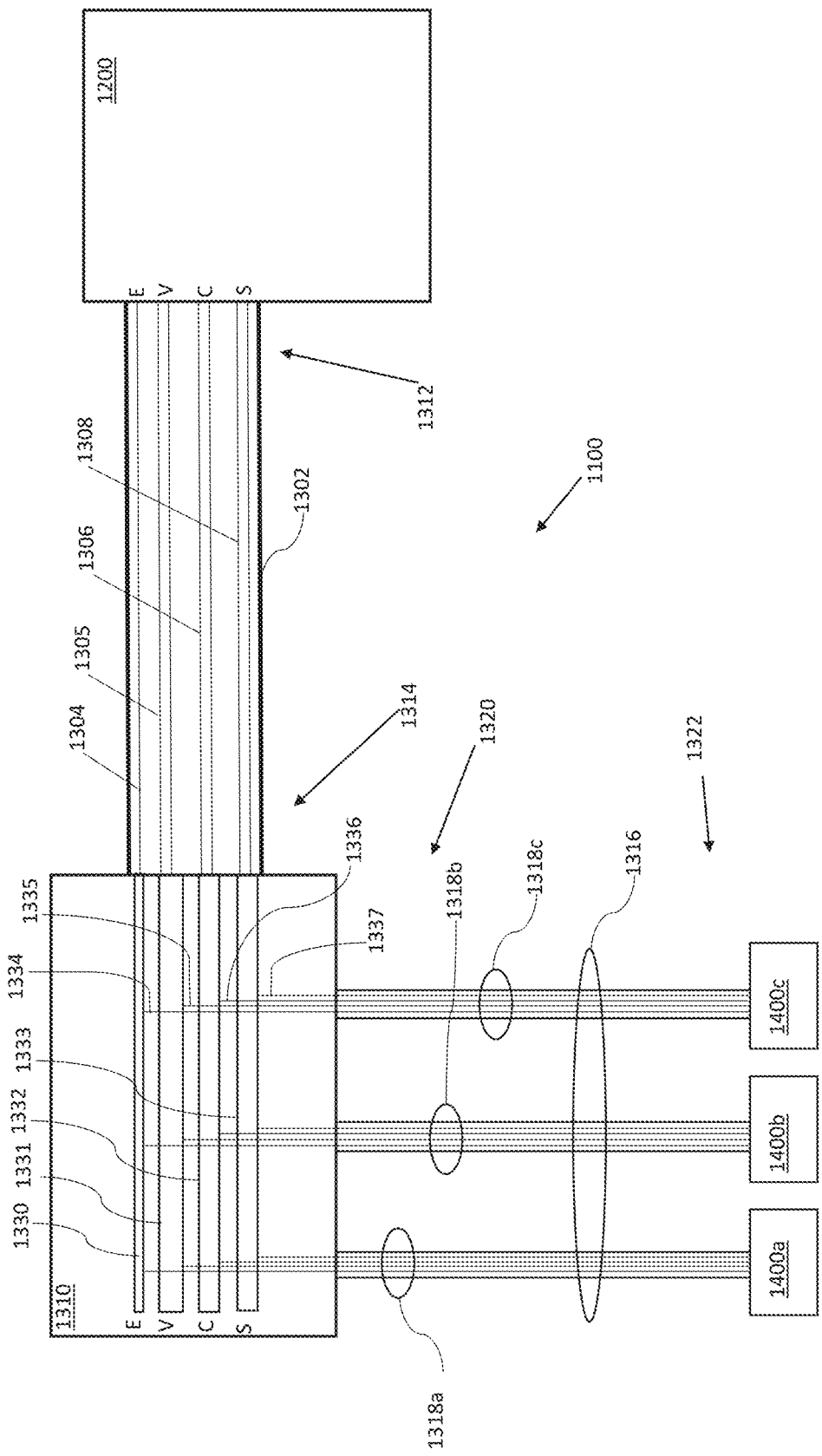
FIG. 66 is a schematic illustrating an example of a fluidics assembly that includes a cassette, a splitter, and one or more mounts, a first tubing set coupled to the cassette and splitter, and a second tubing set coupled between the splitter and the one or more mounts, the first tubing set having channels for providing saline, contrast and vacuum to the splitter, and the second tubing set having groups of channels (or subchannels) providing saline, contrast, and vacuum to each of the one or more mounts, the first and second tubing set and the splitter also providing electrical connections between the cassette and one or more connected mounts.

FIG. 66 is a schematic of an example of the fluidics assembly 1100 illustrated in FIG. 65 illustrating some additional features. The fluidics assembly 1100 includes cassette 1200, splitter 1310, and one or more mounts 1400, first tubing set 1302 coupled to the cassette 1200 and splitter 1310, and second tubing set 1316 coupled between the splitter 1310 and the one or more mounts 1400, the first tubing set 1316 having a saline channel 1308, a contrast channel 1306, and a vacuum channel 1305 for providing saline, contrast, and vacuum to the splitter 1310. In this example, the fluidics assembly 1100 is shown having three mounts 1400*a-c* that receive saline, contrast, and vacuum from the cassette 1200. The first tubing set 1302 also includes an electrical channel 1304 having a plurality of electrical leads for connecting electrical components in the mounts 1400 to an electrical interface of the cassette 1200. The second tubing set 1316 includes tube groups 1318*a-c* providing saline, contrast, and vacuum to mounts 1400*a-c*. Each of the tube groups 1318*ac* includes a saline subchannel 1333, a contrast subchannel 1332, a vacuum subchannel 1335, and an electrical subchannel 1334.

The splitter 1310 is structured to provide fluid communication of saline from the saline channel 1308 to the multiple saline subchannels 1333 in the tube groups 1316, to provide fluid communication of contrast from the contrast channel 1306 to the multiple contrast subchannels 1336 in the tube groups 1316, to provide fluid communication of saline from the single saline channel 1308 to the multiple saline subchannels 1333 in the tube groups 1316, and to provide fluid communication of vacuum from the vacuum channel 1305 to the multiple vacuum subchannels 1335 in the tube groups 1316. Also, the splitter 1310 is structured to provide electrical connection between the electrical channel 1304 and the electrical subchannels 1334 in the tube groups 1316. As illustrated in FIG. 66, the splitter 1310 includes a saline manifold 1333 coupled to the saline channel 1308 and the saline subchannels 1337 of each tube group 1318*a-c* in the second tubing set 1316, a contrast manifold 1332 coupled to the contrast channel 1308 and the contrast subchannels 1336 of each tube group 1318*a-c* in the second tubing set 1316, a vacuum manifold 1331 coupled to the vacuum channel 1305 and the vacuum subchannel of each tube group 1318*a-c* in the second tubing set 1316, and an electrical bus 1330 coupled to the electrical subchannels 1334 of each tube group 1318*a-c* in the second tubing set 1316. The saline manifold 1333, contrast manifold 1332, and vacuum manifold 1331 can be structured in various configurations that include tubes, splitters, manifolds, or any other structures to provide fluid communication from a single channel in the first tubing set 1302 to multiple subchannels in the second tubing set 1316. The electrical bus 1330 can be any electrical structure that provides electrical communication between the electrical subchannels of the tub groups 1318 in the second tubing set 1316 and the electrical channel 1304 in the first tubing set, including separate electrical wires (leads) or other electrical connections. For example, the electrical subchannels in the tube groups 1318 can include a plurality of electrical leads which are bundled together in the splitter 1310 and form the electrical channel 1304 in the first tubing set. As shown in FIG. 65, the electrical bus 1330 can also electrically connect the electrical channel 1304 of the first tubing set 1302 to the electrical connection 1328 to guide wire mount 1400*d*. Other embodiments having more or fewer mounts and corresponding connections are also possible. In some embodiments, the splitter 1310 may be referred to as a relay cassette. In some embodiments, the splitter 1310 may be located outside of the sterile field or within the sterile field. In some embodiments, the splitter 1310, second tubing set 1316, and associated hub assemblies (e.g., mounts 1400*a*, 1400*b*, and 1440*c* and associated hubs) can be positioned within the sterile field.

The embodiment of communication channels 1300 illustrated in FIGS. 65 and 66 is designed to minimize the time needed for inspecting the fluid lines. In this example, the fluid communication channels 1300 include a first tubing set 1302 having a proximal end 1312 coupled to the cassette 1200 and a distal end 1314 coupled to a splitter 1310. The fluid communication channels also include a second tubing set 1316 having one or more tube groups 1318, each tube group 1318 having a proximal end 1320 coupled to the splitter 1310 and a distal end 1312 coupled to one of the mounts 1400*a-c*. However, use of connectors in fluidic systems can cause air bubbles to be formed and/or trapped in a portion of the connector. In some preferred embodiments, advantageously connectors (i.e., releasable connectors) are not used to couple the first tubing set 1302 to the cassette 1200 and the splitter 1310, and are not used to connect the second tubing set 1316 to the splitter 1310. Instead, the first tubing set 1302 is coupled to the cassette 1200 and the splitter 1310 in a persistent coupling (e.g., permanent connection, semi-permanent coupling using glue, clamped fittings, integrally molded portions, and/or other suitable couplings) that it is not meant to be decoupled prior to or during a medical procedure. In preferred embodiments, the first tubing set 1302 and the second tubing set 1316 comprises transparent tubing. The cassette 1200 can comprise fluid communication channels (including portions of components) configured to communicate saline, contrast, and vacuum in first saline, contrast, and vacuum flow-paths, respectively. For example, as described in reference to FIG. 67. The splitter 1310 can comprise fluid communication channels configured to communicate saline, contrast, and vacuum in the second saline, contrast, and vacuum flow-paths, respectively. For example, as described in reference to FIG. 66. The fluid communication channels in the cassette 1200 and the splitter 1310 can include one or more tubes, channels (e.g., molded channels), portions of components (e.g., a drip chamber, clot pod, at least a portion of peristaltic saline pump, at least a portion of a contrast pump, robotically controlled valves, etc.) and other suitable fluid communication structures. The proximal end of the first tubing set can be coupled to the cassette 1200 using a persistent coupling. In some embodiments, the proximal end of the first tubing set 1302 extends into the cassette 1200 and forms a portion of a channel in the cassette 1200. The distal end of the first tubing set can be coupled to the splitter 1310 using a persistent coupling. In some embodiments, the distal end of the first tubing set 1302 extend into the splitter 1310 and can form a portion of a channel in the splitter 1310. In some embodiments, a portion of, or all of, the fluid communication channels of the first tubing set 1302 are integrally formed with a portion of, or all of, and the fluid communication channels of the splitter 1310. In an example, tubes forming each of a saline channel 1308, a contrast channel 1306, and a vacuum channel 1305 of the first tubing set 1302 are integrally formed with tubes forming saline, contrast, and vacuum fluid communication channels of the splitter 1310. In some embodiments, a portion of, or all of, the fluid communication channels of the second tubing set 1316 are integrally formed with a portion of, or all of, and the fluid communication channels of the splitter 1310. In an example, a portion, or all of, tubes forming a saline subchannel, a contrast subchannel, and a vacuum subchannel in each of one or more tube groups 1318 are formed to be integral with structures (e.g., tubes) forming the fluid communication channels of the splitter (e.g., channel 1337, channel 1336, channel 1335, manifolds 1333, 1332, 1331). In some embodiments, all or part of the fluid communication channels of the first tubing set 1302, the splitter 1310, and the second tubing set 1316 are formed as in integral structure and are persistently connected. In some embodiments, all or part of the fluid communication channels of the first tubing set 1302, the splitter 1310, the second tubing set 1316 and at least some of the fluid communication structures in the mounts 1400 are formed as an integral structure such that they are persistently connected. In some embodiments, all of the fluid communication channels in the first tubing set 1302, the splitter 1310, the second tubing set 1316 comprise tubing. For example, tubing that is coupled to the cassette 1200, split into multiple tube groups in the splitter, and tubing that is coupled to the splitter and the mounts. In some embodiments, all of the fluid communication channels in the first tubing set 1302, the splitter 1310, the second tubing set 1316 and the mounts 1400 comprise tubing. Some embodiments can include non-persistent coupling of fluid communication channels, for example, it is determined that such connections do not heighten the likelihood trapping air bubbles. In certain embodiments, tubes that are integrally formed with one another may be referred to as "tube sections" that together form a tube.

FIGS. 2, 3, 4, 14, 20, and 21 illustrate some examples of components of a fluidic system including configurations of a cassette. FIG. 67 is a schematic illustrating another example of a cassette 1200 of the fluidics assembly having a housing 1209 supports portions of a saline subsystem 1201, a contrast subsystem 1202, and a vacuum subsystem 1203 enclosed in, or partially enclosed in, the housing 1209. FIG. 67 also illustrates components of an example of a saline subsystem 1201, a contrast subsystem 1202, and a vacuum subsystem 1203 coupled to the cassette 1200, according to some embodiments. Other examples of cassettes may have different components, for example, fewer or more components. The control valves in the saline subsystem 1201, contrast subsystem 1202, and vacuum subsystem 1203 are robotically controlled to be actuated based on a user input, sensor signals received by a controller, and/or executable instructions that one or more hardware processors of a controller are configured to execute to prime the saline, contrast, and vacuum subsystems 1201, 1202, 1203, to prime fluid communication channels coupled to the saline, contrast, and vacuum subsystems 1201, 1202, 1203, prime fluidic channels in hubs/mounts, and provide saline, contrast, and vacuum from the saline, contrast, and vacuum subsystems 1201, 1202, 1203 to the hubs/mounts and ultimately to catheters connected to the hubs/mounts.

One or more saline sources can be coupled to the cassette 1200 to be selectively placed in fluid communication with the saline subsystem 1201. Flow-paths 1206 communicate saline through the saline subsystem 1201. In this example, two saline sources 1106a and 1106b (e.g., saline bags) are coupled to saline input ports 1204a, 1204b for providing a flow of saline to the saline subsystem 1201. The cassette 1200 includes a saline flow-path 1206 that receives saline through input ports 1204 and provides saline to the first tubing set 1302 through saline output port 1230, and also provides saline to the contrast subsystem 1202. Control valve 1214 can be actuated to connect channel 1206c to channel 1206f which is coupled to the vacuum subsystem 1203 vacuum channel 1282a to evacuate saline and air from the saline subsystem 1201 (i.e., channel 1206f can be used as a waste linc). Input ports 1204a, 1204b are in fluid communication with a saline first control valve 1220, which can be controlled to select the saline source 1106a, 1106b to receive saline from. In some embodiments the saline sources 1106a, 1106b are supported by a weight sensor 1210 that is connected to a controller (e.g., in pump station) and provides a signal associated with the weight of each saline source to the controller. The saline subsystem 1201 also includes a peristaltic pump 1213 having an inlet 1207 and an outlet 1208, and an air sensor 1205 positioned between the peristaltic pump 1213 and the first control valve 1220. In some embodiments, the air sensor 1205 is incorporated in the cassette 1200. In other embodiments, the air sensor 1205 is capital equipment (not disposable) and is not included in the cassette 1200, instead it can be included in the pump station and is positioned near channel 1206ab (e.g., near a piece of tubing 1206ab that engages with/into the air sensor 1205. In this embodiment, the portion of the peristaltic pump 1213 in the cassette includes tubing that, when the cassette 1200 is coupled to the pump station, the tubing interfaces with a movable portion of a peristaltic pump on the pump station which is configured to move saline through the saline flow-path 1206 of the saline subsystem 1201. An air sensor 1205 is positioned to sense air in the saline flow-path (channel) 1206ab between the peristaltic pump 1213 and the first control valve 1220, and is configured to generate a signal indicative of air detected. In some embodiments, the air sensor 1205 is capital equipment and located (for example, on the pump station). In such embodiments, channel 1206ab can include a portion of tubing that engages into the air sensor. In some embodiments, the air sensor is located in the cassette 1200 and is connected to the electrical interface 1236 such that a signal generated by the air sensor 1205 can be provided to the pump station (or another controller).

The saline subsystem 1201 also includes a pressure sensor 1212, positioned downstream of the peristaltic pump 1213, and configured to generate a signal indicative of pressure in the saline flow-path. The saline subsystem further includes a saline second control valve 1214 that is configured to selectively, as controlled by a controller, provide saline to a channel 1222 which is connected to the vacuum subsystem 1203. In operation, a controller may align the second control valve 1214 to diverge the saline flow-path to the vacuum subsystem 1203 to prime the upstream portion of the saline flow-path 1206*a-c*, for example, when the saline sources are first connected to the saline flow-path or when the saline source is switched from the first saline source 1106*a* a second saline source 1106*b*. The saline subsystem 1201 also includes a saline third control valve 1218 that is configured to selectively, as controlled by a controller, provide saline to a channel 1256 which is connected to the contrast subsystem 1202 for priming the contrast subsystem 1202 with saline. In a normal operational configuration for providing saline to catheters, a controller aligns the first control valve 1220 to receive saline from one of the two connected saline sources 1106, aligns the second control valve 1214 to provide saline from peristaltic pump 1213 to the third control valve 1218, and the lines the third control valve 1218 to provide saline to the saline output port 1230 to flow into the first tubing set 1302.

Still referring to the example illustrated in FIG. 67, the contrast subsystem 1202 includes a contrast flow-path 1244 that receives contrast from a contrast source 1108 through contrast inlet port 1242 along flow-path 1244*ab*, communicates contrast to the first tubing set 1302 via contrast outlet port 1264 along flow-path 1244*bd*, and communicates air and/or contrast from a contrast pump 810 to the vacuum subsystem 1203 along flow-path 1244*c*. In some embodiments, the contrast subsystem 1202 includes a control valve 1211 coupled to channels 1244*abd* that can be actuated to connect the contrast pump 810 to the contrast source 1108 (connecting channels 1244*b* and 1244*a*), or connecting the contrast pump 810 to channel 1244*d* and the contrast channel of the first tubing set 1302. An air sensor 1246 is positioned along the contrast flow-path between the contrast source 1108 and the contrast pump 810, and is configured to sense air in the contrast flow-path (channel) 1244*a* and generate a signal indicative of air being in the contrast flow-path. In some embodiments, the air sensor 1246 is capital equipment and located (for example, on the pump station). In such embodiments, channel 1244*a* can include a portion of tubing that engages into the air sensor 1246. In some embodiments, the air sensor 1246 is located in the cassette 1200 and is connected to the electrical interface 1236 such that a signal generated by the air sensor 1246 can be provided to the pump station (or another controller). In some embodiments, based on receiving a signal from the air sensor 1246 indicating presence of air in flow-path 1244*a*, the controller may pause contrast pump operation, indicate another contrast source is needed on a user display or with an audible alarm. When a new contrast source is attached to contrast inlet port 1242, in some embodiments the controller can initiate a priming sequence that includes actuating the contrast control valve 1247 to provide vacuum to the contrast pump 810 (connecting channel 1244*c* to port 1250) and actuating valve 1211 to connect channels 1244*a* and 1244*b* to expel air in the contrast pump 810 and channels 1244*ab* through channel 1244*c*. When changing contrast sources (bottles), channel 1244*b* and the contrast pump (syringe) 810 are already full of contrast, but 1244*a* has air in it. Instead of pulling air through the primed syringe, control valve 1247 can be actuated to block channel 1244*c* from being in fluid communication with port 1250 (if not already so aligned) and control valve 1211 can be actuated to connect channel 1244*a* to be in fluid communication with contrast pump outlet port 1254, and the contrast pump 810 can be actuated to push air in channel 1244*a* into the contrast source 1108.

The contrast pump 810 receives contrast into a chamber in the contrast pump 810 from the contrast source 1108 through contrast (outlet) port 1254 to fill the contrast pump 810. A contrast pump port 1250 connects the contrast pump 810 to channel 1244*c*, 1249 which is connected to the vacuum subsystem 1203, and may be used to remove air from the contrast pump 810. Contrast control valve 1247 is positioned between contrast pump port 1250 and the vacuum subsystem, and is selectively controlled by a controller to align the contrast control valve 1247 to open or to shut the air/contrast flow-path between the contrast pump 810 and the vacuum subsystem 1203. When filling the contrast pump 810 with contrast from contrast source 1108, in some embodiments, the contrast control valve 1247 can be opened to provide vacuum to the contrast pump 810 through port 1250 to evacuate air in the contrast pump 810 along flow-path 1244*c*, and help cause contrast from the contrast source to flow along flow-paths 1244*a* and 1244*b* into port 1254 to fill the pump 810. In an example, the contrast control valve 1247 is opened for a predetermined amount of time to prime the contrast pump 810. In other examples, vacuum is not used during the priming process. For example, once the contrast pump 810 is at least partially filled with contrast, the contrast pump can be actuated to expel any air in the pump through channel 1244*c* and/or through channel 1244*b* (e.g., to the contrast source). The contrast control valve 1247 is closed for operation of the contrast pump 810. FIG. 67 illustrates one example of a contrast subsystem 1202, but other configurations are also contemplated. For example, FIGS. 70A-C and Figures D-E illustrate two other configurations that also can be incorporated in the cassette 1200.

The vacuum subsystem 1203 of the cassette 1200 includes a vacuum port 1271 coupled to a vacuum canister 1270, which can be coupled to a vacuum filter 1269, and a vacuum source assembly (collectively "vacuum source") 1267 which can include a vacuum pump, a vacuum regulator, and other components for providing a consistent vacuum controlled robotically. The vacuum source 1267 can be controlled by a controller to provide a desired amount of vacuum to a vacuum flow-path. As illustrated in FIG. 67, in this example the vacuum canister 1270, and vacuum source 1267 are positioned outside of the cassette 1200. Vacuum flow-path 1282 extends from the vacuum inlet port 1271, through clot pod assembly 1272 to vacuum port 1289, which is coupled to the first tubing set 1302. A portion of the vacuum flow-path 1282 extends from the vacuum port 1271 to the clot pod assembly 1272. The contrast subsystem 1202 and the saline subsystem 1201 are connected to the vacuum flow-path 1282 through channels 1249 and 1222, respectively, connecting between the clot pod assembly 1272 and vacuum port 1271 such that fluid and air from the saline subsystem 1201 and the contrast subsystem 1202 do not go through the clot pod assembly 1272, instead flowing through vacuum port 1271 and into vacuum canister 1270. The clot pod assembly 1272 includes clot pod 1273, drip chamber 1278, and a first three-way control valve 1275 positioned in the vacuum flow-path 1282 between the drip pod 1278 and the clot pod 1273. The first control valve 1275 is controlled by a controller to align the vacuum flow-path 1282 to connect clot pod inlet line 1274 to either the drip pod outlet line 1276 or the drip pod bypass line 1277. The first control valve 1275 can also be controlled by a controller to align the vacuum flow-path 1282 to neither the drip pod outlet line 1276 or the drip pod bypass line 1277. Drip pod inlet line 1279 connects the vacuum flow-path to second three-way control valve 1280, which is controlled by a controller to align the vacuum flow-path 1282 to vacuum port 1289 and the first tubing set 1302, or to the local atmosphere. A pressure sensor 1283 is positioned along the flow-path 1282 between control valve 1280 and vacuum port 1289. Pressure sensor 1283 also connected to the electrical interface 1236, and is configured to detect pressure in the vacuum flow-path 1282 and provide a signal indicative of the detected pressure to the electrical interface 1236.

At least a portion of the clot pod assembly 1272 can be transparent to allow a medical practitioner to view the drip chamber 1278 and the clot pod 1273. For example, to see a fluid flow into the drip chamber and to determine a level of fluid accumulated in the drip chamber, and to view and assess material captured in the clot pod. In an example, the clot pod assembly 1272 can be structured to be positioned along a surface of the cassette 1200. In some embodiments, one side of the clot pod assembly 1272 can be transparent to such that the drip chamber and the clot pod are visible to a medical practitioner when the cassette is mounted on the pump station, and the opposite side is transparent or translucent to allow light illuminate the drip chamber and/or clot pod for easier viewing. An imaging sensor (e.g., a camera) 1292 can be positioned to generate an image of the clot pod 1273 and/or the drip pod 1278, and the image can be displayed locally or remotely to provide information on the contents of the clot pod 1273 and/or the drip pod 1273. In this embodiment, the imaging sensor 1292 is not included in the cassette 1200, but instead the imaging sensor 1292 can be incorporated in the pump station or another suitable location (locally) such that it can generate an image of the clot pod 1273 and/or drip pod 1278. In some embodiments, the imaging sensor 1292 can be incorporated in the cassette, however, having the imaging sensor positioned in the disposable cassette may increase cost. In embodiments where the imaging sensor is disposed external to the cassette 1200, a portion of the cassette 1200 can be transparent to allow the imaging sensor 1292 to image the clot pod assembly 1272, or a portion thereof.

Saline subsystem 1201 can include air sensor 1205 and pressure sensor 1212, the contrast subsystem 1202 includes air sensor 1246, and the vacuum subsystem 1203 includes pressure sensor 1283. Signals from these sensors are received by a controller, which can use these signals to align control valves in the cassette 1200 to vary the saline, contrast, and vacuum flow-paths in the cassette and perform processes described herein, and other processes. A purpose of these sensors is to detect potentially hazardous situations, for example, running out of a fluid source, a kink or occlusion in a fluid line, etc. Although the saline and contrast air sensors 1205, 1246 can be located in a pump station and engage a portion of saline or contrast tubing in the cassette, or they can be located in the cassette, such air sensors can be considered and referred to as being a part of the saline subsystem 1201 or the contrast subsystem 1202.

The configuration of the cassette 1200 in FIG. 67 has a certain different features than cassettes described above, which can provide operational and cost advantages. For example, in embodiments in FIGS. 14 and 22, the vacuum canister is positioned in the cassette, where in FIG. 67 the vacuum canister 1270 (and vacuum regulator 1269 and the vacuum pump 1267) are positioned outside of the cassette in the line from the vacuum canister 1270 is coupled to the cassette at port 1271. This may allow the disposable cassette to be less expensive, and allow various configurations of vacuum source assemblies (e.g., the vacuum canister, the vacuum regulator, and the vacuum pump) to be used with the system, and any changes or improvements to the vacuum canister will not affect the design of the cassette. The configuration of the cassette 1200 in FIG. 67 includes two saline sources 1106a, 1106b in a control valve 1220 that a controller can align to select either one of the saline sources, either based on a manual input or automatically based on the sensed condition (e.g., the signal from weight sensor 1210 that a saline source is depleted below a predetermined threshold, a signal from air sensor 1205 that air is present in the saline flow-path 1206). The saline subsystem 1201 in FIG. 67 includes channel 1222 from the saline subsystem to the vacuum subsystem 1203 which allows for a simplified priming procedure compared to configurations illustrated in FIGS. 14 and 22. In some embodiments, if air is detected, the controller can be configured to automatically, or based on user input, to prime the saline subsystem by directing the saline flow-path 1206 upstream of the second control valve 1214 to vacuum such that saline and the air in the saline subsystem 1201 upstream of the second control valve 1214 is evacuated into the vacuum canister 1270. Also, the contrast subsystem 1202 has advantageously been simplified and no longer includes a contrast manifold and the three control valves (as illustrated in FIG. 14) can be aligned to select the catheter to receive contrast. Instead, control valves that the controller can align to provide contrast from the contrast subsystem 1202 to a catheter are located in the mounts as shown in an example, in FIG. 69 (e.g., control valve 1426). Similarly, control valves that the controller can align to provide saline from the saline subsystem 12012 a catheter located in the mounts (e.g., FIG. 69). Having these control valves in the mounts also advantageously obviates the need for having multiple individually controllable saline lines and contrast lines extending from the cassette 1200 to the mounts 1400, such that the fluid communication channels 1300 (FIG. 66) are also simplified and include less tubing. Also, unlike some of the previous embodiments described above, the example configuration illustrated in FIG. 67 advantageously does not include saline lines or control valves for providing saline to a femoral sheath, thus further simplifying the design of the cassette 1200 and may lower manufacturing costs. Instead, in this example, saline can be provided to a femoral sheath from a separate system (not shown here).

In reference to FIG. 64-67, examples of a fluidics management system can comprise a cassette configured to receive saline from a saline source (e.g., two or more saline sources), receive contrast from a contrast source, and receive vacuum from a vacuum source. The cassette can include saline subsystem having a first saline flow-path; a contrast subsystem having a first contrast flow-path; and a vacuum subsystem including a first vacuum flow-path. The first saline, contrast, and vacuum flow-paths can include channels, tubes, line, and portions of other components (e.g., one or more of a valve, drip chamber, clot pod, pump, etc. in the cassette). The fluidics management system can also include a splitter having a second saline flow-path, a second contrast flow-path, and a second vacuum flow-path. Each of the second saline, contrast, and vacuum flow-paths has single proximal end and a plurality of distal ends. The single proximal end of the second saline flow-path is in fluid communication with a single saline channel in a first tubing set, the proximal end of the second contrast flow-path is in fluid communication with a single channel of the first tubing set. The second vacuum flow-path proximal end is in fluid communication with the single vacuum channel of the first tubing set. The first tubing set has a first length, as measured between the cassette and the splitter, and is coupled to the cassette and splitter. The first tubing set includes a single saline channel coupled to the first saline flow-path and the proximal end of the second saline flow-path, the single contrast channel coupled to the first contrast flow-path and the proximal end of the second contrast flow-path, and a single vacuum channel coupled to the first vacuum flow-path and the proximal end of the second vacuum flow-path. The fluidics management system can also include two or more mounts, for example, three mounts, or four mounts. The mounts can be configured in various ways to provide saline, contrast, and vacuum to catheters coupled to each respective mount. Each mount can be configured to have a third saline flow-path, a third contrast flow-path, and a third vacuum flow-path to provide saline, contrast and vacuum to a catheter via a connector configured to couple to a catheter. In some embodiments, the catheter is coupled to another assembly (e.g., a hub) which is coupled to the mount, and the lumen of the catheter is coupled to the connector to be in fluid communication with the connector. A mount can include a plurality of robotically actuated control valves controlled by a control system to selectively align the third saline flow-path, the third contrast flow-path, and the third vacuum flow-path to be in fluid communication with the connector. The fluidics management system can also include a second tubing set having a second length, the second tubing set comprising a plurality of tube groups, each tube group coupled to the splitter on a proximal end of the tube group and to one of the two or more mounts on a distal end of the tube group. Each tube group including a saline subchannel coupled to the distal end of the second saline flow-path of the splitter, a contrast subchannel coupled to the distal end of the second contrast flow-path of the splitter, and a vacuum subchannel coupled to the distal end of the second vacuum flow-path of the splitter. The first tubing set has a first length and the second tubing set has a second length, the first length being greater than the second length to minimize the amount of tubing that needs to be visually inspected for air bubbles. In some examples, first tubing set has a first length and the second tubing set has a second length, and the first length of the first tubing set is at least two times as long as the second length of the second tubing set.

Priming of the saline subsystem 1201 can include robotically actuating control valves of the saline subsystem 1201, robotically actuating a peristaltic saline pump, and robotically controlling vacuum in the vacuum subsystem to perform a priming process. In one example of priming of the saline subsystem 1201, the cassette 1200 is coupled to a pump station and the saline sources 1106 are coupled to the saline subsystem. To be able to switch from one saline source to another connected saline source seamlessly, channels connecting both saline sources to the saline subsystem 1201 must be primed. Control valve 1220 can be robotically controlled to couple a first saline source to peristaltic pump inlet 1207. The control valve 1214 can be aligned to connect the peristaltic pump outlet 1208 to channel 1222 which is connected to the vacuum subsystem 1203 to purge air from the saline subsystem. The vacuum subsystem can be robotically controlled to provide vacuum to channel 1222 to purge air during priming, or to not provide vacuum and instead channel 1222 and cannister 1270 is used to purge air without applying vacuum using channel 1222. In this configuration, the saline peristaltic pump can be run (e.g., for a predetermined time) to evacuate air in the saline flow-path from the first saline source to control valve 1214. During this priming, signals from air sensor 1205 should eventually indicate no air is detected. The control valve can be actuated to connect a second saline source to peristaltic pump inlet 1207. The control valve 1214 can continue to be aligned to connect the peristaltic pump outlet 1208 to channel 1222 which is connected to the vacuum subsystem 1203. The vacuum subsystem can again be robotically controlled to provide vacuum to channel 1222. In this configuration, the saline peristaltic pump can be run (e.g., for a predetermined time) to evacuate air in the saline flow-path from the second saline source to control valve 1214. During this priming, signals from air sensor 1205 should eventually indicate no air is detected. Control valve 1214 can be actuated to connect the outlet port 1208 to the second control valve 1218, which can be actuated to connect the outlet port 1208 to the contrast subsystem 1202 for priming the contrast subsystem, or connect outlet port 1208 to a saline communication channel to provide saline to a plurality of mounts 1400.

Priming of the contrast subsystem 1202 can include robotically actuating control valve 1247, robotically actuating contrast pump 810, and robotically controlling the vacuum subsystem 1203 to perform a priming process. In an example of a priming process of the contrast subsystem 1202, the contrast subsystem 1202 is connected to a contrast source 1108. Control valve 1247 is robotically actuated to connect outlet port 1250 to the vacuum subsystem 1203. In some embodiments of a contrast priming process, the vacuum pump 1267 is robotically actuated to provide vacuum to the contrast pump 810 and the contrast flow-path 1244, which evacuates air from the contrast flow-path (channel) 1244 and the contrast pump 810 as it fills with contrast. In other embodiments of a contrast priming process, vacuum is not provided to the contrast pump 810 via channel 1244, instead channel 1244 is used to evacuate air which evacuate air from channels 1244 and the contrast pump 810 as the pump is filled with contrast. Subsequently, control valve 1247 is closed and the contrast pump 810 can be robotically actuated to provide contrast to a prime a contrast communication channel, to prime the plurality of mounts, and to provide contrast to the plurality of mounts 1400. As part of priming the contrast communication channels connect the cassette to the mounts, control valve 1218 can robotically actuated to connect outlet port 1208 to the contrast flow-path 1244, and the saline peristaltic pump can be actuated to provide saline to the contrast subsystem such that it fills the contrast communication channels to the mounts and in the mounts. The vacuum subsystem 1203 can be robotically controlled to provide vacuum to the mounts 1400 via a vacuum communication channel. In each mount, one or more control valves can be robotically actuated to place a contrast channel in the mount, that is being provided saline from the cassette, in fluid communication with a vacuum channel to facilitate priming the contrast communication channel between the cassette and the mount, and in the mount, with saline to evacuate all air in these channels. Subsequently, control valve 1218 can be actuated to connect the outlet port 1208 with saline outlet port 1230 and the saline communication channel that is coupled to the mounts.

As indicated above for other embodiments of a fluidics system, saline and contrast channels in the fluidics assembly 1100 and in hub assemblies (e.g., mounts and/or hubs) are also primed prior to use in a medical procedure. In an example, once the saline subsystem 1201 is primed, the control valve 1218 be actuated to connect the outlet of the saline pump to the saline channels in the fluidics assembly 1100 and the saline pump 1213 can be actuated to provide saline to fill the saline 1308, the saline manifold 1333, the saline subchannels 1337 of each tube group in the second tubing set 1316, and the saline channel 1412 of each mount 1400 with saline. To facilitate the flow of saline through these saline channels, the control valves 1426 and 1428 can be actuated to connect the saline channel 1412 with the vacuum channel 1416 while controlling the vacuum subsystem 1203 to provide vacuum to the mounts 1400. Once the saline subsystem 1201 is primed, the control valve 1218 be actuated to connect the outlet of the saline pump 1213 to the contrast subsystem 1202, and the saline pump 1213 can be actuated to provide saline into the contrast subsystem 1202, to fill the contrast channel 1306, the contrast manifold 1333, the contrast subchannels 1336 of the second tubing set, and the contrast channel 1414 of each mount 1400 with saline. To facilitate the flow of saline through the contrast channels, the control valves 1426 and 1428 can be actuated to connect the contrast channel 1414 with the vacuum channel 1416 while controlling the vacuum subsystem to provide vacuum to the mount. A controller can use signals received from the saline and contrast air sensors 1418, 1420 to determine when no air is detected in the saline channel 1412 and the contrast channel 1414, indicating the saline and contrast channels between the mounts and the cassette are primed with saline. Similar to the priming processes described above, once the contrast channels from the cassette to the mounts are primed with saline, and the contrast channel 1414 is primed with saline, Channels of the fluidic assembly can also be prime.

Figure 68A:
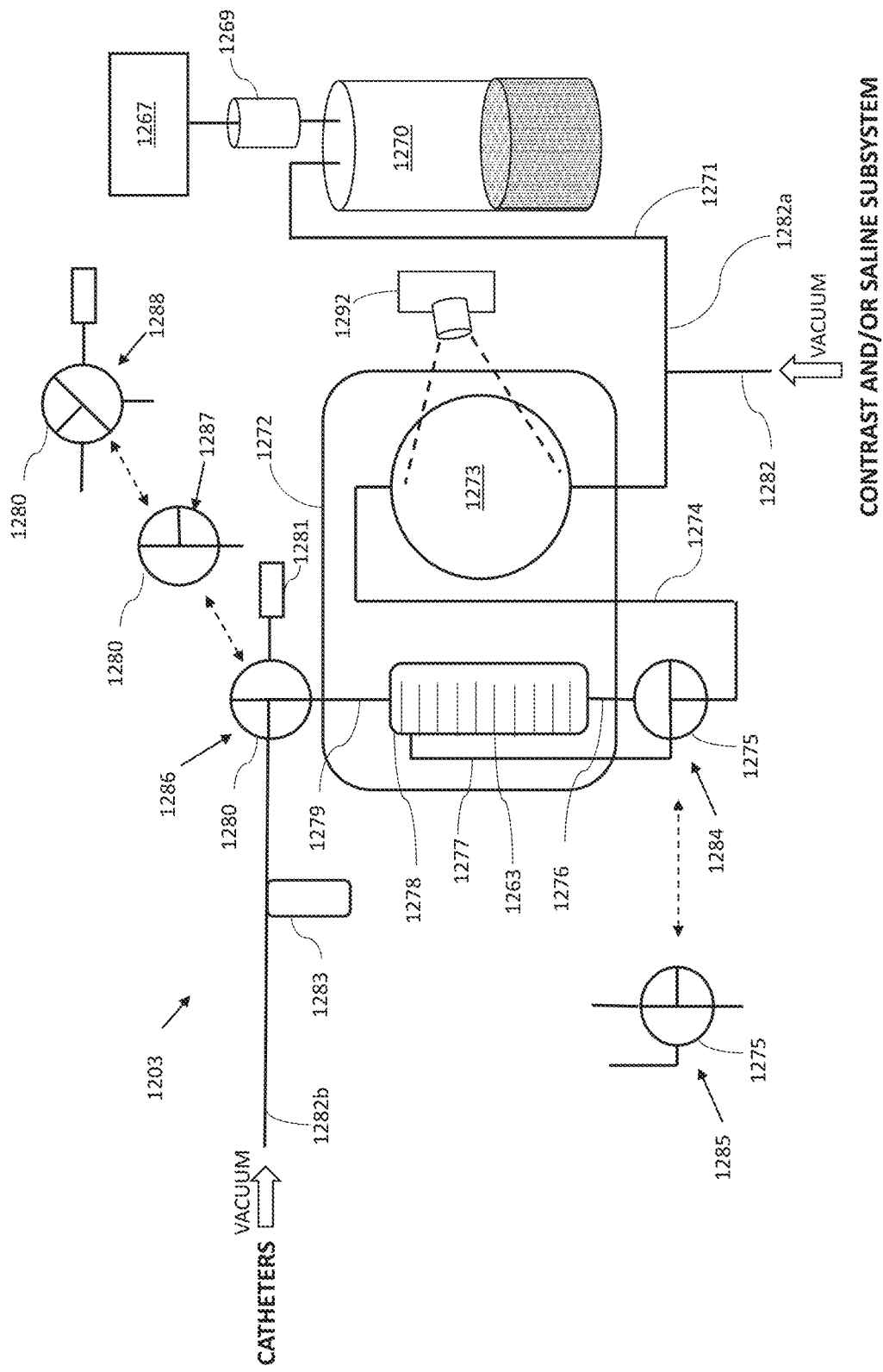
FIG. 68A is a schematic illustrating an example of a drip pod and clot pod assembly.
Figure 85:
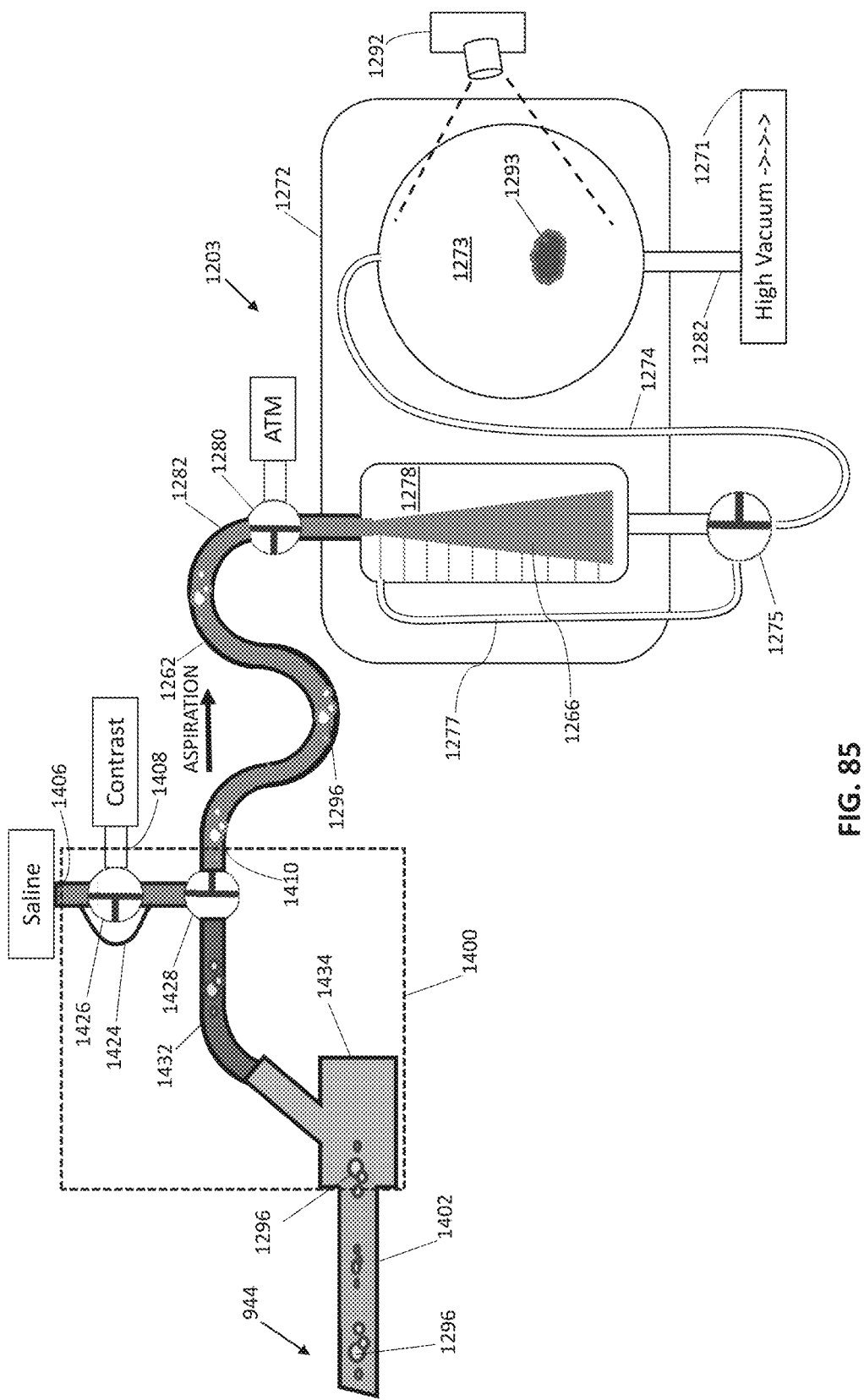

FIG. 68A is a schematic illustrating an example of clot pod assembly 1272 shown in FIG. 67, and illustrates positions of the control valves 1275, 1280 to connect the vacuum flow-path 1282 through different channels of the clot pod assembly 1272 and to the first tubing set 1302. When control valve 1275 is aligned in position 1284, the vacuum flow-path is though the drip chamber bypass channel 1277. This allows vacuum to be in the drip chamber 1278 but does not flush fluid straight through the drip chamber 1278. When the first control valve 1280 is aligned in position 1284, the controller can control the vacuum regulator to provide the vacuum to be at a lower vacuum level (less vacuum) compared to when the first control valve 1275 is aligned in position 1285. In this configuration, when the second control valve 1280 is aligned in position 1286 and the vacuum flow-path in the associated mount is aligned to provide vacuum to the attached catheter, the low vacuum causes a slow flow of fluid from the catheter to the vacuum subsystem 1203 such that the fluid drips into the drip chamber 1278, and the cumulative amount of fluid flowing into the drip chamber 1278 can be visually determined using drip chamber graduation lines 1263, along the length of the drip chamber 1278, as the fluid fills the drip chamber 1278. When the first control valve 1275 is aligned in position 1285, the vacuum flow-path is through the drip chamber 1278, through drip chamber outlet line 1276, through the first control valve 1275 and to the clot pod 1273. When the first control valve 1275 is aligned in position 1285 and the second control valve is aligned in position 1286, and the associated mount is aligned to provide vacuum to the catheter, a controller can control the amount of vacuum to be high vacuum (a higher amount than when in position 1284) such that fluid flows more rapidly through the drip chamber 1278, through the first control valve 1275 to the clot pod 1273, and further to the vacuum canister 1270. Such a configuration can be used, for example, for aspirating a clot or providing a saline flush of the clot pod 1273 (for example, as illustrated in FIG. 85). A controller can align the second control valve 1280 to align vacuum flow-path to a first position 1286 to provide vacuum to the associated mount 1400, to position 1287 to provide vacuum flow-path to atmosphere (for example, to quickly flush out the drip chamber 1278 and the clot pod 1273), or to position 1288 to cut off the vacuum flow-path from an associated mount and atmosphere 128 (for example, when receiving fluid from the saline subsystem 1201 or the contrast subsystem 1202.

Figure 68B:
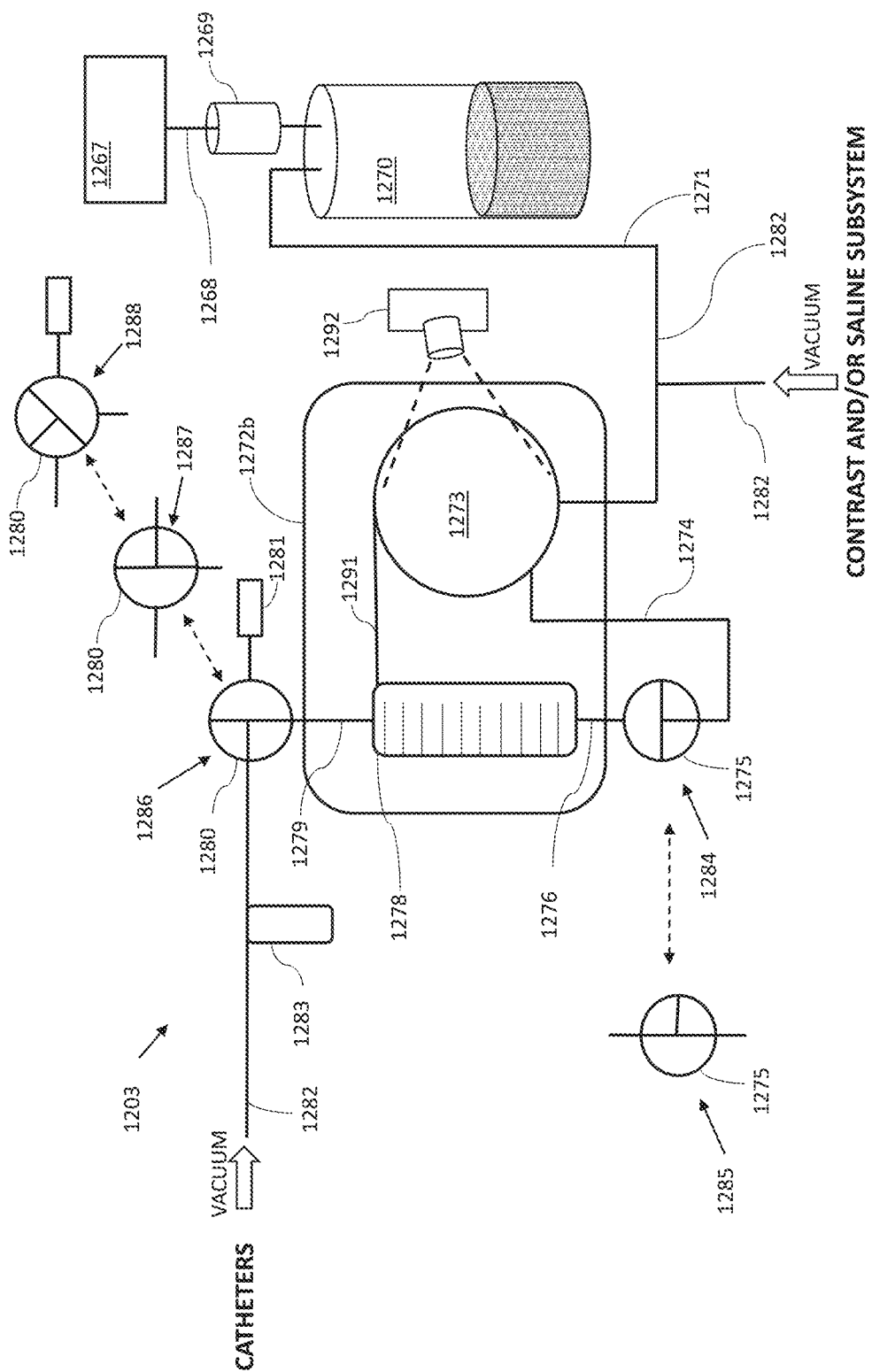
FIG. 68B is a schematic illustrating another example of a drip pod and clot pod assembly.

FIG. 68B is a schematic illustrating another example of a clot pod assembly. This example is similar to the example illustrated in FIG. 68A except instead of having a drip chamber bypass line 1277, there is a line 1291 from the clot pod 1273 to the distal end of the drip chamber 1278 such that the vacuum flow-path can go directly from the clot pod 1273 to the drip chamber 1278, and the first control valve 1275 can be aligned by a controller to be in a first position 1284 to block vacuum flow-path to the drip chamber 1278 and to be in a second position 1285 to connect vacuum flow-path to the drip chamber 1278. Accordingly, in various embodiments the cassette further includes a vacuum subsystem having a clot pod. The clot pod can have at least one transparent surface positioned in/on the cassette to be visible from outside of the cassette. The cassette can further comprise a vacuum subsystem with a drip chamber in fluid communication with the first vacuum flow-path. The drip chamber can have at least one transparent surface. Also, the drip chamber can be positioned in/on the cassette to be visible from outside of the cassette. The drip chamber can be positioned in the first vacuum flow-path between the clot pod and the first tubing set. The vacuum subsystem can include a plurality of robotically actuated valves configured to be controlled by a control system for controlling the vacuum flow-path through the drip chamber and the clot pod. As an example, the plurality of robotically actuated valves includes a first valve positioned in the first vacuum flow-path between the drip chamber and the clot pod and a second valve positioned on an opposite side of the drip chamber in the first vacuum flow-path between the drip chamber and the first tubing set, wherein first valve and second valve can be aligned to control the flow of fluid and material from the mounts through the drip chamber and the clot pod. In various embodiments, the control system includes a controller, for example, controller 2230, controller 2220, or the pump station (e.g., a controller in the pump station). The control system can include a controller including non-transitory computer storage medium configured to store computer-executable instructions, and including one or more computer hardware processors in communication with the non-transitory computer storage medium, the one or more computer hardware processors configured to execute the computer-executable instructions to control the pump station to actuate the saline subsystem, the contrast subsystem, and the vacuum subsystem, to independently provide to each hub in the set of hubs contrast, saline, and vacuum via the fluid communication system. Such a controller can be configured to robotically actuate valves and pumps in the fluidics management system at least partially based on a user input, sensed characteristics, and/or executable instructions.

FIG. 69 is a schematic illustrating an example of a fluidic system components in one or more mounts 1400 coupled to the second tubing set 1316. This example includes three mounts 1400a-c that have the same components relating to the fluidic system. Each mount 1400 has fluidic connections to the second tubing set 1316 to receive saline, contrast, and vacuum, and an electrical connection that includes one or more electrical leads, which are coupled to one or more sensors in the mounts 1400 to communicate signals from one or more sensors in the mount to the cassette, and ultimately to a controller (e.g., controller 2220) when the cassette is coupled to the pump station. The controller uses the received signals to align valves in the mounts to provide saline, contrast, and aspiration automatically or semi-automatically (e.g., based on a user input) as needed during different portions of a medical procedure. In this example, mount 1400a has a common connector 1434a for providing saline, contrast, and vacuum to the lumen of catheter 1402a, mount 1400b has a connector 1434b for providing saline, contrast, and vacuum to the lumen of catheter 1402b, and mount 1400c has a connector 1434c for providing saline, contrast, and vacuum to the lumen of catheter 1402c. The connectors 1434 can be in fluid communication with the lumens of catheters 1402 by coupling the connectors to a corresponding connector on a hub (or other assembly) that the catheters are coupled to, where the hubs can include a fluid communication channel from the connector 1434 to the lumen of the catheter coupled to the hub. Such hubs can be removably coupled to the mounts 1400. The hub can include structure that operates as a hemostasis valve, such that the hub can provide fluid to the lumen of a first catheter coupled to the hub that for discharging at the distal end of the first catheter, or can provide vacuum to the lumen of a first catheter coupled to the hub for providing aspiration at the distal end of the first catheter, while another elongated device is positioned partially or fully in the lumen of the first catheter in a concentric nested configuration. For example, when catheter 1402b is positioned in the lumen of catheter 1402a, when catheter 1402c is positioned in the lumen of catheter 1402b, or when an elongated device (e.g., a catheter, a guidewire, etc.) is positioned in the lumen of catheter 1402c. In some embodiments, catheter 1402a is a guide catheter, catheter 1402 is a procedure catheter, and catheter 1402c is an access (or insert) catheter.

Still referring to FIG. 69, a mount 1400 includes a saline port 1406, a contrast port 1408, a vacuum port 1410, and an electrical connection 1411 that are coupled to saline subchannel 1337, contrast subchannel 1336, vacuum subchannel 1335, and electrical channel 1334, respectively, of a tube group 1318 (of second tubing set 1316) coupled to the mount 1400. Preferably, the mount 1400 is coupled to the tube group 1318 without using connectors, for example, in a persistent connection that is not meant to be decoupled before or during its use in a medical procedure. An air sensor 1418 is positioned along the saline channel (flow-path) 1412 and is in electrical communication with electrical connection 1411. The air sensor 1418 is configured to detect air in the saline channel 1412 and generate a signal indicative of detecting air which is provided to the cassette 1200 and ultimately a controller, via the second tubing set 1316, splitter 1310, first tubing set 1302, and the cassette 1200. An air sensor 1420 is positioned along contrast channel (flow-path) 1414 and is in electrical communication with electrical connection 1411. The air sensor 1420 is configured to detect air in the contrast channel 1414 and generate a signal indicative of detecting air which is provided to cassette 1200 and ultimately a controller via the second tubing set 1316, splitter 1310, first tubing set 1302, and the cassette 1200.

Mount 1400 includes a first control valve 1426 that is controllable by a controller to align saline channel 1412, or contrast channel 1414, to a second control valve 1428. Check valve 1422 in the saline channel 1412 prevents any upstream fluid flow on the saline channel 1412. Along the saline channel 1412 between the first control valve 1426 and the check valve 1422 is a saline drip channel (saline restricted-flow channel) 1424 which connects the saline channel 1412 upstream of the first control valve 1426 a fluid flow-path to the second control valve 1428, bypassing the first control valve 1426. In this configuration, at least some saline that enters the mount 1400 can flow to via the saline restricted-flow channel 1424 to the second control valve 1428 regardless of the position of the first control valve 1426. The saline drip flow-path 1423 includes a saline restricted-flow channel 1424 designed to allow a desired flow-rate of saline (e.g, mL/minute) to flow to the connector 1434 and to the lumen of a catheter in fluid communication with the connector 1434 when the second control valve 1428 is aligned to provide saline or contrast to the connector 1434, regardless of the alignment of the first control valve 1426. The saline restricted-flow channel 1424 is configured to provide a lower flow-rate of saline than the saline channel 1412 provides to the saline-contrast channel 1421 through the first control valve 1426. The saline restricted-flow channel 1424 can have, for example, a smaller cross-sectional dimension then the cross-sectional dimension of the flow-path from the saline channel 1412 to the saline-contrast channel 1421 through the first control valve 1426. As an example, the saline restricted-flow channel 1424 can have narrow portion of the saline drip flow-path designed such that the saline restricted-flow channel 1424 provides about 1 mL/minute of saline to the lumen of an associated catheter. For example, in the range of about 0.85 mL/minute to about 1.35 mL/minute. In systems with multiple catheters, the catheters can be positioned in a concentric configuration, that is, such that catheter 1402c can be positioned at least partially in the lumen of catheter 1402b, and catheter 1402b can be positioned at least partially in the lumen of catheter 1402a. In the example illustrated in FIG. 69, flow restrictor FR1 is associated with catheter 1402a, flow restrictor FR2 is associated with catheter 1402b, and flow restrictor FR3 is associated with catheter 1402c. As an example, the saline restricted-flow channel 1424a can have a flow restrictor (value, size) FR1 designed such that the saline restricted-flow channel 1424 provides about 1 mL/minute of saline to the lumen of a catheter having a lumen inner diameter (ID) of about 0.088 inches (for example, a Zoom 88 catheter). As an example, the saline restricted-flow channel 1424b can have a flow restrictor FR2 designed such that the saline restricted-flow channel 1424b provides about 1 mL/minute of saline to the lumen of a catheter having an ID of about 0.071 inches (for example, a Zoom 71 catheter). As an example, the saline restricted-flow channel 1424c can have a flow restrictor FR3 designed such that the saline restricted-flow channel 1424c provides about 1 ml of saline to the lumen of a catheter having a lumen inner diameter (ID) of about 0.035 inches (for example, a Zoom 35 catheter). The flow restrictor FR1, FR2, FR3 can be all about the same size (e.g., having the same or about the same ID), or can be sized differently based on the catheter size a flow restrictor is associated with such that a saline drip flow of about 1 mL/minute is achieved to the catheter in fluid communication with the connector 1434.

The second control valve 1428 is a three-way valve that connects either vacuum to or saline/contrast to connector 1434 via a fluid primary channel 1432. The primary channel provides saline, contrast and vacuum to a catheter coupled to the mount 1400, for example, provides saline, contrast and vacuum to the lumen of the catheter through connector 1434. The primary channel also receives material (e.g., fluids, clots, etc.) from a catheter coupled to the mount 1400 when vacuum is provided to the catheter. Pressure sensor 929 (e.g., a hemodynamic pressure sensor) is positioned to detect pressure in the primary channel 1432 and is in electrical communication with electrical connection 1411. Pressure sensor 929 is configured to generate a signal, indicative of the detected pressure, which is provided to cassette 1200 and ultimately a controller via the second tubing set 1316, splitter 1310, first tubing set 1302, and the cassette 1200. The configuration of mounts 1400 includes several advantages over previous configurations described above. For example, in this configuration a mount 1400 includes an air sensor 1418 in the saline channel 1412 and includes air sensor 1420 and the contrast channel 1414, instead of a bubble filter 922 (FIG. 18) in a combined saline/contrast fluid channel 940 providing extra safety detecting air in any fluid provided to catheter 1402. If the controller receives a signal from the saline air sensor 1418 or the contrast air sensor 1420, it can provide an alarm and/or align the second control valve 1428 to evacuate fluid in saline-contrast channel 1421 and upstream of saline-contrast channel 1421 via vacuum channel (flow-path) 1416. Subsequently, the saline and/or the contrast channels can be re-primed. In some embodiments, the controller may also align the first control valve 1426 to prevent contrast and saline to flow through the first control valve 1246.

FIGS. 70A-70C are schematics illustrating another example of a configuration of a contrast subsystem that can be included in a cassette, for example, instead of the contrast subsystem 1202 illustrated in FIG. 67. In this example, the contrast subsystem is coupled to a contrast source 1108 which is located exterior to the cassette. Air sensor 1248 is positioned along contrast channel (flow-path) 1244c. A first control valve 1255a and a second control valve 1255b are three-way control valves controllable by a controller to align contrast channels 1244 for various processes. For example, first control valve 1255a and second control valve 1255b are controllable to align flow-path 1244c to flow-path 1244f and 1244h for filling contrast pump 810 with contrast through inlet port 1251, as illustrated in FIG. 70A. Second control valve 1255b can be aligned to disconnect flow-paths 1244f and 1244h, and first control valve 1255a can be aligned to connect flow-paths 1244g and 1244e for purging air from contrast pump 810 through outlet port 1253, as illustrated in FIG. 70B. As illustrated in FIG. 70C, first control valve 1255a can be aligned to disconnect flow-paths 1244c and 1244f, and disconnect flow-paths 1244c and 1244g, and second control valve 1255b can be aligned to connect flow-path 1244h and 1244i to the second tubing set ("to catheters") to provide contrast to an associated mount.

Figure 70E:
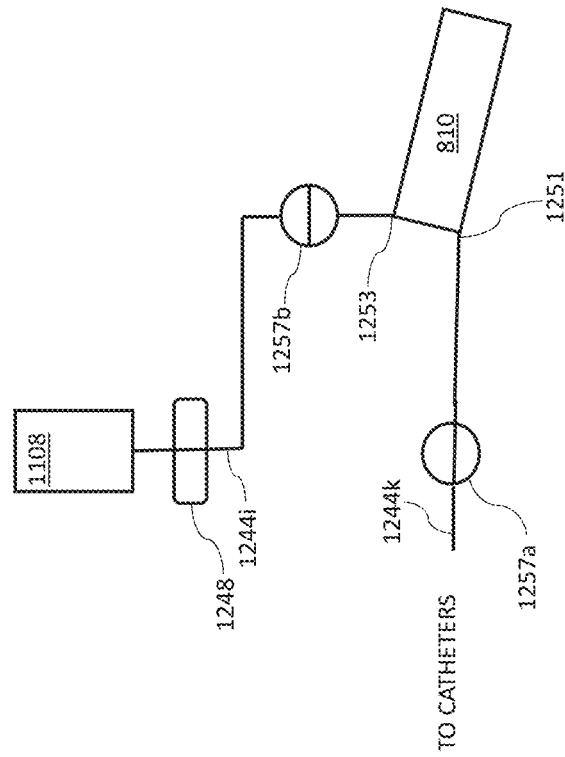
FIGS. 70D-70E are schematics illustrating another example of a contrast subsystem that can be included in a cassette.
Figure 70D:
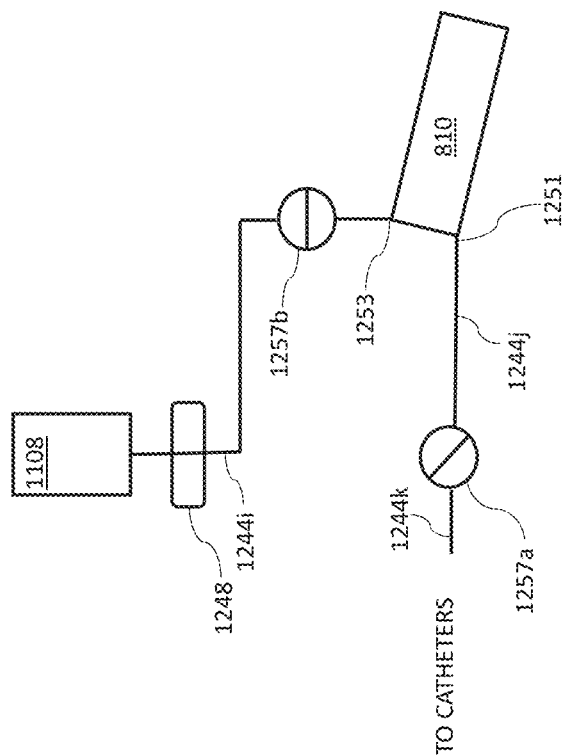

FIGS. 70D-70E are schematics illustrating another example of a contrast subsystem that can be included in a cassette, instead of the contrast subsystem of FIG. 67. In this example, the contrast subsystem is coupled to a contrast source 1108 located exterior to the cassette and includes air sensor 1248 along the contrast flow-path 1244i. The contrast subsystem includes first control valve 1257a and second control valve 1257b which are controllable by a controller to align flow-paths 1244 for various processes. For example, first control valve 1257b can be aligned to connect contrast flow-path 1244i from contrast source 1104 to port 1253 of contrast pump 810, and second control valve 1257b can be aligned to disconnect flow-path 1244k from port 1251 for filing the contrast pump 810, as shown in FIG. 70D. Second control valve 1257b can also be aligned to disconnect flow-path 1244i from port 1253, and first control valve 1257a can be aligned to connect output port 1251 to flow-path 1444k to provide contrast to the second tubing set 1302 and to an associated mount, as illustrated in FIG. 70E.

FIGS. 71-77 illustrate examples of configurations of saline, contrast, and vacuum flow-paths of mount 1400, that has components described in reference to FIG. 69, during different processes prior to or during a medical procedure using the robotic catheter system. Other configurations to provide a saline drip, contrast injection, saline flush, aspiration, and priming of mounts and the fluidic system are also possible with different components are also possible. In each of these configurations, the mount 1400 is being provided saline, contrast, and vacuum via the second tubing set 1316, the splitter 1310, the first tubing set 1302, in the cassette 1200. The various configurations allow saline, contrast and vacuum provided to the mount 1400 to be provided to connector 1434 into the lumen of a catheter coupled to, and in fluid communication with, connector 1434. In some embodiments, the connector 1434 is connected to a hub to which the catheter is coupled to, the hub including the fluid path such that saline, contrast, or vacuum provided to the hub is also provided to the lumen of the catheter. Accordingly, reference to a fluid being provided to connector 1434 also indicates the fluid is provided to the catheter in fluid communication with connector 1434. The different configurations of saline, contrast, and vacuum flow-paths are achieved by different alignments of first control valve 1426 and second control valve 1428. The controller (e.g., controller 2230, controller 2220) can control the alignment the first control valve 1426 and the second control valve 1428 based on user input from the remote control system 2210, user input from a local control system (e.g., interface 2235), predetermined instructions that the controller is configured to carry out, and/or signals from one or more sensors that provide the controller information about the system. In an example, the first control valve 1426 and second control valve 1428 can be aligned by the actuators in a drive system mount 1400 is coupled to. In some embodiments, actuators are coupled to the first control valve in the second control valve by a magnetic coupling. In other embodiments, actuators are coupled to the first and second control valves 1426, 1428 by a mechanical coupling.

Figure 71:
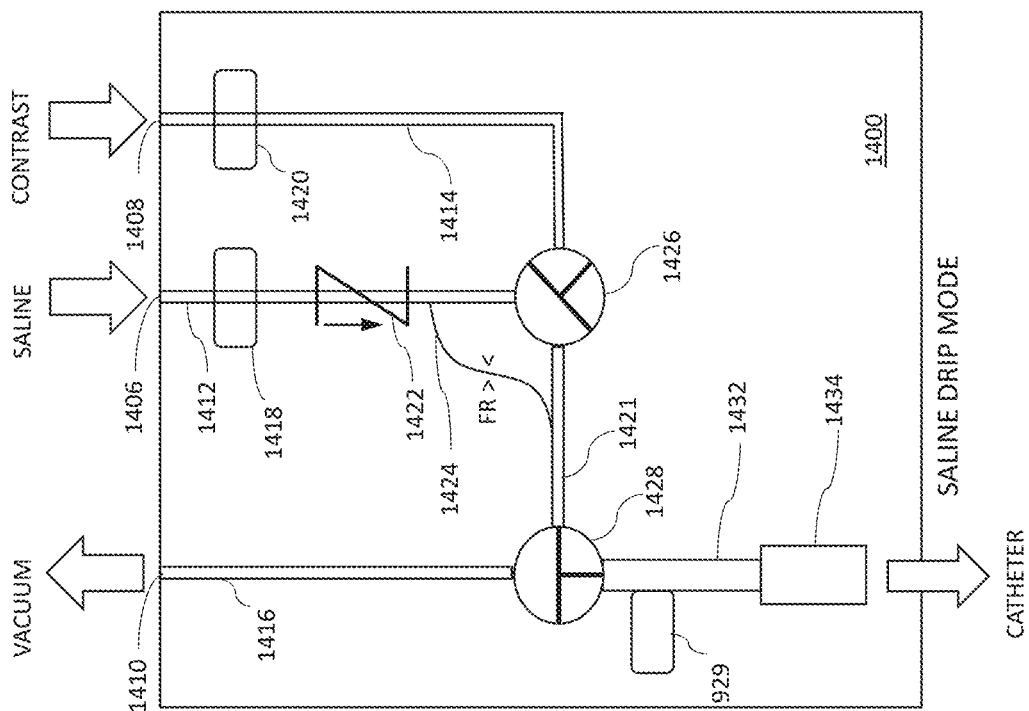
FIG. 71 is a schematic illustrating an example of the configuration of the fluidic system components shown in FIG. 69, where two three-way valves are configured in a "saline drip mode" to provide a saline drip to a connector that is coupled to a catheter for providing saline flow-path to a lumen of the coupled-to catheter.

FIG. 71 is a schematic illustrating an example of a configuration of the fluidic system components of a mount 1400 shown in FIG. 69, where valves in the mount are aligned in a "saline drip mode" fluid flow to the connector 1434, and to a catheter lumen in fluid communication with the connector 1434. A mount 1400 can be configured to be in the saline drip mode after the fluidic system, including the mount, has been primed. In operation, each mount with a catheter coupled thereto can configured to be in saline drip mode while the catheters are being moved towards and in a patient, or after another process. For example, a mount 1400 can be configured in saline drip mode after injecting contrast. In this configuration, the first control valve 1426 is aligned to prevent saline channel 1412 and contrast channel 1414 from being in fluid communication with saline-contrast channel 1421 and the second control valve 1428, except for a saline flow-path through saline restricted-flow channel 1424. The second control valve 1428 is aligned to prevent fluid communication of the vacuum channel 1416 in the connector 1434, and to allow the fluid communication of saline from saline-contrast channel 1421 to connector 1434, and to a catheter lumen in fluid communication with the connector 1434.

Figure 72:
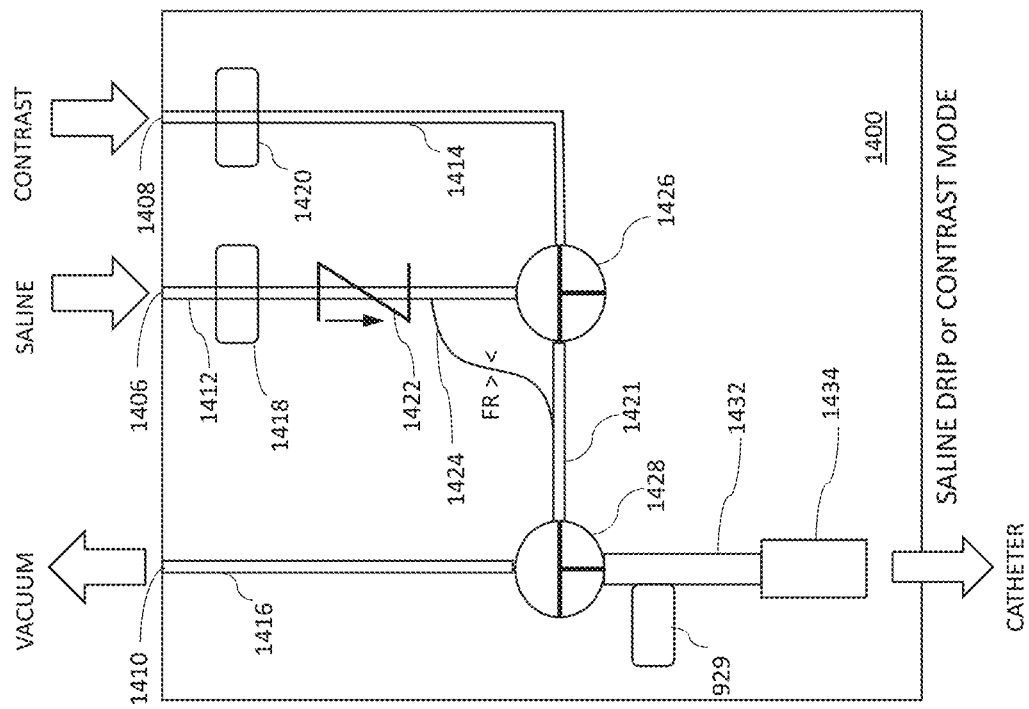
FIG. 72 is a schematic illustrating an example of the configuration of the fluidic system components shown in FIG. 69, where two three-way valves are configured in a "saline drip or contrast mode" to provide a saline drip or contrast to a connector that is coupled to a catheter for providing a saline flow-path and/or a contrast flow-path to a lumen of the coupled-to catheter.

FIG. 72 is a schematic illustrating an example of a configuration of the fluidic system components of a mount 1400 shown in FIG. 69, where valves in the mount are aligned in a "saline drip or contrast mode" fluid flow to the connector 1434, and to a catheter lumen in fluid communication with the connector 1434. A mount 1400 can be configured to be in the "saline drip or contrast mode" after the fluidic system, including the mount, has been primed. In operation, each mount with a catheter coupled thereto can configured to be in saline drip mode while the catheters are being moved towards and in a patient, or after another process. For example, a mount 1400 can be configured in saline drip mode after injecting contrast. In this configuration, the first control valve 1426 is aligned to prevent saline channel 1412 from being in fluid communication with saline-contrast channel 1421 and the second control valve 1428, except for a saline flow-path through saline restricted-flow channel 1424, and the first control valve 1428 is also aligned to place the contrast channel 1414 in fluid communication with saline-contrast channel 1421 and the second control valve 1428. The second control valve 1428 is aligned to prevent fluid communication of the vacuum channel 1416 in the connector 1434, and to allow the fluid communication of saline from a saline drip flow-path and contrast (when injected) in saline-contrast channel 1421 with connector 1434 and to a catheter lumen in fluid communication with the connector 1434. In the configuration illustrated in FIG. 72, in some embodiments contrast can be injected and then a saline drip will continue to be provided to the connector 1434 without needing to change the alignment of the first control valve 1426 and the second control valve 1428.

Figure 73:
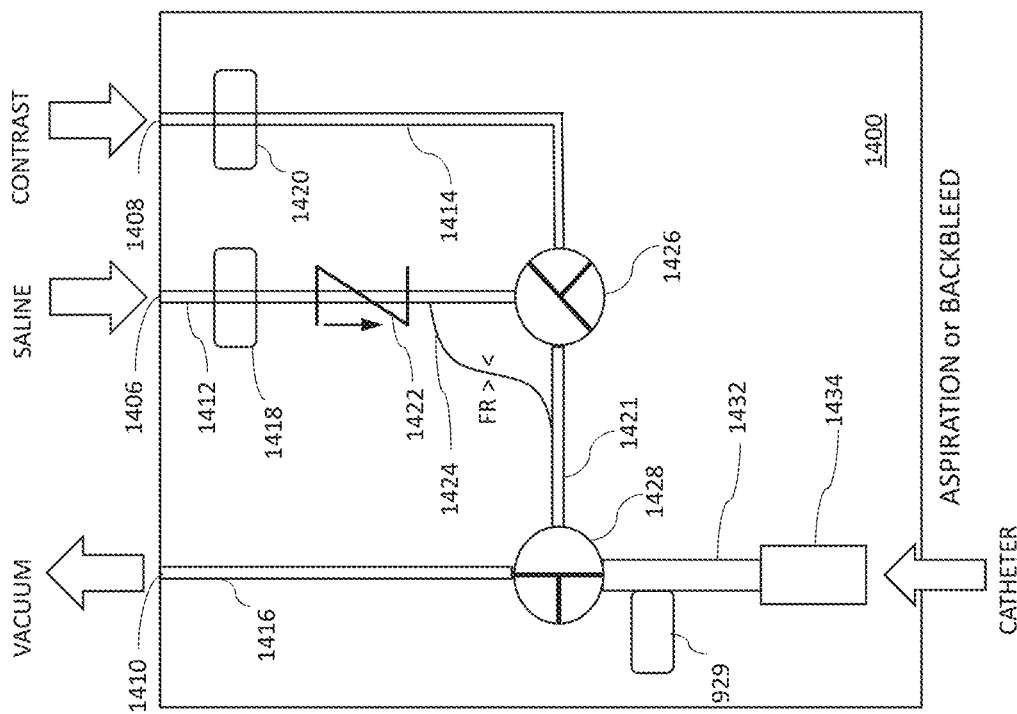
FIG. 73 is a schematic illustrating an example of the configuration of the fluidic system components shown in FIG. 69, where two three-way valves are configured in a "aspiration or backbleed mode" to provide apply atmospheric pressure or a vacuum to a connector that is coupled to a catheter for aspirating or backbleeding a lumen of the coupled-to catheter.

FIG. 73 is a schematic illustrating an example of a configuration of the fluidic system components of a mount 1400 shown in FIG. 69, where valves in the mount are aligned in a "aspiration or back-bleed mode" fluid flow to connector 1434, and to a catheter lumen in fluid communication with the connector 1434. This configuration can be used, for example, when aspirating a clot or aspirating air and fluid (e.g., blood) that may reside in a catheter in fluid communication with the connector 1434 and the portion of the flow-path between the second control valve 1428 and the catheter. In this configuration, the first control valve 1426 is aligned to prevent saline channel 1412 from being in fluid communication with saline-contrast channel 1421 and the second control valve 1428, except for a saline flow-path through saline restricted-flow channel 1424 to saline-contrast channel 1421, and the first control valve 1428 is also aligned to prevent the contrast channel 1414 from being in fluid communication with saline-contrast channel 1421 and the second control valve 1428. The second control valve 1428 is aligned to prevent fluid communication of saline or contrast from saline-contrast channel 1421 to connector 1434, and to allow fluid communication of vacuum with connector 1434 and to a catheter lumen in fluid communication with the connector 1434.

Figure 74:
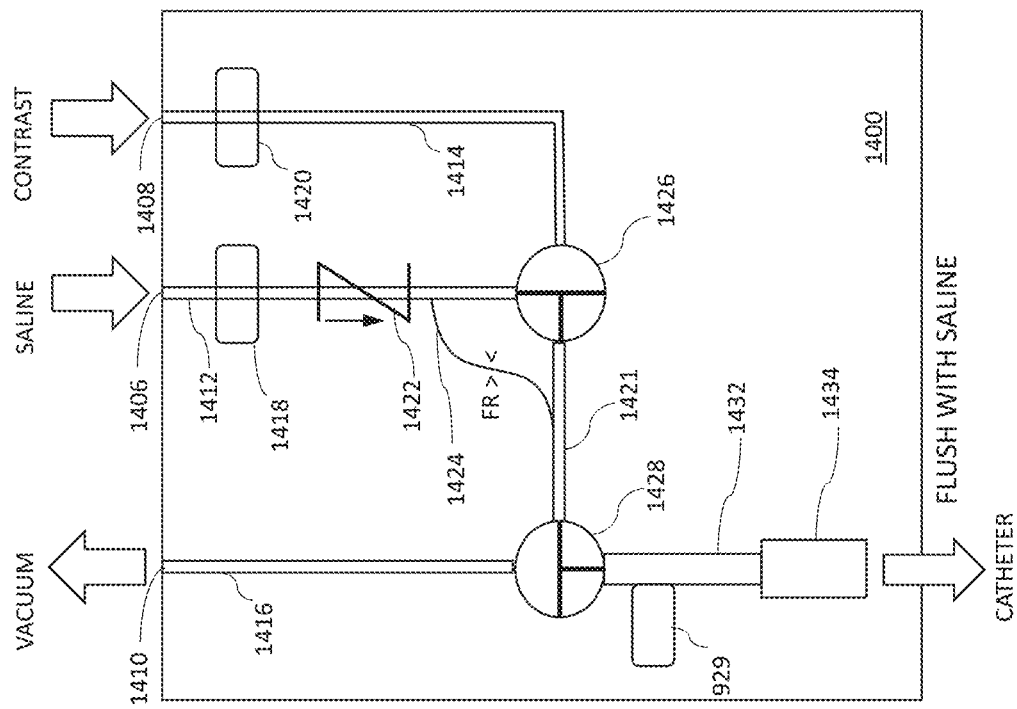
FIG. 74 is a schematic illustrating an example of the configuration of the fluidic system components shown in FIG. 69, where two three-way valves are configured in a "flush with saline mode" to provide a saline flow-path with a relatively higher flow of saline (i.e., higher than when in "saline drip mode") to a lumen of the coupled-to catheter for flushing the fluidic channels and/or the catheter with saline.

FIG. 74 is a schematic illustrating an example of a configuration of the fluidic system components of a mount 1400 shown in FIG. 69, where valves in the mount are aligned in a "flush with saline mode" fluid flow to the connector 1434, and to a catheter lumen in fluid communication with the connector 1434. As a nonlimiting example, a mount 1400 can be configured to be in the "flush with saline mode" after a contrast injection has been performed to clear contrast from the saline flow-path and the catheter. In this configuration, the first control valve 1426 is aligned to communicate saline from saline channel 1412 to the saline-contrast channel 1421 and second control valve 1428, and the first control valve 1426 is further aligned to prevent the contrast channel 1414 from being in fluid communication with saline-contrast channel 1421 and the second control valve 1428. The second control valve 1428 is aligned to prevent fluid communication of the vacuum channel 1416 to the connector 1434, and to allow the fluid communication of saline from a saline drip flow-path and the saline channel 1412 through saline-contrast channel 1421 with connector 1434 and to a catheter lumen in fluid communication with the connector 1434.

Figure 75:
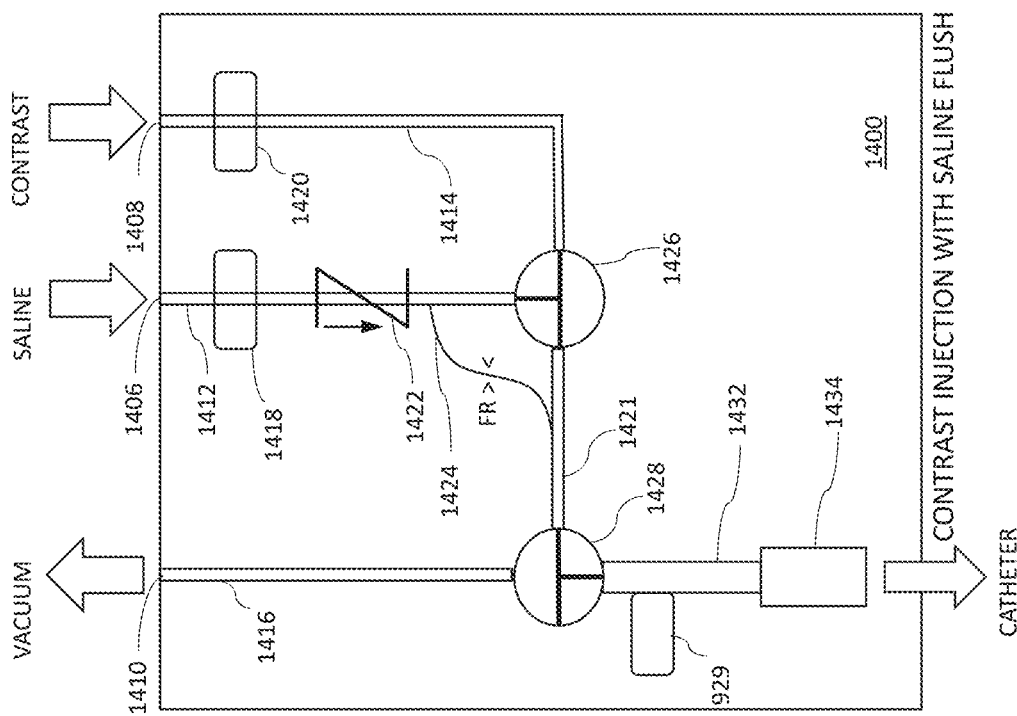
FIG. 75 is a schematic illustrating an example of the configuration of the fluidic system components shown in FIG. 69, where two three-way valves are configured in a "saline drip or contrast mode" to provide a saline drip or contrast flow to a connector that is coupled to a catheter for providing saline and/or to a lumen of the coupled-to catheter.

FIG. 75 is a schematic illustrating an example of the configuration of the fluidic system components shown in FIG. 69, where two three-way valves are configured in a "contrast injection with saline flush mode" to provide contrast to a catheter in fluid connection with connector 1434 and then flush the catheter with saline. In this configuration, first control valve 1426 is aligned to allow contrast channel 1414 to be in fluid communication with saline-contrast channel 1421 the second control valve 1428 and allow saline channel 1412 to be in fluid communication with saline-contrast channel 1421 and the second control valve 1428, that is, to allow saline flow to the second control valve 1428 through the saline restricted-flow channel 1424 and through the first control valve 1426 and saline-contrast channel 1421. The second control valve 1428 is aligned to provide fluid communication from saline-contrast channel 1421 that can contain saline and/or contrast to connector 1434 and to a catheter coupled to connector 1434, and prevent connection of the vacuum channel 1416 with connector 1434.

Figure 76:
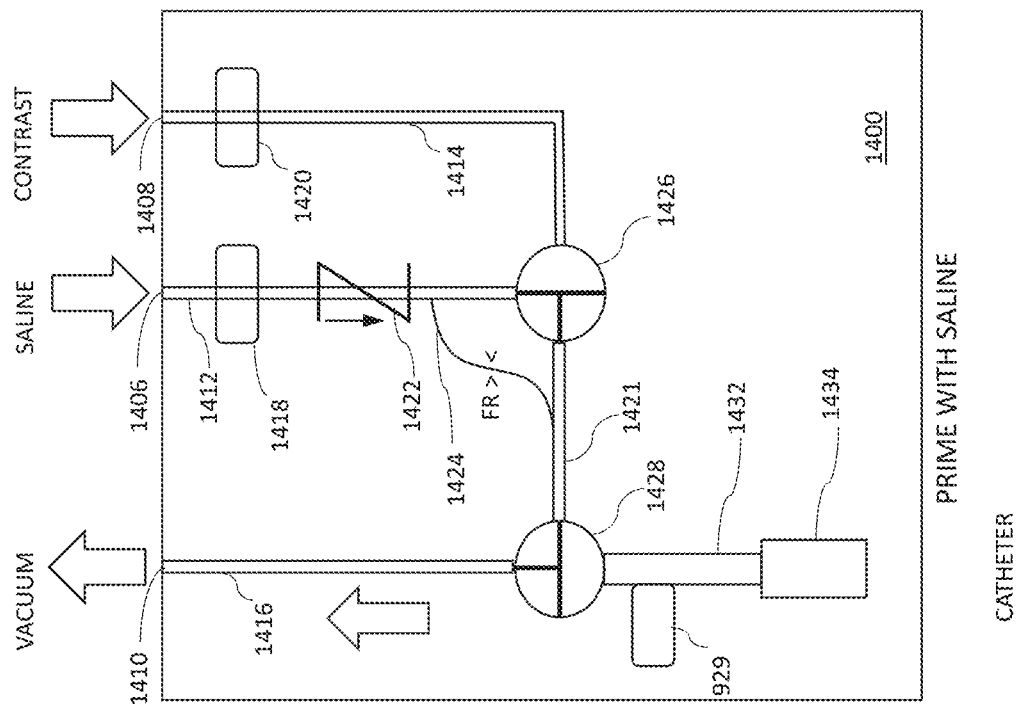
FIG. 76 is a schematic illustrating an example of the configuration of the fluidic system components shown in FIG. 69, where two three-way valves are configured in a "prime with saline mode" to align a saline flow-path with a relatively high volume saline flow (for example, a higher volume than a saline flow from a saline restrictor channel) for priming the mount with saline.

FIG. 76 is a schematic illustrating an example of a configuration of the fluidic system components shown in FIG. 69, where the control valves are configured in a "prime with saline mode" to align fluid communication of a saline channel 1412 with a relatively high saline flow (i.e., higher than a saline flow from the saline drip flow-path) to the vacuum flow-path. To prime the vacuum flow-path. In this configuration, first control valve 1426 is aligned to prevent fluid communication between the contrast channel 1414 and saline-contrast channel 1421. The second control valve 1428 is aligned to connect saline-contrast channel 1421 to the vacuum channel 1416 to provide saline to the vacuum channel 1416 for priming the vacuum channel 1416 with saline.

Figure 77:
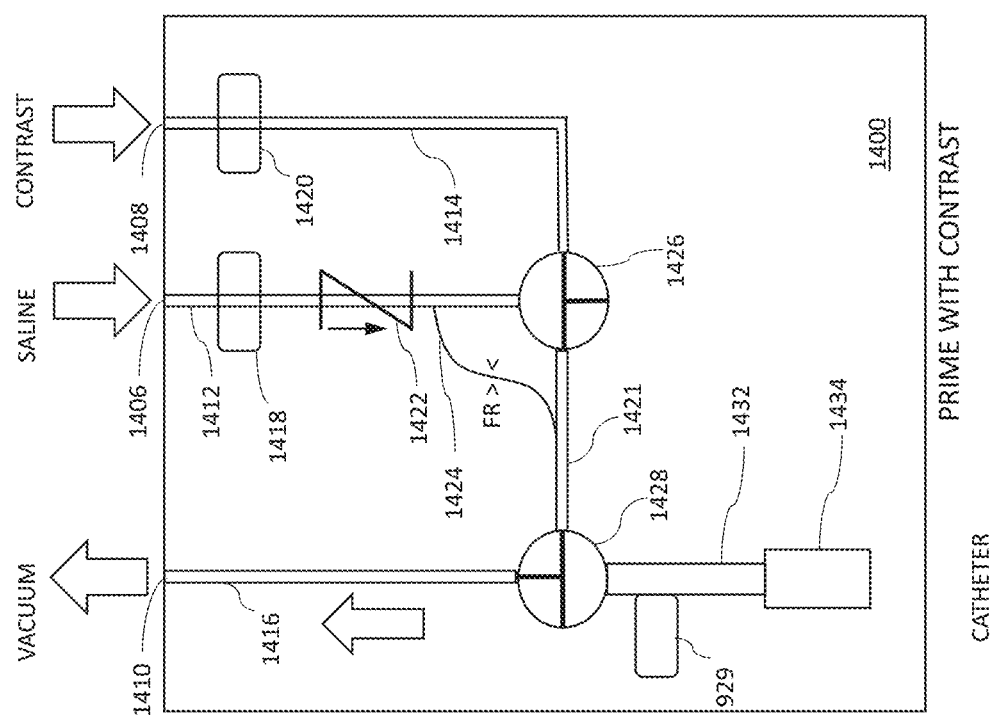
FIG. 77 is a schematic illustrating an example of the configuration of the fluidic system components shown in FIG. 69, where two three-way valves are configured in a "prime with contrast mode" to align a contrast flow-path for priming the mount with contrast.

FIG. 77 is a schematic illustrating an example of the configuration of the fluidic system components shown in FIG. 69, where control valves in the mount 1400 are configured in a "prime with contrast mode" for priming the mount 1400 with contrast. In this configuration, the first control valve 1426 is aligned to connect contrast channel 1414 to saline-contrast channel 1421 to provide contrast to the second control valve 1428 and to prevent fluid communication between the saline channel 1412 and saline-contrast channel 1421, except through a saline restricted-flow channel 1424. The second control valve 1428 is aligned to connect channel 1412 to the vacuum channel 1416 and prevent fluid communication from vacuum channel 1416 and saline-contrast channel 1421 to the connector 1434. In this configuration, contrast can be provided to the mount in the contrast channel 1414 can be filled (primed) with contrast. The second control valve 1428 can connect saline-contrast channel 1421 to the vacuum channel 1416 to facilitate the flow of contrast through channel 14142 the first control valve 1426. In some embodiment, once the mount 1400 is primed with contrast, the first control valve 1426 and the second control valve 1428 can be aligned as illustrated in FIG. 71 to provide a saline drip to the connector 1434 (and catheter), or the first control valve 1426 and the second control valve 1428 can be aligned as illustrated in FIG. 72 to provide a saline drip or contrast injection to connector 1431 and the catheter coupled to the connector 1434.

Figure 78:
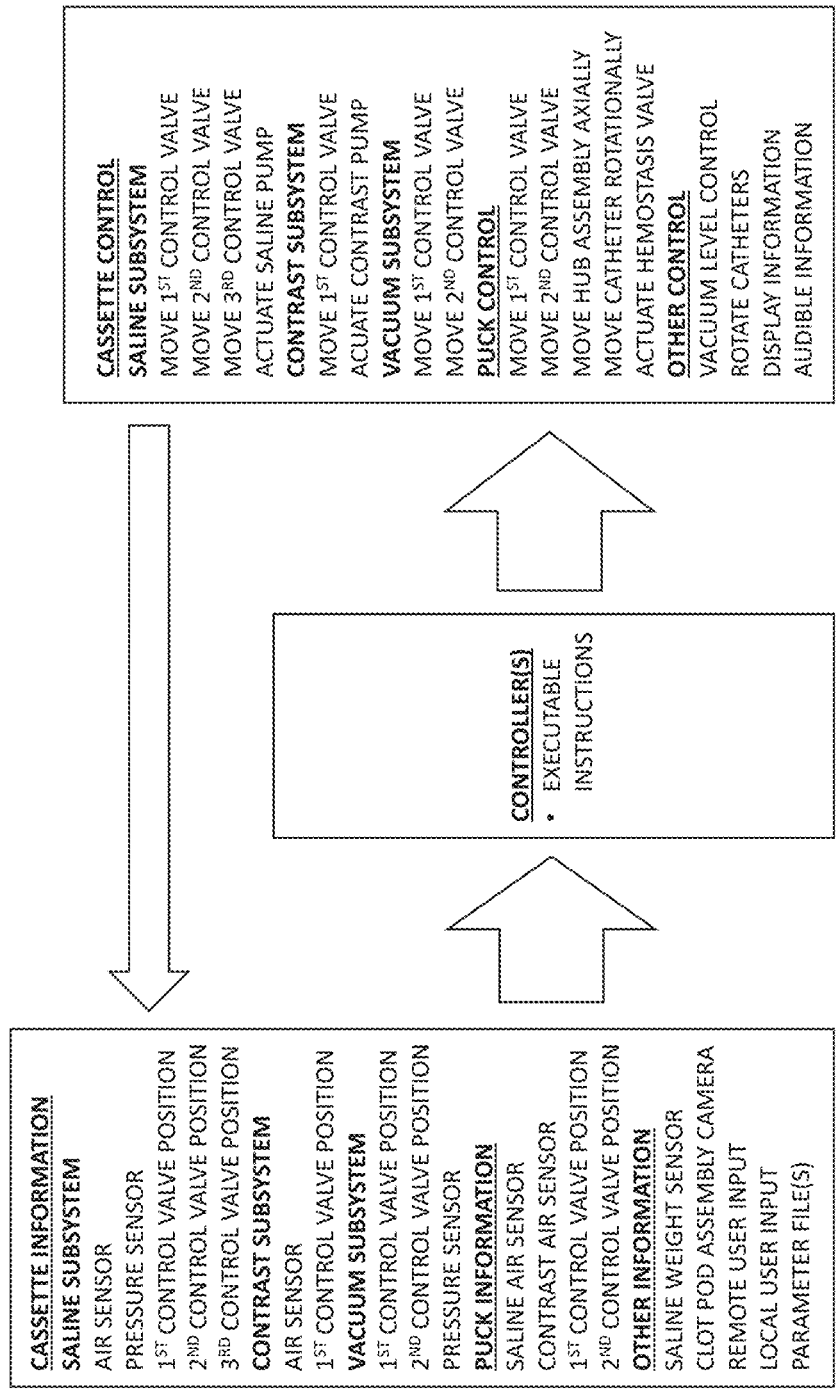
FIG. 78 is a flowchart illustrating a process performed by a fluidics system to monitor saline flow and switch from a first saline source to a second saline source.

FIG. 78 illustrates examples of components of a robotic catheter system that a controller can control components (e.g., hubs, valves, pumps, etc.) to actuate and move to perform processes for a medical procedure, and examples of information that the controller can use to determine to control the components. As described in reference to FIGS. 64-77 and throughout this disclosure, information can be provided to a controller from the cassette via a communication interface, for example, the electrical interface 1236. The information from the cassette can include information from the saline subsystem air sensor, the saline subsystem pressure sensor, the contrast subsystem air sensor, the contrast subsystem pressure sensor, and the vacuum subsystem pressure sensor. If valve position sensors are included in the cassette, information from the cassette can include position information from the control valves of the saline subsystem, the contrast subsystem, and the vacuum subsystem. For example, in reference to the embodiment illustrated in FIG. 67, position information of the first, second, third control valve of the saline subsystem, the first control valve of the contrast subsystem in the first and second control valves of the vacuum subsystem. Information from one or more mounts can be provided to the controller via the communication interface on the cassette. The information from the one or more hub assemblies (e.g., mounts and/or hubs) can include information from a saline air sensor and a contrast air sensor. If valve position sensors are included in the one or more hub assemblies, information from the one or more hub assembly can include position information of control valves in the one or more hub assemblies. For example, in reference the embodiment illustrated in FIG. 69, position information of the first and second control valves. If valve position sensors are not included in the cassette and/or the one or more hub assemblies, the controller can receive valve position information from actuators moving the valves. The controller can receive other information as well including, in some embodiments, information from a saline weight sensor (s), the clot pod assembly camera, information and control signals from the remote medical practitioner, information control signals from a local medical practitioner, and one or more parameter files that can include specific information relating to the catheters being used, a medical procedure being performed, the medical practitioner(s) performing the procedure, and system itself.

Using the received information, and instructions (e.g., software) that the controller is configured to execute, the controller can actuate/move components of the saline subsystem, the contrast subsystem, the vacuum subsystem, and the one or more mounts. For example, in reference to the embodiment illustrated in FIG. 67, the controller can move the first, second, third control valves of the saline subsystem, the first control valve of the contrast subsystem, the first and second control valves of the vacuum subsystem, and the first and second control valves of the one or more hub assemblies (e.g., mounts and/or hubs) to align the control valves in certain positions to communicate saline, contrast, and vacuum to fluidic connectors of the one or more hub assemblies into catheters coupled to the connectors. The controller can also actuate the contrast pump in the saline pump is necessary for a particular procedure. In addition, the controller can cause each of the one or more hub assemblies to be moved separately or together in an axial direction, and cause the one or more hub assemblies to individually rotate the catheters coupled to the hub assemblies, such that the catheters rotated separately or simultaneously. In addition, the controller can display information received, and information determines from the received information, on displays positioned locally or remotely. Also, in some embodiments, the controller can provide audible information (alarms, signals, etc.) based on the received information.

As an example of certain embodiments, the fluidics management system can comprise a plurality of catheters, one of the plurality of catheters coupled to the connector of each hub assembly (e.g., mount and/or hub) to place a lumen of the catheter in fluid communication with the connector. In some embodiments, each of the two or more hub assemblies can include a saline air sensor positioned to detect air in the third saline flow-path, and a contrast air sensor positioned to detect air in the third contrast flow-path. In some embodiments of the fluidics system, the saline air sensor and contrast air sensor are positioned in the saline and contrast third flow-paths, respectively, between the plurality of robotically actuated control valves and the second tubing set for detecting air in the saline and contrast flow-paths before it reaches the plurality of robotically actuated control valves. In some embodiments of the fluidics management system, one or more plurality of robotically actuated control valves are controlled by a control system to block the saline and contrast flow-paths to the connector based on a signal from one or both of the saline and contrast air detectors. In some embodiments, each of the two or more hub assemblies (e.g., mounts and/or hubs) includes a plurality of sensors, and wherein the first tubing set, the splitter, and each tube group of the second tubing set further comprises an electrical channel coupled to the plurality of sensors in respective hub assemblies, the electrical channel configured to communicate electrical signals from the plurality of sensors to an electrical interface on the cassette that is configured to electrically connect to a corresponding electrical interface on a pump station to provide a control system with the signals from the plurality of sensors in the mounts. In some examples, the plurality of sensors can include a saline air sensor positioned to detect air in the third saline flow-path, a contrast air sensor positioned to detect air in the third contrast flow-path, and a pressure sensor configure to sense pressure of fluid flowing through the connector. In some embodiments, the third saline flow-path in each hub assembly includes a saline restricted-flow channel the allows for a low-volume of saline flow that bypasses the first control valve that's configured to select one or both of the third saline flow-path and the contrast flow-path such that saline can be provided from the second tubing set to the connector without passing through the first control valve.

Figure 79A:
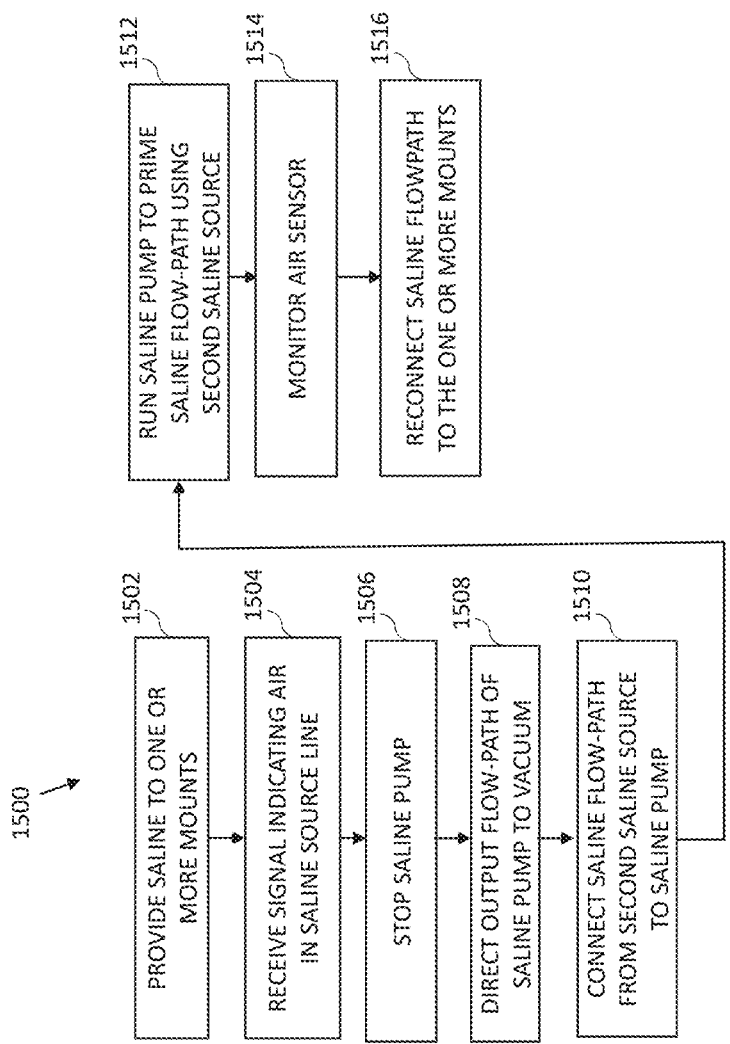
FIG. 79A is a schematic illustrating an example of a fluidics system configuration for monitoring saline flow and switching from a first saline source to a second saline source.

FIG. 79A is a schematic illustrating an example of a process 1500 for a controller to control providing a constant saline flow to one or more mounts (or hub assemblies). Specifically, FIG. 79A illustrates a process 1500 for monitoring saline flow and switching from a first saline source to a second saline source, and is described in reference to the embodiment of the cassette 1200 illustrated in FIG. 67. The actuation of the pump and the valves is performed by the controller based in part on information received from an air sensor monitoring a channel providing saline from a saline source. As indicated above, the air sensor can be positioned in the cassette or in the pump station at a location to engage the saline channel providing saline from the saline source. In this example, at block 1502, the system is controlled to provide saline to one or more mounts. Saline pump 1213 is actuated for providing saline from a saline source 1106a, and the first control valve 1220 is aligned to communicate saline from saline source 1106a to the peristaltic pump 1213. The second and third control valves 1214, 1218 are aligned to communicate saline output from the saline pump 1213 to the first tubing set 1302. At block 1504, the controller receives a signal from air sensor 1205 indicating the presence of air in the saline flow-path from the saline source 1106a. Based on receiving the signal from the air sensor 1205, the controller stops the saline pump 1213. At block 1508 the controller directs the output of the saline pump to vacuum, for example, by aligning the second control valve 1214 to form a flow-path from the output of the saline pump to channel 1222 connected to the vacuum subsystem. In saline subsystems that are configured to use one saline source (e.g., saline bag), a user can swap the depleted saline source for another saline source. In saline subsystems that are configured to use two (or more) saline sources as illustrated in FIG. 67, at block 1510 the first control valve 1220 can be aligned to connect a flow-path from the second saline source 1106*b* to the saline pump 1213. At block 1512, the controller can direct the saline pump 1213 to run such that a predetermined amount of saline passes through the saline pump 1213 (e.g., the pump is robotically controlled to run for a predetermined amount of time) and flows to the vacuum subsystem 1203 to the vacuum canister 1270, priming the saline source line from the second saline source to the second control valve 1214. While the saline pump 1213 is running, at block 1514 the controller monitors signals received from the air sensor 1205 for an indication of air in the saline flow-path. When a saline passes through the pump 1213 and air is not detected in the saline flow-path from the second saline source, at block 1514 the controller can realign the second control valve 1214 to connect the saline flow-path downstream to the first tubing set 1302 and the mounts 1400. In some processes, a user inspection of the cassette saline paths can be performed between blocks 1514 and blocks 1516.

Figure 79B:
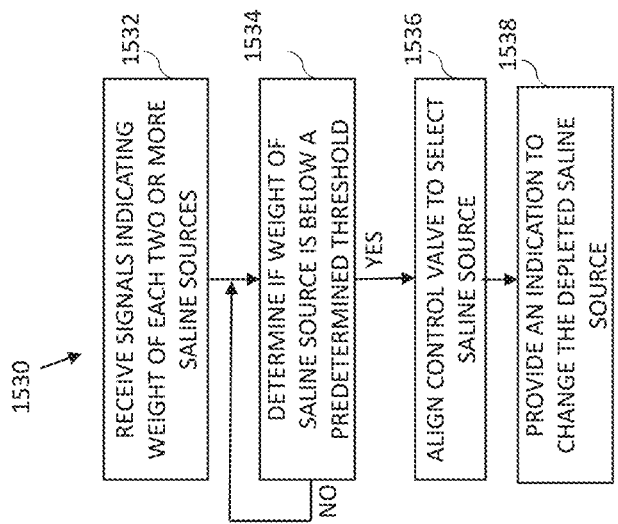
FIG. 79B is a schematic illustrating an example of process for monitoring saline flow and switching from a first saline source to a second saline source based on a signal from a weight sensor, and is described in reference to the embodiment of the cassette illustrated in FIG. 67.

FIG. 79B is a schematic illustrating an example of another process 1530 for a controller to control providing a constant saline flow to one or more mounts, and is described in reference to an embodiment illustrated in FIG. 67. In some configurations, saline can be supplied to the saline subsystem 1201 by two or more saline sources 1106*a*, 1106*b*. FIG. 67 shows the first control valve 1220 aligned to provide saline from the first saline source 1106*a* to the saline flow-path 1206*a*. One or more weight sensor 1210 can support the two or more saline sources 1106*a*, 1106*b*. At the beginning of process 1530 the saline subsystem 1201 is primed and configured to receive saline from one of the two or more saline sources 1106*a*, 1106*b*. At block 1532 of process 1500, the weight sensor 1210 detects the weight of each saline source 1106*a*, 1106*b*, and the controller receives a signal indicating the weight of each saline source. At block 1534, the controller monitors the weight of each saline source based on the received signals from the weight sensor 1210, and determines if the weight of a saline source 1106*a* currently providing saline to the saline subsystem 1201 is below the predetermined threshold. If the weight of the saline source 1106*a* is not below a predetermined threshold, the controller continues to monitor the weight of the saline source. If the weight of the saline source 1106*a* is below a predetermined threshold indicating that the saline source 1106*a* is running out of saline, the process proceeds to block 1536 with the controller aligns the first control valve 1220 to place the saline flow-path 1206*a* in fluid communication with the second saline source 1106*b*. If the system has been properly primed, and the first saline source 1106*a* was not completely depleted, no air should be in the saline flow-path 1206 and another saline priming process should not need to be performed. If the air sensor 1205 indicates air is present in the saline flow-path 1206, the controller can perform a priming process for the saline subsystem 1201. Finally, at block 1536, the controller can provide an indication (e.g., an audible signal, a visible signal on a user interface at the remote and/or local location) for the medical practitioner to change the depleted saline source.

FIG. 80 is a flowchart illustrating an example of a process 1550 for providing contrast to one or more catheters. The process 1550 can be performed by a controller of a fluidics system in a robotic catheter system configured as described herein, the fluidics system being configurable to provide saline and contrast to two or more catheters coupled to mounts (e.g., hub assemblies) in various combinations. For example, to provide saline to all of the two or more catheters (for example, three catheters), or a subset of the two or more catheters (for example, catheters that are not being utilized for aspiration). The fluidics system can include, for example, a cassette 1200 as illustrated in FIG. 67, one or more mounts 1400 as illustrated in FIG. 69, and the fluid communication channels 1300 coupled to the one or more mounts 1400 and the cassette 1200, is illustrated in FIG. 65. At block 1552 of process 1550, the controller aligns the saline subsystem 1201 in a cassette 1200 that is coupled to a pump station 2240 to provide saline to two or more mounts. In an example, FIG. 67 illustrates a configuration of the saline subsystem 1201 where the controller has aligned first control valve 1220, second control valve 1214, and third control valve 1218, and actuated peristaltic pump 1213, to provide a saline flow along flow-path 1206 to the fluid communication channels 1300.

At block 1554 of process 1550, the controller aligns the contrast subsystem 1202 in the cassette 1200 to provide contrast to two or more mounts. In an example, FIG. 67 illustrates a configuration of the contrast subsystem 1202 where the controller has aligned first control valve 1247 such that when actuated the contrast pump 810 can provide contrast to the fluid communication channels 1300. At block 1556 of process 1550, the controller aligns a flow-path in mounts to provide a constant flow of saline to a catheter coupled to the mount. FIGS. 71 and 72 illustrate two different configuration of fluidic flow-paths in a mount to provide a constant flow of saline to the catheter (e.g., a low flow rate of saline). At block 1558 of process 1550, the controller receives input that indicates a selected catheter for injecting contrast. The input can be provided, for example, from a remote controller at a remote location operated by medical practitioner. When the controller receives the selection of the catheter for a contrast injection, at block 1560 the controller aligns (if not already aligned) the contrast flow-path in the selected mount such that the contrast channel 1414 is in fluid communication with the saline-contrast channel 1421, for example, as illustrated in FIG. 72. At block 1562 of the process 1550, the controller align contrast flow-paths in non-selected mounts such that the contrast channel 1414 is not in fluid communication with a saline-contrast channel 1421. For example, in a configuration illustrated in FIG. 71. If a saline flush of the catheter is desired after contrast injection has been performed (for example, for a larger ID catheter), the controller can align flow-paths in the selected mount such that both the contrast channel 1414 and the saline channel 1412 are in fluid communication with saline-contrast channel 1421. For example, as illustrated FIG. 75. Finally at block 1564, the controller actuates the contrast pump to provide contrast through the fluid communication channels 1300 and to the selected catheter. If the mount 1400 coupled to the selected catheter is configured as illustrated in FIG. 75, after the contrast injection occurs a saline flush immediately occurs due to the connection between the saline channel 1412 and the saline-contrast channel 1421 by the first control valve 1426, to allow the full volume of saline being provided to the mount 1400 to flow through the first control valve 1426, through the saline-contrast channel 1421, through the second control valve 1428, threw primary channel 1432, and through connector 1434 to the attached catheter.

FIGS. 81-86 illustrates a representation of an example of a portion of fluidics system during processes of ingesting a clot and performing a backbleed process for a catheter. Some components may not be illustrated for clarity. Such a process can be used with fluidic system configurations disclosed herein, for example, with the vacuum subsystem 1203 illustrated in FIG. 67 and the mount configurations illustrated in FIG. 69. In FIGS. 81-86, the mount 1400 is shown as including a hemostasis valve 1434 for case of illustration. In some embodiments, the mount 1400 can include the hemostasis valve 1434. In other embodiments, the hemostasis valve 1434 can be incorporated in a hub 1436 that mechanically and fluidically releasably couples to the mount 1400. For example, the hub 1436 can connect to the mount via a luer connector, for example, at connector 1434 (FIG. 69). In this representation, channel 1262 represents a fluid communication channel coupled to the vacuum flow-path 1282 of the vacuum subsystem 1203 and coupled to vacuum port 1410 on the mount 1400, for example, a portion of first tubing set 1302, splitter 1310, and second tubing set 1316 (FIG. 66).

Figure 81:
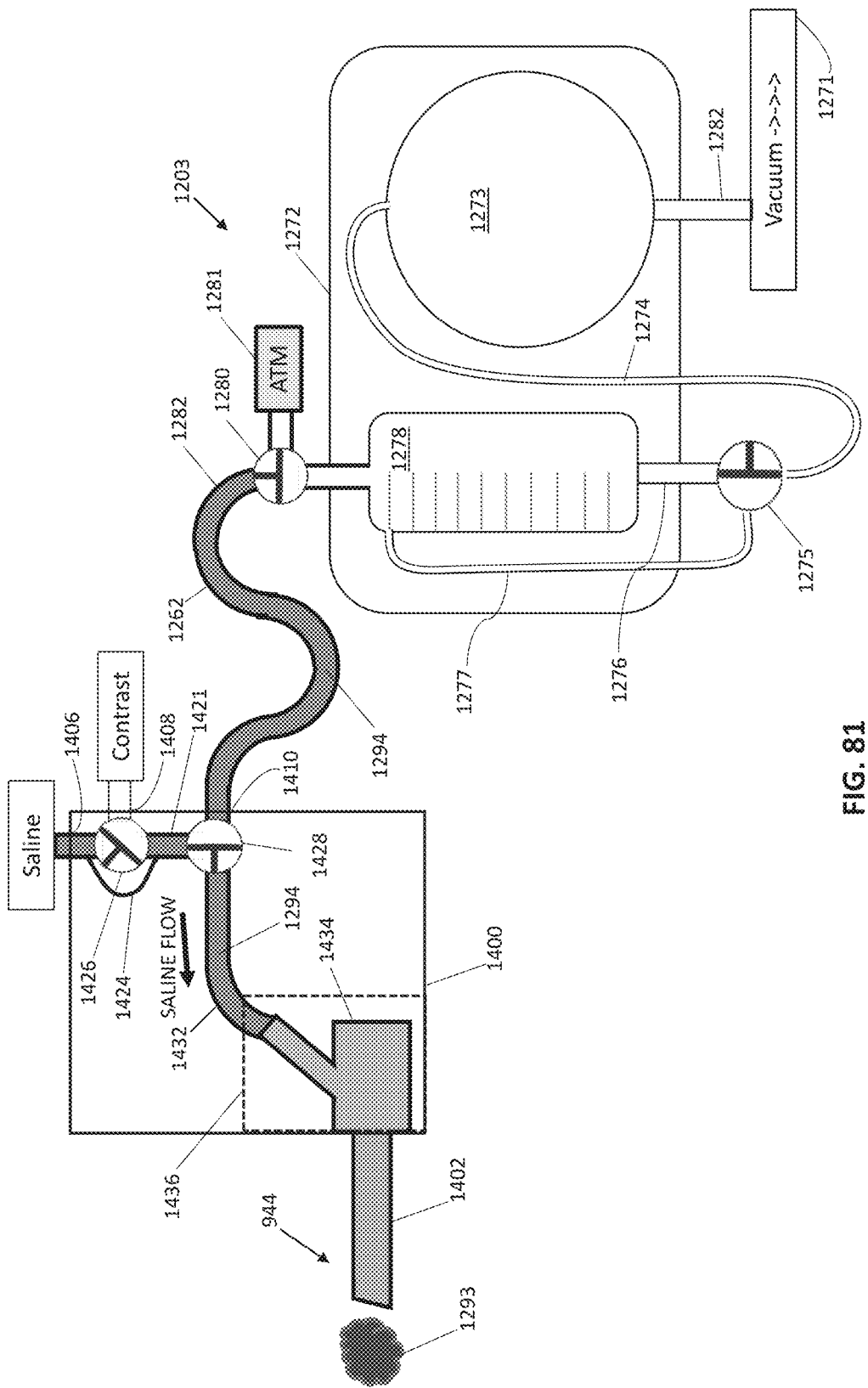
FIGS. 81-86 illustrate configurations of a fluidics system during a backbleed process, FIG. 81 illustrating an example configuration of a fluidics system where saline is provided to a catheter, for example, before a clot is ingested.

In the configuration show in FIG. 81, a low volume saline flow 1294 is being provided to the mount 1400 and catheter 1402. The configuration illustrated in FIG. 81 is an example of an alignment of control valves of the vacuum subsystem 1203 and control valves of the mount 1400 while a distal end 944 of the catheter 1402 is positioned near a clot 1293 prior to aspirating the clot 1293. In this representation, although the first control valve 1426 is aligned to prevent a high volume of saline or contrast to flow to the second control valve 1428, a small volume of saline is flowing from the saline subsystem through a saline restricted-flow channel 1424 (shown in FIG. 69, not shown in FIGS. 81-86,) to second control valve 1428 and downstream through primary channel 1432 to the mount 1400 and the catheter 1402. In an alternative configuration, the first control valve 1426 and the second control valve can be aligned as illustrated in FIG. 72 in a saline drip or contrast mode. The clot pod assembly 1272 is receiving vacuum from a vacuum source (e.g., vacuum canister 1270, vacuum regulator 1259, and vacuum pump 1267 FIG. 67). The first control valve 1275 of the vacuum subsystem is aligned such that the vacuum is provided to the drip chamber 1278. The second control valve 1280 of the vacuum subsystem is aligned to stop the vacuum flow-path downstream of the clot pod assembly 1272, such that the vacuum flow-path 1282 between the second control valve 1280 and the second control valve 1428 may contain saline 1294.

Figure 82:
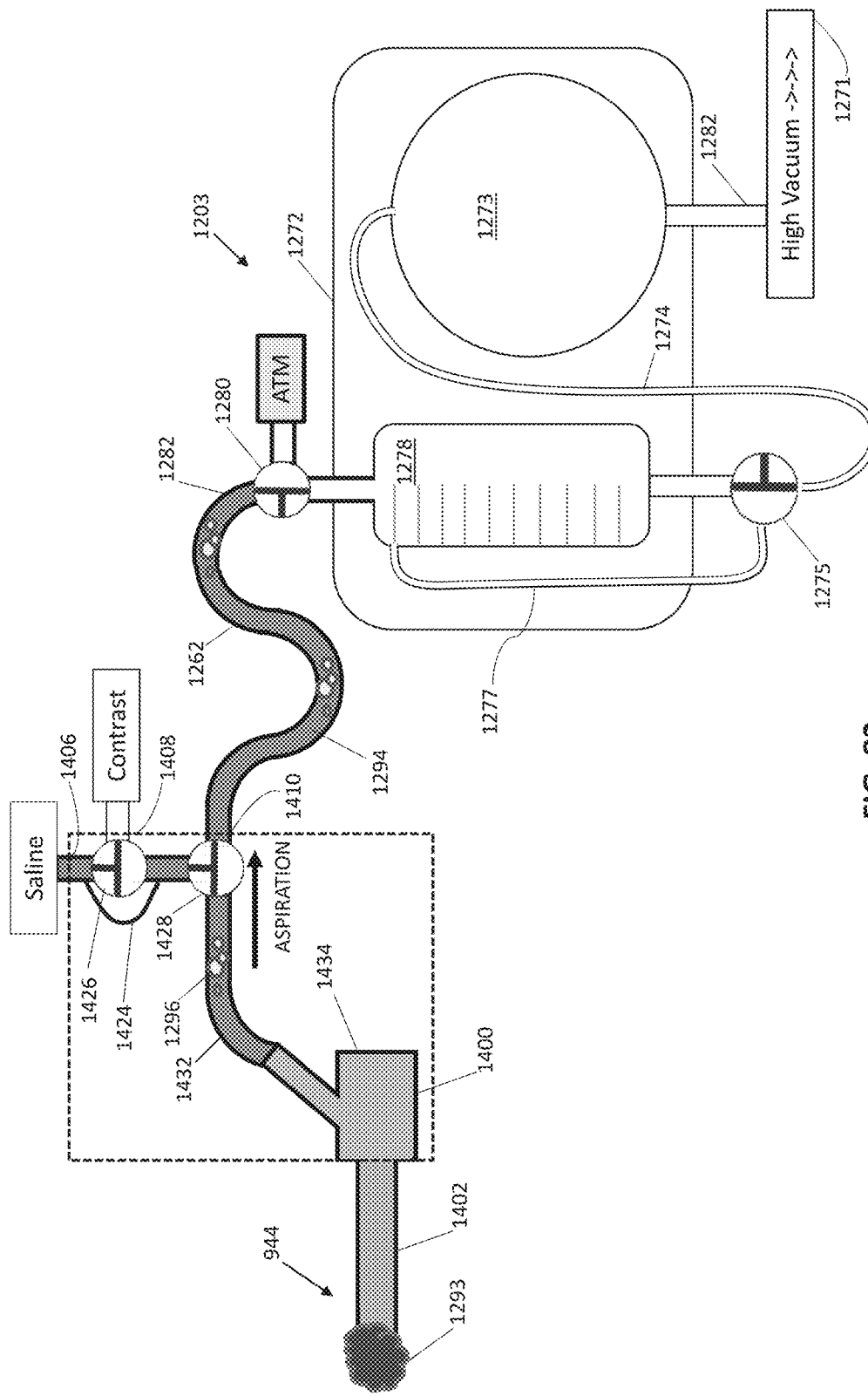

FIG. 82 illustrates an example of the portion of the fluidics system represented in FIG. 81 where "high" vacuum is provided to the catheter 1402 to aspirate a clot when the distal end 944 of the catheter 14022 is in contact with the clot 1293 such that the clot can be ingested and captured in the clot pod 1273. In this configuration, the vacuum subsystem first control valve 1275 and second control valve 1280 are aligned to provide a vacuum flow-path 1282 through the clot pod assembly 1272 to the mount second control valve 1428 such that high vacuum is applied to the mounts 1400 in the catheter 1402. During aspiration, a controller can control the vacuum regulator to provide a high vacuum flow-path to the mount 1400 which causes air bubbles 1296 to form in the vacuum flow-path between the mount 1400 and the clot pod assembly 1272, and in the catheter 1402 and in the mount 1400.

Figure 83:
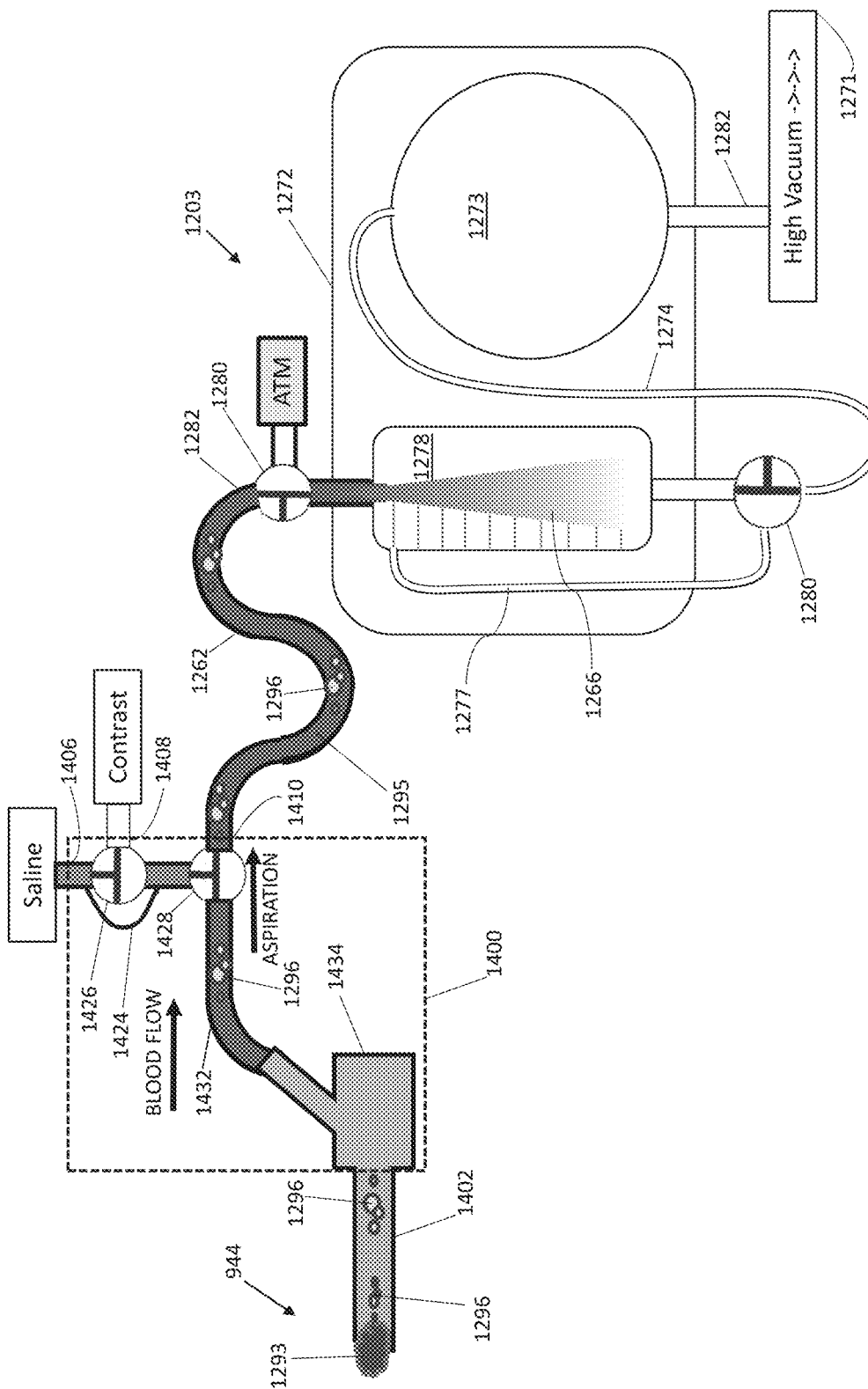

FIG. 83 illustrates same configuration of a fluidics system as illustrated in FIG. 82 where "high" vacuum is provided to a catheter 1402 at slightly later time than the example illustrated in FIG. 82. In the representation illustrated in FIG. 83, the clot 1293 has at least partially into the catheter 1402 and the vacuum flow-path from the catheter 1402 to the trip chamber 1278 causes the clot 1293 and blood from the patient to be ingested by the catheter 1402 and flow through the mount second control valve 1428 to the clot pod assembly 1272 blood enters the chamber 1278 and a high flow rate 1266. The high vacuum causes air bubbles 1296 to be formed in the aspirated blood flow and the catheter 1402.

Figure 84:
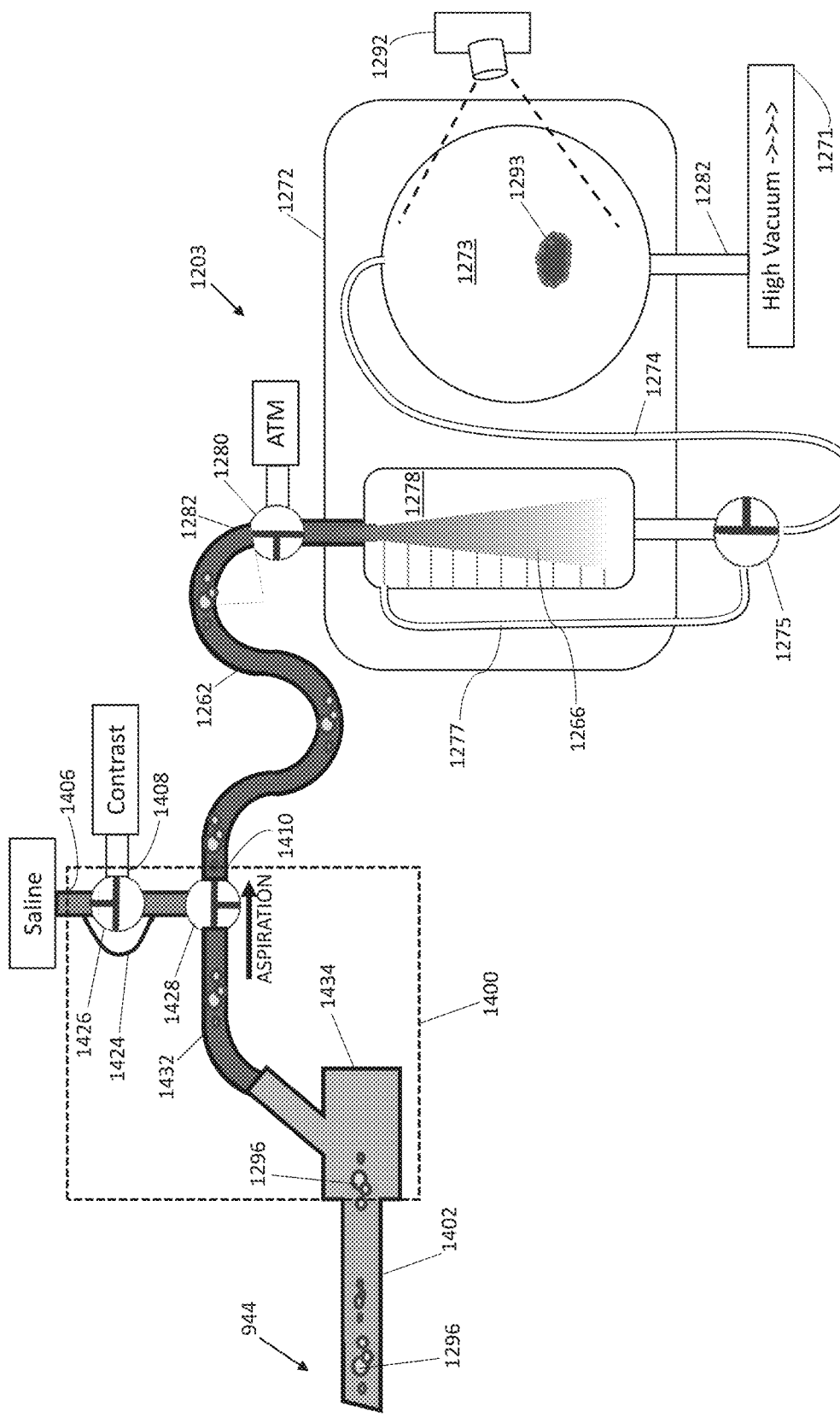

FIG. 84 illustrates same configuration of a fluidics system as illustrated in FIG. 82 where "high" vacuum is still provided to a catheter 1402 but FIG. 84 represents a later time than the example illustrated in FIG. 83. In the representation illustrated in FIG. 83, high vacuum is still being applied to the vacuum flow-path, the clot 1293 is ingested is captured in the clot pod 1273. When the control valves are aligned to provide a high vacuum flow-path to the catheter, air bubbles 1296 are formed in the stream of blood flowing back from the catheter distal tip to the clot pod assembly 1272. An imaging sensor 1292 can be positioned to generate an image of the clot pod 1273, and the image can be displayed locally and/or displayed at the remote location for viewing by a medical practitioner. In some embodiments, the generated image can be processed by the controller using feature detection functionality (e.g., image processing) to assess the presence of a clot in the image, and/or size or characteristics of the clot or clot material, and this information can be displayed locally or at the remote location. However, at this portion of the process the clot pod may include a mix of blood, air, and clot material in the clot pod and it can be hard to determine if the clot is in the clot pod until a saline flush is performed. In some embodiments, the clot is assessed and the controller uses the assessed information to determine one or more subsequent actions, For example, to notify a medical practitioner of the presence of the clot in the clot pod 1273, to start another process or process step (e.g., begin to perform a saline flush).

FIG. 85 illustrates the fluidics system shown in FIG. 84 where the controller is controlling the vacuum regulator to provide "high" vacuum in the vacuum flow-path 1282 to facilitate a saline flush of vacuum channel 1262 and a saline flush of the clot pod assembly 1272, including the clot pod 1273. Saline flow during a "saline flush" is a relatively high volume of saline compared to the low volume of saline flowing through a saline restricted-flow channel 1424 in the mount in a normal operating configuration. To perform a saline flush, the controller can receive an input to perform a saline flush, for example, from a remote control operated be a medical practitioner at the remote location, or from a process being run by the controller (e.g., computer executable instructions). In some examples, a medical practitioner sees sufficient flow of fluid through the drip chamber and then the physician turns off aspiration, and the system can flush the clot pod either automatically or as controlled by an input of a medical practitioner. In some examples, signals from the pressure sensors 1279, 929 in the cassette and mount can used by a controller to detect a detect high-flow condition and the controller can automatically turn off aspiration by actuating a control valve in the mount or the vacuum subsystem.

In some examples, the imaging sensor 1292 generates an image of the clot pod 1273, the controller processes the image using image processing (e.g., feature detection), a signal is generated to indicate a clot has been captured in the clot pod 1273, and the controller begins a saline flush process based at least in part on such a signal. When a controller receives the signal to perform the saline flush, if not already so aligned, the controller can align the vacuum subsystem first control valve 1275 to provide vacuum through the drip chamber 1278, align the first control valve 1426 of the mount 1400 to provide a saline flow-path through the first control valve 1426 to the second control valve 1428, and align the second control valve 1428 to provide a high volume saline flow-path through the second control valve 1428 and channel 1262 to the second control valve 1280 of the vacuum subsystem. The controller can further align the second control valve 1280 to allow a saline into the clot pod assembly 1272. In the example illustrated in FIG. 85, a relatively high volume of saline flows through channel 1282, into the drip chamber 1278, and flows through the vacuum subsystem first control valve 1275 and the clot pod 1273, flushing blood and any clot material from the drip chamber 1278 into the clot pod 1273, and flushing blood from the clot pod 1273 out through vacuum port 1271 to a vacuum canister such that the clot 1293 is more easily visible for viewing and assessment by a medical practitioner and/or an imaging sensor 1292. While the saline flush is occurring, fluid (e.g., blood, saline) in the vacuum flow-path 1282 will likely contain air bubbles due to the high vacuum, which necessitates a backbleed process (e.g., described in reference to FIG. 86) to remove the air filled blood from the system and prevent it from flowing back into the patient.

Figure 86:
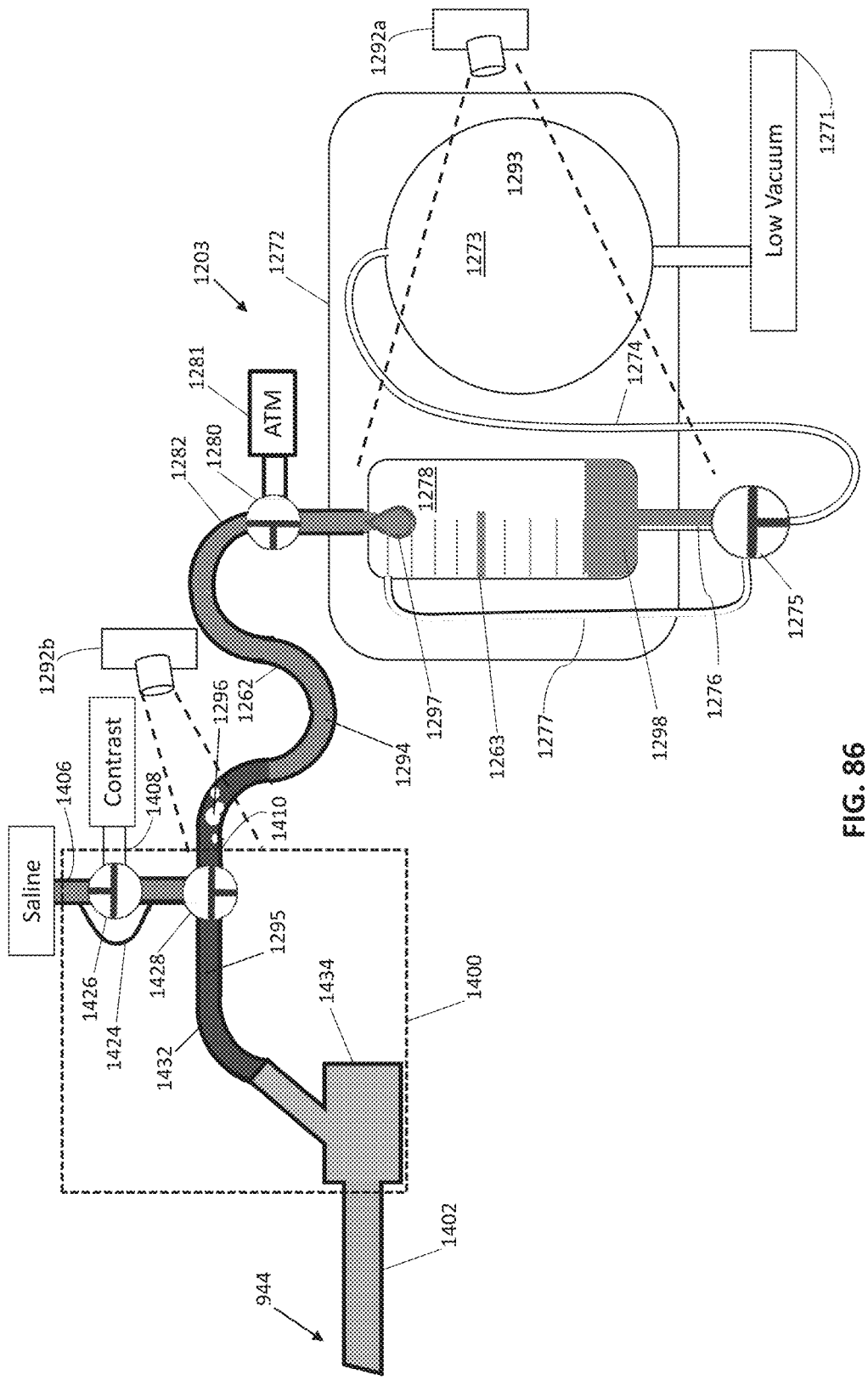

FIG. 86 illustrates an example configuration of the fluidics system shown in FIG. 85 during a "backbleed" process. In the representation shown in FIG. 86, channel 1262 represents the vacuum communication channel between the vacuum subsystem 1203 in the mounts 1400. During backbleed, a "low" level vacuum is provided to the vacuum channel 1262, mount 1400, and catheter 1402 to cause a slow flow of blood foam and fluid containing air from the catheter and mount into the vacuum channel 1262 towards the vacuum subsystem 1203, removing blood foam from the catheter and mount. The blood foam is moved out of the mount and at least past the mount second control valve 1428 of the mount and into the vacuum channel 1282 so that subsequent fluid provided to the catheter will not include any blood foam. A backbleed process can be performed to clear blood foam from the catheter and/or the mount, and is typically performed after aspiration or whenever a high level of vacuum has been applied to the catheter such that there is a likelihood of blood foam in the catheter or the mount. In some embodiments, prior to starting the backbleed process, the controller can align the second control valve 1280 to place the drip chamber 1278, which is subjected to vacuum, in fluid communication with a connector 1281 open to atmospheric pressure, and align the first control valve 1275 to align channel 1276 to the clot pod inlet 1274 to quickly flush out the drip chamber and the clot pod 1273 with air, and then once it has been flushed the controller can align the second control valve 1280 to close the connection to atmospheric pressure and align the first control valve 1275 to place the clot pod inlet 1274 in fluid communication with drip chamber bypass channel 1277. The controller can receive a signal indicating to begin a backbleed process, the signal based on an input provided by medical practitioner at a remote location or at the locally. In some embodiments, the signal may be based on another process controlled by the controller, for example, that a saline flush process has been completed. In some embodiments, the controller may provide a visual or audio indication that a backbleed process may be necessary, for example, if a pressure sensor 929 (FIG. 69) in the mount indicates a vacuum level sufficient to cause blood foam to occur. Similar to the actions performed in FIGS. 81-85, the controller aligns control valves in the mount and the vacuum subsystem, and controls the level of vacuum provided by the vacuum subsystem to perform the backbleed process.

In an example, prior to starting the backbleed process the control valves in the vacuum subsystem 1203 and the mount 1400 may be aligned as illustrated in FIG. 85 with blood foam present in the catheter 1402 and the mount 1400. When the controller receives a signal to begin backbleed, the vacuum source is controlled to provide low vacuum through the vacuum subsystem 1203, and the first control valve 1426 of the mount is aligned to prevent flow of saline or contrast to the second control valve 1428 (note: a small amount of saline may still be flowing towards the second control valve 1428 via the saline restricted-flow channel 1424). The second control valve 1428 is aligned to place the catheter 1402 and primary channel 1432 in fluid communication with the vacuum channel 1262. In the vacuum subsystem, first control valve 1275 is aligned to provide vacuum to the drip chamber 1728 via bypass channel 1277 and stopping fluid flow from the clot pod inlet line 1274 to the drip chamber outlet line 1276, and the second control valve 1280 is aligned (or maintains its alignment) to provide fluid flow from channel 1262 to the drip chamber 1278. This alignment of the control valves with the low vacuum level causes blood foam other fluid to slowly flow from the catheter 1402 in the mount 1400 through the park second control valve 1428 and into channel 1262 towards the drip chamber 1278, and drip into the drip chamber 1278. The level of vacuum is set to be a low level that causes this slow fluid flow to occur such that the fluid can be visually seen dripping into and filling the drip chamber 1278, such that fluid 1298 accumulates in the bottom of the drip chamber 1278. One or more graduations (lines) 1263 along the side of the drip chamber 1278 allow a medical practitioner to visually determine how much fluid has been backbled from the catheter/mount. As shown in FIG. 86, channel 1262 between the vacuum subsystem 1203 in the mount 1400 contains saline at the beginning of the backbleed process (for example, if being done after saline flush). During the backbleed process, saline in channel 1262 slowly flows to and into the drip chamber 1278, and the drip chamber 1278 is configured to be visible so a user can see it filling with fluid. Blood foam and other fluid in the mount and the catheter flows from the catheter lumen and from primary channel 1432 through the second control valve 1428, out of the mount 1400 into channel 1262 and flows towards the drip chamber 1278, while saline in the channel 1262 upstream of the blood foam 1296 flows into the drip chamber 1278.

Channel 1262 represents the vacuum communication in the first tubing set 1302, the splitter 1310, and the second tubing set 1316. In some embodiments, the total length of channel 1262 is about 14 feet which is longer than a total length of any fluid flow-path in the mount 1400 and the catheter 1402, for example, between two and four times longer. Correspondingly, the volume of fluid (blood foam, saline) in channel 1262 is also two to four times the volume of blood foam and fluid in the catheter 1402 and the mount 1400. Accordingly, removing blood foam from the catheter and mount during a backbleed process does not require all of the blood foam flow through the entire channel 1262 to reach the drip chamber 1278. Instead, the blood foam need only to be removed from the catheter 1402 and the mount 1400 and flow into the channel 1262. FIG. 86 illustrates this fluid flow, showing blood foam 1296, that has been removed from the catheter 1402 and the mount 1400 resides in distal portion of channel 1262 while a proximal portion of the channel 1262 contain saline which is dripping into the drip chamber 1278. Blood 1295 in primary channel 1432 of the mount is free of blood foam. Thus, to minimize the loss of blood from the patient, only a predetermined amount of fluid needs to be backbled to remove blood foam from the mounts 1400 and the catheter 1402, the predetermined amount of fluid being dependent at least in part on volume of liquid that can be in the mounts 1400 and the catheter 1402, which is determined based on the size of the catheter 1402 and the size of primary channel 1432. In an example, if the volume of the catheter 1402 and the primary channel 1432 is 5 mL, to ensure blood foam has been sufficiently removed from the catheter and mount, a fluid volume of greater than 5 mL (e.g., at least about 6 mL, 7 mL, 8 mL, 9 mL, or 10 mL) should flow into the drip chamber 1278 during backbleed. The amount of blood flowing into the drip chamber 1278 can be monitored using the graduation lines 1263, and when the fluid level reaches a certain amount (e.g., 10 mL) the vacuum subsystem first control valve 1275 can be aligned to connect the drip chamber outlet line 1276 to the clot pod inlet line 1276, allowing fluid collected in the drip chamber 1278 to be flushed to the vacuum canister. In an example, backbleed is performed to fill the drip chamber 1278 with about 10 mL of fluid, the fluid in the drip chamber 1278 is flushed to the vacuum canister, and the first control valve 1275 is realigned such that the vacuum flow-path is from the clot pod inlet line 1274 to the bypass line 1277. Then, a second volume of 10 mL of fluid is allowed to fill the drip chamber 1278, the first control valve 1275 is aligned to connect the drip chamber outlet line 1276 to the clot pod inlet line 1276, the fluid in the drip chamber 1278 is again flushed to the vacuum canister.

In some embodiments, an imaging sensor 1292 can be positioned to generate an image of the drip chamber 1278 and the image can be displayed on user interfaces locally and at the remote location such that the flow of fluid (e.g., saline) dripping into the drip chamber can be visually seen by a medical practitioner to verify backbleed is occurring and determine when to flush out the fluid in the drip chamber. Images generated of the drip chamber can be displayed in various ways on user interfaces on a local display or a remote display to help determine the amount of back-bled fluid. In an example, an image of the drip chamber can be displayed and a target volume mark can be shown at a certain level on the drip chamber (e.g., as an overlay) to help a viewer determine when enough fluid has been back-bled. In an example, placement of the target volume mark can be at a predetermined level. In an example, placement of the target mark can be at a level based in part on characteristics of the system, for example, which catheters are used, lengths of certain fluid channels in the hub assemblies, and the like. The target mark can be displayed in a color unique in the displayed image to be more visible to a user. In some embodiments, image processing can be performed on images of the drip chamber to determine quantitatively the volume of the back-bled fluid, and the determined amount can be shown on a user interface on a local display or a remotely located display.

The amount of fluid that is needed to be backbled is dependent on the effective ID of the catheter 1402 (which may be affected if another elongated device is positioned in the lumen of the catheter) and the volume of the primary channel 1432. In some embodiments, this information can be predetermined and stored in a parameter file, and used by the controller determine how much backbleed is needed and indicate the amount or status to a medical practitioner at the remote location or locally. In some embodiments, the controller can perform the backbleed process automatically (while being monitored by a medical practitioner based at least in part on predetermined information about the size of the catheters being used. In one example, the predetermined information assumes that there are no other elongated devices in the catheter lumen, such that the estimated volume of the catheter is its maximum volume.

During a backbleed process, in typical embodiments, channel 1262 is transparent and the fluid flow out of the mount vacuum port 1410 through channel 1262 can be visually monitored by a medical practitioner locally. When blood exiting the vacuum port 1410 no longer includes blood foam, the backbleed process can be stopped, for example, by providing an input to the controller to end the backbleed process. If additional procedures are required, the controller can configure the system for such processes (e.g., saline drip and contrast mode). In some embodiments, an imaging sensor 1292*b* can be positioned to generate an image of a portion of channel 1262 proximate to the mount vacuum port 1410. For example, the portion of the second tubing set 1316 coupled to mount 1400 that includes the vacuum subchannel 1335, or another portion of the first tubing set or the second tubing set, preferably a portion of vacuum tubing close to the mount. In some embodiments, the system can include two or more imaging sensors to generate images of the drip chamber, the clot pod, and/or a portion of tubing near the mount (e.g., to see whether blood backbled from the mount includes blood foam). The image can be displayed locally and/or provided to the remote location for medical practitioner performing the procedure can see the characteristics of the blood flowing out of the mount to determine if it contains blood foam. In this embodiment, the imaging sensor 1292 can be positioned as a suitable place in the local operating environment.

Figure 87:
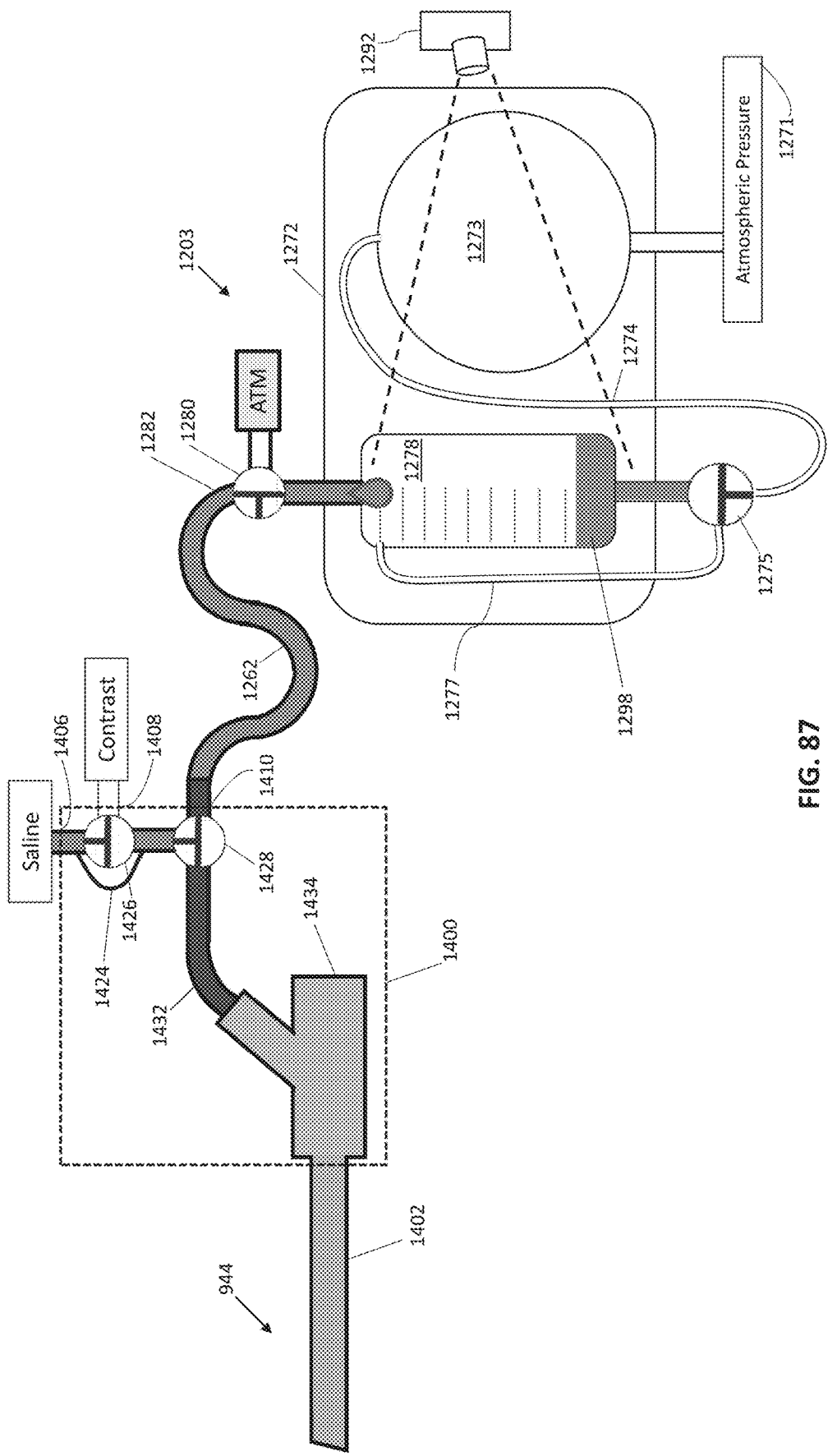
FIG. 87 illustrates an example configuration of a fluidics system during patency check of a catheter.

FIG. 87 illustrates a representation of an example configuration of a fluidics system for performing a patency check of a catheter. In this example, a controller can receive an input to perform a patency check of a selected one of the one or more catheters of the system, for example, guide catheter 1402*a* (FIG. 69), procedure catheter 1420*b*, or access catheter 1402*c*. A patency check can be performed with no other elongated device in the lumen of the catheter, or the patency check can be performed with an elongated device in the lumen of the catheter. In this example, the controller aligns the mount first control valve 1426 to prevent saline or contrast flow to the second control valve 1428, except for saline flowing in a saline restricted-flow channel 1424 (FIG. 69) and aligns the second control valve 1428 to put primary channel 1432 of the mount 1400 in fluid communication with vacuum channel 1262. The controller also aligns the vacuum subsystem 1203 first control valve 1280 to allow fluid flow from channel 1262 into the drip chamber 1278, aligns the second control valve 1275 such that the clot pod inlet line 1274 is in fluid communication with the bypass line 1277, and controls a vacuum source/vacuum regulator to set a vacuum level provided to the vacuum subsystem 1203 at about atmospheric pressure, or at a low vacuum level. Because the channel 1262 contain saline prior to the patency check being performed, in this configuration if the catheter is "clear" then saline should drip into the drip chamber 1278 at a rate that can be predetermined, for example, based on the size of the specific catheter used for the patency check, the level of vacuum, and other system parameters.

Various fluidics systems and methods are described herein primarily in the context of providing saline, contrast, and vacuum to an interventional device. However, in certain embodiments, other fluids, such as one or more drugs or components thereof (e.g., therapeutic drugs, anti-complication drugs, lytic drugs, non-lytic drugs, post thrombectomy drugs, interventional oncology drugs), can be provided using the fluidics systems and/or methods described herein. For example, a drug may be delivered through an interventional device alternatively to saline, contrast, and/or vacuum or additionally to saline, contrast, and/or vacuum using a subsystem that is the same as or generally similar to the saline subsystem or the contrast subsystem.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processor on a hubs, RHVs, and/or a computing device associated with the fluidics management systems described herein. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

Various systems and methods are described herein primarily in the context of a neurovascular access or procedure. However, the inventors contemplate applicability of the disclosed catheters, systems and methods to any of a wide variety of alternative applications, including within the coronary vascular or peripheral vascular systems as well as other hollow organs or tubular structures in the body.

As used in the description and claims, the singular form "a", "an" and "the" include both singular and plural references unless the context clearly dictates otherwise. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A fluidics system, comprising:
 a cassette configured to be releasably coupled to a pump station, and configured to receive saline from a saline source, receive contrast from a contrast source, and receive vacuum from a vacuum source, the cassette comprising:
  a housing;
  a saline subsystem supported by the housing, the saline subsystem having a first saline flow-path and one or more robotically actuated saline control valves arranged for directing saline through the first saline flow-path, the one or more robotically actuated saline control valves configured to operatively couple to one or more saline actuators located in the pump station such that each saline valve is coupled to a unique saline actuator when the cassette is coupled to the pump station,
  a contrast subsystem supported by the housing, the contrast subsystem having a first contrast flow-path and one or more robotically actuated contrast control valves arranged for directing contrast through the first contrast flow-path, the one or more robotically actuated contrast control valves configured to operatively couple to one or more contrast actuators located in the pump station such that each contrast valve is coupled to a unique contrast actuator when the cassette is coupled to the pump station, and
  a vacuum subsystem supported by the housing, the vacuum subsystem having a first vacuum flow-path and one or more robotically actuated vacuum control valves arranged for directing vacuum through the first vacuum flow-path, the one or more robotically actuated vacuum control valves configured to operatively couple to one or more vacuum actuators located in the pump station such that each vacuum valve is coupled to a unique vacuum actuator when the cassette is coupled to the pump station;
 a splitter having a second saline flow-path, a second contrast flow-path, and a second vacuum flow-path, each of the second saline flow-path, second contrast flow-path, and second vacuum flow-path having a single proximal end and a plurality of distal ends;
 a first tubing set having a first length and coupled to the cassette and the splitter, the first tubing set including:
  a single saline channel coupled to the first saline flow-path and the proximal end of the second saline flow-path,
  a single contrast channel coupled to the first contrast flow-path and the proximal end of the second contrast flow-path, and a single vacuum channel coupled to the first vacuum flow-path and the proximal end of the second vacuum flow-path;

two or more hub assemblies, the two or more hub assemblies comprising a first hub assembly configured to have a third saline flow-path, a third contrast flow-path, and a third vacuum flow-path for providing saline, contrast, and vacuum to a lumen of a first catheter coupled to the first hub assembly; and a second tubing set having a second length that is shorter than the first length, the second tubing set comprising a plurality of tube groups, a proximal end of each tube group of the plurality of tube groups coupled to the splitter and a distal end of each tube group of the plurality of tube groups coupled to one of the two or more hub assemblies, at least one of the plurality of tube groups including:

a saline subchannel coupled to the distal end of the second saline flow-path of the splitter, a contrast subchannel coupled to the distal end of the second contrast flow-path of the splitter, and a vacuum subchannel coupled to the distal end of the second vacuum flow-path of the splitter.

2. The fluidics system of claim 1, wherein the first hub assembly comprises a mount, and wherein the mount comprises the third saline flow-path, the third contrast flow-path, and the third vacuum flow-path.

3. The fluidics system of claim 2, wherein the mount further comprises a connector, wherein the mount is configured to provide saline, contrast, and vacuum through the connector to the lumen of the first catheter.

4. The fluidics system of claim 3, wherein the first hub assembly comprises one or more robotically actuated control valves controlled by a control system to selectively align the third saline flow-path, the third contrast flow-path, and the third vacuum flow-path to be in fluid communication with the lumen of the first catheter via the connector.

5. The fluidics system of claim 1, wherein the first length of the first tubing set is at least twice as long as the second length of the second tubing set.

6. The fluidics system of claim 1, wherein a ratio of the first length to the second length is greater than 1:4.

7. The fluidics system of claim 1, wherein the saline source comprises a first saline source, wherein the saline subsystem is configured to receive saline from the first saline source and a second saline source, wherein the one or more robotically actuated saline control valves includes a first robotically actuated valve controlled by a control system to place the first saline flow-path in fluid communication with the first saline source or the second saline source.

8. The fluidics system of claim 7, wherein the control system controls the first robotically actuated valve to switch to receiving saline from a different one of the first and second saline sources based on receiving a signal from a sensor.

9. The fluidics system of claim 8, wherein the sensor is a weight sensor configured to sense the weight of the first saline source and the second saline source.

10. The fluidics system of claim 8, wherein the sensor is an air sensor configured to detect air in the first saline flow-path.

11. The fluidics system of claim 1, wherein the contrast subsystem comprises a contrast pump actuatable by a control system to provide contrast to the first hub assembly.

12. The fluidics system of claim 1, wherein the vacuum subsystem comprises a clot pod.

13. The fluidics system of claim 12, wherein the clot pod includes at least one transparent surface positioned such that contents of the clot pod are visible from outside of the cassette.

14. The fluidics system of claim 1, wherein the vacuum subsystem comprises a drip chamber in fluid communication with the first vacuum flow-path, wherein the one or more robotically actuated vacuum valves are configured to be controlled by a control system such that fluid aspirated by the vacuum subsystem is collected in the drip chamber.

15. The fluidics system of claim 14, wherein the drip chamber includes at least one transparent surface positioned such that contents of the drip chamber are visible from outside of the cassette.

16. The fluidics system of claim 14, wherein the vacuum subsystem further comprises a clot pod, and wherein the drip chamber is positioned in the first vacuum flow-path between the clot pod and the first tubing set.

17. The fluidics system of claim 14, wherein the one or more robotically actuated vacuum valves are configured to be controlled by the control system for controlling the first vacuum flow-path through the drip chamber and a clot pod.

18. The fluidics system of claim 17, wherein the one or more robotically actuated vacuum valves include a first valve positioned in the first vacuum flow-path between the drip chamber and the clot pod and a second valve positioned on an opposite side of the drip chamber in the first vacuum flow-path between the drip chamber and the first tubing set, wherein the first valve and the second valve are selectively controlled to control the flow of fluid and material from the two or more hub assemblies to the drip chamber and the clot pod.

19. The fluidics system of claim 1, further comprising a plurality of catheters, wherein the plurality of catheters includes the first catheter and a second catheter, the second catheter connected to a second hub assembly of the two or more hub assemblies.

20. The fluidics system of claim 1, wherein the first hub assembly includes a saline air sensor positioned to detect air in the third saline flow-path, and a contrast air sensor positioned to detect air in the third contrast flow-path.

21. The fluidics system of claim 20, wherein the first hub assembly comprises one or more robotically actuated control valves controlled by a control system to selectively align the third saline flow-path and the third contrast flow-path of the first hub assembly to be in fluid communication with the lumen of the first catheter, and wherein the saline and contrast air sensors are positioned in the third saline and contrast flow-paths of the first hub assembly, respectively, between the one or more robotically actuated control valves and the second tubing set for detecting air in the third saline and contrast flow-paths before the air reaches the one or more robotically actuated control valves.

22. The fluidics system of claim 21, wherein the first hub assembly further comprises a connector to provide saline, contrast, and vacuum through the connector to the lumen of the catheter, wherein one or more of the one or more robotically actuated control valves of the first hub assembly are controlled by a control system to block the saline and contrast flow-paths to the connector based on a signal from one of the saline and contrast air sensors.

23. The fluidics system of claim 1, wherein each of the two or more hub assemblies includes a plurality of sensors, and wherein the first tubing set, the splitter, and each tube group of the second tubing set further comprises an electrical channel coupled to the plurality of sensors in the two or more hub assemblies, the electrical channel configured to communicate electrical signals from the plurality of sensors to an electrical interface on the cassette that is configured to electrically connect to a corresponding electrical interface on the pump station to provide the signals from the plurality of sensors in the hub assemblies to a control system.

24. The fluidics system of claim 23, wherein the plurality of sensors includes a saline air sensor positioned to detect air in the third saline flow-path, a contrast air sensor positioned to detect air in the third contrast flow-path, and a pressure sensor.

* * * * *